United States Patent
Kataoka et al.

(10) Patent No.: US 10,248,019 B2
(45) Date of Patent: Apr. 2, 2019

(54) PATTERN FORMING METHOD, ACTINIC RAY-SENSITIVE OR RADIATION-SENSITIVE RESIN COMPOSITION AND RESIST FILM

(71) Applicant: FUJIFILM CORPORATION, Tokyo (JP)

(72) Inventors: Shohei Kataoka, Shizuoka (JP); Kaoru Iwato, Shizuoka (JP); Kana Fujii, Shizuoka (JP); Sou Kamimura, Shizuoka (JP); Yuichiro Enomoto, Shizuoka (JP); Keita Kato, Shizuoka (JP); Shuhei Yamaguchi, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 2 days.

(21) Appl. No.: 13/725,483

(22) Filed: Dec. 21, 2012

(65) Prior Publication Data

US 2013/0122427 A1 May 16, 2013

Related U.S. Application Data

(63) Continuation of application No. PCT/JP2011/064850, filed on Jun. 22, 2011.

(30) Foreign Application Priority Data

Jun. 25, 2010 (JP) .................................. 2010-145618
Dec. 22, 2010 (JP) .................................. 2010-286766

(51) Int. Cl.
| | | |
|---|---|---|
| G03F 7/004 | (2006.01) | |
| C07C 303/32 | (2006.01) | |
| C07C 309/04 | (2006.01) | |
| C07C 309/06 | (2006.01) | |
| C07C 309/07 | (2006.01) | |
| C07C 309/10 | (2006.01) | |
| C07C 309/12 | (2006.01) | |
| C07C 309/13 | (2006.01) | |
| C07C 309/14 | (2006.01) | |
| C07D 211/96 | (2006.01) | |
| G03F 7/039 | (2006.01) | |
| G03F 7/20 | (2006.01) | |
| G03F 7/32 | (2006.01) | |
| G03F 7/075 | (2006.01) | |
| G03F 7/11 | (2006.01) | |

(52) U.S. Cl.
CPC ............ *G03F 7/004* (2013.01); *C07C 303/32* (2013.01); *C07C 309/04* (2013.01); *C07C 309/06* (2013.01); *C07C 309/07* (2013.01); *C07C 309/10* (2013.01); *C07C 309/12* (2013.01); *C07C 309/13* (2013.01); *C07C 309/14* (2013.01); *G03F 7/0045* (2013.01); *G03F 7/0046* (2013.01); *G03F 7/0392* (2013.01); *G03F 7/0397* (2013.01); *G03F 7/2041* (2013.01); *G03F 7/325* (2013.01); *C07D 211/96* (2013.01); *G03F 7/0755* (2013.01); *G03F 7/11* (2013.01)

(58) Field of Classification Search
CPC ... G03F 7/0045; G03F 7/2041; C07C 309/04; C07C 309/06; C07C 309/07; C07C 309/10; C07C 309/12; C07C 309/13; C07C 309/14; C07C 303/32; C07D 211/96
USPC ........ 430/325, 326, 330, 921, 922; 562/113, 562/105, 100, 109; 546/245
See application file for complete search history.

(56) References Cited

U.S. PATENT DOCUMENTS

| | | | | |
|---|---|---|---|---|
| 4,743,529 A | * | 5/1988 | Farid et al. ................. | 430/281.1 |
| 7,498,116 B2 | * | 3/2009 | Hirano et al. .............. | 430/270.1 |
| 7,524,609 B2 | * | 4/2009 | Wada .................... | G03F 7/0045 |
| | | | | 430/270.1 |
| 8,227,183 B2 | * | 7/2012 | Tsubaki et al. ............... | 430/434 |
| 8,247,160 B2 | * | 8/2012 | Utsumi et al. ............. | 430/270.1 |
| 2005/0123859 A1 | * | 6/2005 | Wada et al. .................... | 430/313 |
| 2006/0166135 A1 | | 7/2006 | Wada | |
| 2007/0141512 A1 | | 6/2007 | Wada et al. | |
| 2007/0298352 A1 | * | 12/2007 | Kobayashi et al. .......... | 430/302 |
| 2008/0187860 A1 | | 8/2008 | Tsubaki et al. | |
| 2008/0187863 A1 | * | 8/2008 | Shibuya ...................... | 430/281.1 |
| 2008/0248419 A1 | * | 10/2008 | Hirano ........................ | 430/281.1 |
| 2009/0011366 A1 | | 1/2009 | Tsubaki et al. | |
| 2009/0023096 A1 | * | 1/2009 | Tarutani et al. ........... | 430/281.1 |
| 2010/0330507 A1 | | 12/2010 | Tsubaki et al. | |
| 2011/0300485 A1 | | 12/2011 | Tsubaki et al. | |

FOREIGN PATENT DOCUMENTS

| | | |
|---|---|---|
| JP | 2008189601 A | 8/2002 |
| JP | 3606291 B2 | 1/2005 |
| JP | 2006201711 A | 8/2006 |

(Continued)

OTHER PUBLICATIONS

Office Action dated Jul. 14, 2014, issued by the Taiwanese Patent Office in Taiwanese Application No. 100122270.

(Continued)

*Primary Examiner* — John S Chu
(74) *Attorney, Agent, or Firm* — Sughrue Mion, PLLC

(57) ABSTRACT

A pattern forming, method, includes: (i) forming a film from an actinic ray-sensitive or radiation-sensitive resin composition that contains (A) a compound capable of generating an acid upon irradiation with an actinic ray or radiation and decomposing by an action of an acid to decrease a solubility of the compound (A) for an organic solvent; (ii) exposing the film; and (iii) performing development by using a developer containing an organic solvent.

9 Claims, No Drawings

(56) References Cited

FOREIGN PATENT DOCUMENTS

| JP | 2007199692 A | | 8/2007 |
|---|---|---|---|
| JP | 2008189597 A | | 8/2008 |
| JP | 2008281974 A | | 11/2008 |
| JP | 2008281975 A | | 11/2008 |
| JP | 2008292975 A | | 12/2008 |
| JP | 2009025708 A | | 2/2009 |
| JP | 2010134279 | * | 6/2010 |
| KR | 10-2008-0000527 A | | 1/2008 |
| TW | 201039055 A1 | | 11/2010 |
| WO | 2010/095763 A1 | | 8/2010 |

OTHER PUBLICATIONS

International Search Report (PCT/ISA/210) dated Aug. 2, 2011 issued by the International Searching Authority in counterpart International Application No. PCT/JP2011/064850.
Written Opinion (PCT/ISA/237) dated Aug. 2, 2011 of the International Searching Authority issued in counterpart International Application No. PCT/JP2011/064850.
Office Action issued by the Korean Intellectual Property Office, dated Oct. 22, 2014, in counterpart Korean Application No. 10-2012-7033917.

* cited by examiner

PATTERN FORMING METHOD, ACTINIC RAY-SENSITIVE OR RADIATION-SENSITIVE RESIN COMPOSITION AND RESIST FILM

CROSS REFERENCE TO RELATED APPLICATIONS

This application is a continuation of International Application No. PCT/JP2011/064850 filed Jun. 22, 2011, and claims priority from Japanese Patent Application 2010-145618 filed Jun. 25, 2010, and Japanese Patent Application 2010-286766 filed Dec. 22, 2010, the contents of all of which are incorporated herein by reference in their entirety.

TECHNICAL FIELD

The present invention relates to a pattern forming method, and an actinic ray-sensitive or radiation-sensitive resin composition and a resist film each used for the pattern forming method. More specifically, the present invention relates to a pattern forming method suitable for lithography in the process of producing a semiconductor such as IC or the production of a liquid crystal device or a circuit board such as thermal head and further in other photo-fabrication processes; and an actinic ray-sensitive or radiation-sensitive resin composition and a resist film each used for the pattern forming method. In particular, the present invention relates to a pattern forming method suitable for when performing exposure by an ArF exposure apparatus, an ArF immersion projection exposure apparatus or an EUV exposure apparatus each using a light source capable of emitting far ultraviolet ray at a wavelength of 300 nm or less; and an actinic ray-sensitive or radiation-sensitive resin composition and a resist film used for the pattern forming method.

BACKGROUND ART

Since the advent of a resist for KrF excimer laser (248 nm), a pattern forming method utilizing chemical amplification is being used so as to compensate for sensitivity reduction due to light absorption. For example, in the positive chemical amplification method, a photoacid generator contained in the exposed area decomposes upon irradiation with light to produce an acid and, for example, in the baking process after exposure (PEB: Post Exposure Bake), an alkali-insoluble group contained in the photosensitive composition is changed into an alkali-soluble group by the catalytic action of the acid generated. Thereafter, development is performed using, for example, an alkali solution, whereby the exposed area is removed and a desired pattern is obtained.

As for the alkali developer used in the method above, various alkali developers have been proposed, but an aqueous alkali developer of 2.38 mass % TMAH (an aqueous tetramethylammonium hydroxide solution) is being used as the alkali developer for general purposes.

Furthermore, in view of enhancement of the pattern forming performance, such as enhancement of resolution in the positive chemical amplification method, it is being attempted to incorporate a group capable of decomposing by the action of an acid also into the photoacid generator (see, for example, Japanese Patent No. 3606291, JP-A-2006-201711 (the term "JP-A" as used herein means an "unexamined published Japanese patent application") and JP-A-2007-199692).

Due to the miniaturization of a semiconductor device, the trend is moving toward a shorter wavelength of the exposure light source and a higher numerical aperture (higher NA) of the projection lens, and an exposure machine using an ArF excimer laser with a wavelength of 193 nm as a light source has been developed at present. As a technique for more enhancing the resolution, a method of filling a high refractive-index liquid (hereinafter sometimes referred to as an "immersion liquid") between the projection lens and the sample (that is, an immersion method) has been proposed. Furthermore, EUV lithography of performing exposure to ultraviolet light at a shorter wavelength (13.5 nm) have been also proposed.

However, it is actually very difficult to find out an appropriate combination of a resist composition, a developer, a rinsing solution and the like necessary for forming a pattern with overall good performance. In particular, as the resolved line width of resist becomes finer, improvements of the line edge roughness performance of a line pattern and the in-plane uniformity of the pattern dimension are being demanded.

Recently, a pattern forming method using an organic solvent-containing developer has been developed (see, for example, JP-A-2008-281974, JP-A-2008-281975 and JP-A-2008-292975). For example, JP-A-2008-292975 discloses a pattern forming method including a step of applying, on a substrate, a resist composition capable of increasing the solubility for an alkali developer and decreasing the solubility for an organic solvent developer upon irradiation with an actinic ray or radiation, an exposure step, and a step of performing development by using an organic solvent developer. According to this method, a high-precision fine pattern can be stably formed.

However, the composition above is demanded to be more improved with respect to resolution, roughness performance and development time dependency.

SUMMARY OF INVENTION

An object of the present invention is to provide a pattern forming method ensuring excellent performance in terms of resolution such as pre-bridge dimension, roughness such as line edge roughness, and development time dependency, and an actinic ray-sensitive or radiation-sensitive resin composition and a resist film each used for the pattern forming method.

The present invention includes the following configurations, and the above-described object of the present invention can be attained by these configurations.

[1] A pattern forming method, comprising:
(i) forming a film from an actinic ray-sensitive or radiation-sensitive resin composition that contains (A) a compound capable of generating an acid upon irradiation with an actinic ray or radiation and decomposing by an action of an acid to decrease a solubility of the compound (A) for an organic solvent;
(ii) exposing the film; and
(iii) performing development by using a developer containing an organic solvent.

[2] The pattern forming method as described in [1] above, wherein a content of the organic solvent contained in the developer containing the organic solvent is from 90 to 100 mass % based on the entire amount of the developer.

[3] The pattern forming method as described in [1] or [2] above,
wherein the compound (A) has (B) a moiety capable of decomposing by an action of an acid to produce a hydroxyl group or a carboxyl group.

[4] The pattern forming method as described in [3] above,
wherein the moiety (B) capable of decomposing by an action of an acid to produce a hydroxyl group or a carboxyl group is represented by at least one formula selected from the group consisting of the following formulae (I-1) to (I-6):

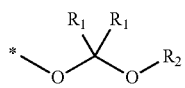
(I-1)

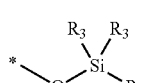
(I-2)

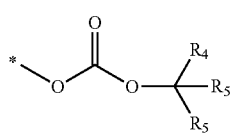
(I-3)

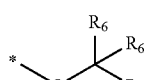
(I-4)

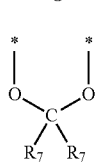
(I-5)

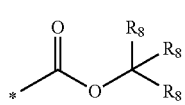
(I-6)

wherein in formula (I-1), each $R_1$ independently represents a hydrogen atom or a monovalent organic group, and two $R_1$'s may combine with each other to form a ring;

$R_2$ represents a monovalent organic group, and one $R_1$ and $R_2$ may combine with each other to form a ring;

in formula (I-2), each $R_3$ independently represents a monovalent organic group, and two $R_3$'s may combine with each other to form a ring;

in formula (I-3), $R_4$ represents a hydrogen atom or a monovalent organic group;

each $R_5$ independently represents a monovalent organic group, $R_5$'s may combine with each other to form a ring, and one $R_5$ and $R_4$ may combine with each other to form a ring;

in formula (I-4), each $R_6$ independently represents a hydrogen atom, an alkyl group, a cycloalkyl group, an aryl group, an alkenyl group or an alkynyl group, and two $R_6$'s may combine with each other to form a ring, provided that when one or two of three $R_6$'s are a hydrogen atom, at least one of the remaining $R_6$'s represents an aryl group, an alkenyl group or an alkynyl group;

in formula (I-5), each $R_7$ independently represents a hydrogen atom or a monovalent organic group, and $R_7$'s may combine with each other to form a ring;

in formula (I-6), each $R_8$ independently represents a monovalent organic group, and two $R_8$'s may combine with each other to form a ring; and in formulae (I-1) to (I-6), * represents a bond.

[5] The pattern forming method as described in [3] or [4] above,
wherein the compound (A) is an ionic compound having, in a cation moiety, (B) a moiety capable of decomposing by an action of an acid to produce a hydroxyl group or a carboxyl group.

[6] The pattern forming method as described in any one of [1] to [5] above,
wherein the compound (A) is represented by at least one formula selected from the group consisting of the following formulae (II-1) to (II-3):

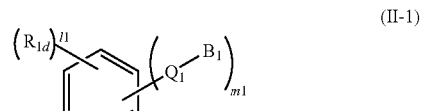
(II-1)

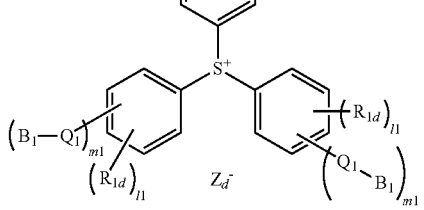
(II-2)

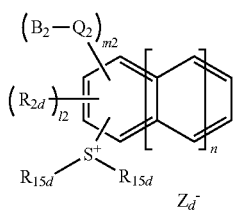

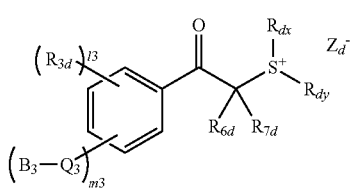
(II-3)

wherein in formula (II-1), each $R_{1d}$ independently represents a hydrogen atom or a monovalent organic group, and two $R_{1d}$'s may combine with each other to form a ring;

$Q_1$ represents a single bond or a divalent linking group;

$B_1$ represents (B) a moiety capable of decomposing by an action of an acid to produce a hydroxyl group or a carboxyl group;

$Z_1^-$ represents a non-nucleophilic counter anion having X number of groups represented by ($B_1$-$Q_1$);

each l1 independently represents an integer of 0 to 5;

each m1 independently represents an integer of 0 to 5;

X represents an integer of 0 to 3;

provided that at least one of m1's and X represents an integer of 1 or more;

in formula (II-2), each $R_{2d}$ independently represents a hydrogen atom or a monovalent organic group, and two $R_{2d}$'s may combine with each other to form a ring;

each $R_{15d}$ independently represents an alkyl group, and two $R_{15d}$'s may combine with each other to form a ring;

$Q_2$ represents a single bond or a divalent linking group;

$B_2$ represents (B) a moiety capable of decomposing by an action of an acid to produce a hydroxyl group or a carboxyl group;

$Z_d^-$ represents a non-nucleophilic counter anion having X number of groups represented by ($B_2$-$Q_2$);

n represents 0 or 1;

each l2 independently represents an integer of 0 to 5;

each m2 independently represents an integer of 0 to 5;

X represents an integer of 0 to 3;

provided that at least one of m2 and X represents an integer of 1 or more;

in formula (II-3), each $R_{3d}$ independently represents a hydrogen atom or a monovalent organic group, and two $R_{3d}$'s may combine with each other to form a ring;

each of $R_{6d}$ and $R_{7d}$ independently represents a hydrogen atom or a monovalent organic group, and $R_{6d}$ and $R_{7d}$ may combine with each other to form a ring;

each of $R_{dx}$ and $R_{dy}$ independently represents an alkyl group, $R_{dx}$ and $R_{dy}$ may combine with each other to form a ring;

$Q_3$ represents a single bond or a divalent linking group;

$B_3$ represents (B) a moiety capable of decomposing by an action of an acid to produce a hydroxyl group or a carboxyl group;

$Z_d^-$ represents a non-nucleophilic counter anion having X number of groups represented by $(B_3-Q_3)$;

each l3 independently represents an integer of 0 to 5;

each m3 independently represents an integer of 0 to 5;

X represents an integer of 0 to 3; and provided that at least one of m3 and X represents an integer of 1 or more.

[7] The pattern forming method as described in any one of [3] to [6] above, wherein the moiety (B) is (B') a moiety capable of decomposing by an action of an acid to produce an alcoholic hydroxyl group.

[8] The pattern forming method as described in any one of [1] to [7] above, wherein the compound (A) is a compound represented by the following formula (II-4) or (II-5):

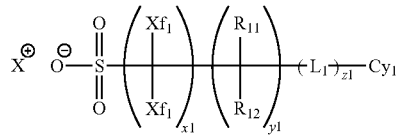

wherein each $X^+$ independently represents a counter cation;

Rf represents an alkyl group having at least one fluorine atom, a cycloalkyl group having at least one fluorine atom, or an aryl group having at least one fluorine atom;

each of $Xf_1$ and $Xf_2$ independently represents a fluorine atom or an alkyl group substituted with at least one fluorine atom;

each of $R_{11}$, $R_{12}$, $R_{21}$ and $R_{22}$ independently represents a hydrogen atom, a fluorine atom or an alkyl group, and when a plurality of $R_{11}$'s, $R_{12}$'s, $R_{21}$'s or $R_{22}$'s are present, each may be the same as or different from every others;

each of $L_1$ and $L_2$ independently represents a divalent linking group and when a plurality of $L_1$'s or $L_2$'s are present, each may be the same as or different from every others;

each of $Cy_1$ and $Cy_2$ independently represents a cyclic organic group;

provided that at least one of $Xf_1$, $R_{11}$, $R_{12}$, $L_1$ and $Cy_1$ is substituted with a group having a structure in which a polarity group is protected with a leaving group capable of decomposing and leaving by an action of an acid and that at least one of $Xf_2$, $R_{21}$, $R_{22}$, $L_2$, $Cy_2$ and Rf is substituted with a group having a structure in which a polarity group is protected with a leaving group capable of decomposing and leaving by an action of an acid;

each of x1 and x2 independently represents an integer of 1 to 20;

each of y1 and y2 independently represents an integer of 0 to 10; and each of z1 and z2 independently represents an integer of 0 to 10.

[9] The pattern forming method as described in any one of [1] to [8] above, wherein the compound (A) is a compound represented by the following formula (III):

$$B-Y-A^-X^+ \qquad (III)$$

wherein $A^-$ represents an organic acid anion;

Y represents a divalent linking group;

$X^+$ represents a counter cation; and

B represents a moiety capable of decomposing by an action of an acid to produce a hydroxyl group or a carboxyl group.

[10] The pattern forming method as described in any one of [1] to [9] above, wherein exposure in the step (ii) is immersion exposure.

[11] An actinic ray-sensitive or radiation-sensitive resin composition used for the pattern forming method as described in any one of [1] to [10] above, the composition comprising:

(A) an ionic compound capable of generating an acid upon irradiation with an actinic ray or radiation and having, in a cation moiety, (B') a moiety capable of decomposing by an action of an acid to produce an alcoholic hydroxyl group.

[12] The actinic ray-sensitive or radiation-sensitive resin composition as described in [11] above, wherein the moiety (B') capable of decomposing by an action of an acid to produce an alcoholic hydroxyl group is represented by at least one formula selected from the group consisting of the following formulae (I-1) to (I-5):

(I-1)

(I-2)

(I-3)

(I-4)

-continued (I-5)

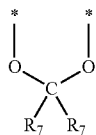

wherein in formula (I-1), each $R_1$ independently represents a hydrogen atom or a monovalent organic group, and two $R_1$'s may combine with each other to form a ring;

$R_2$, represents a monovalent organic group, and one $R_1$ and $R_2$ may combine with each other to form a ring;

in formula (I-2), each $R_3$ independently represents a monovalent organic, group, and two $R_3$ may combine with each other to form a ring;

in formula (I-3), $R_4$ represents a hydrogen atom or a monovalent organic group;

each $R_5$ independently represents a monovalent organic group, $R_5$'s may combine with each other to form a ring, and one $R_5$ and $R_4$ may combine with each other to form a ring;

in formula (I-4), each $R_6$ independently represents a hydrogen atom, an alkyl group, a cycloalkyl group, an aryl group, an alkenyl group or an alkynyl group, and two $R_6$'s may combine with each other to form a ring, provided that when one or two of three $R_6$'s are a hydrogen atom, at least one of the remaining $R_6$'s represents an aryl group, an alkenyl group or an alkynyl group;

in formula (I-5), each $R_7$ independently represents a hydrogen atom or a monovalent organic group, and $R_7$'s may combine with each other to form a ring; and in formulae (I-1) to (I-5), * represents a bond.

[13] The actinic ray-sensitive or radiation-sensitive resin composition as described in [11] for or [12] above, wherein the compound (A) is represented by at least one formula selected from the group consisting of the following formulae (II-1) to (II-3):

(II-1)

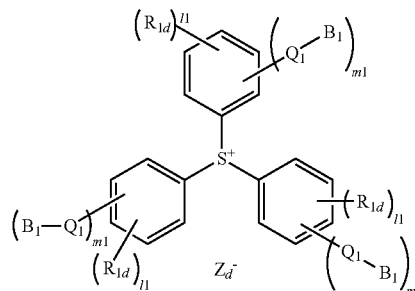

(II-2)

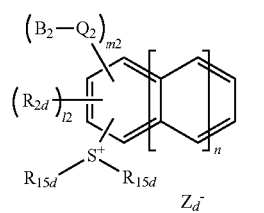

(II-3)

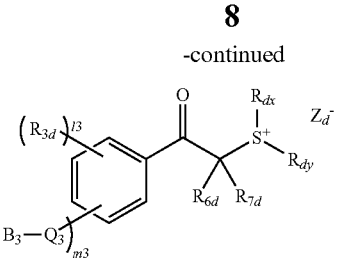

wherein in formula (II-1), each $R_{1d}$ independently represents a hydrogen atom or a monovalent organic group, and two $R_{1d}$'s may combine with each other to form a ring;

$Q_1$ represents a single bond or a divalent linking group;

$B_1$ represents (B') a moiety capable of decomposing by an action of an acid to produce an alcoholic hydroxyl group;

$Z_d^-$ represents a non-nucleophilic counter anion having X number of groups represented by ($B_1$-$Q_1$);

each l1 independently represents an integer of 0 to 5;

each m1 independently represents an integer of 0 to 5;

X represents an integer of 0 to 3;

provided that at least one of a plurality of m1's is an integer of 1 or more;

in formula (II-2), each $R_{2d}$ independently represents a hydrogen atom or a monovalent organic group, and two $R_{2d}$'s may combine with each other to form a ring;

each $R_{15d}$ independently represents an alkyl group, and two $R_{15d}$'s may combine with each other to form a ring;

$Q_2$ represents a single bond or a divalent linking group;

$B_2$ represents (B') a moiety capable of decomposing by an action of an acid to produce an alcoholic hydroxyl group;

$Z_d^-$ represents a non-nucleophilic counter anion having X number of groups represented by ($B_2$-$Q_2$);

n represents 0 or 1;

each l2 independently represents an integer of 0 to 5;

each m2 independently represents an integer of 1 to 5;

X represents an integer of 0 to 3;

in formula (II-3), each $R_{3d}$ independently represents a hydrogen atom or a monovalent organic group, and two $R_{3d}$'s may combine with each other to form a ring;

each of $R_{6d}$ and $R_{7d}$ independently represents a hydrogen atom or a monovalent organic group, and $R_{6d}$ and $R_{7d}$ may combine with each other to form a ring;

each of $R_{dx}$ and $R_{dy}$ independently represents an alkyl group, and $R_{dx}$ and $R_{dy}$ may combine with each other to form a ring;

$Q_3$ represents a single bond or a divalent linking group;

$B_3$ represents (B') a moiety capable of decomposing by an action of an acid to produce an alcoholic hydroxyl group;

$Z_d^-$ represents a non-nucleophilic counter anion having X number of groups represented by ($B_3$-$Q_3$);

each l3 independently represents an integer of 0 to 5;

each m3 independently represents an integer of 1 to 5; and

X represents an integer of 0 to 3.

[14] The actinic ray-sensitive or radiation-sensitive resin composition as described in any one of [11] to [13] above, wherein the compound (A) is represented by the following formula (III):

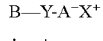 (III)

wherein $A^-$ represents an organic acid anion;

Y represents a divalent linking group;

$X^+$ represents a counter cation; and

B represents (B') a moiety capable of decomposing by an action of an acid to produce an alcoholic hydroxyl group.

[15] An actinic ray-sensitive or radiation-sensitive resin composition used for the pattern forming method as described in any one of [1] to [10] above, the composition comprising:

(A) an ionic compound capable of generating an acid upon irradiation with an actinic ray or radiation, represented by the following formula (II-4) or (II-5):

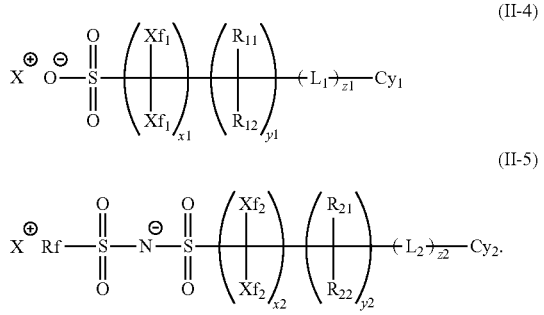

wherein each $X^+$ independently represents a counter cation;

Rf represents an alkyl group having at least one fluorine atom, a cycloalkyl group having at least one fluorine atom, or an aryl group having at least one fluorine atom;

each of $Xf_1$ and $Xf_2$ independently represents a fluorine atom or an alkyl group substituted with at least one fluorine atom;

each of $R_{11}$, $R_{12}$, $R_{21}$ and $R_{22}$ independently represents a hydrogen atom, a fluorine atom or an alkyl group, and when a plurality of $R_{11}$'s, $R_{12}$'s, $R_{21}$'s or $R_{22}$'s are present, each may be the same as or different from every others;

each of $L_1$ and $L_2$ independently represents a divalent linking group and when a plurality of $L_1$'s or $L_2$'s are present, each may be the same as or different from every others;

each of $Cy_1$ and $Cy_2$ independently represents a cyclic organic group;

provided that at least one of $Xf_1$, $R_{11}$, $R_{12}$, $L_1$ and $Cy_1$ is substituted with a group having a structure in which a polarity group is protected with a leaving group capable of decomposing and leaving by an action of an acid and that at least one of $Xf_2$, $R_{21}$, $R_{22}$, $L_2$, $Cy_2$ and Rf is substituted with a group having a structure in which a polarity group is protected with a leaving group capable of decomposing and leaving by an action of an acid;

each of x1 and x2 independently represents an integer of 1 to 20;

each of y1 and y2 independently represents an integer of 0 to 10; and each of z1 and z2 independently represents an integer of 0 to 10.

[16] A resist film, which is formed by using the actinic ray-sensitive or radiation-sensitive resin composition as described in any one of [11] to [15] above, The present invention preferably further includes the following configurations.

[17] The pattern forming method as described in any one of [6] to [10] above, wherein each of $Q_1$, $Q_2$ and $Q_3$ is independently a divalent linking group.

[18] The pattern forming method as described in any one of [6] to [10] and [17] above, wherein each of $Q_1$, $Q_2$ and $Q_3$ is independently an alkylene group which may contain an oxygen atom or a sulfur atom in the alkylene chain.

[19] The pattern forming method as described in any one of [6] to [10], [17] and [18] above, wherein the developer containing an organic solvent is a developer containing at least one kind of an organic solvent selected from the group consisting of a ketone-based solvent, an ester-based solvent, an alcohol-based solvent, an amide-based solvent and an ether-based solvent.

[20] The pattern forming method as described in any one of [6] to [10] and [17] to [19] above, further comprising:

(iv) rinsing the film with a rinsing solution containing an organic solvent.

[21] The actinic ray-sensitive or radiation-sensitive resin composition as described in [13] or [14] above, wherein each of $Q_1$, $Q_2$ and $Q_3$ is independently a divalent linking group,

[22] The actinic ray-sensitive or radiation-sensitive resin, composition as described in any one of [13], [14] and [21] above, wherein each of $Q_1$, $Q_2$ and $Q_3$ is independently an alkylene group which may contain an oxygen atom or a sulfur atom in the alkylene chain.

[23] The actinic ray-sensitive or radiation-sensitive resin composition as described in any one of [13] to [15], [21] and [22] above, further comprising:

a hydrophobic resin.

[24] the actinic ray-sensitive or radiation-sensitive resin composition as described in any one of [13] to [15] and [21] to [23] above, which is used for organic solvent development.

[25] The actinic ray-sensitive or radiation-sensitive resin composition as described in any one of [13] to [15] and [21] to [24] above, which is used for immersion exposure.

DESCRIPTION OF EMBODIMENTS

The mode for carrying out the present invention is described below.

In the description of the present invention, when a group (atomic group) is denoted without specifying whether substituted or unsubstituted, the group includes both a group having no substituent and a group having a substituent. For example, "an alkyl group" includes not only an alkyl group having no substituent (unsubstituted alkyl group) but also an alkyl group having a substituent (substituted alkyl group).

In the description of the present invention, the term "actinic ray" or "radiation" indicates, for example, a bright line spectrum of mercury lamp, a far ultraviolet ray typified by excimer laser, an extreme-ultraviolet ray (EUV light), an X-ray or an electron beam (EB). Also, in the present invention, the "light" means an actinic ray or radiation.

Furthermore, in the description of the present invention, unless otherwise indicated, the "exposure" includes not only exposure to a mercury lamp, a far ultraviolet ray typified by excimer laser, an extreme-ultraviolet ray, an X-ray, EUV light or the like but also lithography with a particle beam such as electron beam and ion beam.

The pattern forming method of the present invention comprises:

(i) a step of forming a film from an actinic ray-sensitive or radiation-sensitive resin composition containing (A) a compound capable of generating an acid upon irradiation with an actinic ray or radiation and decomposing by the action of an acid to decrease the solubility for an organic solvent, (ii) a step of exposing the film, and (iii) a step of performing development by using a developer containing an organic solvent (hereafter also referred to as "an organic solvent-containing developer").

The present inventors have found that in the case of performing development by using an organic solvent-containing developer, when the (A) compound capable of generating an acid upon irradiation with an actinic ray or radiation decomposes by the action of an acid to decrease the solubility for an organic solvent, the resolution, roughness performance and development time dependency can be improved.

The reasons therefor are not necessarily clarified, but the present invention presumes as follows. That is, the compound (A) as an acid generator is a compound capable of decreasing the solubility for an organic, solvent by the action of an acid and is considered to exert a function of dissolving with an organic solvent in the unexposed area but more suppressing dissolution for an organic solvent in the exposed area, whereby the dissolution contrast for an organic solvent between the exposed area and the unexposed area can be made larger, as a result, the resolution such as pre-bridge dimension is increased.

Furthermore, for achieving various performances required of a chemical amplification resist, it is important that the acid generator is uniformly dispersed in a resist reason whose hydrophobicity is high because, for example, a resin is the main component. In general, an acid generator with low hydrophobicity (for example, an ionic acid generator) is liable to be hardly uniformly dispersed in a highly hydrophobic resist film and depending on the case, may aggregate to adversely affect the resist performance.

On the other hand, in the case where the acid generator is increased in the hydrophobicity for the purpose of uniform dispersion in a resist film, the above-described adverse effect associated with insufficient dispersion in a resist film may be reduced, but in the exposed area, the acid generator exhibits a tendency to accelerate the dissolution for an organic solvent and this is considered to give rise to reduction in the dissolution contrast.

However, the compound (A) is a compound capable of decreasing the dissolution for an organic solvent by the action of an acid and even in the case of an acid generator with low hydrophobicity such as ionic acid generator, can be designed as a compound whose hydrophobicity is reduced after being subjected to the action of an acid, as compared with the hydrophobicity before the action of an acid is exerted. As a result, while obtaining the above-described larger dissolution contrast for an organic solvent between the exposed area and the unexposed area, the compound (A) is uniformly dispersed in a resist film and this is considered to bring out excellent performance in terms of not only resolution hut also roughness such as line edge roughness.

In addition, when a resist film containing such a compound (A) is subjected to pattern formation using an organic solvent-containing developer, a very excellent performance is also exhibited in terms of dependency of the obtained pattern size oil the development time, but the mechanism of such an action is not known.

In the pattern forming method of the present invention, the developer is preferably a developer containing at least one kind of an organic solvent selected from the group consisting of a ketone-based solvent, an ester-based solvent, an alcohol-based solvent, an amide-based solvent and an ether-based solvent.

The pattern forming method of the present invention preferably further comprises (iv) a step of rinsing the film with a rinsing solution containing an organic solvent (hereafter also referred to as "an organic solvent-containing rinsing solution").

The rinsing solution is preferably a rinsing solution containing at least one kind of an organic solvent selected from the group consisting of a hydrocarbon-based solvent, a ketone-based solvent, an ester-based solvent, an alcohol-based solvent, an amide-based solvent and an ether-based solvent.

The pattern forming method of the present invention preferably comprises (v) a heating step after the exposure step (ii).

In the pattern forming method of the present invention, the later-described resin (a) may be a resin capable of increasing the polarity by the action of an acid to increase the solubility for an alkali developer and the method may further comprise (vi) a step of performing development by using an alkali developer.

In the pattern forming method of the present invention, the exposure step (ii) may be performed a plurality of times.

In the pattern forming method of the present invention, the heating step (v) may be performed a plurality of times.

The resist film of the present invention is a film formed of the above-described actinic ray-sensitive or radiation-sensitive resin composition, and this film is formed, for example, by applying the actinic ray-sensitive or radiation-sensitive resin composition on a base material.

The actinic ray-sensitive or radiation-sensitive resin composition which can be used in the present invention is described below.

The present invention also relates to the actinic ray-sensitive or radiation-sensitive resin composition described below.

The actinic ray-sensitive or radiation-sensitive resin composition of the present invention contains (b) a compound capable of generating an acid upon irradiation with an actinic ray or radiation (hereinafter, sometimes referred to as an "acid generator"), and it is preferred to contain (a) a resin capable of increasing the polarity by the action of an acid to decrease the solubility for an organic solvent-containing developer.

Also, the actinic ray-sensitive or radiation-sensitive resin composition may further contain at least one of (c) a solvent, (d) a hydrophobic resin, (e) a basic compound, (f) surfactant and (g) other additives. These components are described in sequence below.

[1] (a) Acid-Decomposable Resin

The resin capable of increasing the polarity by the action of an acid to decrease the solubility for an organic solvent-containing developer (hereinafter, sometimes referred to as an "acid-decomposable resin" or a "resin (a)"), which is used for the actinic ray-sensitive or radiation-sensitive resin composition of the present invention, is a resin having a structure where a polar group is protected with a group capable of decomposing and leaving by the action of an acid (hereinafter, sometimes referred to as an "acid-decomposable group").

The resin (a) includes, for example, a resin having an acid-decomposable group on either one or both of the main chain and the side chain of the resin.

Incidentally, this resin (a) is at the same time a resin capable of increasing the polarity by the action of an acid to increase the solubility for an alkali developer.

The polar group is not particularly limited as long as it is a group capable of being sparingly solubilized or insolubilized in an organic solvent-containing developer, but examples thereof include a phenolic hydroxyl group, a carboxyl group, a fluorinated alcohol group (preferably hexafluoroisopropanol group), a sulfonic acid group, a sulfonamide group, a sulfonylimide group, an (alkylsulfonyl)(alkylcarbonyl)methylene group, an (alkylsulfonyl)(alkylcarbonyl)imide group, a bis(alkylcarbonyl)methylene group, a bis(alkylcarbonyl)imide group, a bis(alkylsulfonyl)methylene group, a bis(alkylsulfenyl)imide group, a tris(alkylcarbonyl)methylene group and a tris(alkylsulfonyl)methylene group.

Preferred examples of the polar group include a carboxyl group, a sulfonic acid group and an alcoholic hydroxyl group.

In the present invention, the alcoholic hydroxyl (hereinafter, sometimes referred to as an "alcoholic hydroxyl group") is a hydroxyl (hydroxyl group) bonded to a hydrocarbon group and indicates a hydroxyl group except for a hydroxyl group directly bonded on an aromatic ring (phenolic hydroxyl group) and a hydroxyl group in an aliphatic alcohol where the α-position carbon (the carbon atom to which the hydroxyl group is bonded) is substituted with a fluorine atom, and the alcoholic hydroxyl group is typically a hydroxyl group with pKa of 12 to 20.

The structure where a polar group is protected with a leaving group capable of decomposing and leaving by the action of an acid is preferably (i) a structure represented by the following formula (a), which decomposes by the action of an acid to generate a carboxyl group, (ii) a structure represented by the following formula (b), which decomposes by the action of an acid to generate one alcoholic hydroxyl group, or (iii) a structure represented by the following formula (c), which decomposes by the action of an acid to generate two or three alcoholic hydroxyl groups.

$$*-\underset{\underset{O}{\|}}{C}-O-P_1 \qquad (a)$$

$$*-O-P_2 \qquad (b)$$

$$(*-O)_z-P_3 \qquad (c)$$

wherein each of $P_1$ and $P_2$ independently represents a monovalent group capable of decomposing and leaving by the action of an acid, $P_3$ represents a z-valent group capable of decomposing and leaving by the action of an acid, z represents 2 or 3, and

* represents a bond to the main or side chain of the resin above.

The structure (i) is preferably a group represented by the following formula (a-1):

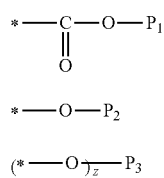

wherein each of $Rx_1$ to $Rx_3$ independently represents a monovalent organic group, $Rx_1$ and $Rx_2$ may combine to form a ring, and

* represents a bond to the main chain or side chain of the resin above.

The monovalent organic group as $Rx_1$ to $Rx_3$ is preferably an alkyl group (linear or branched) or a cycloalkyl group (monocyclic or polycyclic).

The alkyl group of $Rx_1$ to $Rx_3$ is preferably an alkyl group having a carbon number of 1 to 4, such as methyl group, ethyl group, n-propyl group, isopropyl group, n-butyl group, isobutyl group and tert-butyl group.

The cycloalkyl group of $Rx_1$ to $Rx_3$ is preferably a monocyclic cycloalkyl group having a carbon number of 3 to 20, such as cyclopentyl group and cyclohexyl group, or a polycyclic cycloalkyl group having a carbon number of 4 to 20, such as norbornyl group, tetracyclodecanyl group, tetracyclododecanyl group and adamantly group.

The ring formed by combining $Rx_1$ and $Rx_2$ is preferably a cycloalkyl group (monocyclic or polycyclic). The cycloalkyl group is preferably a monocyclic cycloalkyl group such as cyclopentyl group and cyclohexyl group, or a polycyclic cycloalkyl group such as norbornyl group, tetracyclodecanyl group, tetracyclododecanyl group and adamantyl group. A monocyclic cycloalkyl group having a carbon number of 5 to 6 is more preferred, and a monocyclic cycloalkyl group having a carbon number of 5 is still more preferred.

An embodiment where $Rx_3$ is a methyl group or an ethyl group and $Rx_1$ and $Rx_2$ are combined to form the above-described cycloalkyl group is preferred.

Each of $Rx_1$ to $Rx_3$ may have a substituent, and examples of the substituent include an alkyl group (having a carbon number of 1 to 4), a halogen atom, a hydroxyl group, an alkoxy group (having a carbon number of 1 to 4), a carboxyl group, an alkoxycarbonyl group (having a carbon number of 2 to 6) and an aryl group (having a carbon number of 6 to 10). The carbon number is preferably 8 or less.

The structure (ii) is preferably a group represented by the following formula (b-1), (b-2), (b-3) or (b-4), more preferably a group represented by the following formula (b-1):

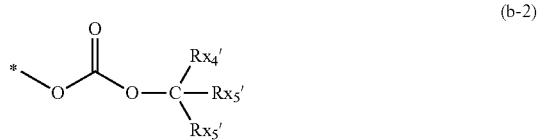

In formula (b-1), each $Rx_4$ independently represents a hydrogen atom or a monovalent organic group, and $Rx_4$s may combine with each other to form a ring.

$Rx_5$ represents a monovalent organic group, and one $Rx_4$ and $Rx_5$ may combine with each other to form a ring.

In formula (b-2), $Rx_4$' represents a hydrogen atom or a monovalent organic group.

Each $Rx_5'$ independently represents a monovalent organic group, and $Rx_5'$'s may combine with each other to form a ring. Also, one $Rx_5'$ and $Rx_4'$ may combine with each other to form a ring.

In formula (b-3), each $Rx_6$ independently represents a hydrogen atom, an alkyl group, cycloalkyl group, an aryl group, an alkenyl group or an alkynyl group, and two $Rx_6$s may combine with each other to form a ring, provided that when one or two out of three $Rx_6$s are a hydrogen atom, at least one of the remaining $Rx_6$s represents an aryl group, an alkenyl group or an alkynyl group.

In formula (b-4), each $Rx_6'$ independently represents a monovalent organic group, and two $Rx_6$'s may combine with each other to form a ring.

In formulae (b-1) to (b-4), * represents a bond to the main chain or side chain of the resin above.

As described above, each of $Rx_4$ and $Rx_4'$ independently represents a hydrogen atom or a monovalent organic group. Each of $Rx_4$ and $Rx_4'$ is independently preferably a hydrogen atom, an alkyl group or a cycloalkyl group, more preferably a hydrogen atom or an alkyl group.

The alkyl group of $Rx_4$ and $Rx_4'$ may be linear or branched. The carbon number of the alkyl group is preferably from 1 to 10, more preferably from 1 to 3. Examples of the alkyl group of $Rx_4$ include a methyl group, an ethyl group, an n-propyl group, an isopropyl group and an n-butyl group.

The cycloalkyl group of $Rx_4$ and $Rx_4'$ may be monocyclic or polycyclic. The carbon number of the cycloalkyl group is preferably 3 to 10, more preferably 4 to 8. Examples of the cycloalkyl group of $Rx_4$ include a cyclopropyl group, a cyclobutyl group, a cyclopentyl group, a cyclohexyl group, a norbornyl group and an adamantyl group.

In formula (b-1), at least one $Rx_4$ is preferably a monovalent organic group. When such a configuration is employed, particularly high sensitivity can be achieved.

The alkyl group and cycloalkyl group as $Rx_4$ and $Rx_4'$ may further have a substituent, and examples of the substituent include the same groups as described for the substituent which each of $Rx_1$ to $Rx_3$ may have.

As described above, each of $Rx_5$ and $Rx_5'$ independently represents a monovalent organic group. Each of $Rx_5$ and $Rx_5'$ is independently preferably an alkyl group or a cycloalkyl group, more preferably an alkyl group. The alkyl group and cycloalkyl group may further have a substituent, and examples of the substituent include the same groups as described for the substituent which each of $Rx_1$ to $Rx_3$ may have.

The alkyl group of $Rx_5$ and $Rx_5'$ preferably has no substituent or has one or more aryl groups and/or one or more silyl groups as the substituent. The carbon number of the unsubstituted alkyl group is preferably from 1 to 20, more preferably from 1 to 10. The carbon number of the alkyl group moiety in the alkyl group substituted with one or more aryl groups is preferably from 1 to 25.

Specific examples of the alkyl group of $Rx_5$ and $Rx_5'$ are the same as specific examples of the alkyl group of $Rx_4$ and $Rx_4'$. The aryl group in the alkyl group substituted with one or more aryl group is preferably an aryl group having a carbon number of 6 to 10 and specifically includes a phenyl group and a naphthyl group.

The carbon number of the alkyl group moiety in the alkyl group substituted with one or more silyl groups is preferably from 1 to 30. Also, in the case where the cycloalkyl group of $Rx_5$ and $Rx_5'$ does not have a substituent, the carbon number thereof is preferably from 3 to 20, more preferably from 3 to 15.

Specific examples of the cycloalkyl group of $Rx_5$ and $Rx_5'$ are the same as specific examples of the cycloalkyl group of $Rx_4$ and $Rx_4'$.

$Rx_6$ represents a hydrogen atom, an alkyl group, a cycloalkyl group, an aryl group, an alkenyl group or an alkynyl group. However, when one or two out of three $Rx_6$s are a hydrogen atom, at least one of the remaining $Rx_6$s represents an aryl group, an alkenyl group or an alkynyl group. $Rx_6$ is preferably a hydrogen atom or an alkyl group.

The alkyl group, cycloalkyl group, aryl group, alkenyl group and alkynyl group as $Rx_6$ may further have a substituent, and examples of the substituent include the same groups as described for the substituent which each of $Rx_1$ to $Rx_3$ may have.

Examples of the alkyl group and cycloalkyl group as $Rx_6$ are the same as those described for the alkyl group and cycloalkyl group of $Rx_4$ and $Rx_4'$. In particular, when the alkyl group has no substituent, the carbon number thereof is preferably from 1 to 6, more preferably from 1 to 3.

The aryl group of $Rx_6$ includes, for example, an aryl group having a carbon number of 6 to 10, such as phenyl group and naphthyl group.

The alkenyl group of $Rx_6$ includes, for example, an alkenyl group having a carbon number of 2 to 5, such as vinyl group, propenyl group and allyl group.

The alkynyl group of $Rx_6$ includes, for example, an alkynyl group having a carbon number of 2 to 5, such as ethynyl group, propynyl group and butynyl group.

Each $Rx_6'$ is independently preferably an alkyl group, a cycloalkyl group or an aryl group, more preferably an alkyl group or a cycloalkyl group, still more preferably an alkyl group.

Specific examples and preferred examples of the alkyl group, cycloalkyl group and aryl group of $Rx_6$ are the same as those described for the alkyl group and cycloalkyl group of $Rx_4$ and $Rx_4'$ and the aryl group of $Rx_6$.

These alkyl group, cycloalkyl group and aryl group may further have a substituent, and examples of the substituent include the same groups as described for the substituent which each of $Rx_1$ to $Rx_3$ may have.

The structure (iii) is preferably a group represented by the following formula (c-1), (c-2) or (c-3):

(c-1)

(c-2)

(c-3)

In formula (c-1), each $Rx_7$ independently represents a hydrogen atom or a monovalent organic group, and $Rx_7$s may combine with each other to form a ring.

In formula (c-2), each $Rx_8$ independently represents a monovalent organic group, and $Rx_8$s may combine with each other to form a ring.

In formula (c-3), $Rx_8'$ represents a monovalent organic group.

In formulae (c-1) to (c-3), * represents a bond to the main chain or side chain of the resin above.

As described above, $Rx_7$ represents a hydrogen atom or a monovalent organic group. $Rx_7$ is preferably a hydrogen atom, an alkyl group or a cycloalkyl group, more preferably a hydrogen atom or an alkyl group, still more preferably a hydrogen atom or an alkyl group having no substituent.

$Rx_7$ is preferably a hydrogen atom or an alkyl group having a carbon number of 1 to 10, more preferably a hydrogen atom or an alkyl group having a carbon number of 1 to 10 and having no substituent.

The alkyl group and cycloalkyl group as $Rx_7$ may further have a substituent, and examples of the substituent include the same groups as described for the substituent which each of $Rx_1$ to $Rx_3$ may have.

Specific examples of the alkyl group and cycloalkyl group of $Rx_7$ are the same as specific examples of the alkyl group and cycloalkyl group of $Rx_4$ and $Rx_4'$.

As described above, each of $Rx_8$ and $Rx_8'$ represents a hydrogen atom or a monovalent organic group. Each of $Rx_8$ and $Rx_8'$ is independently preferably a hydrogen atom, an alkyl group or a cycloalkyl group, more preferably a hydrogen atom or an alkyl group.

Examples of the alkyl group and cycloalkyl group of $Rx_8$ and $Rx_8'$ are the same as those described for the alkyl group and cycloalkyl group of $Rx_4$ and $Rx_4'$.

The resin (a) preferably contains a repeating unit having a structure where a polar group is protected with the above-described leaving group capable of decomposing and leaving by the action of an acid (hereinafter, sometimes referred to as an "acid-decomposable repeating unit (a)"), more preferably a repeating unit having any one of the structures (i) to (iii) above.

The repeating unit having any one of the structures (i) to (iii) includes a repeating unit represented by the following formula (I-1) or (I-2):

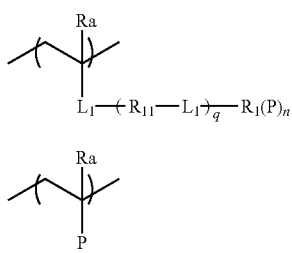

In the formulae, each Ra independently represents a hydrogen atom, an alkyl group or a group represented by —$CH_2$—O—$Ra_2$, wherein $Ra_2$ represents a hydrogen atom, an alkyl group or an acyl group.

P represents the structure (i) or (ii) and when a plurality of P's are present, each P may be the same as or different from every other P or they may combine with each other to form a ring. in the case where a plurality of P's combine with each other to form a ring, the bonded P may represents the structure (iii) and in this case, * of formula (c) in the structure (iii) represents a bond to $R_1$.

$R_1$ represents an (n+1)-valent organic group.

$R_{11}$ represents a divalent organic group, and when a plurality of $R_{11}$'s are present, each $R_{11}$ may be the same as or different from every other $R_{11}$.

n represents an integer of 1 or more.

$L_1$ represents a linking group represented by —COO—, —OCO—, —CONH—, —O—, —Ar—, —$SO_3$— or —$SO_2$NH—, wherein Ar represents a divalent aromatic ring group. In the case where a plurality of $L_1$'s are present, each $L_1$ may be the same as or different from every other $L_1$.

q is the repetition number of the group represented by —$R_{11}$-$L_1$-and represents an integer of 0 to 3.

Ra represents a hydrogen atom, an alkyl group or a group represented by —$CH_2$—O—$Ra_2$.

The carbon number of the alkyl group of Ra is preferably 6 or less, and the carbon number of the alkyl group and acyl group of $Ra_2$ is preferably 5 or less. The alkyl group of Ra and the alkyl group and acyl group of $Ra_2$ may have a substituent.

Ra is preferably a hydrogen atom, an alkyl group having a carbon number of 1 to 10, or an alkoxyalkyl group having a carbon number of 1 to 10, specifically, preferably a hydrogen, a methyl group, a trifluoromethyl group or a hydroxymethyl group, more preferably a hydrogen atom or a methyl group.

$R_1$ represents an (n+1)-valent organic group. $R_1$ is preferably a non-aromatic hydrocarbon group. In this case, $R_1$ may be a chain hydrocarbon group or an alicyclic hydrocarbon group. $R_1$ is more preferably an alicyclic hydrocarbon group.

The chain hydrocarbon group as $R_1$ may be linear or branched. The carbon number of the chain hydrocarbon group is preferably from 1 to 8. For example, when the chain hydrocarbon group is an alkylene group, the alkylene group is preferably a methylene group, an ethylene group, an n-propylene group, an isopropylene group, an n-butylene group, an isobutylene group or a sec-butylene group.

The alicyclic hydrocarbon group as $R_1$ may be monocyclic or polycyclic. The alicylcic hydrocarbon group has, for example, a monocyclo, bicyclo, tricyclo or tetracyclo structure. The carbon number of the alicyclic hydrocarbon group is usually 5 or more, preferably from 6 to 30, more preferably from 7 to 25.

The alicyclic hydrocarbon group includes, for example, those having a partial structure illustrated below. Each of these partial structures may have a substituent. Also, in each of these partial structures, the methylene group (—$CH_2$—) may be substituted with an oxygen atom (—O—), a sulfur atom (—S—), a carbonyl group [—C(=O)—], a sulfonyl group [—S(=O)$_2$—], a sulfinyl group [—S(=O)—] or an imino group [—N(R)—] (wherein R is a hydrogen atom or an alkyl group).

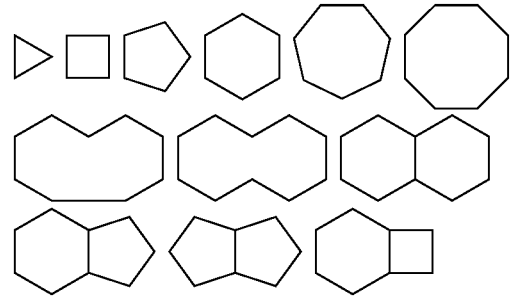

-continued

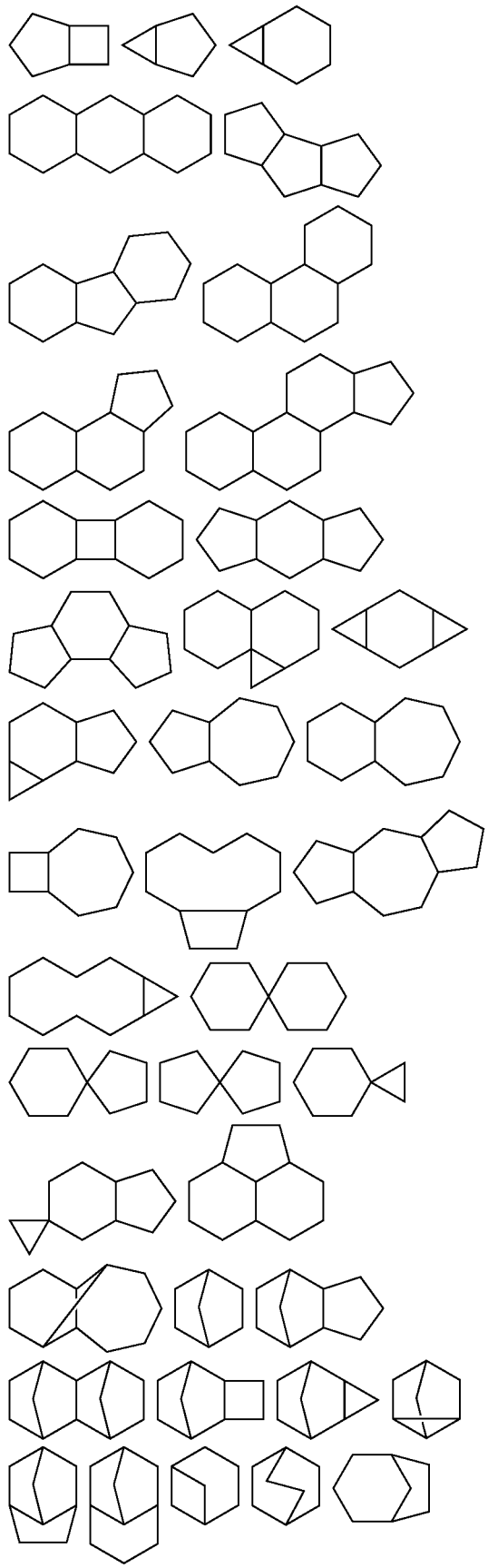

-continued

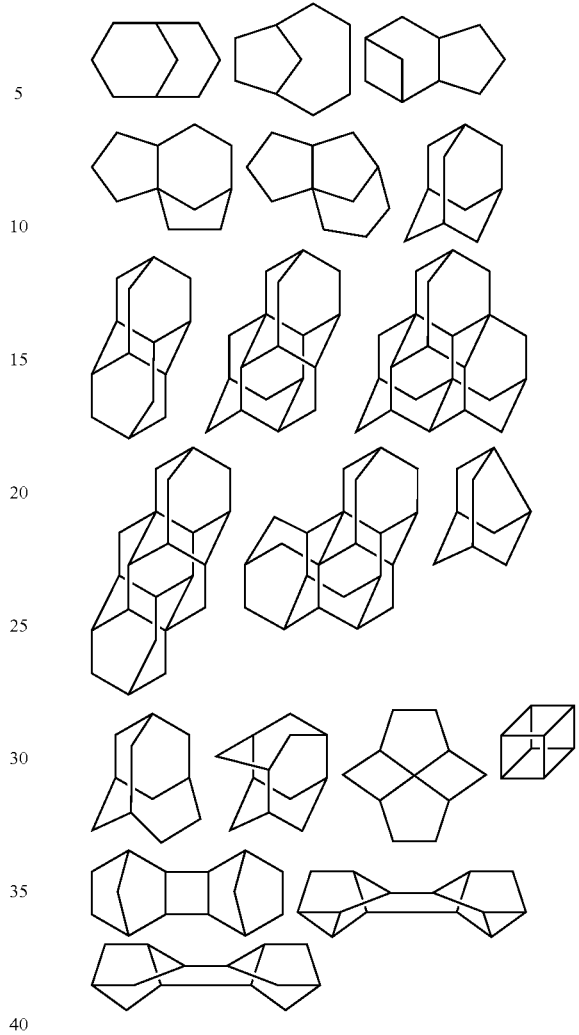

For example, when $R_1$ is a cycloalkylene group, $R_1$ is preferably an adamantylene group, a noradamantylene group, a decahydronaphthylene group, a tricyclodecanylene group, a tetracyclododecanylene group, a norbornylene group, a cyclopentylene group, a cyclohexylene group, a cycloheptylene group, a cyclooctylene group, a cyclodecanylene group or a cyclododecanylene group, more preferably an adamantylene group, a norbornylene group, a cyclohexylene group, a cyclopentylene group, a tetracyclododecanylene group or a tricyclodecanylene group.

The non-aromatic hydrocarbon group of $R_1$ may have a substituent. Examples of this substituent include an alkyl group having a carbon number of 1 to 4, a halogen atom, a hydroxy group, an alkoxy group having a carbon number of 1 to 4, a carboxy group, and an alkoxycarbonyl group having a carbon number of 2 to 6. These alkyl group, alkoxy group and alkoxycarbonyl group may further have a substituent, and examples of the substituent include a hydroxy group, a halogen atom and an alkoxy group.

Details of the divalent organic group of $R_{11}$ are the same as those of the (n+1)-valent organic group where n=1, that is, the divalent organic group, of $R_1$, and specific examples thereof are also the same.

$L_1$ represents a linking group represented by —COO—, —OCO—, —CONH—, —O—, —Ar—, —SO$_3$— or —SO₂NH— (in these linking groups, "-" on the left side is connected to the main chain of the resin), wherein Ar represents a divalent aromatic ring group and is preferably, for example, a divalent aromatic group having a carbon number of 6 to 10, such as phenylene group and naphthylene group. $L_1$ is preferably a linking group represented by —COO—, —CONH— or —Ar—, more preferably a linking group represented by —COO— or —CONH—.

n is an integer of 1 or more. n is preferably an integer of 1 to 3, more preferably 1 or 2. Also, when n is an integer of 2 or more, the dissolution contrast for an organic solvent-containing developer can be more increased and in turn, not only the resolution can be more enhanced but also LWR can be more reduced.

q is the repetition number of the group represented by —$R_1$-$L_4$- and represents an integer of 0 to 3. q is preferably an integer of 0 to 2, more preferably 0 or 1.

Specific examples of the acid-decomposable repeating unit (a) are illustrated below. In specific examples, Ra and P have the same meanings as Ra and P in formula (I-1) or (I-2). $P_1$ has the same meaning as $P_1$ in formula (a). $P_3$ has the same meaning as $P_3$ in formula (c) where z is 2.

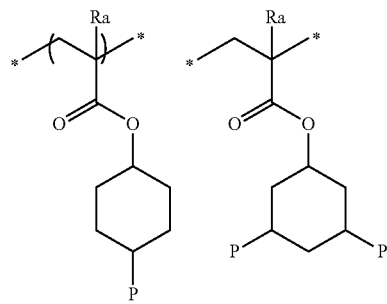

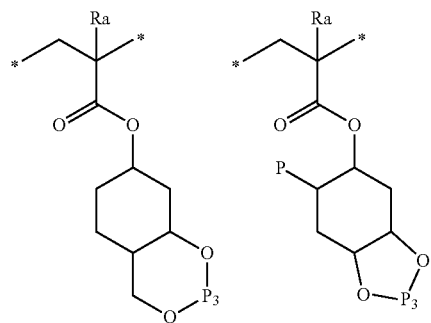

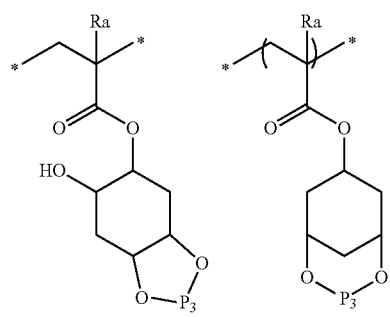

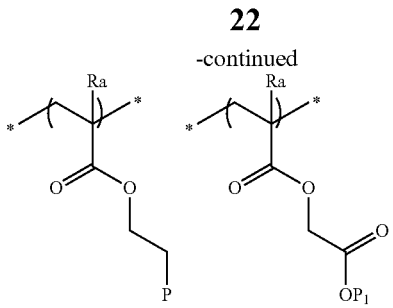

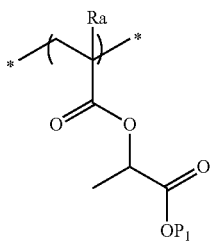

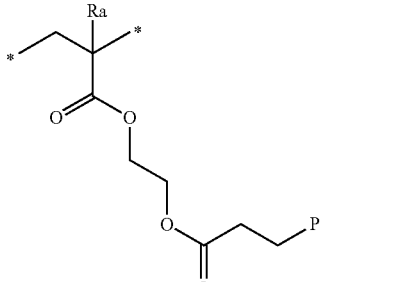

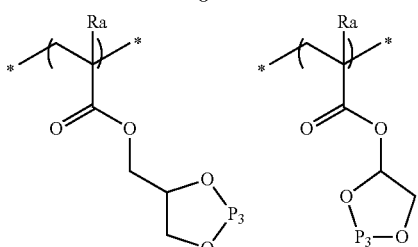

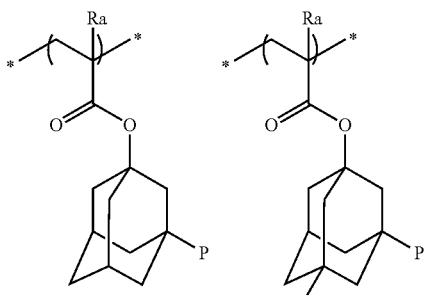

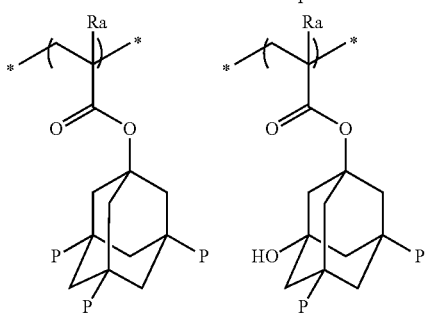

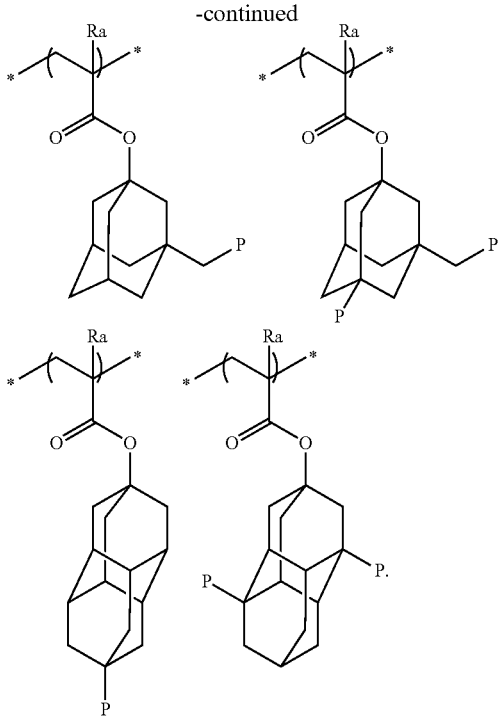

Preferred examples of the group capable of leaving by the action of an acid, in the acid-decomposable repeating unit (a), also include —C($R_{36}$)($R_{37}$)($R_{38}$), —C($R_{36}$)($R_{37}$)(O$R_{39}$) and —C($R_{01}$)($R_{02}$)(O$R_{39}$).

In the formulae, each of $R_{36}$ to $R_{39}$ independently represents an alkyl group, a cycloalkyl group, an aryl group, an aralkyl group or an alkenyl group. $R_{36}$ and $R_{37}$ may combine with each other to form a ring.

Each of $R_{01}$ and $R_{02}$ independently represents a hydrogen atom, an alkyl group, a cycloalkyl group, an aryl group, an aralkyl group or an alkenyl group.

The acid-decomposable group is preferably a cumyl ester group, an enol ester group, an acetal ester group, a tertiary alkyl ester group or the like, more preferably a tertiary alkyl ester group.

The acid-decomposable repeating unit (a) which can be contained in the resin (a) is preferably a repeating unit represented by the following formula (a1) or (a2):

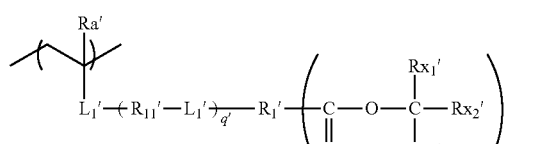

(a1)

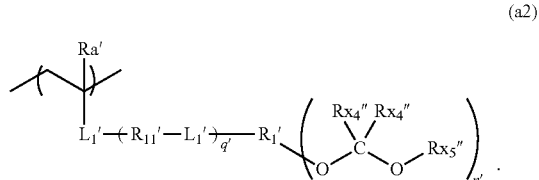

(a2)

in formulae (a1) and (a2), each Ra'0 independently represents a hydrogen atom, an alkyl group or a group represented by —CH$_2$—O—Ra$_2$', wherein Ra$_2$' represents a hydrogen atom, an alkyl group or an acyl group.

$R_1$' represents an (n+1)-valent organic group.

$R_{11}$' represents a divalent organic group, and when a plurality of $R_{11}$'s are present, each $R_{11}$' may be the same as or different from every other $R_{11}$'.

$L_1$' represents a linking group represented by —COO—, —OCO—, —CONH—, —O—, —Ar'—, —SO$_3$— or —SO$_2$NH—, wherein Ar' represents a divalent aromatic ring group. In the case where a plurality of $L_1$'s are present, each $L_1$' may be the same as or different from every other $L_1$'.

Each of Rx$_1$' to Rx$_3$' independently represents a monovalent organic group.

Rx$_1$' and Rx$_3$' may combine to form a ring.

q' is the repetition number of the group represented by —$R_{11}$'-$L_1$'- and represents an integer of 0 to 3.

n' represents an integer of 1 or more.

Each Rx$_4$" independently represents a hydrogen atom or a monovalent organic group, and Rx$_4$"s may combine with each other to form a ring.

Rx$_5$" represents a monovalent organic group, and one Rx$_4$" and Rx$_5$" may combine with each other to form a ring.

Details of Ra', Ra$_2$', $R_1$', $R_{11}$', $L_1$',Ar', Rx$_1$' to Rx$_3$', Rx$_4$" and Rx$_5$" are the same as those described for Ra, Ra$_2$, $R_1$, $R_{11}$, $L_1$ and Ar in formula (I-1), Rx$_1$ to Rx$_3$ in formula (a-1), and Rx$_4$ and Rx$_5$ in formula (b-1). Also, preferred ranges of n' and q' are the same as preferred ranges of n and q in formula (I-1).

The resin (a) may contain two or more kinds of acid-decomposable repeating units (a). When such a configuration is employed, the reactivity and/or the developability can be subtly adjusted to facilitate optimization of various performances.

The content of the acid-decomposable repeating unit (a) is, in total, preferably from 20 to 80 mol %, more preferably from 30 to 70 mol %, based on all repeating units.

Specific preferred examples of the acid-decomposable repeating unit (a) are illustrated below, but the present invention is not limited thereto.

In specific examples, each of Rx and Xa$_1$ represents a hydrogen atom, CH$_3$, CF$_3$ or CH$_2$OH, and each of Rxa and Rxb represents an alkyl group having a carbon number of 1 to 4. Z represents a substituent containing a polar group, and when a plurality of Z's are present, each Z may be the same as or different from every other Z. p represents 0 or a positive integer. Specific examples and preferred examples of Z include a hydroxyl group, a cyano group, an amino group, an alkylamide group, a sulfonamide group itself, and a linear or branched alkyl group or cycloalkyl group having at least one of these groups. An alkyl group having a hydroxyl group is preferred, and a branched alkyl group having a hydroxyl group is more preferred. The branched alkyl group is preferably an isopropyl group. In the case were a plurality of Z's are present, each Z may be the same as or different from every other Z.

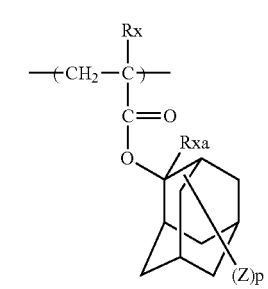

1

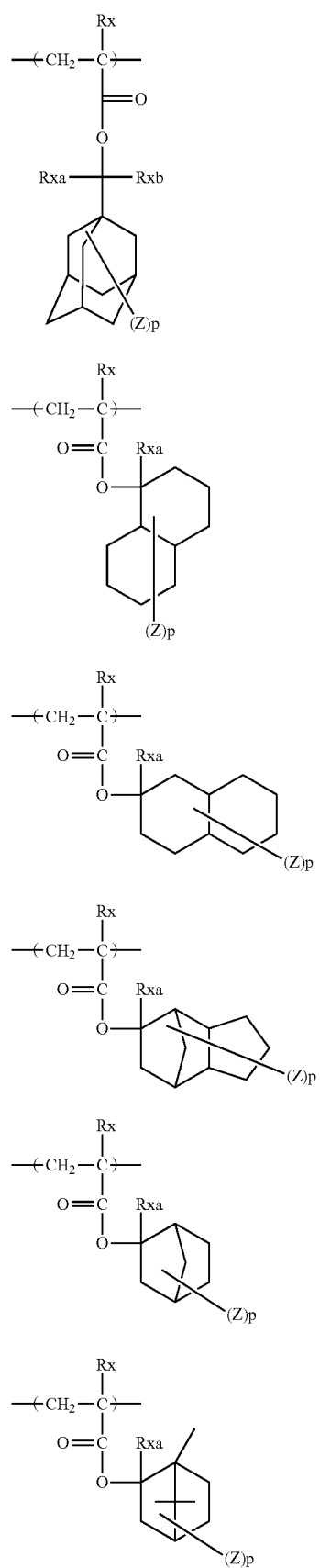
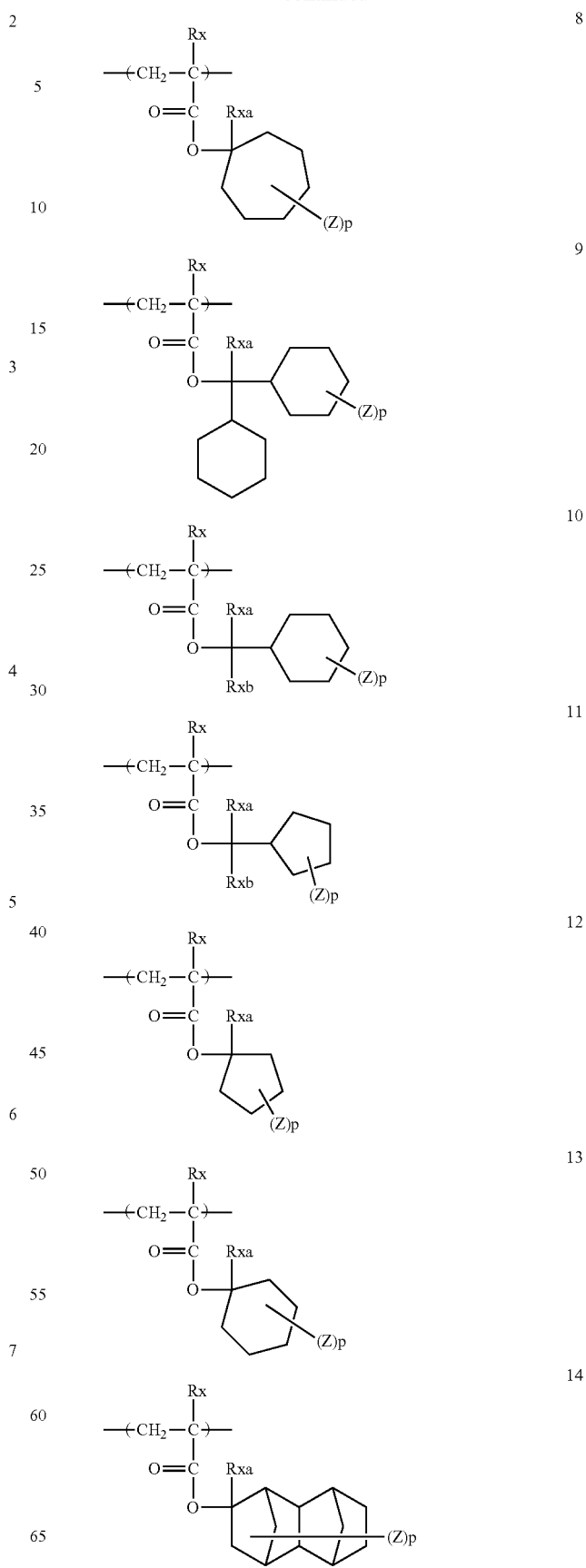

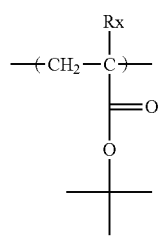
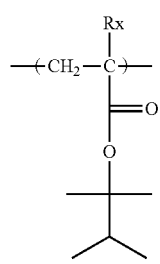
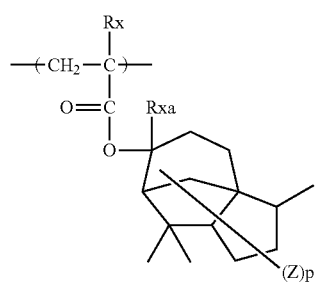
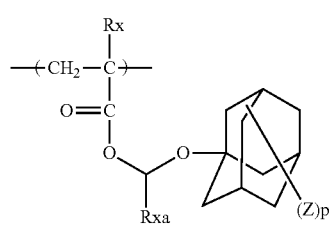
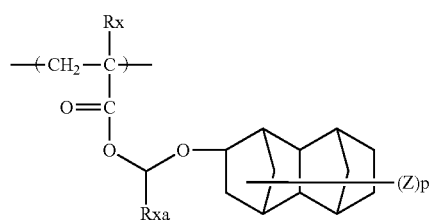
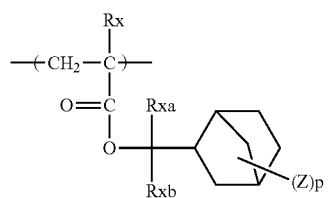
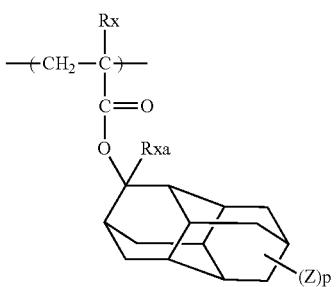
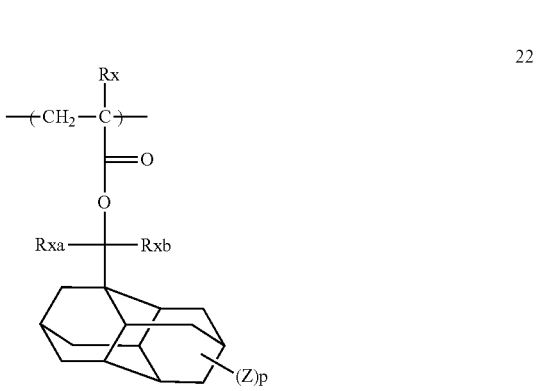
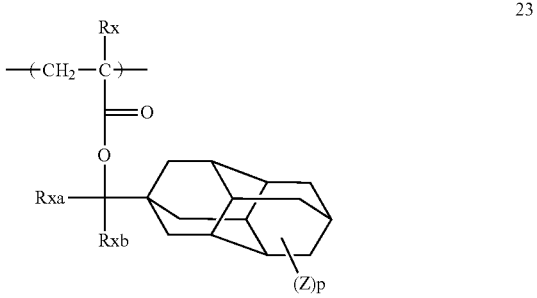
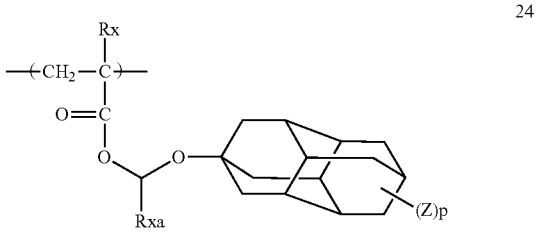
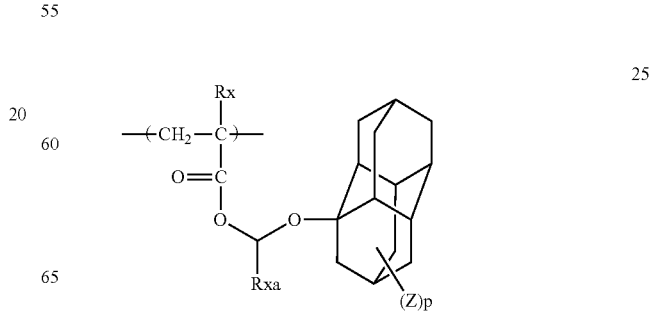

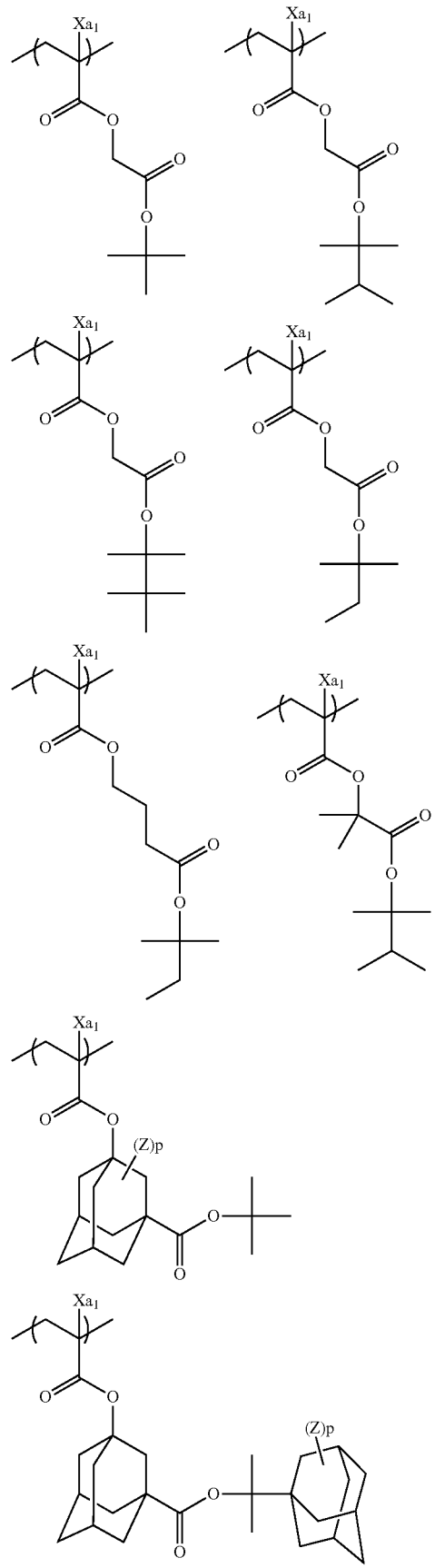
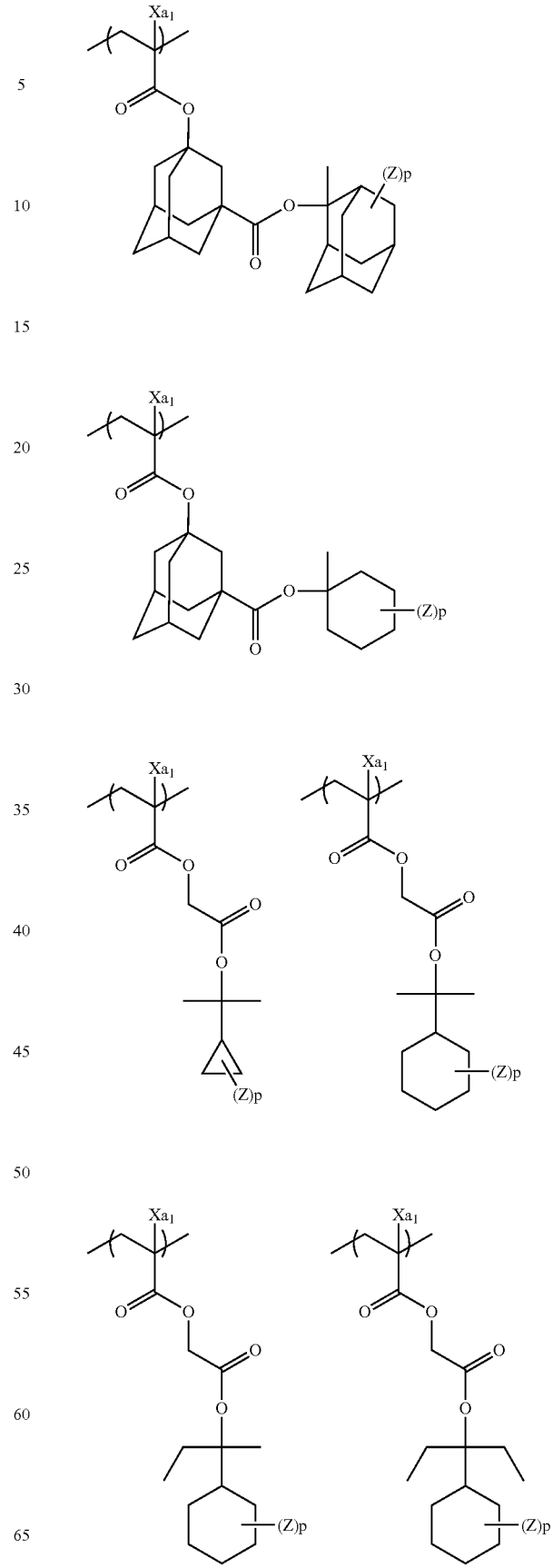

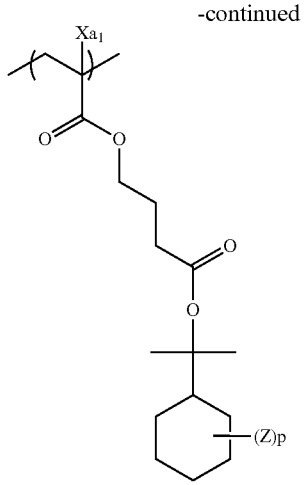
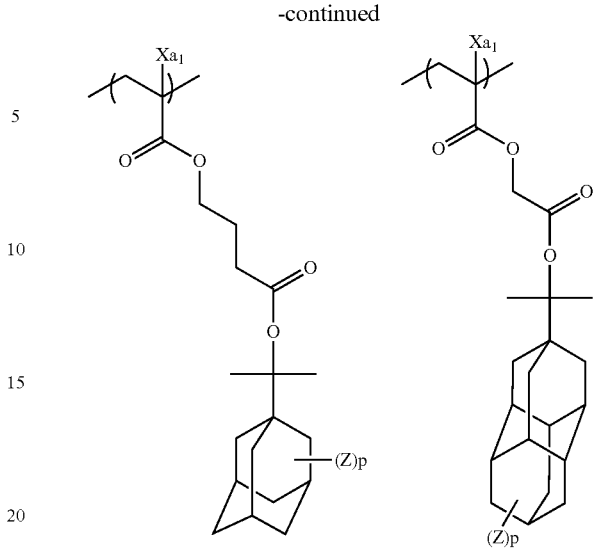
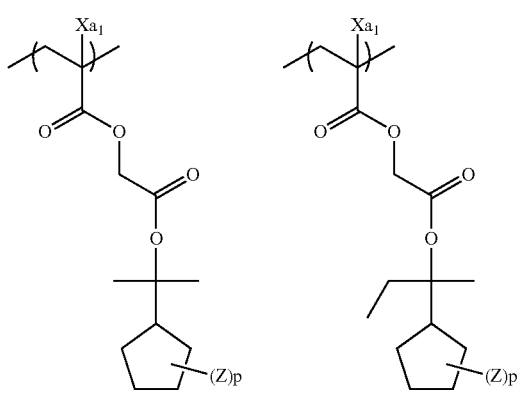
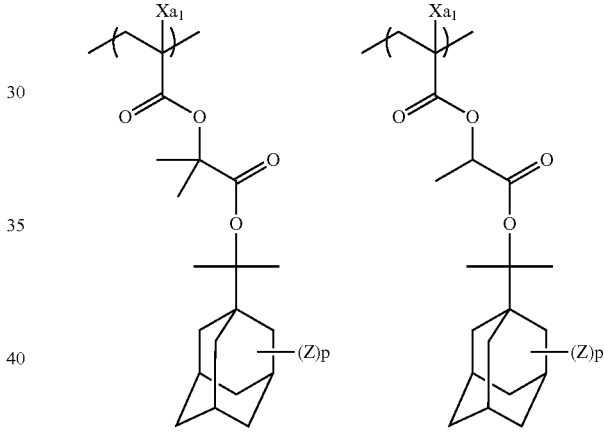
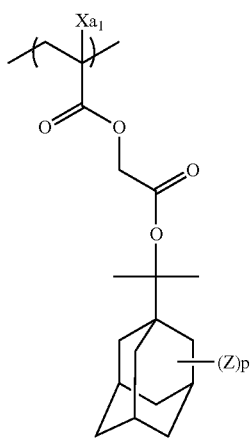
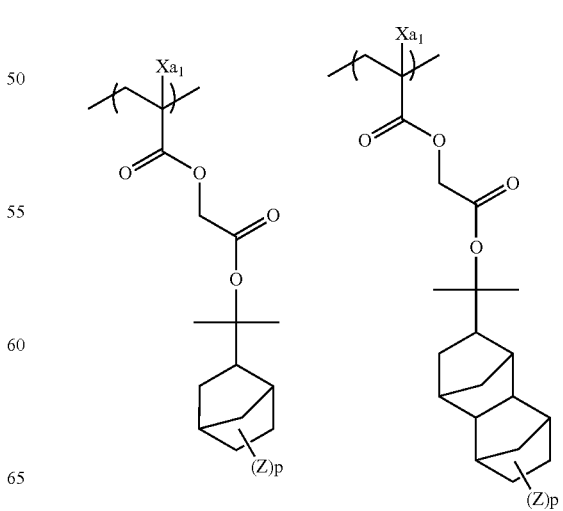

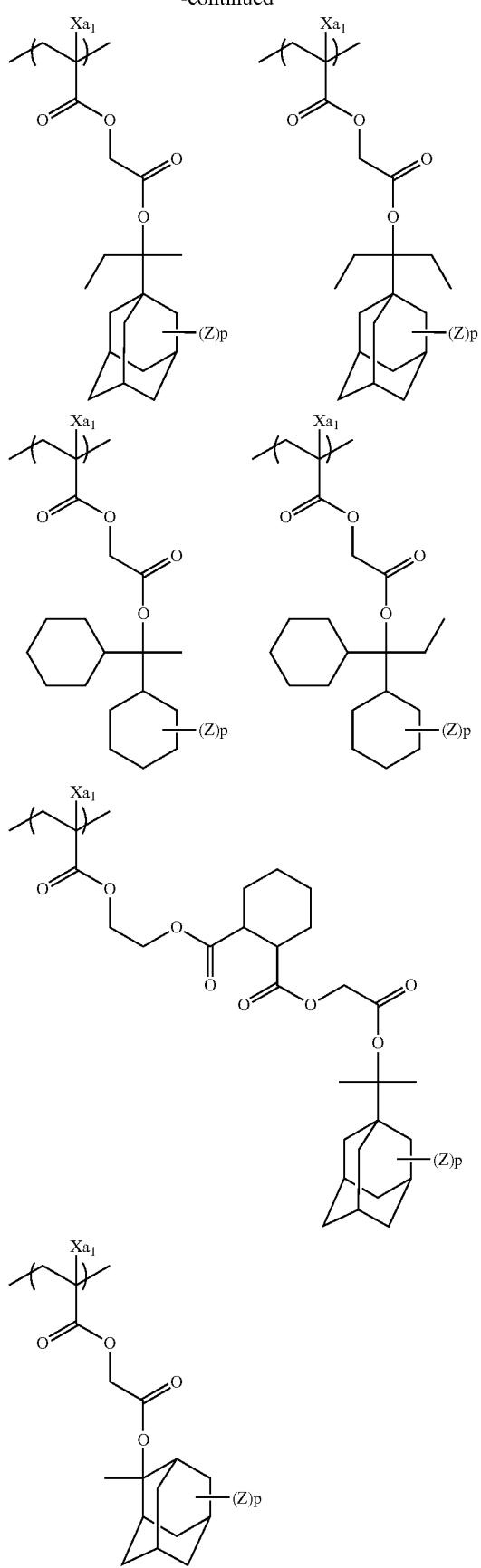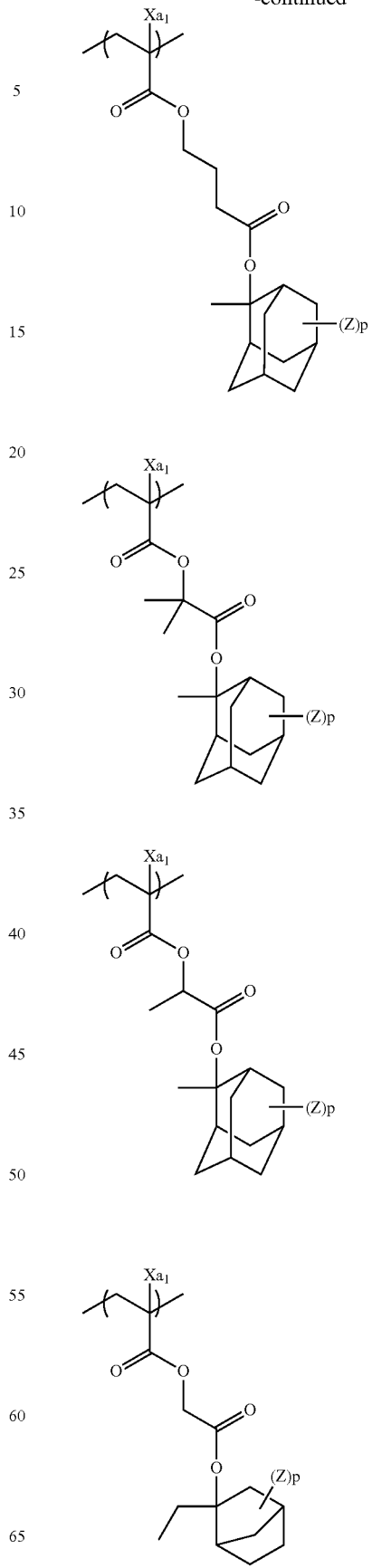

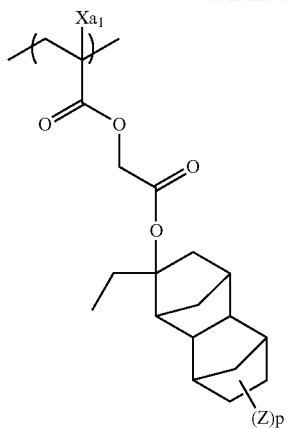
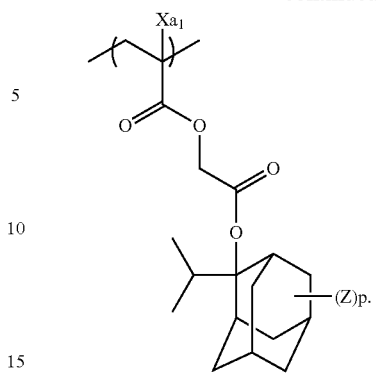
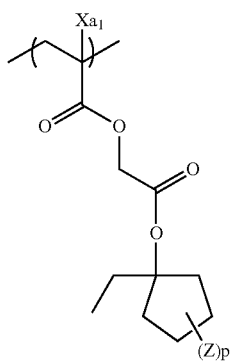
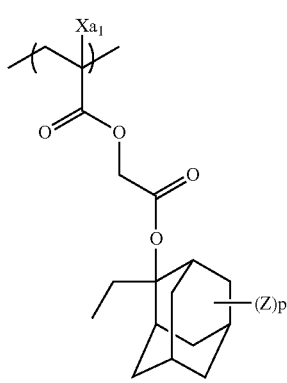

The resin (a) preferably contains a repeating unit having a lactone structure.

Any lactone structure may be used as long as it has a lactone structure, but a 5- to 7-membered ring lactone structure is preferred, and a 5- to 7-membered ring lactone structure to which another ring structure is fused to form a bicyclo structure or a spiro structure is preferred. It is more preferred to contain a repeating unit having a lactone structure represented by any of the following formulae (LC1-1) to (LC1-17). The lactone structure may be bonded directly to the main chain. Among these lactone structures, (LC1-1), (LC1-4), (LC1-5), (LC1-6), (LC1-13), (LC1-14) and (LC1-17) are preferred, and the lactone structure of (LC1-4) is more preferred. By virtue of using such a specific lactone structure, LWR and development defect are improved.

LC1-1
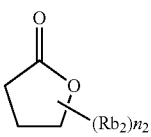

LC1-2
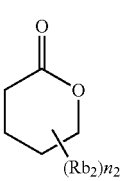

LC1-3
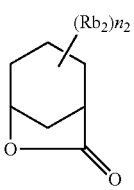

LC1-4
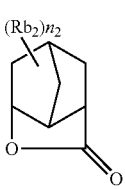

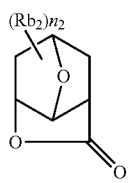 LC1-5

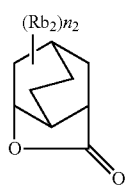 LC1-6

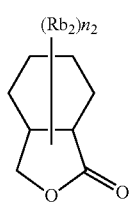 LC1-7

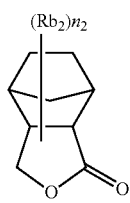 LC1-8

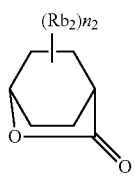 LC1-9

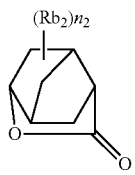 LC1-10

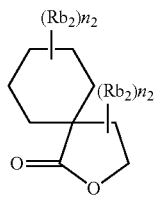 LC1-11

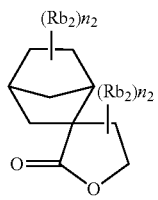 LC1-12

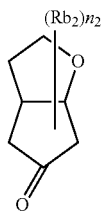 LC1-13

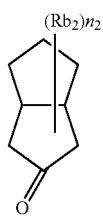 LC1-14

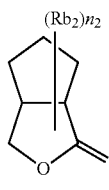 LC1-15

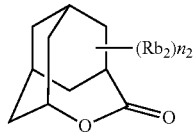 LC1-16

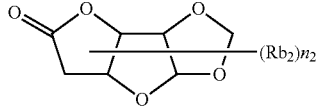 LC1-17

The lactone structure moiety may or may not have a substituent ($Rb_2$). Preferred examples of the substituent ($Rb_2$) include an alkyl group having a carbon number of 1 to 8, a cycloalkyl group having a carbon number of 4 to 7, an alkoxy group having a carbon number of 1 to 8, an alkoxycarbonyl group having a carbon number of 2 to 8, a carboxyl group, a halogen atom, a hydroxyl group, a cyano group and an acid-decomposable group. Among these, an alkyl group having a carbon number of 1 to 4, a cyano group and an acid-decomposable group are more preferred. $n_2$ represents an integer of 0 to 4. When $n_2$ is an integer of 2 or more, each substituent ($Rb_2$) may be the same as or different from every other substituents ($Rb_2$), and also, the plurality of substituents ($Rb_2$) may combine together to form a ring.

The repeating unit having a lactone group usually has an optical isomer, but any optical isomer may be used. One optical isomer may be used alone or a mixture of a plurality of optical isomers may be used. In the case of mainly using one optical isomer, the optical purity (ee) thereof is preferably 90% or more, more preferably 95% or more.

The lactone structure-containing repeating unit is preferably a unit represented by the following formula (III):

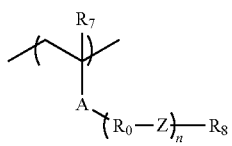

(III)

In formula (III), A represents an ester bond (a group represented by —COO—) or an amido bond (a group represented by —CONH—).

$R_0$ represents, when a plurality of $R_0$s are present, each independently represents, an alkylene group, a cycloalkylene group or a combination thereof.

Z represents, when a plurality of Z's are present, each independently represents, a single bond, an ether bond, an ester bond, an amide bond, a urethane bond (a group represented by

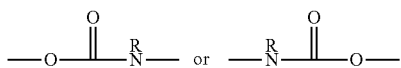

or a urea bond (a group represented by

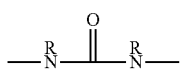

wherein each R independently represents a hydrogen atom, an alkyl group, a cycloalkyl group or an aryl group.

$R_8$ represents a monovalent organic group having a lactone structure.

n is the repetition number of the structure represented by —$R_0$—Z— and represents an integer of 0 to 5, preferably 0 or 1, more preferably 0. When n is 0, —$R_0$—Z— is not present and a single bond is formed.

$R_7$ represents a hydrogen atom, a halogen atom or an alkyl group.

The alkylene group and cycloalkylene group of $R_0$ may have a substituent.

Z is preferably an ether bond or an ester bond, more preferably an ester bond.

The alkyl group of $R_7$ is preferably an alkyl group having a carbon number of 1 to 4, more preferably a methyl group or an ethyl group, still more preferably a methyl group.

The alkylene group and cycloalkylene group of $R_0$ and the alkyl group of $R_7$ may be substituted, and examples of the substituent include a halogen atom such as fluorine atom, chlorine atom and bromine atom, a mercapto group, a hydroxyl group, an alkoxy group such as methoxy group, ethoxy group, isopropoxy group, tert-butoxy group and benzyloxy group, and an acyloxy group such as acetyloxy group and propionyloxy group.

$R_7$ is preferably a hydrogen atom, a methyl group, a trifluoromethyl group or a hydroxymethyl group.

The chain alkylene group in $R_0$ is preferably a chain alkylene group having a carbon number of 1 to 10, more preferably from 1 to 5, and examples thereof include a methylene group, an ethylene group and a propylene group. The cycloalkylene group is preferably a cycloalkylene group having a carbon number of 3 to 20, and examples thereof include a cyclohexylene group, a cyclopentylene group, a norbornylene group and an adamantylene group. For bringing out the effects of the present invention, a chain alkylene group is more preferred, and a methylene group is still more preferred.

The lactone structure-containing monovalent organic group represented by $R_8$ is not limited as long as it has a lactone structure. Specific examples thereof include lactone structures represented by formulae (LC1-1) to (LC1-17) and among these, a structure represented by (LC1-4) is preferred. Also, structures where $n_2$ in (LC1-1) to (LC1-17) is an integer of 2 or less are more preferred.

$R_8$ is preferably a monovalent organic group having an unsubstituted lactone structure, or a monovalent organic group having a lactone structure containing a methyl group, a cyano group or an alkoxycarbonyl group as the substituent, more preferably a monovalent organic group having a lactone structure containing a cyano group as the substituent (cyanolactone).

Specific examples of the repeating unit containing a group having a lactone structure are illustrated below, but the present invention is not limited thereto.

In specific examples, R represents a hydrogen atom, an alkyl group which may have a substituent, or a halogen atom, preferably a hydrogen atom, a methyl group, a hydroxymethyl group or an acetyloxymethyl group.

(In the formulae, Rx represents H, $CH_3$, $CH_2OH$ or $CF_3$.)

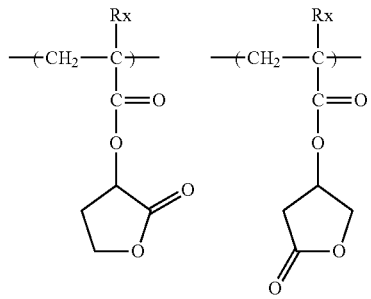

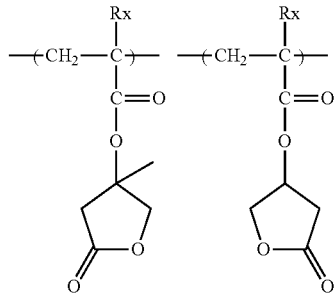

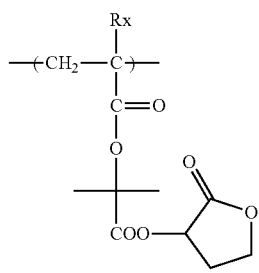

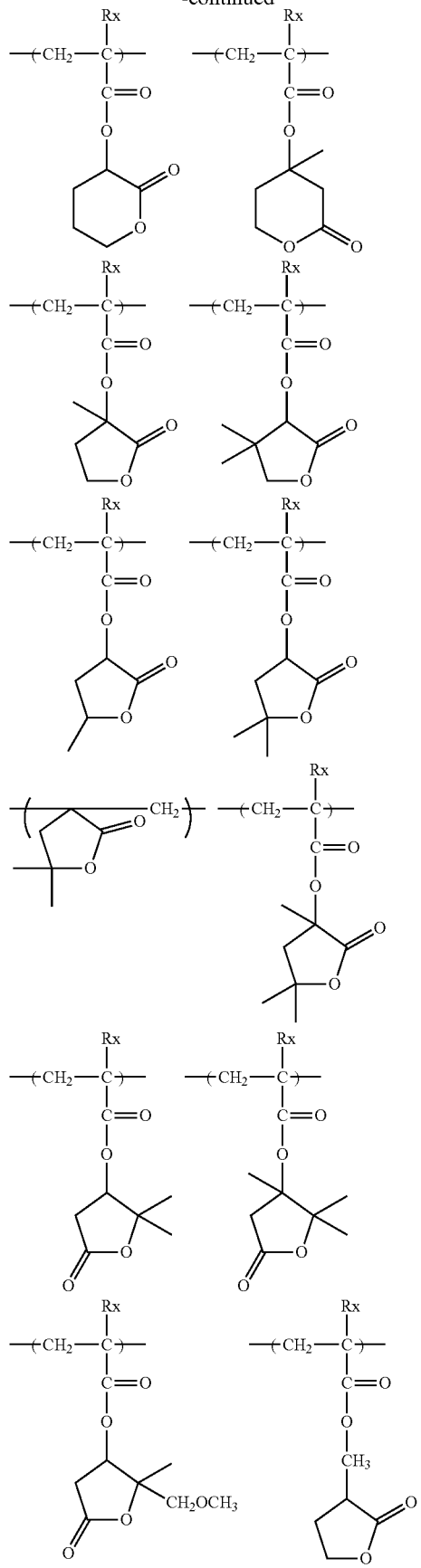
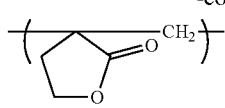
(In the formulae, Rx represents H, CH$_3$, CH$_2$OH or CF$_3$.)
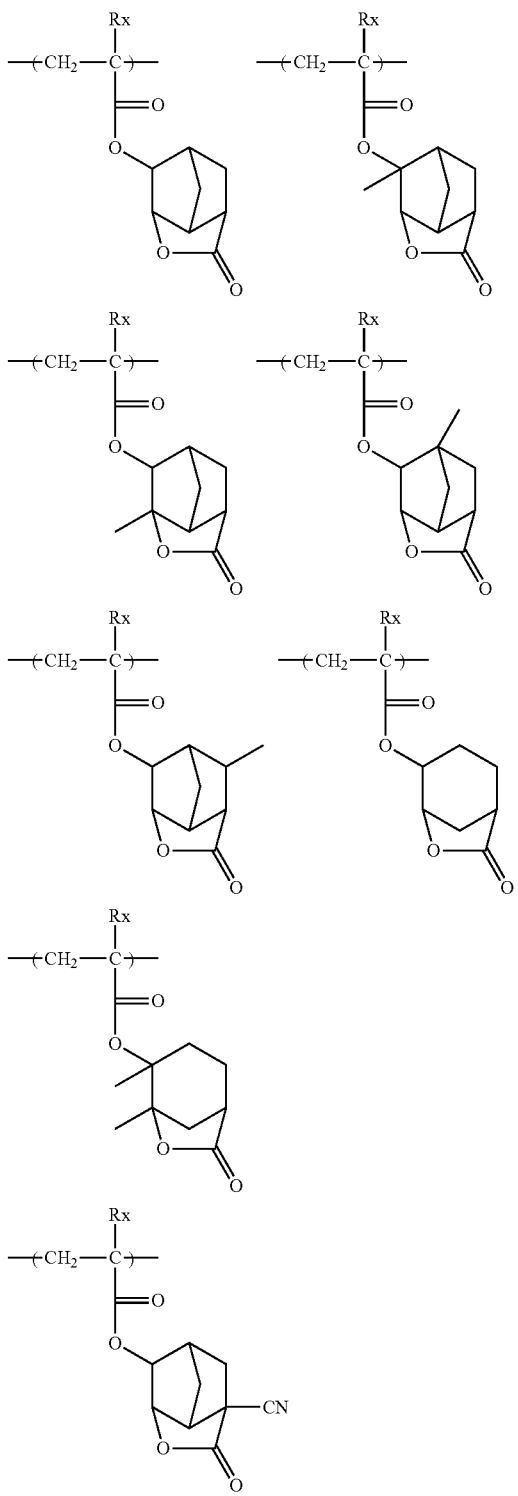

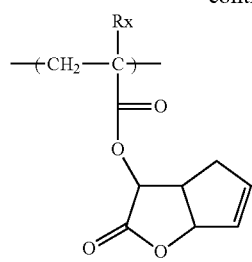
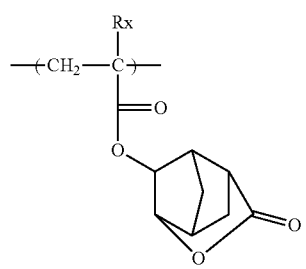
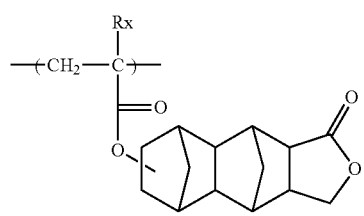
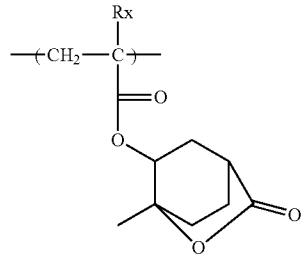
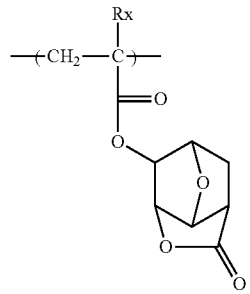
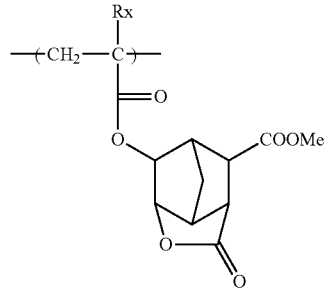
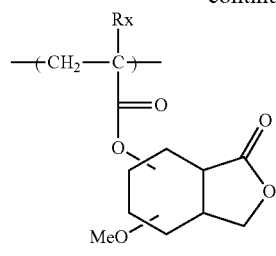
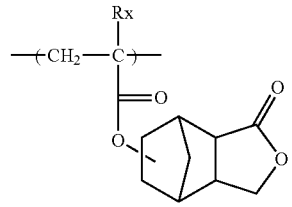
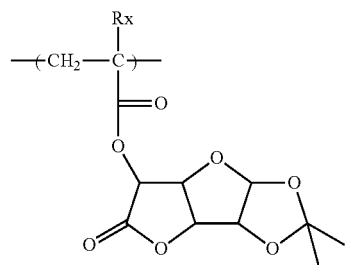
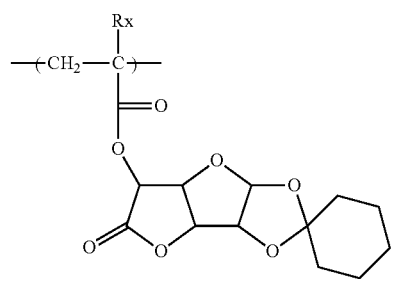
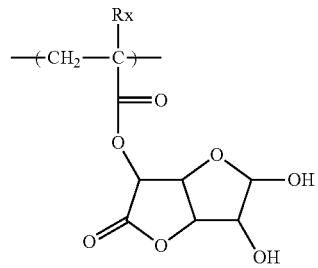
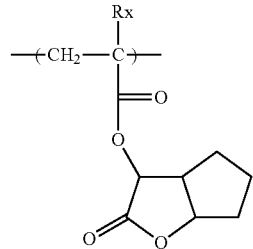

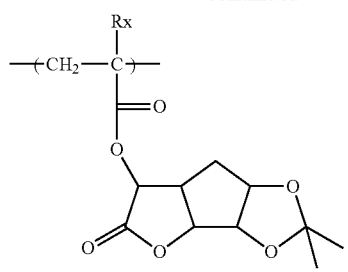
In the formulae, Rx represents H, CH$_3$, CH$_2$OH or CF$_3$.)
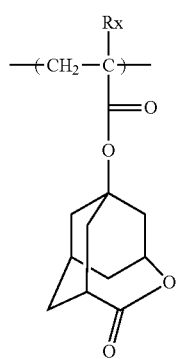 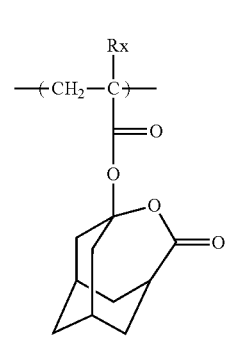
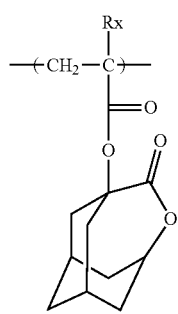 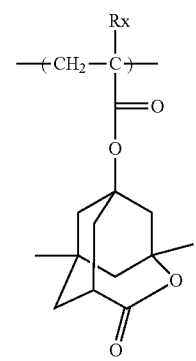
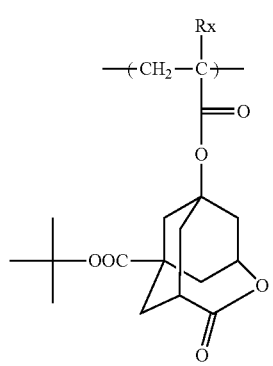 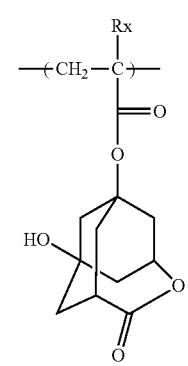
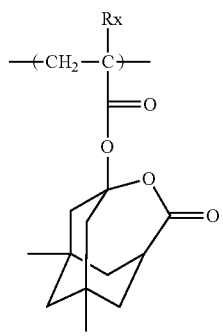 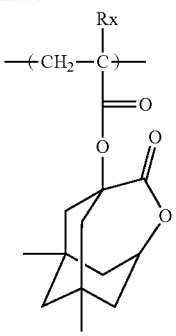
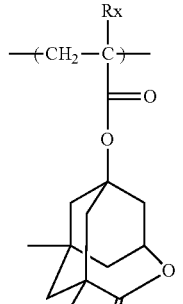 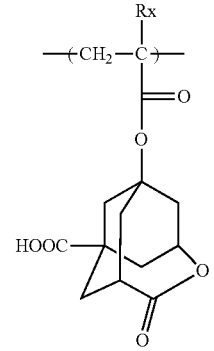
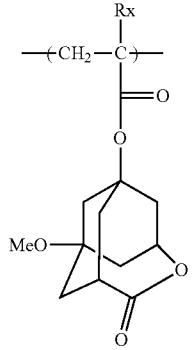 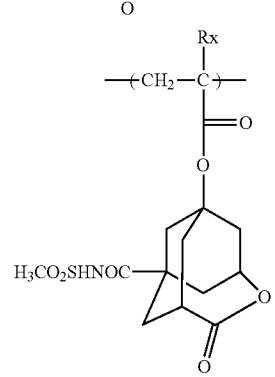
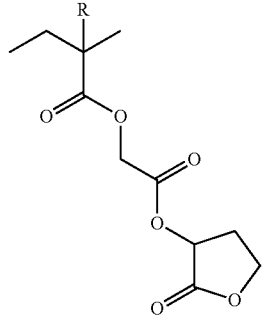
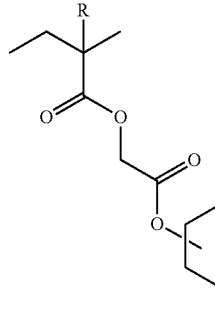

47
-continued
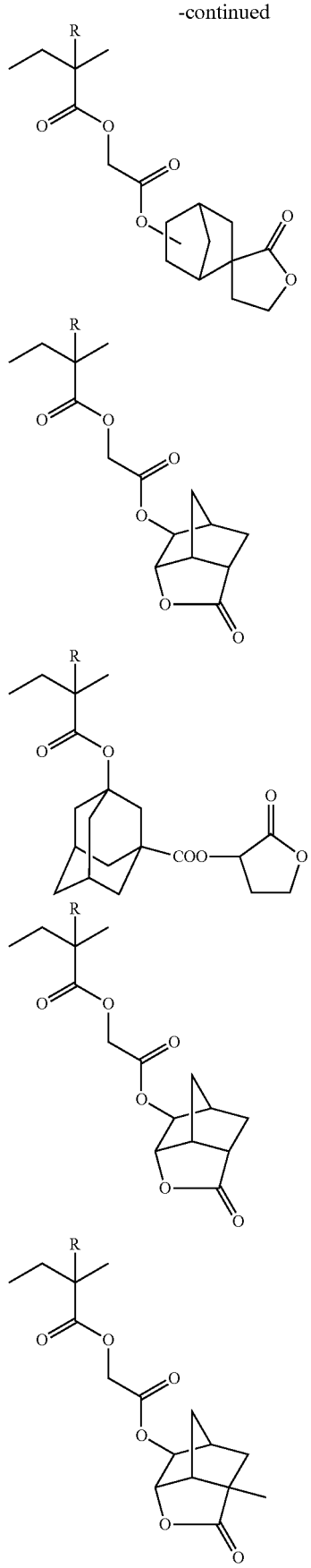
48
-continued
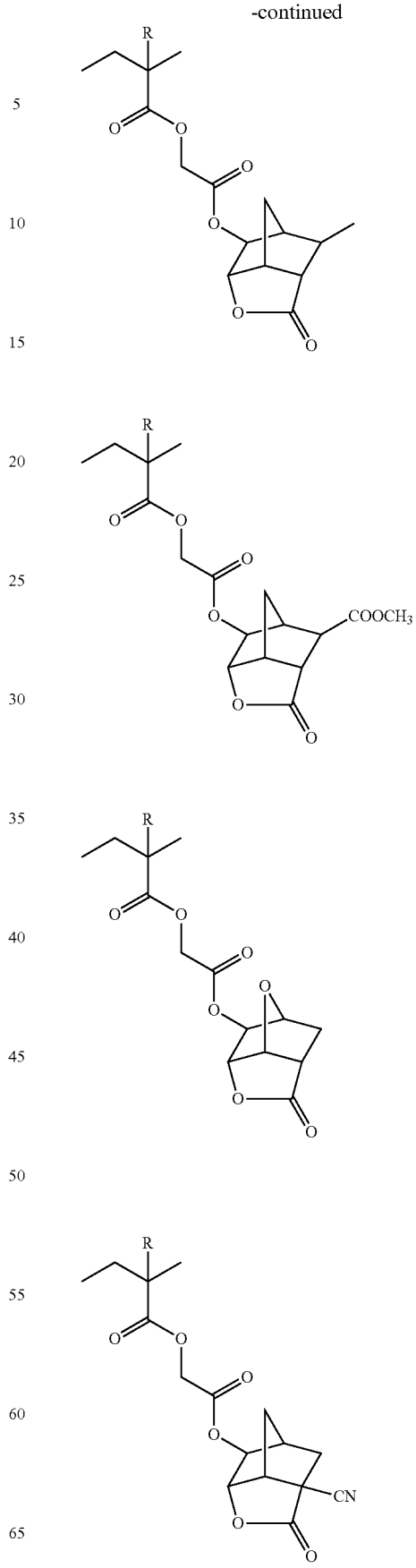

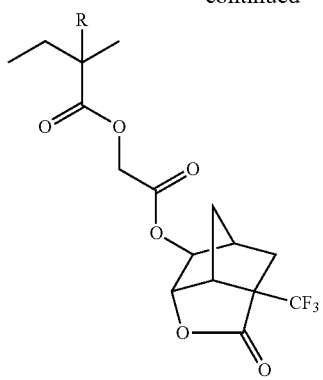
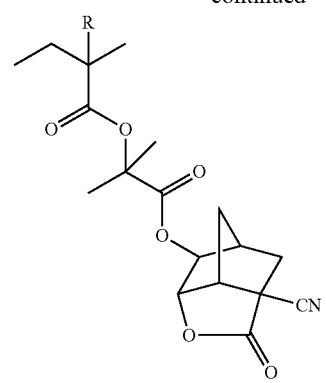
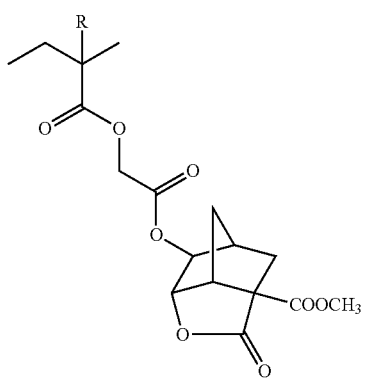
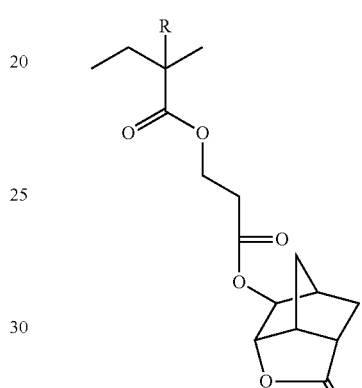
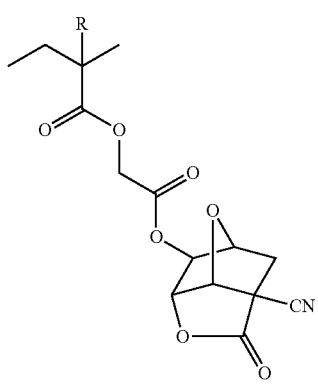
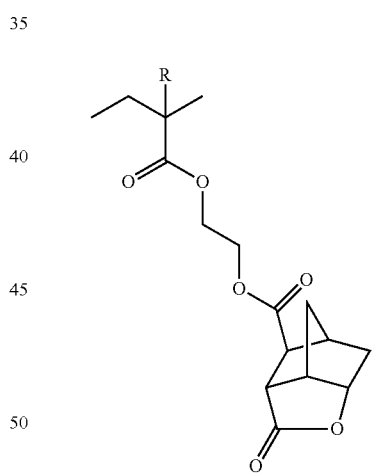
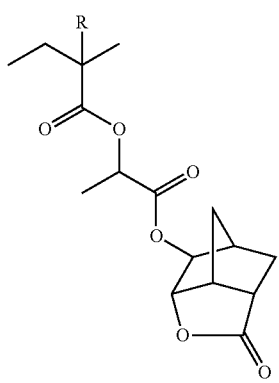
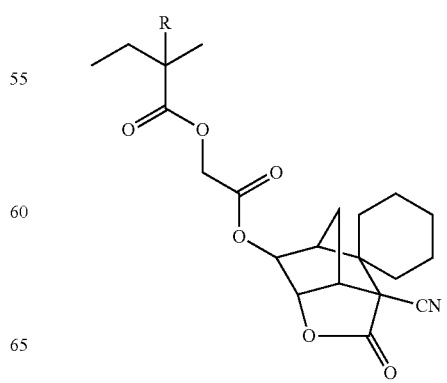

51
-continued
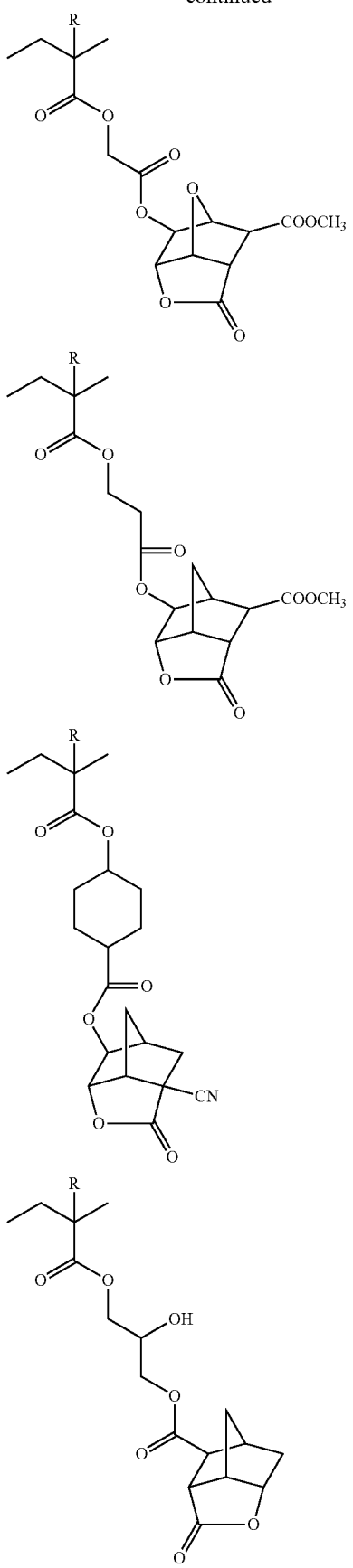
52
-continued
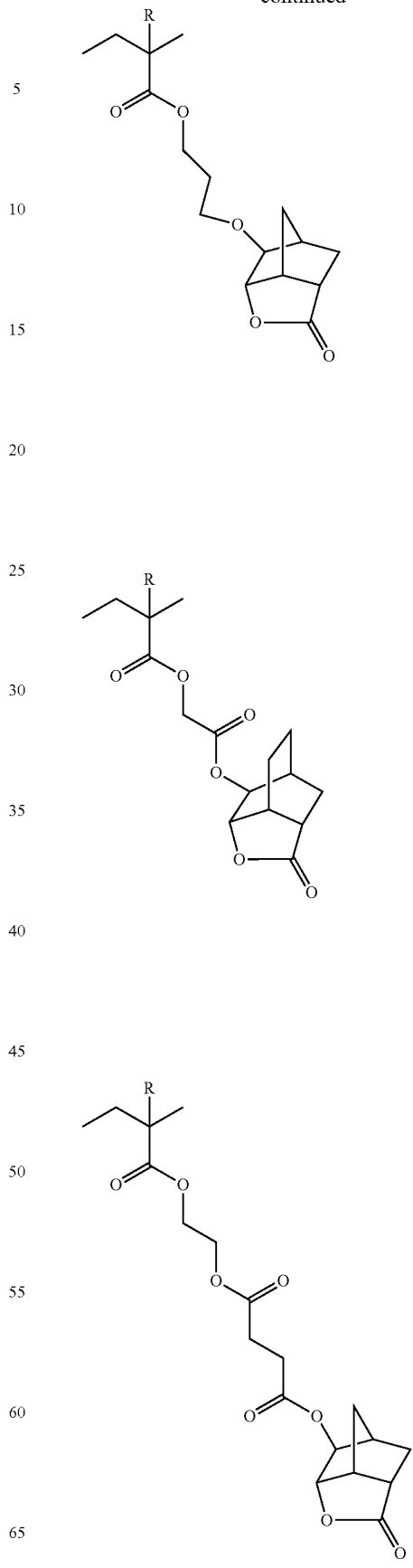

-continued

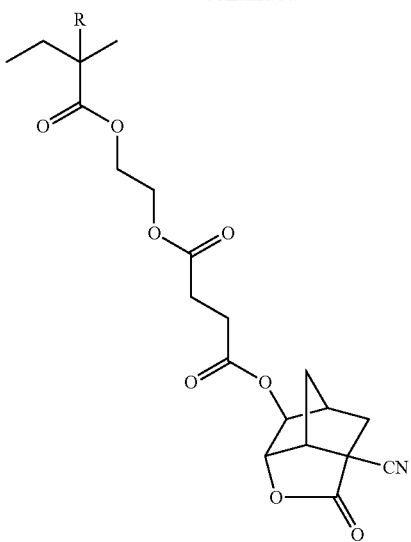

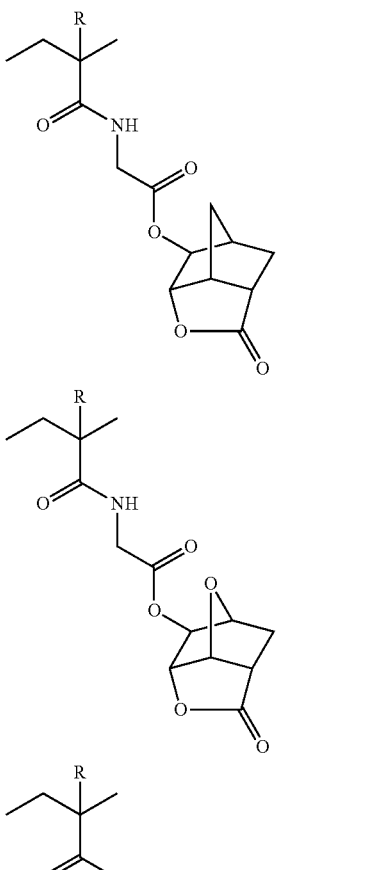

Two or more kinds of lactone structure-containing repeating units may be also used in combination for increasing the effects of the present invention.

The content of the repeating unit having a lactone structure is preferably from 15 to 60 mol %, more preferably from 20 to 50 mol %, still more preferably from 30 to 50 mol %, based on all repeating, units in the resin (a).

The resin (a) preferably contains a repeating unit having a hydroxy group or a cyano group, other than formula (III). Thanks to this repeating unit, adherence to substrate and affinity for developer are enhanced. The repeating unit having a hydroxyl group or a cyano group is preferably a repeating unit having an alicyclic hydrocarbon structure substituted with a hydroxyl group or a cyano group and preferably has no acid-decomposable group. The alicyclic hydrocarbon structure in the alicyclic hydrocarbon structure substituted with a hydroxyl group or a cyano group is preferably an adamantyl group, a diamantyl group or a norbornane group. The alicyclic hydrocarbon structure substituted with a hydroxyl group or a cyano group is preferably a partial structure represented by the following formulae (VIIa) to (VIId):

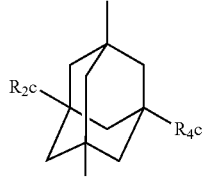
(VIIa)

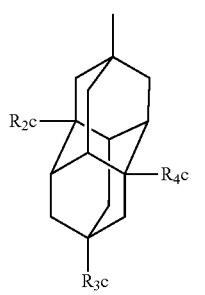
(VIIb)

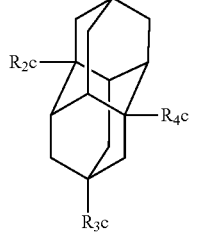
(VIIc)

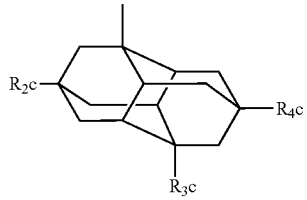
(VIId)

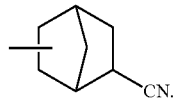

In formulae (VIIa) to (VIIc), each of $R_2c$ to $R_4c$ independently represents a hydrogen atom, a hydroxyl group or a cyano group. However, at least one of $R_2c$ to $R_4c$ represents a hydroxyl group or a cyano group. A structure where one or two members out of $R_2c$ to $R_4c$ are a hydroxyl group with the remaining being a hydrogen atom is preferred. In formula (VIIa), it is more preferred that two members out of $R_2c$ to $R_4c$ are a hydroxyl group and the remaining is a hydrogen atom.

The repeating unit having a partial structure represented by formulae (VIIa) to (VIId) includes repeating units represented by the following formulae (AIIa) to (AIId):

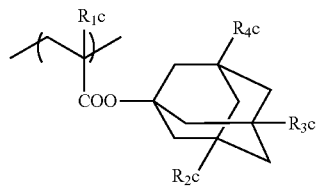
(AIIa)

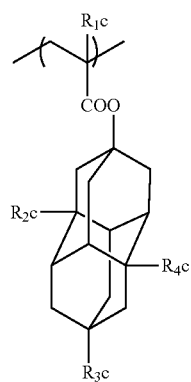
(AIIb)

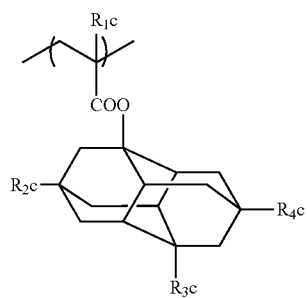
(AIIc)

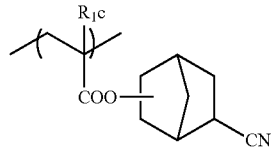
(AIId)

In formulae (AIIa) to (AIId), $R_1c$ represents a hydrogen atom, a methyl group, a trifluoromethyl group or a hydroxymethyl group.

$R_2c$ to $R_4c$ have the same meanings as $R_2c$ to $R_4c$ in formulae (VIIa) to (VIIc).

The content of the repeating unit having a hydroxy group or a cyano group is preferably from 5 to 40 mol %, more preferably from 5 to 30 mol %, still more preferably from 5 to 25 mol %, based on all repeating units in the resin (a).

Specific examples of the repeating unit having a hydroxy group or a cyano group are illustrated below, but the present invention is not limited thereto.

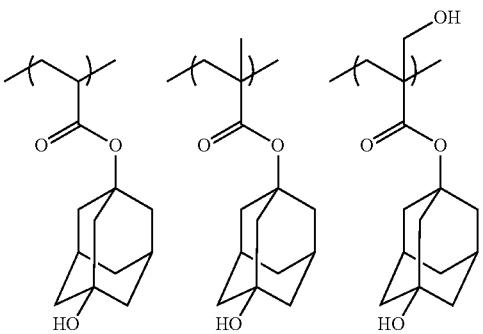

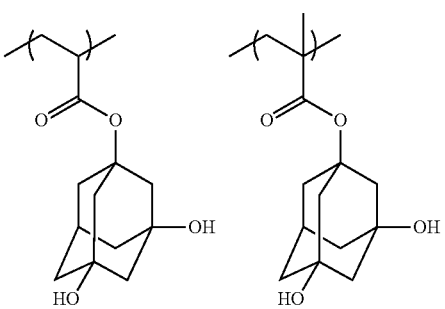

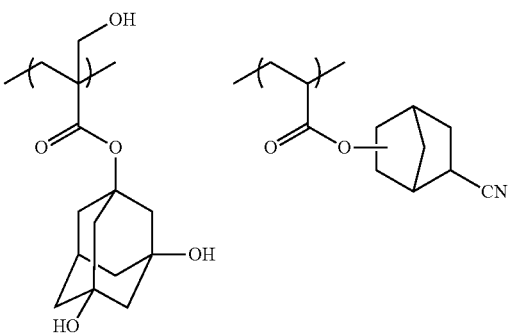

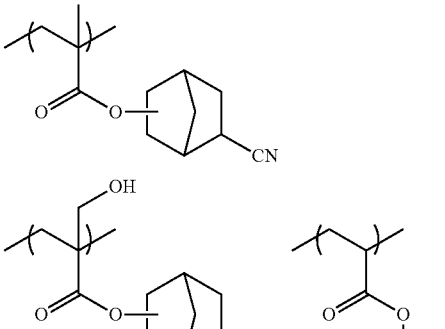

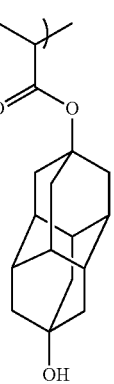

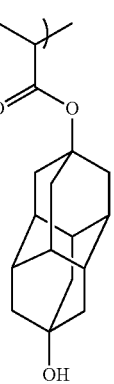

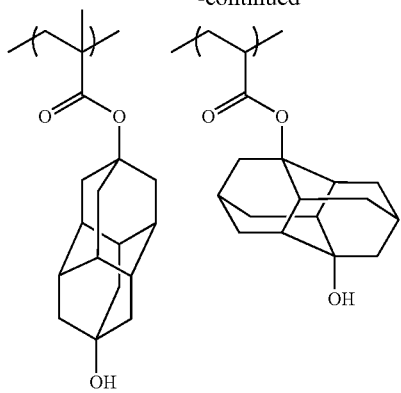

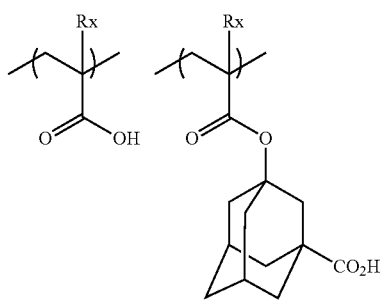

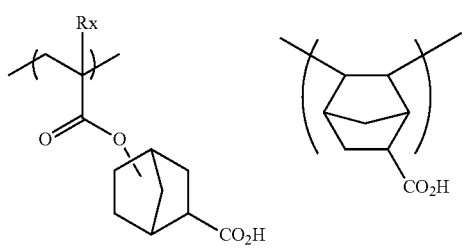

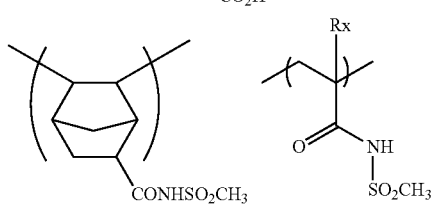

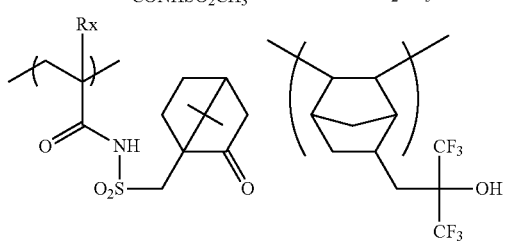

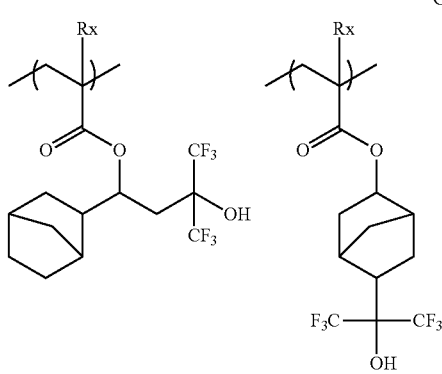

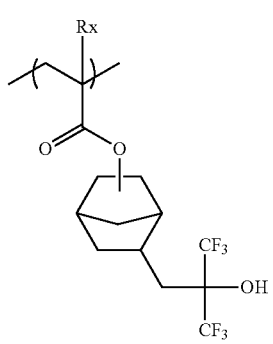

The resin (a) may contain a repeating unit having an acid group. The acid group includes a carboxyl group, a sulfonamide group, a sulfonylimide group, a bissulfonylimide group, and an aliphatic alcohol group substituted with an electron-withdrawing group at the α-position (e.g. hexafluoroisopropanol). It is more preferred to contain a repeating unit having a carboxy group. By virtue of containing a repeating unit having an acid group, the resolution increases in the usage of forming contact holes. As for the repeating unit having an acid group, a repeating unit where the acid group is directly bonded to the main chain of the resin, such as repeating unit by an acrylic acid or a methacrylic acid, a repeating unit where the acid group is bonded to the main chain of the resin through a linking group, and a repeating unit where the acid group is introduced into the terminal of the polymer chain by using an acid group-containing polymerization initiator or chain transfer agent at the polymerization, all are preferred. The linking group may have a monocyclic or polycyclic, cyclic hydrocarbon structure. A repeating unit by an acrylic acid or a methacrylic acid is more preferred.

The resin (a) may or may not contain a repeating unit having an acid group, but in the case of containing a repeating unit having an acid group, the content thereof is preferably 10 mol % or less, more preferably 5 mol % or less, based on all repeating units in the resin (a). In the case where the rein (a) contains a repeating unit having an acid group, the content of the acid group-containing repeating unit in the resin (a) is usually 1 mol % or more Specific examples of the repeating unit having an acid group are illustrated below, but the present invention is not limited thereto.

In specific examples, Rx represents H, $CH_3$, $CH_2OH$ or $CF_3$.

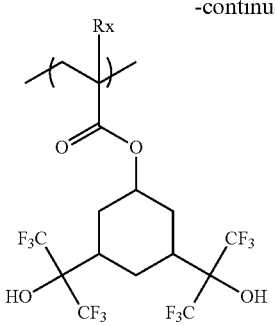

The resin (a) may further contain a repeating unit having an alicyclic hydrocarbon structure free from a polar group (for example, the above-described acid group, a hydroxyl group or a cyano group) and not exhibiting acid decomposability. Thanks to this repeating unit, not only dissolving out of low molecular components from the resist film into the immersion liquid at the immersion exposure can be reduced but also the solubility of the resin at the development using an organic solvent-containing developer can be appropriately adjusted. Such a repeating unit includes a repeating unit represented by formula (IV):

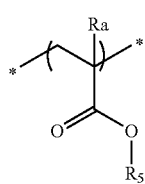

(IV)

in formula (IV), $R_5$ represents a hydrocarbon group having at least one cyclic structure and having no polar group.

Ra represents a hydrogen atom, an alkyl group, or a —$CH_2$—O—$Ra_2$ group, wherein $Ra_2$ represents a hydrogen atom, an alkyl group or an acyl group. Ra is preferably a hydrogen atom, a methyl group, a hydroxyl group or a trifluoromethyl group, more preferably a hydrogen atom or a methyl group.

The cyclic structure contained in $R_5$ includes a monocyclic hydrocarbon group and a polycyclic hydrocarbon group. Examples of the monocyclic hydrocarbon group include a cycloalkyl group having a carbon number of 3 to 12, such as cyclopentyl group, cyclohexyl group, cycloheptyl group and cyclooctyl group, and a cycloalkenyl group having a carbon number of 3 to 12, such as cyclohexenyl group. The monocyclic hydrocarbon group is preferably a monocyclic hydrocarbon group having a carbon number of 3 to 7, more preferably a cyclopentyl group or a cyclohexyl group.

The polycyclic hydrocarbon group includes a ring assembly hydrocarbon group and a crosslinked cyclic hydrocarbon group. Examples of the ring assembly hydrocarbon group include a bicyclohexyl group and a perhydronaphthalenyl group. Examples of the crosslinked cyclic hydrocarbon ring include a bicyclic hydrocarbon ring such as pinane ring, bornane ring, norpinane ring, norbornane ring and bicyclooctane ring (e.g., bicyclo[2.2.2]octane ring, bicyclo[3.2.1]octane ring), a tricyclic hydrocarbon ring such as homobledane ring, adamantane ring, tricyclo[5.2.1.0$^{2,6}$]decane ring and tricyclo[4.3.1.1$^{2,5}$]undecane ring, and a tetracyclic hydrocarbon ring such as tetracyclo[4.4.0.1$^{2,5}$.1$^{7,10}$]dodecane ring and perhydro-1,4-methano-5,8-methanonaphthalene ring. The crosslinked cyclic hydrocarbon ring also includes a condensed cyclic hydrocarbon ring, for example, a condensed ring formed by fusing a plurality of 5- to 8-membered cycloalkane rings, such as perhydronaphthalene (decalin) ring, perhydroanthracene ring, perhydrophenathrene ring, perhydroacenaphthene ring, perhydrofluorene ring, perhydroindene ring and perhydrophenalene ring.

Preferred examples of the crosslinked cyclic hydrocarbon ring include a norbornyl group, an adamantyl group, a bicyclooctanyl group and a tricycle[5,2,1,0$^{2,6}$]decanyl group. Of these crosslinked cyclic hydrocarbon rings, a norbornyl group and an adamantyl group are more preferred.

These alicyclic hydrocarbon groups may have a substituent, and preferred examples of the substituent include a halogen atom, an alkyl group, a hydroxyl group with a hydrogen atom being substituted for, and an amino group with a hydrogen atom being substituted for. The halogen atom is preferably bromine atom, chlorine atom or fluorine atom, and the alkyl group is preferably a methyl group, an ethyl group, a butyl group or a tert-butyl group. This alkyl group may further have a substituent, and the substituent which the alkyl group may further have includes a halogen atom, an alkyl group, a hydroxyl group with a hydrogen atom being substituted for, and an amino group with a hydrogen atom being substituted for.

Examples of the substituent for hydrogen atom include an alkyl group, a cycloalkyl group, an aralkyl group, a substituted methyl group, a substituted ethyl group, an alkoxycarbonyl group and an aralkyloxycarbonyl group. The alkyl group is preferably an alkyl group having a carbon number of 1 to 4; the substituted methyl group is preferably a methoxymethyl group, a methoxythiomethyl group, a benzyloxymethyl group, a tert-butoxymethyl group or a 2-methoxyethoxymethyl group; the substituted ethyl group is preferably a 1-ethoxyethyl group or a 1-methyl-1-methoxyethyl group; the acyl group is preferably an aliphatic acyl group having a carbon number of 1 to 6, such as formyl group, acetyl group, propionyl group, butyryl group, isobutyryl group, valeryl group and pivaloyl group; and the alkoxycarbonyl group includes, for example, an alkoxycarbonyl group having a carbon number of 1 to 4.

The resin (a) may or may not contain a repeating unit having a polar group-free alicyclic hydrocarbon structure and not exhibiting acid decomposability, but in the case of containing the repeating unit, the content thereof is preferably from 1 to 40 mol %, more preferably from 5 to 20 mol %, based on all repeating units in the resin (a).

Specific examples of the repeating unit having a polar group-free alicyclic hydrocarbon structure and not exhibiting acid decomposability are illustrated below, but the present invention is not limited thereto. In the formulae, Ra represents H, $CH_3$, $CH_2OH$ or $CF_3$.

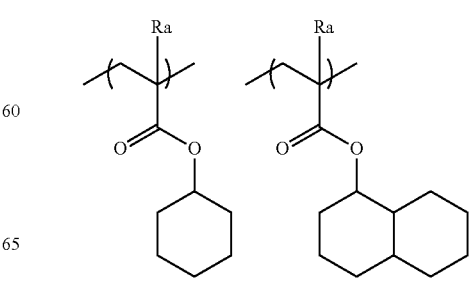

-continued

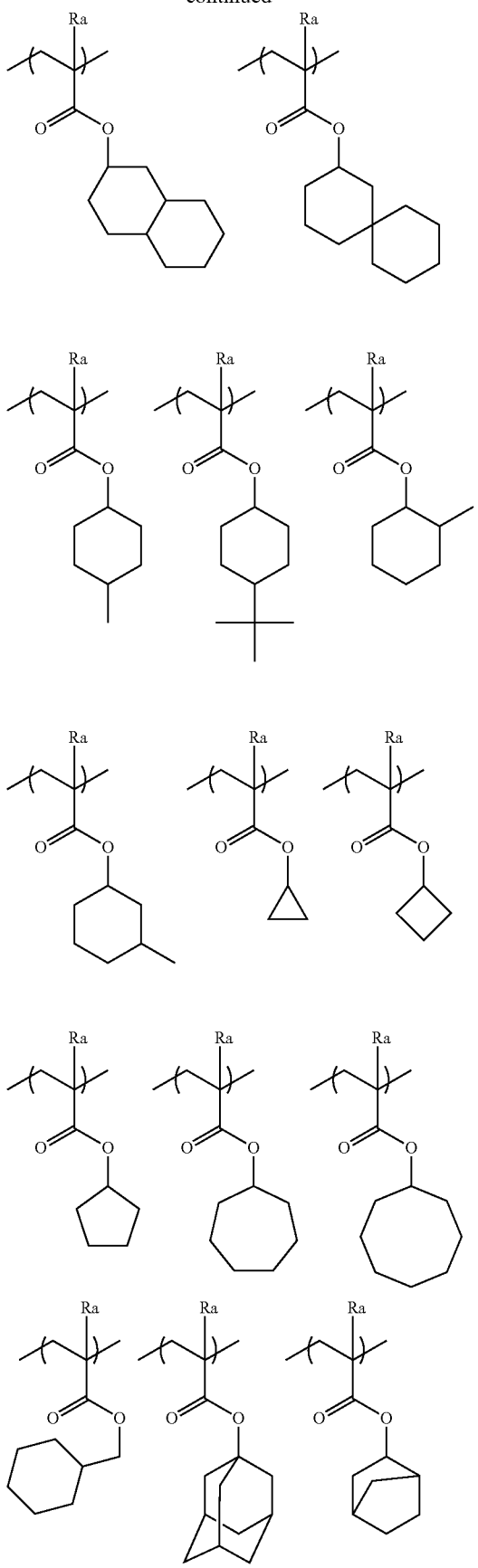

-continued

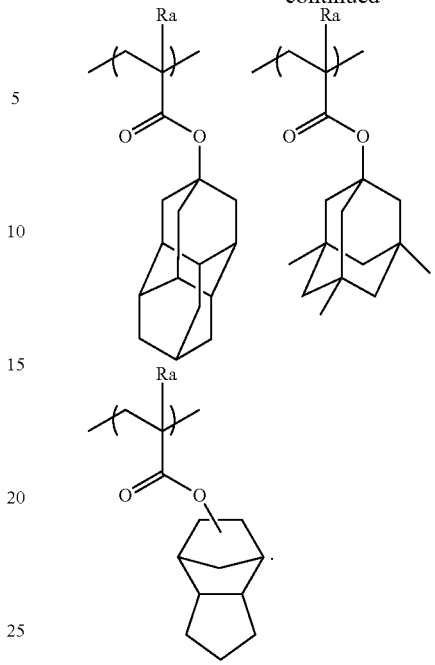

The resin (a) for use in the composition of the present invention may contain, in addition to the above-described repeating structural units, various repeating structural units for the purpose of controlling the dry etching resistance, suitability for standard developer, adherence to substrate, resist profile and properties generally required of an actinic ray-sensitive or radiation-sensitive resin composition, such as resolution, heat resistance and sensitivity.

Examples of such a repeating structural unit include, but are not limited to, repeating structural units corresponding to the monomers described below.

Thanks to such a repeating structural unit, the performance required of the resin used in the composition of the present invention, particularly (1) solubility for coating solvent,
(2) film-forming property (glass transition point),
(3) alkali developability,
(4) film loss (selection of hydrophilic, hydrophobic or alkali-soluble group).
(5) adherence of unexposed area to substrate,
(6) dry etching resistance, and the like, can be subtly controlled.

Examples of the monomer include a compound having one addition-polymerizable unsaturated bond selected from acrylic acid esters, methacrylic acid esters, acrylamides, methacrylamides, allyl compounds, vinyl ethers and vinyl esters.

Other than these, an addition-polymerizable unsaturated compound copolymerizable with the monomers corresponding to the above-described various repeating structural units may be copolymerized.

In the resin (a) for use in the composition of the present invention, the molar ratio of respective repeating structural units contained is appropriately set to control dry etching resistance of the actinic ray-sensitive or radiation-sensitive resin composition, suitability for standard developer, adherence to substrate, resist profile and performances generally required of the actinic ray-sensitive or radiation-sensitive resin composition, such as resolution, heat resistance and sensitivity.

In the case where the composition of the present invention is used for ArF exposure, in view of transparency to ArF light, the resin (a) for use in the composition of the present invention preferably has substantially no aromatic group (specifically, the ratio of an aromatic group-containing repeating unit in the resin is preferably 5 mol % or less, more preferably 3 mol % or less, and ideally 0 mol %, that is, the resin does not have an aromatic group), and the resin (a) preferably has a monocyclic or polycyclic alicyclic hydrocarbon structure.

Also, in the case where the composition of the present invention contains the later-described resin (d), the resin (a) preferably contains no fluorine atom and no silicon atom in view of compatibility with the resin (d).

The resin (a) for use in the composition of the present invention is preferably a resin where all repeating units are composed of a (meth)acrylate-based repeating unit. In this case, all repeating units may be a methacrylate-based repeating unit, all repeating units may be an acrylate-based repeating unit, or all repeating units may be composed of a methacrylate-based repeating unit and an acrylate-based repeating unit, but the content of the acrylate-based repeating unit is preferably 50 mol % or less based on all repeating units. A copolymerized polymer containing from 20 to 50 mol % of an acid decomposable group-containing (meth) acrylate-based repeating unit, from 20 to 50 mol % of a lactone group-containing (meth)acrylate-based repeating unit, from 5 to 30 mol % of a (meth)acrylate-based repeating unit having an alicyclic hydrocarbon structure substituted with a hydroxyl group or a cyano group, and from 0 to 20 mol % of other (meth)acrylate-based repeating units is also preferred.

In the case of irradiating the composition of the present invention with KrF excimer laser light, electron beam, X-ray or high-energy beam at a wavelength of 50 nm or less (e.g., EUV), the resin (a) preferably further contains a hydroxystyrene-based repeating unit. It is more preferred to contain a hydroxystyrene-based repeating unit, a hydroxystyrene-based repeating unit protected with an acid-decomposable group, and an acid-decomposable repeating unit such as tertiary alkyl(meth)acrylate.

Preferred examples of the hydroxystyrene-based repeating unit having an acid-decomposable group include repeating units composed of a tert-butoxycarbonyloxystyrene, a 1-alkoxyethoxystyrene and a tertiary alkyl(meth)acrylate. Repeating units composed of a 2-alkyl-2-adamantyl(meth) acrylate and a dialkyl(1-adamantyl)methyl(meth)acrylate are more preferred.

The resin (a) for use in the present invention can be synthesized by a conventional method (for example, radical polymerization). Examples of the general synthesis method include a hatch polymerization method of dissolving monomer species and an initiator in a solvent and heating the solution, thereby effecting the polymerization, and a dropping polymerization method of adding dropwise a solution containing monomer species and an initiator to a heated solvent over 1 to 10 hours. A dropping polymerization method is preferred. Examples of the reaction solvent include ethers such as tetrahydrofuran, 1,4-dioxane and diisopropyl ether, ketones such as methyl ethyl ketone and methyl isobutyl ketone, an ester solvent such as ethyl acetate, an amide solvent such as dimethylformamide and dimethylacetamide, and the later-described solvent capable of dissolving the composition of the present invention, such as propylene glycol monomethyl ether acetate, propylene glycol monomethyl ether and cyclohexanone. The polymerization is more preferably performed using the same solvent as the solvent used in the photosensitive composition of the present invention. By the use of the same solvent, production of particles during storage can be suppressed.

The polymerization reaction is preferably performed in an inert gas atmosphere such as nitrogen or argon. As for the polymerization initiator, the polymerization is started using a commercially available radical initiator (e.g., azo-based initiator, peroxide). The radical initiator is preferably an azo-based initiator, and an azo-based initiator having an ester group, a cyano group or a carboxyl group is preferred. Preferred examples of the initiator include azobisisobutyronitrile, azobisdimethylvaleronitrile and dimethyl 2,2'-azobis(2-methylpropionate). The initiator is added additionally or in parts, if desired. After the completion of reaction, the reaction solution is poured in a solvent, and the desired polymer is collected, for example, by a powder or solid recovery method. The concentration at the reaction is from 5 to 50 mass %, preferably from 10 to 30 mass %, and the reaction temperature is usually from 10 to 150° C., preferably from 30 to 120° C., more preferably from 60 to 100° C. (In this specification, mass ratio is equal to weight ratio.)

After the completion of reaction, the reaction solution is allowed to cool to room temperature and purified. The purification may be performed by a normal method, for example, a liquid-liquid extraction method of applying water washing or combining an appropriate solvent to remove residual monomers or oligomer components; a purification method in a solution sate, such as ultrafiltration of extracting and removing only polymers having a molecular weight not more than a specific value; a reprecipitation method of adding dropwise the resin solution in a poor solvent to solidify the resin in the poor solvent and thereby remove residual monomers and the like; and a purification method in a solid state, such as washing of a resin slurry with a poor solvent after separation of the slurry by filtration. For example, the resin is precipitated as a solid by contacting the reaction solution with a solvent in which the resin is sparingly soluble or insoluble (poor solvent) and which is in a volumetric amount of 10 times or less, preferably from 10 to 5 times, the reaction solution.

The solvent used at the operation of precipitation or reprecipitation from the polymer solution (precipitation or reprecipitation solvent) may be sufficient if it is a poor solvent for the polymer, and the solvent which can be used may be appropriately selected from, for example, a hydrocarbon, a halogenated hydrocarbon, a nitro compound, an ether, a ketone, an ester, a carbonate, an alcohol, a carboxylic acid, water, and a mixed solvent containing such a solvent, according to the kind of the polymer. Among these solvents, a solvent containing at least an alcohol (particularly, methanol or the like) or water is preferred as the precipitation or reprecipitation solvent.

The amount of the precipitation or reprecipitation solvent used may be appropriately selected by taking into consideration the efficiency, yield and the like, but in general, the amount used is from 100 to 10,000 parts by mass, preferably from 200 to 2,000 parts by mass, more preferably from 300 to 1,000 parts by mass, per 100 parts by mass of the polymer solution.

The temperature at the precipitation or reprecipitation may be appropriately selected by taking into consideration the efficiency or operability but is usually on the order of 0 to 50° C., preferably in the vicinity of room temperature (for example, approximately from 20 to 35° C.). The precipitation or reprecipitation operation may be performed using a commonly employed mixing vessel such as stirring tank by a known method such as batch system and continuous system.

The precipitated or reprecipitated polymer is usually subjected to commonly employed solid-liquid separation such as filtration and centrifugation, then dried and used. The filtration is performed using a solvent-resistant filter element preferably under pressure. The drying is performed wider atmospheric pressure or reduced pressure (preferably under reduced pressure) at a temperature of approximately from 30 to 100° C., preferably on the order of 30 to 50'C.

Incidentally, after the resin is once precipitated and separated, the resin may be again dissolved in a solvent and then put into contact with a solvent in which the resin is sparingly soluble or insoluble. That is, there may be used a method comprising, after the completion of radical polymerization reaction, bringing the polymer into contact with a solvent in which the polymer is sparingly soluble or insoluble, to precipitate a resin (step a), separating the resin from the solution (step b), anew dissolving the resin in a solvent to prepare a resin solution A (step c), bringing the resin solution A into contact with a solvent in which the resin is sparingly soluble or insoluble and which is in a volumetric amount of less than 10 times (preferably 5 times or less) the resin solution A, to precipitate a resin solid (step d), and separating the precipitated resin (step e).

The weight average molecular weight of the resin (a) for use in the present invention is preferably from 1,000 to 200,000, more preferably from 2,000 to 20,000, still more preferably from 3,000 to 15,000, yet still more preferably from 3,000 to 10,000, in terms of polystyrene by the GPC method. When the weight average molecular weight is from 1,000 to 200,000, reduction in the heat resistance and dry etching resistance can be avoided and at the same time, the film-forming property can be prevented from deterioration due to impairment of developability or increase in the viscosity.

The polydispersity (molecular weight distribution) is usually from 1.0 to 3.0, preferably from 1.0 to 2.6, more preferably from 1.0 to 2.0, still more preferably from 1.4 to 2.0. As the molecular weight distribution is smaller, the resolution and resist profile are more excellent, the side wall of the resist pattern is smoother, and the roughness is more improved.

In the actinic ray-sensitive or radiation-sensitive resin composition of the present invention, the blending ratio of the resin (a) in the entire composition is preferably from 30 to 99 mass %, more preferably from 60 to 95 mass %, based on the entire solid content.

In the present invention, as for the resin (a), one kind of a resin may be used or a plurality of kinds of resins may be used in combination.

[2] (b) Acid Generator

The actinic ray-sensitive or radiation-sensitive resin composition of the present invention contains, as the acid generator (b), (A) a compound capable of generating an acid upon irradiation with an actinic ray or radiation acid and decomposing by the action of an acid to decrease the solubility for an organic solvent (hereinafter, sometimes referred to as a "compound (A)").

The compound (A) is a compound having a structure where the polar group is protected with a leaving group capable of decomposing and leaving by the action of an acid, (hereinafter, sometimes referred to as an "acid-decomposable group", similarly to that described for the acid-decomposable resin (a)).

Specific examples and preferred examples of the polar group are the same as specific examples and preferred examples of the polar group described above for the acid-decomposable resin (a).

Specific examples and preferred examples of the acid-decomposable group are the same as specific examples and preferred examples of the "structure where a polar group is protected with a leaving group capable of decomposing and leaving by the action of an acid" described above for the acid-decomposable resin (a).

In the compound (A) for use in the present invention, from the standpoint of more decreasing the solubility for an organic solvent-containing developer, the acid-decomposable group is preferably (B) a moiety capable of decomposing by the action of an acid to produce a hydroxyl group or a carboxyl group, more preferably a moiety capable of decomposing by the action of an acid to produce a hydroxyl group, still more preferably (B') a moiety capable of decomposing by the action of an acid to produce an alcoholic hydroxyl group.

The moiety (B) capable of decomposing by the action of an acid to produce a hydroxyl group or a carboxyl group is preferably a structure represented by at least one formula selected from the group consisting of the following formulae (I-1) to (I-6), more preferably a structure represented by at least one formula selected from the group consisting of the following formulae (I-1) to (I-5) from the standpoint of more decreasing the solubility for an organic solvent-containing developer:

(I-1)

(I-2)

(I-3)

(I-4)

(I-5)

(I-6)

In formula (I-1), each $R_1$ independently represents a hydrogen atom or a monovalent organic group. Two $R_1$'s may combine with each other to form a ring.

$R_2$ represents a monovalent organic group. One $R_1$ and $R_2$ may combine with each other to form a ring.

In formula (I-2), each $R_3$ independently represents a monovalent organic group. Two $R_3$'s may combine with each other to form a ring.

In formula (I-3), $R_4$ represents a hydrogen atom or a monovalent organic group.

Each $R_5$ independently represents a monovalent organic group. $R_5$'s may combine with each other to form a ring, One $R_5$ and $R_4$ may combine with each other to form a ring.

In formula (I-4), each $R_6$ independently represents a hydrogen atom, an alkyl group, a cycloalkyl group, an aryl group, an alkenyl group or an alkynyl group. Two $R_6$'s may combine with each other to form a ring. However, when one or two of three $R_6$'s are a hydrogen atom, at least one of the remaining $R_6$'s represents an aryl group, an alkenyl group or an alkynyl group.

In formula (I-5), each $R_7$ independently represents a hydrogen atom or a monovalent organic group. $R_7$'s may combine with each other to form a ring.

In formula (I-6), each $R_8$ independently represents a monovalent organic group. Two $R_8$'s may combine with each other to form a ring.

In formulae (I-1) to (I-6), * represents a bond.

Specific examples and preferred examples of $R_1$ are the same as specific examples and preferred examples described above for $Rx_4$ in formula (b-1).

Specific examples and preferred examples of $R_2$ are the same as specific examples and preferred examples described above for $Rx_5$ in formula (b-1).

Specific examples and preferred examples of $R_3$ are the same as specific examples and preferred examples described above for $Rx_6'$ in formula (b-4).

Specific examples and preferred examples of $R_4$ are the same as specific examples and preferred examples described above for $Rx_4'$ in formula (b-2).

Specific examples and preferred examples of $R_5$ are the same as specific examples and preferred examples described above for $Rx_5'$ in formula (b-2).

Specific examples and preferred examples of $Rx_6$ are the same as specific examples and preferred examples described above for $Rx_6$ in formula (b-3).

Specific examples and preferred examples of $Rx_7$ are the same as specific examples and preferred examples described above for $Rx_7$ in formula (c-1).

Specific examples and preferred examples of $R_8$ are the same as specific examples and preferred examples described above for $Rx_1$ to $Rx_3$ in formula (a-1).

The compound (A) capable of generating an acid upon irradiation with an actinic ray or radiation acid and decomposing by the action of an acid to decrease the solubility for an organic solvent includes compounds represented by the following formulae (ZI), (ZII) and (ZIII):

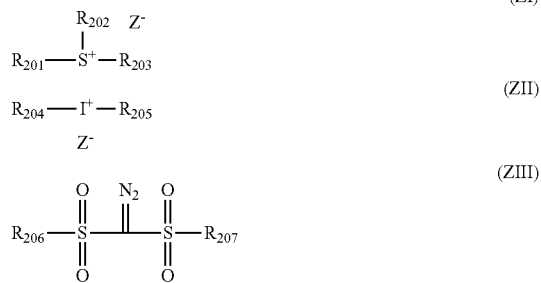

In formula (ZI), each of $R_{201}$, $R_{202}$ and $R_{203}$ independently represents an organic group.

The carbon number of the organic group as $R_{201}$, $R_{202}$ and $R_{203}$ is generally from 1 to 30, preferably from 1 to 20.

Two members out of $R_{201}$ to $R_{203}$ may combine to form a ring structure, and the ring may contain an oxygen atom, a sulfur atom, an ester bond, an amide bond or a carbonyl group. Examples of the group formed by combining two members out of $R_{201}$ to $R_{203}$ include an alkylene group (e.g., butylene, pentylene).

$Z^-$ represents a non-nucleophilic anion.

At least one of $R_{201}$, $R_{202}$, $R_{203}$ and $Z^-$ has an acid-decomposable group. The preferred embodiment of the acid-decomposable group is as described above.

Preferably, at least one of $R_{201}$, $R_{202}$ and $R_{203}$ has an acid-decomposable group, because when an acid-decomposable group is contained in the cation moiety, a dissolution contrast resulting from decomposition by the irradiation with an actinic ray or radiation can be more uniformly imparted by virtue of having an acid-decomposable group in the cation moiety whose decomposition product becomes more hydrophobic.

Examples of the non-nucleophilic anion as include a sulfonate anion, a carboxylate anion, a sulfonylimide anion, a bis(alkylsulfonyl)imide anion and a tris(alkylsulfonyl)methyl anion.

The non-nucleophilic anion is an anion having an extremely low ability of causing a nucleophilic reaction and this anion can suppress the decomposition with aging due to intramolecular nucleophilic reaction. Thanks to this anion, the aging stability of the actinic ray-sensitive or radiation-sensitive resin composition is enhanced.

Examples of the sulfonate anion include an aliphatic sulfonate anion, an aromatic sulfonate anion and a camphorsulfonate anion.

Examples of the carboxylate anion include an aliphatic carboxylate anion, an aromatic carboxylate anion and an aralkylcarboxylate anion.

The aliphatic moiety in the aliphatic sulfonate anion and aliphatic carboxylate anion may be an alkyl group or a cycloalkyl group but is preferably an alkyl group having a carbon number of 1 to 30 or a cycloalkyl group having a carbon number of 3 to 30, and examples thereof include a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbornyl group and a bornyl group.

The aromatic group in the aromatic sulfonate anion and aromatic carboxylate anion is preferably an aryl group having a carbon number of 6 to 14, and examples thereof include a phenyl group, a tolyl group and a naphthyl group.

The alkyl group, cycloalkyl group and aryl group in the aliphatic sulfonate anion and aromatic sulfonate anion may have a substituent. Examples of the substituent of the alkyl group, cycloalkyl group and aryl group in the aliphatic sulfonate anion and aromatic sulfonate anion include a nitro group, a halogen atom (e.g., fluorine, chlorine, bromine, iodine), a carboxyl group, a hydroxyl group, an amino group, a cyano group, an alkoxy group (preferably baying a carbon number of 1 to 15), a cycloalkyl group (preferably having a carbon number of 3 to 15), an aryl group (preferably having a carbon number of 6 to 14), an alkoxycarbonyl group (preferably having a carbon number of 2 to 7), an acyl group (preferably having a carbon number of 2 to 12), an alkoxycarbonyloxy group (preferably having a carbon number of 2 to 7), an alkylthio group (preferably having a carbon number of 1 to 15), an alkylsulfonyl group (preferably having a carbon number of 1 to 15), an alkyliminosulfonyl group (preferably having a carbon number of 1 to 15), an aryloxysulfonyl group (preferably having a carbon number of 6 to 20), an alkylaryloxysulfonyl group (preferably having a carbon number of 7 to 20), a cycloalkylaryloxysulfonyl group (preferably having a carbon number of 10 to 20), an alkyloxyalkyloxy group (preferably having a carbon number of 5 to 20), and a cycloalkylalkyloxyalkyloxy group (preferably having a carbon number of 8 to 20). As for the aryl group or ring structure in each group, examples of the substituent further include an alkyl group (preferably having a carbon number of 1 to 15).

The aralkyl group in the aralkylcarboxylate anion is preferably an aralkyl group having a carbon number of 7 to 12, and examples thereof include a benzyl group, a phenethyl group, a naphthylmethyl group, a naphthylethyl group and a naphthylbutyl group.

The alkyl group, cycloalkyl group, aryl group and aralkyl group in the aliphatic carboxylate anion, aromatic carboxylate anion and aralkylcarboxylate anion may have a substituent. Examples of the substituent include the same halogen atom, alkyl group, cycloalkyl group, alkoxy group and alkylthio group as in the aromatic sulfonate anion.

Examples of the sulfonylimide anion include saccharin anion.

The alkyl group in the bis(alkylsulfonyl)imide anion and tris(alkylsulfonyl)methide anion is preferably an alkyl group having a carbon number of 1 to 5, and examples thereof include a methyl group, an ethyl group, a propyl group, an isopropyl group, an n-butyl group, an isobutyl group, a sec-butyl group, a pentyl group and a neopentyl group. Examples of the substituent on this alkyl group include a halogen atom, a halogen atom-substituted alkyl group, an alkoxy group, an alkylthio group, an alkyloxysulfonyl group, an aryloxysulfonyl group, and a cycloalkylaryloxysulfonyl group, with a fluorine atom-substituted alkyl group being preferred.

Other examples of the non-nucleophilic anion include fluorinated phosphorus, fluorinated boron and fluorinated antimony.

The non-nucleophilic anion of $Z^-$ is preferably an aliphatic sulfonate anion substituted with a fluorine atom at least at the α-position of the sulfonic acid, an aromatic sulfonate anion substituted with a fluorine atom or a fluorine atom-containing group, a bis(alkylsulfonyl)imide anion in which the alkyl group is substituted with a fluorine atom, or a tris(alkylsulfonyl)methide anion in which the alkyl group is substituted with a fluorine atom. The non-nucleophilic anion is more preferably a perfluoroaliphatic sulfonate anion having a carbon number of 4 to 8 or a fluorine atom-containing benzenesulfonate anion, still more preferably nonafluorobutanesulfonate anion, perfluorooctanesulfonate anion, pentafluorobenzenesulfonate anion or 3,5-bis(trifluoromethyl)benzenesulfonate anion.

As the non-nucleophilic anion of $Z^-$, an anion capable of producing an acid represented by the following formula (I) is also preferred.

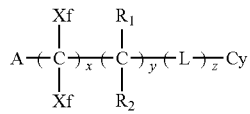
(I)

In the formula, each Xf independently represents a fluorine atom or an alkyl group substituted with at least one fluorine atom.

Each of $R_1$ and $R_2$ independently represents a hydrogen atom, a fluorine atom or an alkyl group, and when a plurality of $R_1$'s or $R_2$'s are present, each $R_1$ or $R_2$ may be the same as or different from every other $R_1$ or $R_2$.

L represents a divalent linking group, and when a plurality of L's are present, each L may be the same as or different from every other L.

Cy represents a cyclic organic group.

A represents $HO_3S$— or $Rf—SO_2—NH—SO_2$—. Rf represents an alkyl group having at least one fluorine atom, a cycloalkyl group having at least one fluorine atom, or an aryl group having at least one fluorine atom (the substitution on cycloalkyl and aryl group may be substitution with an alkyl fluoride such as —$CF_3$ but not with a fluorine atom; specific examples of the alkyl group as Rf having at least one fluorine atom are the same as specific examples of Xf described later, specific examples of the cycloalkyl group as Rf having at least one fluorine atom include perfluorocyclopentyl and perfluorocyclohexyl, specific examples of the aryl group as Rf having at least one fluorine atom include perfluorophenyl, and each of these groups may be substituted with a substituent not containing a fluorine atom).

x represents an integer of 1 to 20, y represents an integer of 0 to 10, and z represents an integer of 0 to 10.

Formula (I) is described in more detail below.

The alkyl group in the fluorine atom-substituted alkyl group of Xf is preferably an alkyl group having a carbon number of 1 to 10, more preferably from 1 to 4. Also, the fluorine atom-substituted alkyl group of Xf is preferably a perfluoroalkyl group.

Xf is preferably a fluorine atom or a perfluoroalkyl group having a carbon number of 1 to 4. Specific examples of Xf include a fluorine atom, $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$ and $CH_2CH_2C_4F_9$, with a fluorine atom and $CF_3$ being preferred. In particular, it is preferred that both Xf's are a fluorine atom.

The alkyl group of $R_1$ and $R_2$ is preferably an alkyl group having a carbon number of 1 to 4, which may have a substituent (preferably fluorine atom), more preferably a perfluoroalkyl group having a carbon number of 1 to 4. Specific examples of the alkyl group having a substituent of $R_1$ and $R_2$ include $CF_3$, $C_2F_5$, $C_3F_7$, $C_4F_9$, $C_5F_{11}$, $C_6F_{13}$, $C_7F_{15}$, $C_8F_{17}$, $CH_2CF_3$, $CH_2CH_2CF_3$, $CH_2C_2F_5$, $CH_2CH_2C_2F_5$, $CH_2C_3F_7$, $CH_2CH_2C_3F_7$, $CH_2C_4F_9$ and $CH_2CH_2C_4F_9$, with $CF_3$ being preferred.

Each of $R_1$ and $R_2$ is preferably a fluorine atom or $CF_3$, y is preferably from 0 to 4, more preferably 0. x is preferably from 1 to 8, more preferably from 1 to 4, still more preferably 1. z is preferably from 0 to 8, more preferably from 0 to 4.

The divalent linking group of L is not particularly limited and includes —COO—, —OCO—, —CO—, —O—, —S—, —SO—, $SO_2$—, an alkylene group, a cycloalkylene group, an alkenylene group, and a linking group formed by combining a plurality of these members, and a linking group having a total carbon number of 12 or less is preferred. Above all, —COO—, —OCO—, —CO—, —O— and —$SO_2$— are preferred, —COO—, —OCO— and —$SO_2$— are more preferred, and —$SO_2$— is still more preferred.

The cyclic organic group of Cy is not particularly limited as long as it has a cyclic structure, and examples thereof include an alicyclic group, an aryl group and a heterocyclic group (including not only those having aromaticity but also those having no aromaticity, for example, a tetrahydropyrane ring and a lactone ring structure).

The alicyclic group may be monocyclic or polycyclic and is preferably a monocyclic cycloalkyl group such as cyclopentyl group, cyclohexyl group and cyclooctyl group, or a polycyclic cycloalkyl group such as norbornyl group, tricyclodecanyl group, tetracyclodecanyl group, tetracyclododecanyl group and adamantyl group. Above all, an alicyclic group having a bulky structure with a carbon number of 7 or more, such as norbornyl group, tricyclodecanyl group, tetracyclodecanyl group, tetracyclododecanyl group and adamantyl group, is preferred from the standpoint that diffusion in the film at the PEB (post-exposure baking) step can be suppressed and MEEF (mask error enhancement factor) can be improved.

The aryl group may be monocyclic or polycyclic and includes a benzene ring, a naphthalene ring, a phenanthrene ring and an anthracene ring. Among these, naphthalene having low absorbance is preferred in view of absorbance for light at 193 nm.

The heterocyclic group may be monocyclic or polycyclic includes those derived from a furan ring, a thiophene ring, a benzofuran ring, a benzothiophene ring, a dibenzofuran ring, a dibenzothiophene ring, a pyridine ring and a decahydroisoquinoline ring. In particular, those derived from a furan ring, a thiophene ring, a pyridine ring and a decahydroisoquinoline ring are preferred.

The above-described cyclic organic group may have a substituent, and examples of the substituent include an alkyl group (may be any of linear, branched and cyclic, preferably having a carbon number of 1 to 12), a cycloalkyl group (may be any of monocyclic, polycyclic and spirocyclic, preferably having a carbon number of 3 to 20), an aryl group (preferably having a carbon number of 6 to 14), a hydroxyl group, an alkoxy group, an ester group, an amide group, a urethane group, a ureido group, a thioether group, a sulfonamide group, and a sulfonic acid ester group. Incidentally, the carbon constituting the cyclic organic group (the carbon contributing to ring formation) may be carbonyl carbon.

In the case where the anion capable of producing an acid represented by formula (I) has an acid-decomposable group, any group of Xf, $R_1$, $R_2$, L, Cy and Rf may be substituted with an acid-decomposable group, but Cy or Rf is preferably substituted with an acid-decomposable group, and it is more preferred that Cy is substituted with an acid-decomposable group.

The acid-decomposable group is preferably (B) a moiety capable of producing a hydroxyl group or a carboxyl group, having a structure represented by formula (I-1), (I-3) or (I-6), more preferably a moiety capable of producing a carboxyl group, having a structure represented by formula (I-6).

In the case where the anion capable of producing an acid represented by formula (I) has an acid-decomposable group, the acid-decomposable group may be bonded to the anion through a divalent linking group, and examples thereof include an embodiment where Cy is substituted with an acid-decomposable group through a divalent linking group.

This divalent linking group is not particularly limited but includes —COO—, —OCO—, —CO—, —O—, —S—, —SO—, —SO$_2$—, alkylene group, a cycloalkylene group, an alkenylene group, and a linking group formed by combining a plurality of these members.

In the case where the anion capable of producing an acid represented by formula (I) has an acid-decomposable group, the compound (A) is preferably a compound represented by the following formula (II-4) or (II-5):

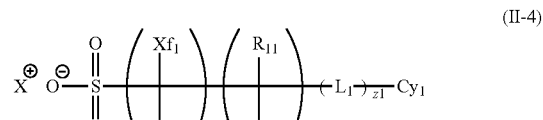

(II-4)

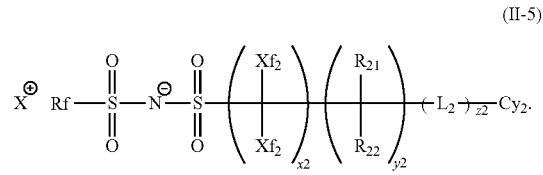

(II-5)

In formulae, each $X^+$ independently represents a counter cation.

Rf has the same meaning as Rf in A of formula (I).

Each of $Xf_1$ and $Xf_2$ independently has the same meaning as Xf in formula (I).

Each of $R_{11}$, $R_{12}$, $R_{21}$ and $R_{22}$ independently has the same meaning as $R_1$ or $R_2$ in formula (I).

Each of $L_1$ and $L_2$ independently has the same meaning as L in formula (I).

Each of $Cy_1$ and $Cy_2$ independently has the same meaning as Cy in formula (I).

Any of $Xf_1$, $R_{11}$, $R_{12}$, and $Cy_1$ may be substituted with a group (acid-decomposable group) having a structure where a polarity group is protected with a leaving group capable of decomposing and leaving by the action of an acid, and any of $Xf_2$, $R_{21}$, $R_{22}$, $L_2$, $Cy_2$ and Rf may be substituted with an acid-decomposable group.

Each of x1 and x2 independently has the same meaning as x in formula (I).

Each of y1 and y2 independently has the same meaning as y in formula (I).

Each of z1 and z2 independently has the same meaning as z in formula (I).

The counter cation of $X^+$ includes a sulfonium cation in formula (ZI) and an iodonium cation in formula (ZII).

Specific examples of the anion having an acid-decomposable group and being capable of producing an acid represented by formula (I) are illustrated below, but the present invention is not limited thereto.

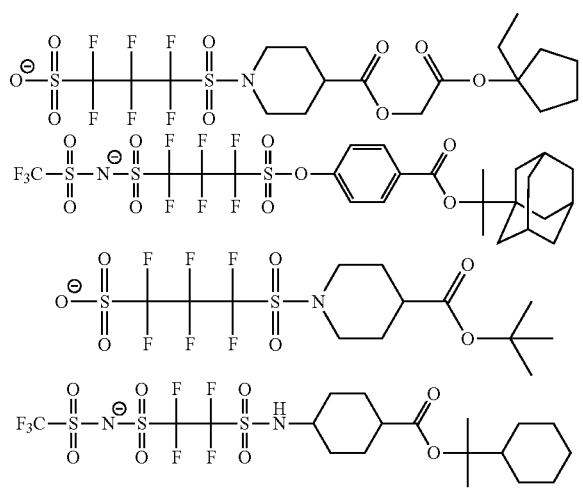

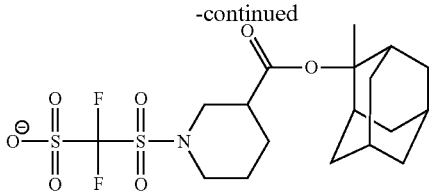

In the case of containing an acid-decomposable group in Z⁻ of formulae (ZI) to (ZIII), an embodiment where the compound (A) is a compound represented by the following formula (III) is also preferred.

B—Y-A⁻X⁺                   (III)

wherein A⁻ represents an organic acid anion,
   Y represents a divalent linking group,
   X⁺ represents a counter cation, and
   B represents an acid-decomposable group.

The organic acid anion of A⁻ includes a sulfonate anion, a carboxylate anion and an imide acid anion and is preferably a sulfonate anion or an imide anion, and in this case, the sensitivity is enhanced.

The divalent linking group as Y is preferably a divalent linking group having a carbon number of 1 to 8, and examples thereof include an alkylene group and an arylene group (preferably phenylene group). The divalent linking group as Y is more preferably an alkylene group, and the carbon number is preferably from 1 to 6, more preferably from 1 to 4. The alkylene chain may have a linking group containing an oxygen atom, a nitrogen atom, a sulfur atom or the like. The alkylene group may be substituted with a fluorine atom and in this case, it is more preferred that the carbon bonded to A⁻ has a fluorine atom.

The counter cation of X⁺ includes a sulfonium cation in formula (ZI) and an iodonium cation in formula (ZII).

B is preferably (B) a moiety capable of decomposing by the action of an acid to produce a hydroxyl group or a carboxyl group, more preferably a structure represented by any of formulae (I-1) to (I-6), still more preferably a structure represented by any of formulae (I-1) to (I-5). It is also preferred that B is a moiety capable of decomposing by the action of an acid to produce an alcoholic hydroxyl group, and in this case, Y is preferably an alkylene group.

Specific examples of the acid anion in formula (III) are illustrated below, but the present invention is not limited thereto.

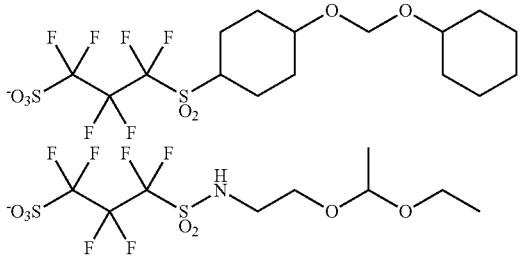

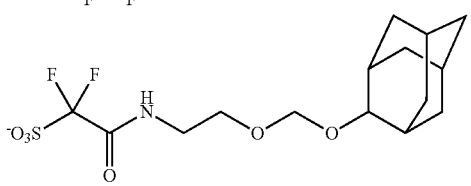

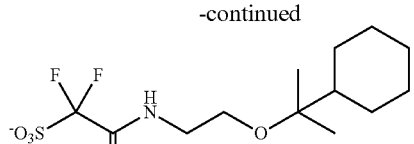

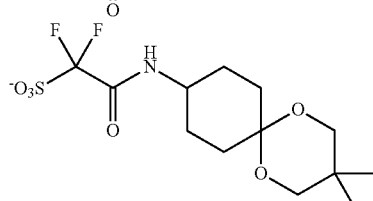

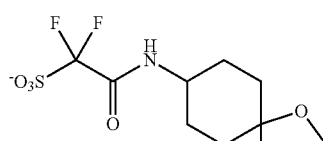

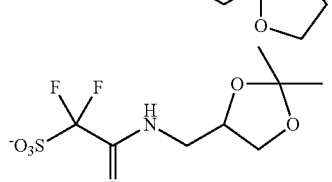

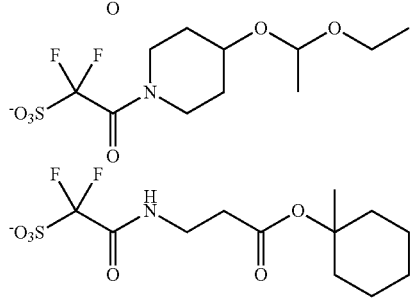

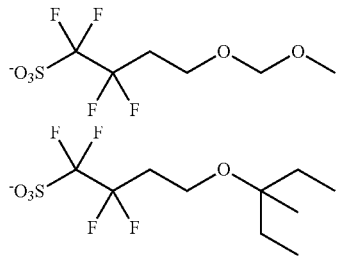

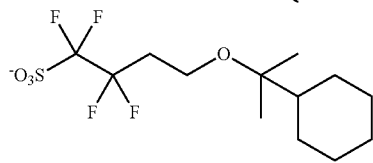

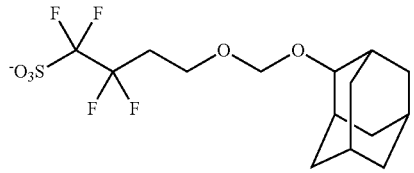

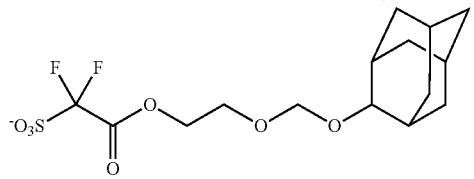

-continued

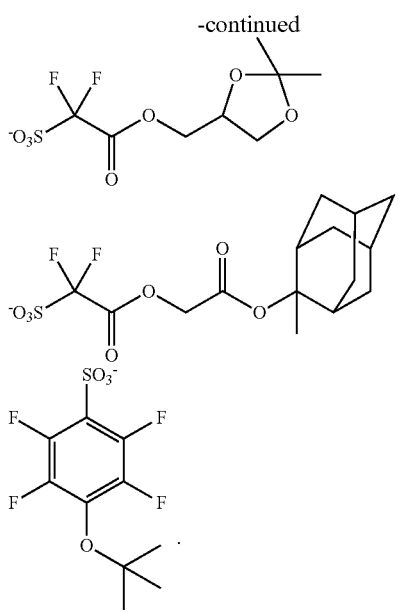

Examples of the organic group represented by $R_{201}$, $R_{202}$ and $R_{203}$ include corresponding groups in the later-described compounds (ZI-1), (ZI-2), (ZI-3) and (ZI-4).

The compound may be a compound having a plurality of structures represented by formula (ZI). For example, the compound may be a compound having a structure where at least one of $R_{201}$ to $R_{203}$ in a compound represented by formula (ZI) is bonded to at least one of $R_{201}$ to $R_{203}$ in another compound represented by formula (ZI) through a single bond or a linking group.

Compounds (ZI-1), (ZI-2), ZI-3) and (ZI-4) described below are more preferred as the component (ZI).

The compound (ZI-1) is an arylsulfonium compound where at least one of $R_{201}$ to $R_{203}$ in formula (ZI) is an aryl group, that is, a compound having an arylsulfonium as the cation.

In the arylsulfonium compound, all of $R_{201}$ to $R_{203}$ may be an aryl group or a part of $R_{201}$ to $R_{203}$ may be an aryl group with the remaining being an alkyl group or a cycloalkyl group.

Examples of the arylsulfonium compound include a triarylsulfonium compound, a diarylalkylsulfonium compound, an aryldialkylsulfonium compound, a diarylcycloalkylsulfonium compound and an aryldicycloalkylsulfonium compound.

The aryl group in the arylsulfonium compound is preferably a phenyl group or a naphthyl group, more preferably a phenyl group. The aryl group may be an aryl group having a heterocyclic structure containing an oxygen atom, a nitrogen atom, a sulfur atom or the like. Examples of the heterocyclic structure include a pyrrole residue group, a furan residue group, a thiophene residue group, indole residue group, a benzofuran residue group and a benzothiophene residue group. In the case where the arylsulfonium compound has two or more aryl groups, these two or more aryl groups may be the same or different.

The alkyl or cycloalkyl group which is present, if desired, in the arylsulfonium compound is preferably a linear or branched alkyl group having a carbon number of 1 to 15 or a cycloalkyl group having a carbon number of 3 to 15, and examples thereof include a methyl group, an ethyl group, a propyl group, an n-butyl group, a sec-butyl group, a tert-butyl group, a cyclopropyl group, a cyclobutyl group and a cyclohexyl group.

At least one of $R_{201}$, $R_{202}$ and $R_{203}$ preferably has an acid-decomposable group. The preferred embodiment of the acid-decomposable group is as described above.

The aryl group, alkyl group and cycloalkyl group of $R_{201}$ to $R_{203}$ may have, as the substituent, an alkyl group (for example, having a carbon number of 1 to 15), a cycloalkyl group (for example, having a carbon number of 3 to 15), an aryl group (for example, having a carbon number of 6 to 14), an alkoxy group (for example, having a carbon number of 1 to 15), a halogen atom, a hydroxyl group or a phenylthio group, other than an acid-decomposable group. The substituent is preferably a linear or branched alkyl group having a carbon number of 1 to 12, a cycloalkyl group having a carbon number of 3 to 12, or a linear, branched or cyclic alkoxy group having a carbon number of 1 to 12, more preferably an alkyl group having a carbon number of 1 to 4, or an alkoxy group having a carbon number of 1 to 4. The substituent may be substituted on any one of three members $R_{201}$ to $R_{203}$ or may be substituted on all of these three members. In the case where $R_{201}$ to $R_{203}$ are an aryl group, the substituent is preferably substituted at the p-position of the aryl group.

The compound (ZI-2) is described below.

The compound (ZI-2) is a compound where each of $R_{201}$ to $R_{203}$ in formula (ZI) independently represents an aromatic ring-free organic group. The aromatic ring as used herein includes an aromatic ring containing a heteroatom.

The aromatic ring-free organic group as $R_{201}$ to $R_{203}$ has a carbon number of generally from 1 to 30, preferably from 1 to 20.

Each of $R_{201}$ to $R_{203}$ independently represents preferably an alkyl group, a cycloalkyl group, an allyl group or a vinyl group, more preferably a linear or branched 2-oxoalkyl group, a 2-oxocycloalkyl group or an alkoxycarbonylmethyl group, still more preferably a linear or branched 2-oxoalkyl group.

The alkyl group and cycloalkyl group of $R_{201}$ to $R_{203}$ are preferably a linear or branched alkyl group having a carbon number of 1 to 10 (e.g., methyl, ethyl, propyl, butyl, pentyl), and a cycloalkyl group having a carbon number of 3 to 10 (e.g., cyclopentyl, cyclohexyl, norbornyl). The alkyl group is more preferably a 2-oxoalkyl group or an alkoxycarbonylmethyl group. The cycloalkyl group is more preferably a 2-oxocycloalkyl group.

The 2-oxoalkyl group may be either linear or branched and is preferably a group having >C=O at the 2-position of the above-described alkyl group.

The 2-oxocycloalkyl group is preferably a group having >C=O at the 2-position of the above-described cycloalkyl group.

The alkoxy group in the alkoxycarbonylmethyl group is preferably an alkoxy group having a carbon number of 1 to 5 (e.g. methoxy, ethoxy, propoxy, butoxy, pentoxy).

At least one of $R_{201}$, $R_{202}$ and $R_{203}$ preferably has an acid-decomposable group. The preferred embodiment of the acid-decomposable group is as described above.

$R_{201}$ to $R_{203}$ may be further substituted with a halogen atom, an alkoxy group (for example, having a carbon number of 1 to 5), a hydroxyl group, a cyano group or a nitro group, other than an acid-decomposable group.

The compound (ZI-3) is described below.

The compound (ZI-3) is a compound represented by the following formula (ZI-3), and this is a compound having a phenacylsulfonium salt structure.

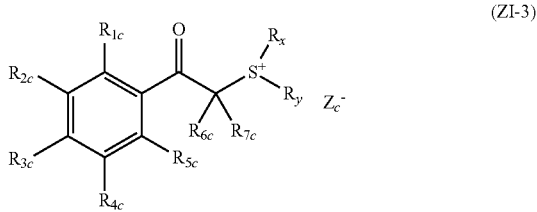

(ZI-3)

In formula (ZI-3), each of $R_{1c}$ to $R_{5c}$ independently represents a hydrogen atom, an alkyl group, a cycloalkyl group, an aryl group, an alkoxy group, an aryloxy group, an alkoxycarbonyl group, an alkylcarbonyloxy group, a cycloalkylcarbonyloxy group, a halogen atom, a hydroxyl group, a nitro group, an alkylthio group or an arylthio group.

Each of $R_{6c}$ and $R_{7c}$ independently represents a hydrogen atom, an alkyl group, a cycloalkyl group, a halogen atom, a cyano group or an aryl group.

Each of $R_x$ and $R_y$ independently represents an alkyl group, a cycloalkyl group, a 2-oxoalkyl group, a 2-oxocycloalkyl group, an alkoxycarbonylalkyl group, an allyl group or a vinyl group.

Any two or more members out of $R_{1c}$ to $R_{5c}$, a pair of $R_{5c}$ and $R_{6c}$, a pair of $R_{6c}$ and $R_{7c}$, a pair of $R_{5c}$ and $R_x$, or a pair of $R_x$ and $R_y$ may combine together to form a ring structure. This ring structure may contain an oxygen atom, a sulfur atom, a ketone group, an ester bond or an amide bond.

The ring structure includes an aromatic or non-aromatic hydrocarbon ring, an aromatic or non-aromatic heterocyclic ring, and a polycyclic condensed ring formed by combining two or more of these rings. The ring structure includes a 3- to 10-membered ring and is preferably a 4- to 8-membered ring, more preferably a 5- or 6-membered ring.

Examples of the group formed by combining any two or more members out of $R_{1c}$ to $R_{5c}$, a pair of $R_{6c}$ and $R_{7c}$, or a pair of $R_x$ and $R_y$ include a butylene group and a pentylene group.

The group formed by combining a pair of $R_{5c}$ and $R_{6c}$ or a pair of $R_{5c}$ and $R_x$ is preferably a single bond or an alkylene group, and examples of the alkylene group include a methylene group and an ethylene group.

$Z_c^-$ represents a non-nucleophilic anion, and examples thereof are the same as those of the non-nucleophilic anion of $Z^-$ in formula (ZI).

The alkyl group as $R_{1c}$ to $R_{7c}$ may be either linear or branched and is, for example, an alkyl group having a carbon number of 1 to 20, preferably a linear or branched alkyl group having a carbon number of 1 to 12 (e.g., methyl, ethyl, linear or branched propyl, linear or branched butyl, linear or branched pentyl). The cycloalkyl group is, for example, a cycloalkyl group having a carbon number of 3 to 10 (e.g., cyclopentyl, cyclohexyl).

The aryl group as $R_{1c}$ to $R_{5c}$ is preferably an aryl group having a carbon number of 5 to 15, and examples thereof include a phenyl group and a naphthyl group.

The alkoxy group as $R_{1c}$ to $R_{5c}$ may be linear, branched or cyclic and is, for example, an alkoxy group having a carbon number of 1 to 10, preferably a linear or branched alkoxy group having a carbon number of 1 to 5 (e.g., methoxy, ethoxy, linear or branched propoxy, linear or branched butoxy, linear or branched pentoxy), or a cyclic alkoxy group having a carbon number of 3 to 10 (e.g., cyclopentyloxy, cyclohexyloxy).

Specific examples of the alkoxy group in the alkoxycarbonyl group of $R_{1c}$ to $R_{5c}$ are the same as specific examples of the alkoxy group of $R_{1c}$ to $R_{5c}$.

Specific examples of the alkyl group in the alkylcarbonyloxy group and alkylthio group of $R_{1c}$ to $R_{5c}$ are the same as specific examples of the alkyl group of $R_{1c}$ to $R_{5c}$.

Specific examples of the cycloalkyl group in the cycloalkylcarbonyloxy group of $R_{1c}$ to $R_{5c}$ are the same as specific examples of the cycloalkyl group of $R_{1c}$ to $R_{5c}$.

Specific examples of the aryl group in the aryloxy group and arylthio group of $R_{1c}$ to $R_{5c}$ are the same as specific examples of the aryl group of $R_{1c}$ to $R_{5c}$.

A compound where any one of $R_{1c}$ to $R_{5c}$ in a linear or branched alkyl group, a cycloalkyl group or a linear, branched or cyclic alkoxy group is preferred, and a compound where the sum of carbon numbers of $R_{1c}$ to $R_{5c}$ is from 2 to 15 is more preferred. Thanks to such a compound, the solvent solubility is more enhanced and production of particles during storage can be suppressed.

The ring structure which may be formed by combining any two or more members out of $R_{1c}$ to $R_{5c}$ with each other is preferably a 5- or 6-membered ring, more preferably a 6-membered ring (for example, phenyl ring).

The ring structure which may be formed by combining $R_{5c}$ and $R_{6c}$ with each other includes a 4- or higher-membered ring (preferably a 5- or 6-membered ring) formed together with the carbonyl carbon atom and carbon atom in formula (I) by combining $R_{5c}$ and $R_{6c}$ with each other to constitute a single bond or an alkylene group (e.g., methylene, ethylene).

The aryl group as $R_{6c}$ and $R_{7c}$ is preferably an aryl group having a carbon number of 5 to 15, and examples thereof include a phenyl group and a naphthyl group.

An embodiment where both $R_{6c}$ and $R_{7c}$ are an alkyl group is preferred, an embodiment where each of $R_{6c}$ and $R_{7c}$ is a linear or branched alkyl group having a carbon number of 1 to 4 is more preferred, and an embodiment where both are a methyl group is still more preferred.

In the case where $R_{6c}$ and $R_{7c}$ are combined to form a ring, the group formed by combining $R_{6c}$ and $R_{7c}$ is preferably an alkylene group having a carbon number of 2 to 10, and examples thereof include an ethylene group, a propylene group, a butylene group, a pentylene group and a hexylene group. Also, the ring formed by combining $R_{6c}$ and $R_{7c}$ may contain a heteroatom such as oxygen atom in the ring.

Examples of the alkyl group and cycloalkyl group as $R_x$ and $R_y$ are the same as those of the alkyl group and cycloalkyl group in $R_{1c}$ to $R_{7c}$.

Examples of the 2-oxoalkyl group and 2-oxocycloalkyl group as $R_x$ and $R_y$ include a group having >C=O at the 2-position of the alkyl group or cycloalkyl group of $R_{1c}$ to $R_{7c}$.

Examples of the alkoxy group in the alkoxycarbonylalkyl group as $R_x$ and $R_y$ are the same as those of the alkoxy group of $R_{1c}$ to $R_{5c}$. The alkyl group is, for example, an alkyl group having a carbon number of 1 to 12, preferably a linear alkyl group having a carbon number of 1 to 5 (e.g., methyl, ethyl).

The allyl group as $R_x$ and $R_y$ is not particularly limited but is preferably an unsubstituted allyl group or an allyl group substituted with a monocyclic or polycyclic cycloalkyl group (preferably a cycloalkyl group having a carbon number of 3 to 10).

The vinyl group as $R_x$ and $R_y$ is not particularly limited but is preferably an unsubstituted vinyl group or a vinyl group substituted with a monocyclic or polycyclic cycloalkyl group (preferably a cycloalkyl group having a carbon number of 3 to 10).

The ring structure which may be formed by combining $R_{5c}$ and $R_x$ with each other includes a 5- or higher-membered ring (preferably a 5-membered ring) formed together with the sulfur atom and carbonyl carbon atom in formula (I) by combining $R_{5c}$ and $R_x$ with each other to constitute a single bond or an alkylene group (e.g., methylene, ethylene).

The ring structure which may be formed by combining $R_x$ and $R_y$ with each other includes a 5- or 6-membered ring formed by divalent $R_x$ and $R_y$ (for example, a methylene group, an ethylene group or a propylene group) together with the sulfur atom in formula (ZI-3), and a 5-membered ring (that is a tetrahydrothiophene ring) is particularly preferred.

Each of $R_x$ and $R_y$ is an alkyl or cycloalkyl group having a carbon number of preferably 4 or more, more preferably 6 or more, still more preferably 8 or more.

At least one of $R_{1c}$ to $R_{7c}$, $R_x$ and $R_y$ preferably has an acid-decomposable group. The preferred embodiment of the acid-decomposable group is as described above.

$R_{1c}$ to $R_{7c}$, $R_x$ and $R_y$ may further have a substituent other than an acid-decomposable group, and examples of the substituent include a halogen atom (e.g., fluorine), a hydroxyl group, a carboxyl group, a cyano group, a nitro group, an alkyl group, a cycloalkyl group, an aryl group, an alkoxy group, an aryloxy group, an acyl group, an arylcarbonyl group, an alkoxyalkyl group, an aryloxyalkyl group, an alkoxycarbonyl group, an aryloxycarbonyl group, an alkoxycarbonyloxy group and an aryloxycarbonyloxy group.

The alkyl group above includes, for example, a linear or branched alkyl group having a carbon number of 1 to 12, such as methyl group, ethyl group, n-propyl group, i-propyl group, n-butyl group, 2-methylpropyl group, 1-methylpropyl group and tert-butyl group.

The cycloalkyl group above includes, for example, a cycloalkyl group having a carbon number of 3 to 10, such as cyclopentyl group and cyclohexyl group.

The aryl group above includes, for example, an aryl group having a carbon number of 6 to 15, such as phenyl group and naphthyl group.

The alkoxy group above includes, for example, a linear, branched or cyclic alkoxy group having a carbon number of 1 to 20, such as methoxy group, ethoxy group, n-propoxy group, i-propoxy group, n-butoxy group, 2-methylpropoxy group, 1-methylpropoxy group, tert-butoxy group, cyclopentyloxy group and cyclohexyloxy group.

The aryloxy group above includes, for example, an aryloxy group having a carbon number of 6 to 10, such as phenyloxy group and naphthyloxy group.

The acyl group above includes, for example, a linear or branched acyl group having a carbon number of 2 to 12, such as acetyl group, propionyl group, n-butanoyl group, i-butanoyl group, n-heptanoyl group, 2-methylbutanoyl group, 1-methylbutanoyl group and tert-heptanoyl group.

The arylcarbonyl group above includes, for example, an arylcarbonyl group having a carbon number of 6 to 10, such as phenylcarbonyl group and naphthylcarbonyl group.

The alkoxyalkyl group above includes, for example, a linear, branched or cyclic alkoxyalkyl group having a carbon number of 2 to 21, such as methoxymethyl group, ethoxymethyl group, 1-methoxyethyl group, 2-methoxyethyl group, 1-ethoxyethyl group and 2-ethoxyethyl group.

The aryloxyalkyl group above includes, for example, an aryloxyalkyl group having a carbon number of 7 to 12, such as phenyloxymethyl group, phenyloxyethyl group, naphthyloxymethyl group and naphthyloxyethyl group.

The alkoxycarbonyl group above includes, for example, a linear, branched or cyclic alkoxycarbonyl group having a carbon number of 2 to 21, such as methoxycarbonyl group, ethoxycarbonyl group, n-propoxycarbonyl group, i-propoxycarbonyl group, n-butoxycarbonyl group, 2-methylpropoxycarbonyl group, 1-methylpropoxycarbonyl group, tert-butoxycarbonyl group, cyclopentyloxycarbonyl group and cyclohexyloxycarbonyl group.

The aryloxycarbonyl group above includes, for example, an aryloxycarbonyl group having a carbon number of 7 to 11, such as phenyloxycarbonyl group and naphthyloxycarbonyl group.

The alkoxycarbonyloxy group above includes, for example, a linear, branched or cyclic alkoxycarbonyloxy group having a carbon number of 2 to 21, such as methoxycarbonyloxy group, ethoxycarbonyloxy group, n-propoxycarbonyloxy group, i-propoxycarbonyloxy group, n-butoxycarbonyloxy group, tert-butoxycarbonyloxy group, cyclopentyloxycarbonyloxy group and cyclohexyloxycarbonyloxy group.

The aryloxycarbonyloxy group above includes, for example, an aryloxycarbonyloxy group having a carbon number of 7 to 11, such as phenyloxycarbonyloxy group and naphthyloxycarbonyloxy group.

In formula (ZI-3), it is more preferred that each of $R_{1c}$, $R_{2c}$, $R_{4c}$, and $R_{5c}$ independently represents a hydrogen atom and $R_{3c}$ represents a group except for hydrogen atom, that is, an alkyl group, a cycloalkyl group, an aryl group, an alkoxy group, an aryloxy group, an alkoxycarbonyl group, an alkylcarbonyloxy group, a cycloalkylcarbonyloxy group, a halogen atom, a hydroxyl group, a nitro group, an alkylthio group or an arylthio group.

The compound (ZI-4) is described below.

The compound (ZI-4) is represented by the following formula (ZI-4):

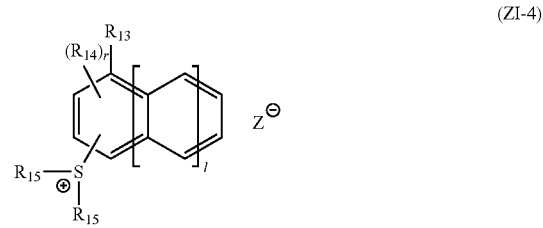

In formula (ZI-4), $R_{13}$ represents a hydrogen atom, a fluorine atom, a hydroxyl group, an alkyl group, a cycloalkyl group, an alkoxy group, an alkoxycarbonyl group, or a group having a cycloalkyl group. These groups may have a substituent.

$R_{14}$ represents, when a plurality of $R_{14}$'s are present, each independently represents, a hydroxyl group, an alkyl group, a cycloalkyl group, an alkoxy group, an alkoxycarbonyl group, alkylcarbonyl group, an alkylsulfonyl group, a cycloalkylsulfonyl group, or a group having a cycloalkyl group. These groups may have a substituent.

Each $R_{15}$ independently represents an alkyl group, a cycloalkyl group or a naphthyl group. Two $R_{15}$'s may combine with each other to form a ring. These groups may have a substituent.

l represents an integer of 0 to 2.

r represents an integer of 0 to 8.

$Z^-$ represents a non-nucleophilic anion, and examples thereof are the same as those of the non-nucleophilic anion of $Z^-$ in formula (ZI).

In formula (ZI-4), the alkyl group of $R_{13}$, $R_{14}$ and $R_{15}$ is a linear or branched alkyl group preferably having a carbon number of 1 to 10, and examples thereof include a methyl group, an ethyl group, an n-propyl group, an i-propyl group, an n-butyl group, a 2-methylpropyl group, a 1-methylpropyl group, a tert-butyl group, an n-pentyl group, a neopentyl group, an n-hexyl group, an n-heptyl group, an n-octyl group, a 2-ethylhexyl group, an n-nonyl group and an n-decyl group. Among these alkyl groups, a methyl group, an ethyl group, an n-butyl group and a tert-butyl group are preferred.

The cycloalkyl group of $R_{13}$, $R_{14}$ and $R_{15}$ includes a monocyclic or polycyclic cycloalkyl group (preferably a cycloalkyl group having a carbon number of 3 to 20), and examples thereof include cyclopropyl, cyclobutyl, cyclopentyl, cyclohexyl, cycloheptyl, cyclooctyl, cyclododecanyl, cyclopentenyl, cyclohexenyl, cyclooctadienyl, norbornyl, tricyclodecanyl, tetracyclodecanyl and adamantyl. Above all, cyclopropyl, cyclopentyl, cyclohexyl, cycloheptyl and cyclooctyl are preferred.

The alkoxy group of $R_{13}$ and $R_{14}$ is a linear or branched alkoxy group preferably having a carbon number of 1 to 10, and examples thereof include methoxy group, an ethoxy group, an n-propoxy group, an i-propoxy group, n-butoxy group, a 2-methylpropoxy group, a 1-methylpropoxy group, a tert-butoxy group, an n-pentyloxy group, a neopentyloxy group, an n-hexyloxy group, an n-heptyloxy group, an n-octyloxy group, a 2-ethylhexyloxy group, an n-nonyloxy group and an n-decyloxy group. Among these alkoxy groups, a methoxy group, an ethoxy group, an n-propoxy group and an n-butoxy group are preferred.

The alkoxycarbonyl group of $R_{13}$ and $R_{14}$ is a linear or branched alkoxycarbonyl group preferably having a carbon number of 2 to 11, and examples thereof include a methoxycarbonyl group, an ethoxycarbonyl group, an n-propoxycarbonyl group, an i-propoxycarbonyl group, n-butoxycarbonyl group, a 2-methylpropoxycarbonyl group, a 1-methylpropoxycarbonyl group, a tert-butoxycarbonyl group, an n-pentyloxycarbonyl group, a neopentyloxycarbonyl group, an n-hexyloxycarbonyl group, an n-heptyloxycarbonyl group, an n-octyloxycarbonyl group, a 2-ethylhexyloxycarbonyl group, an n-nonyloxycarbonyl group and an n-decyloxycarbonyl group. Among these alkoxycarbonyl groups, a methoxycarbonyl group, an ethoxycarbonyl group and an n-butoxycarbonyl group are preferred.

The cycloalkyl group-containing group of $R_{13}$ and $R_{14}$ includes a monocycle or polycyclic cycloalkyl group (preferably a cycloalkyl group having a carbon number of 3 to 20), and examples thereof include a monocyclic or polycyclic cycloalkyloxy group and an alkoxy group containing a monocyclic or polycyclic cycloalkyl group. These groups may further have a substituent.

The monocyclic or polycyclic cycloalkyloxy group of $R_{13}$ and $R_{14}$ preferably has a total carbon number of 7 or more, more preferably a total carbon number of 7 to 15, and is preferably a monocyclic cycloalkyl group. The monocyclic cycloalkyloxy group having a total carbon number of 7 or more indicates a monocyclic cycloalkyloxy group where a cycloalkyloxy group such as cyclopropyloxy group, cyclobutyloxy group, cyclopentyloxy group, cyclohexyloxy group, cycloheptyloxy group, cyclooctyloxy group and cyclododecanyloxy group arbitrarily has a substituent such as alkyl group (e.g., methyl, ethyl, propyl, butyl, pentyl, hexyl, heptyl, octyl, dodecyl, 2-ethylhexyl, isopropyl, sec-butyl, tert-butyl, isoamyl), hydroxyl group, halogen atom (e.g., fluorine, chlorine, bromine, iodine), nitro group, cyano group, amido group, sulfonamido group, alkoxy group (e.g., methoxy, ethoxy, hydroxyethoxy, propoxy, hydroxypropoxy, butoxy), alkoxycarbonyl group (e.g., methoxycarbonyl, ethoxycarbonyl), acyl group (e.g., formyl, acetyl, benzoyl), acyloxy group (e.g., acetoxy, butyryloxy) and carboxy group and where the total carbon number inclusive of the carbon number of an arbitrary substituent on the cycloalkyl group is 7 or more.

Examples of the polycyclic cycloalkyloxy group having a total carbon number of 7 or more include a norbornyloxy group, a tricyclodecanyloxy group, a tetracyclodecanyloxy group and an adamantyloxy group.

The alkoxy group having a monocyclic or polycyclic cycloalkyl group of $R_{13}$ and $R_{14}$ preferably has a total carbon number of 7 or more, more preferably a total carbon number of 7 to 15, and is preferably alkoxy group having a monocycle cycloalkyl group. The alkoxy group having a total carbon number of 7 or more and having a monocyclic cycloalkyl group indicates an alkoxy group where the above-described monocyclic cycloalkyl group which may have a substituent is substituted on an alkoxy group such as methoxy, ethoxy, propoxy, butoxy, pentyloxy, hexyloxy, heptoxy, octyloxy, dodecyloxy, 2-ethylhexyloxy, isopropoxy, sec-butoxy, tert-butoxy and isoamyloxy and where the total carbon number inclusive of the carbon number of the substituent is 7 or more. Examples thereof include a cyclohexylmethoxy group, a cyclopentylethoxy group and a cyclohexylethoxy group, with a cyclohexylmethoxy group being preferred.

Examples of the alkoxy group having a total carbon number of 7 or more and having a polycyclic cycloalkyl group include a norbornylmethoxy group, a norbornylethoxy group, a tricyclodecanylmethoxy group, a tricyclodecanylethoxy group, a tetracyclodecanylmethoxy group, a tetracyclodecanylethoxy group, an adamantylmethoxy group and an adamantylethoxy group, with a norbornylmethoxy group and a norbornylethoxy group being preferred.

Specific examples of the alkyl group in the alkylcarbonyl group of $R_{14}$ are the same as those of the alkyl group of $R_{13}$ to $R_{15}$ above.

The alkylsulfonyl and cycloalkylsulfonyl group of $R_{14}$ are a linear, branched or cyclic alkylsulfonyl group preferably having a carbon number of 1 to 10, and examples thereof include a methanesulfonyl group, an ethanesulfonyl group, an n-propanesulfonyl group, an n-butanesulfonyl group, a tert-butanesulfonyl group, an n-pentanesulfonyl group, a neopentanesulfonyl group, an n-hexanesulfonyl group, an n-heptanesulfonyl group, an n-octanesulfonyl group, a 2-ethylhexanesulfonyl group, an n-nonanesulfonyl group, an n-decanesulfonyl group, a cyclopentanesulfonyl group and a cyclohexanesulfonyl group. Among these alkylsulfonyl groups and cycloalkylsulfonyl groups, a methanesulfonyl group, an ethanesulfonyl group, an n-propanesulfonyl group, an n-butanesulfonyl group, a cyclopentanesulfonyl group and a cyclohexanesulfonyl group are preferred.

Examples of the substituent which each of the groups above may have include a halogen atom (e.g., fluorine), a hydroxyl group, a carboxyl group, a cyano group, a nitro group, an alkoxy group, an alkoxyalkyl group, an alkoxycarbonyl group and an alkoxycarbonyloxy group.

The alkoxy group above includes, for example, a linear, branched or cyclic alkoxy group having a carbon number of 1 to 20, such as methoxy group, ethoxy group, n-propoxy group, i-propoxy group, n-butoxy group, 2-methylpropoxy group, 1-methylpropoxy group, tert-butoxy group, cyclopentyloxy group and cyclohexyloxy group.

The alkoxyalkyl group includes, for example, a linear, branched or cyclic alkoxyalkyl group having a carbon number of 2 to 21, such as methoxymethyl group, ethoxymethyl group, 1-methoxyethyl group, 2-methoxyethyl group, 1-ethoxyethyl group and 2-ethoxyethyl group.

The alkoxycarbonyl group includes, for example, a linear, branched or cyclic alkoxycarbonyl group having a carbon number of 2 to 21, such as methoxycarbonyl group, ethoxycarbonyl group, n-propoxycarbonyl group, i-propoxycarbonyl group, n-butoxycarbonyl group, 2-methylpropoxycarbonyl group, 1-methylpropoxycarbonyl group, tert-butoxycarbonyl group, cyclopentyloxycarbonyl group and cyclohexyloxycarbonyl group.

The alkoxycarbonyloxy group includes, for example, a linear, branched or cyclic alkoxycarbonyloxy group having a carbon number of 2 to 21, such as methoxycarbonyloxy group, ethoxycarbonyloxy group, n-propoxycarbonyloxy group, i-propoxycarbonyloxy group, n-butoxycarbonyloxy group, tert-butoxycarbonyloxy group, cyclopentyloxycarbonyloxy group and cyclohexyloxycarbonyloxy group.

The ring structure which may be formed by combining two $R_{15}$'s with each other includes a 5- or 6-membered ring, preferably a 5-membered ring (that is, tetrahydrothiophene ring), formed by two divalent $R_{15}$'s together with the sulfur atom in formula (ZI-4) and may be fused with an aryl group or a cycloalkyl group. This divalent $R_{15}$ may have a substituent, and examples of the substituent include a hydroxyl group, a carboxyl group, a cyano group, a nitro group, an alkyl group, a cycloalkyl group, an alkoxy group, an alkoxyalkyl group, an alkoxycarbonyl group and an alkoxycarbonyloxy group. A plurality of substituents may be substituted on the ring structure, and these substituents may combine with each other to form a ring (for example, an aromatic or non-aromatic hydrocarbon ring, an aromatic or non-aromatic heterocyclic ring, or a polycyclic condensed ring formed by combining two or more of such rings).

In formula (ZI-4), $R_{15}$ is preferably, for example, a methyl group, an ethyl group, a naphthyl group, or a divalent group capable of forming a tetrahydrothiophene ring structure together with the sulfur atom when two $R_{15}$'s combine with each other.

At least one of $R_{13}$, $R_{14}$ and $R_{15}$ preferably has an acid-decomposable group. The preferred embodiment of the acid-decomposable group is as described above.

The substituent that may be substituted on $R_{13}$, $R_{14}$ and $R_{15}$, other than an acid-decomposable group, is preferably a hydroxyl group, an alkoxy group, an alkoxycarbonyl group or a halogen atom (particularly fluorine atom).

l is preferably 0 or 1, more preferably 1.

r is preferably 0 to 2.

Formulae (ZII) and (ZIII) are described below.

In formulae (ZII) and (ZIII), each of $R_{204}$ to $R_{207}$ independently represents an aryl group, an alkyl group or a cycloalkyl group.

At least one of $R_{204}$, $R_{205}$ and $Z^-$ has an acid-decomposable group.

At least one of $R_{206}$ and $R_{207}$ has an acid-decomposable group. The preferred embodiment of the acid-decomposable group is as described above.

The aryl group of $R_{204}$ to $R_{207}$ is preferably a phenyl group or a naphthyl group, more preferably a phenyl group. The aryl group of $R_{204}$ to $R_{207}$ may be an aryl group having a heterocyclic structure containing an oxygen atom, a nitrogen atom, a sulfur atom or the like. Examples of framework of the aryl group having a heterocyclic structure include pyrrole, furan, thiophene, indole, benzofuran and benzothiophene.

The alkyl group and cycloalkyl group of $R_{204}$ to $R_{207}$ are preferably a linear or branched alkyl group having a carbon number of 1 to 10 (e.g., methyl, ethyl, propyl, butyl, pentyl) and a cycloalkyl group having a carbon number of 3 to 10 (e.g., cyclopentyl, cyclohexyl, norbornyl).

The aryl group, alkyl group and cycloalkyl group of $R_{204}$ to $R_{207}$ may have a substituent other than an acid-decomposable group. Examples of the substituent other than an acid-decomposable group, which may be substituted on the aryl group, alkyl group and cycloalkyl group of $R_{204}$ to $R_{207}$ include an alkyl group (for example, having a carbon number of 1 to 15), a cycloalkyl group (for example, having a carbon number of 3 to 15), an aryl group (for example, having a carbon number of 6 to 15), an alkoxy group (for example, having a carbon number of 1 to 15), a halogen atom, a hydroxyl group and a phenylthio group.

$Z^-$ represents a non-nucleophilic anion, and examples thereof the same as those of the non-nucleophilic anion of $Z^-$ in formula (ZI).

The acid generator further includes compounds represented by the following formulae (ZIV), (ZV) and (ZVI):

$$Ar_3\text{---}SO_2\text{---}SO_2\text{---}Ar_4 \quad (ZIV)$$

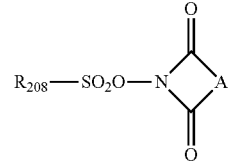

(ZV)

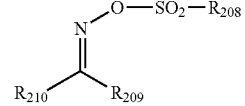

(ZVI)

In formulae (ZIV) to (ZVI), each of $Ar_3$ and $Ar_4$ independently represents an aryl group.

At least one of $Ar_3$ and $Ar_4$ has an acid-decomposable group.

In formula (ZV), $R_{208}$ represents an alkyl group, a cycloalkyl group or an aryl group.

A represents an alkylene group, an alkenylene group or an arylene group.

At least one of $R_{208}$ and A has an acid-decomposable group.

In formula (ZVI), each of $R_{208}$, $R_{209}$ and $R_{210}$ independently represents an alkyl group, a cycloalkyl group or an aryl group.

At least one of $R_{208}$, $R_{209}$ and $R_{210}$ has an acid-decomposable group.

Specific examples of the aryl group of $Ar_3$, $Ar_4$, $R_{208}$, $R_{209}$ and $R_{210}$ are the same as specific examples of the aryl group of $R_{201}$, $R_{202}$ and $R_{203}$ in formula (ZI-1).

Specific examples of the alkyl group and cycloalkyl group of $R_{208}$, $R_{209}$ and $R_{210}$ are the same as specific examples of the alkyl group and cycloalkyl group of $R_{201}$, $R_{202}$ and $R_{203}$ in formula (ZI-2).

The alkylene group of A includes an alkylene group having a carbon number of 1 to 12 (e.g., methylene, ethylene, propylene, isopropylene, butylene, isobutylene); the alkenylene group of A includes an alkenylene group having a carbon number of 2 to 12 (e.g., ethenylene, propenylene, butenylene); and the arylene group of A includes an arylene group having a carbon number of 6 to 10 (e.g., phenylene, tolylene, naphthylene).

In the case where the moiety capable of decomposing by the action of an acid to decrease the solubility for an organic solvent-containing developer is contained in $R_{201}$, $R_{202}$ or $R_{203}$ of formula (ZI), the compound (A) is preferably a compound selected from the following formulae (II-1) to (II-3):

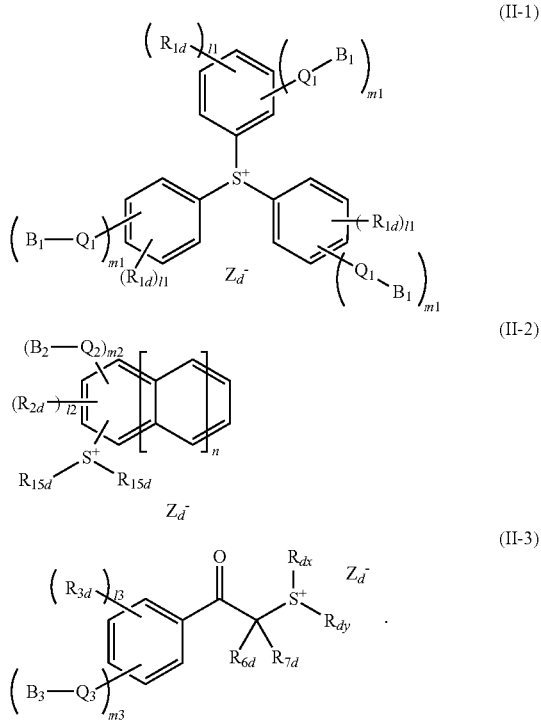

In formula (II-1), each $R_{1d}$ independently represents a hydrogen atom or a monovalent organic group. Two $R_{1d}$'s may combine with each other to form a ring. In other words, two $R_{1d}$'s may combine with each other to form a single bond or a divalent linking group. The divalent linking group is preferably a linking group having a carbon number of 4 or less, and examples thereof include a methylene group, an ethylene group, an ether bond, a carbonyl group and an ester group.

$Q_1$ represents a single bond or a divalent linking group.

$B_1$ represents (B) a moiety capable of decomposing by the action of an acid to produce a hydroxyl group or a carboxyl group.

$Z_d^-$ represents a non-nucleophilic counter anion having X number of groups represented by ($B_1$-$Q_1$).

Each l1 independently represents an integer of 0 to 5.
Each m1 independently represents an integer of 0 to 5.
X represents an integer of 0 to 3.

However, at least one of a plurality of m1's and X represents an integer of 1 or more. Any of a plurality of m1's is preferably an integer of 1 or more.

In formula (II-2), each $R_{2d}$ independently represents a hydrogen atom or a monovalent organic group. Two $R_{2d}$'s may combine with each other to form a ring.

Each $R_{15d}$ independently represents an alkyl group which may have a substituent. Two $R_{15d}$'s may combine with each other to form a ring.

Each of the group represented by —$S^+(R_{15d})(R_{15d})$, m2 number of ($B_2$-$Q_2$), and l2 number of $R_{2d}$ may be substituted on an arbitrary position of any aromatic ring in formula (II-2).

$Q_2$ represents a single bond or a divalent linking group.
$B_2$ represents (B) a moiety capable of decomposing by the action of an acid to produce a hydroxyl group or a carboxyl group.

$Z_d^-$ represents a non-nucleophilic counter anion having X number of groups represented by ($B_2$-$Q_2$).

n represents 0 or 1.
Each l2 independently represents an integer of 0 to 5.
Each m2 independently represents an integer of 0 to 5.
X represents an integer of 0 to 3.

However, at least one of m2 and X represents an integer of 1 or more. m2 is preferably an integer of 1 to 5.

In formula (II-3), each $R_{3d}$ independently represents a hydrogen atom or a monovalent organic group. Two $R_{3d}$'s may combine with each other to form a ring.

Each of $R_{6d}$ and $R_{7d}$ independently represents a hydrogen atom or a monovalent organic group. $R_{6d}$ and $R_{7d}$ may combine with each other to form a ring.

Each of $R_{dx}$ and $R_{dy}$ independently represents an alkyl group which may have a substituent. $R_{dx}$ and $R_{dy}$ may combine with each other to form a ring.

$Q_3$ represents a single bond or a divalent linking group.
$B_3$ represents (B) a moiety capable of decomposing by the action of an acid to produce a hydroxyl group or a carboxyl group.

$Z_d^-$ represents anon-nucleophilic counter anion having X number of groups represented by ($B_3$-$Q_3$).

Each l3 independently represents an integer of 0 to 5.
Each m3 independently represents an integer of 0 to 5.
X represents an integer of 0 to 3.

However, at least one of m3 and X represents an integer of 1 or more. m3 is preferably an integer of 1 to 5.

The organic group as $R_{1d}$, $R_{2d}$ and $R_{3d}$ is preferably an alkyl group, a cycloalkyl group, an alkoxy group or a halogen atom. Two or more $R_4$'s may combine to form a ring structure, and the ring structure may contain an oxygen atom, a sulfur atom, an ester bond or an amido bond. Examples of the group formed by combining two or more $R_4$'s include a butylene group and a pentylene group.

Examples of the alkyl group, cycloalkyl group and alkoxy group as $R_{1d}$, $R_{2d}$ and $R_{3d}$ are the same as those of the alkyl group, cycloalkyl group and alkoxy group of $R_{1c}$ to $R_{5c}$ in formula (ZI-3).

The alkyl group as $R_{15d}$, $R_{dx}$ and $R_{dy}$ is a linear or branched alkyl group preferably having a carbon number of 1 to 10, and examples thereof include a methyl group, an ethyl group, an n-propyl group, an i-propyl group, an n-butyl group, a 2-methylpropyl group, a 1-methylpropyl group, a tert-butyl group, an n-pentyl group, a neopentyl group, an n-hexyl group, an n-heptyl group, an n-octyl group, a 2-ethylhexyl group, an n-nonyl group and an n-decyl group. Among these alkyl groups, a methyl group, an ethyl group, an n-butyl group and a tert-butyl group are preferred, and a methyl group, an ethyl group, an n-propyl group, an n-butyl group, and a divalent group capable of forming a tetrahydrothiophene ring structure together with the sulfur atom when two $R_{15d}$'s combine with each other (or $R_{dx}$ and $R_{dy}$ combine with each other), are more preferred.

The organic group of $R_{6d}$ and $R_{7d}$ is preferably an alkyl group or a cycloalkyl group. $R_{6d}$ and $R_{7d}$ may combine to form a ring structure, and the ring structure may contain an oxygen atom, a sulfur atom, an ester bond or an amide bond.

Examples of the group formed by combining $R_{6d}$ and $R_{7d}$ include a butylene group and a pentylene group.

Examples of the alkyl group and cycloalkyl group of $R_{6d}$ and $R_{7d}$ are the same as those of the alkyl group and cycloalkyl group of $R_{6c}$ and $R_{7c}$ in formula (ZI-3), and a 2-oxoalkyl group, a 2-oxocycloalkyl group and an alkoxycarbonylmethyl group are preferred.

Examples of the 2-oxoalkyl group and 2-oxocycloalkyl group include a group having >C=O at the 2-position of the alkyl group or cycloalkyl group of $R_{1c}$ to $R_{7c}$.

Examples of the alkoxy group in the alkoxycarbonylalkyl group are the same as those of the alkoxy group of $R_{1c}$ to $R_{5c}$.

Each of $R_{6d}$ and $R_{7d}$ is preferably a hydrogen atom or an alkyl or cycloalkyl group having a carbon number of 4 or more, more preferably an alkyl or cycloalkyl group having a carbon number of 6 or more, still more preferably an alkyl or cycloalkyl group having a carbon number of 8 or more.

The divalent linking group of $Q_1$, $Q_2$ and $Q_3$ is preferably a divalent organic group having a carbon number of 1 to 8, and examples thereof include an alkylene group (e.g., methylene, ethylene, propylene, butylene) and an arylene group (e.g., phenylene). The divalent linking group of $Q_1$, $Q_2$ and $Q_3$ is more preferably an alkylene group, and the carbon number thereof is preferably from 1 to 6, more preferably from 1 to 4. The alkylene chain may contain a linking group such as oxygen atom and sulfur atom.

Each of $B_1$, $B_2$ and $B_3$ is preferably a structure represented by formulae (I-1) to (I-5).

$Z_d^-$ represents a non-nucleophilic counter anion, and examples thereof are the same as those of the non-nucleophilic anion of $Z^-$ in formula (ZI). The non-nucleophilic counter anion may be also an acid anion in formula (III).

Specific examples of the cation in the compound (A) are illustrated below, but the present invention is not limited thereto.

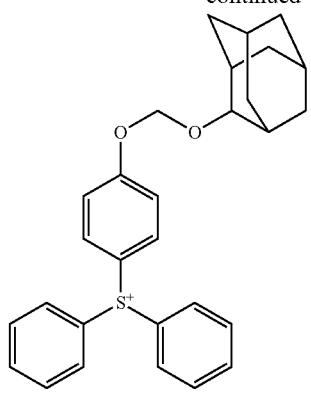

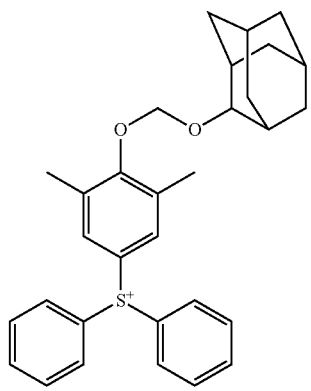

-continued

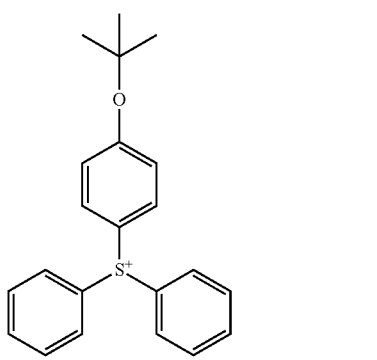

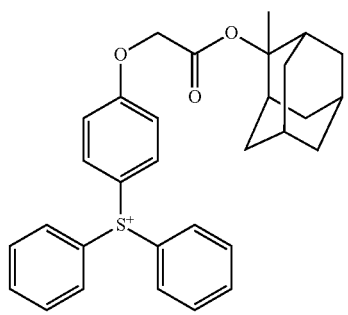

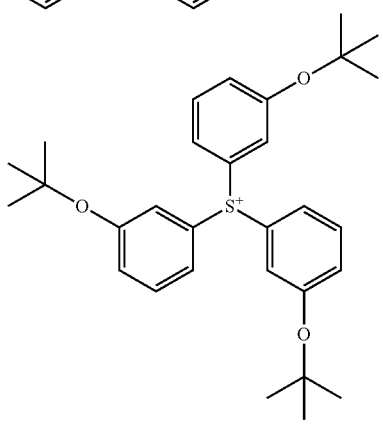

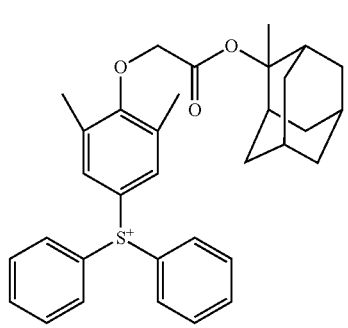

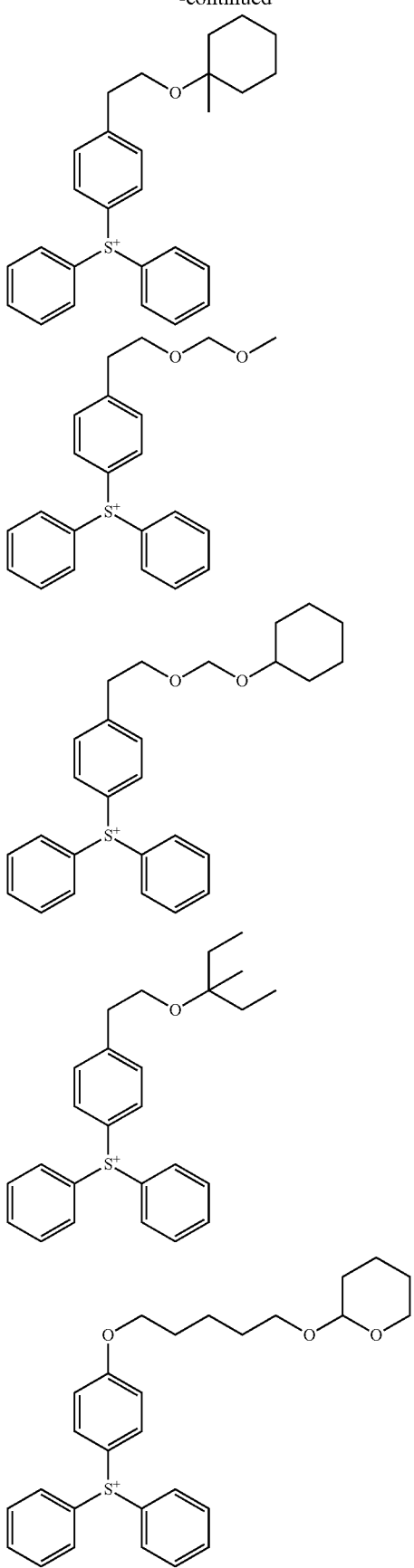
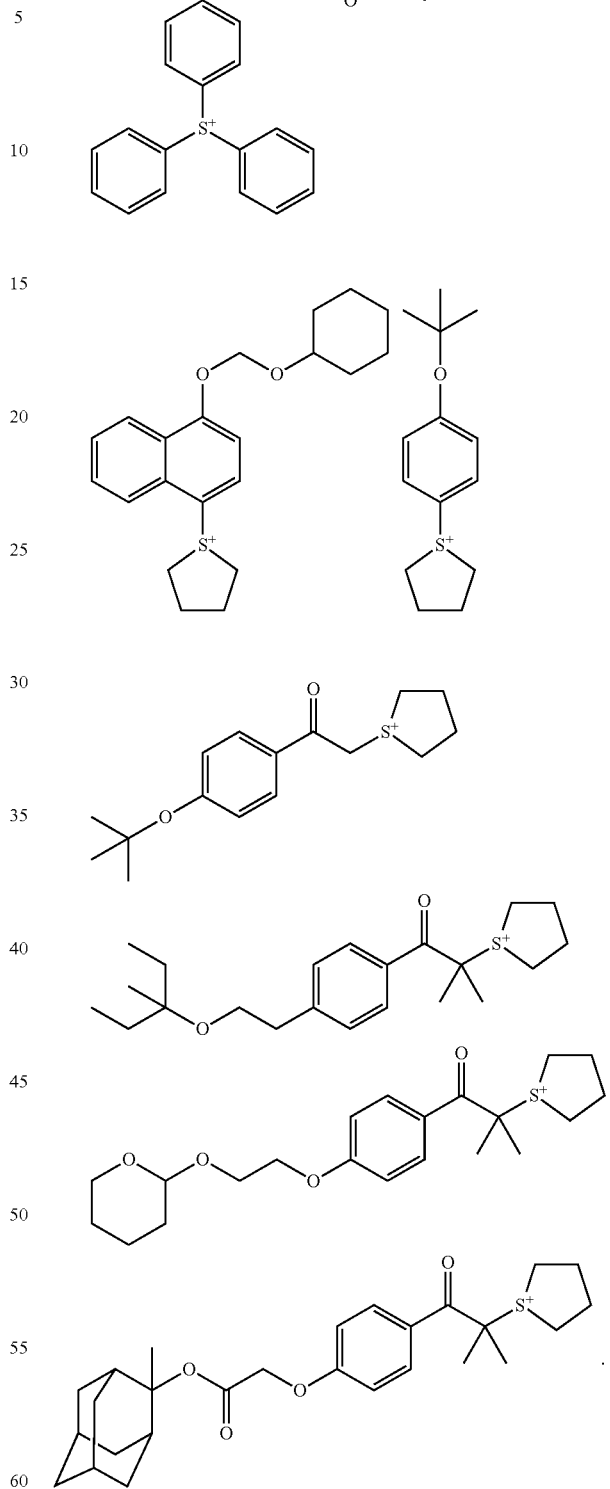
Specific examples of the compound (A) capable of decomposing by the action of an acid to decrease the solubility for an organic solvent and generating an acid upon irradiation with an actinic ray or radiation are illustrated below, but the present invention is not limited thereto.

(b-1) 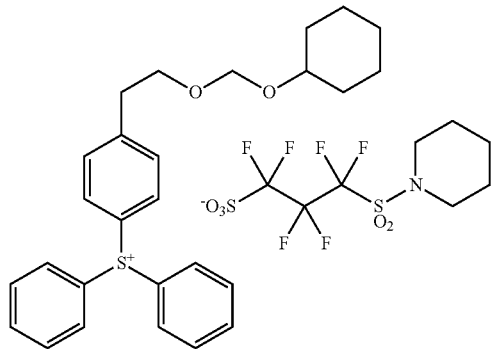
(b-2) 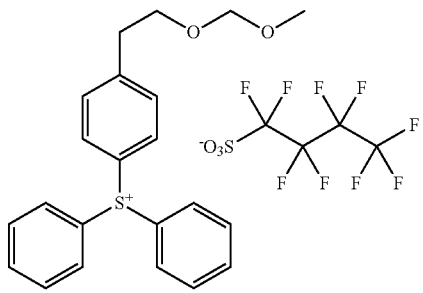
(b-3) 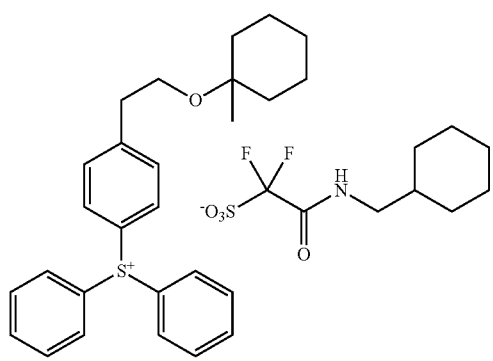
(b-4) 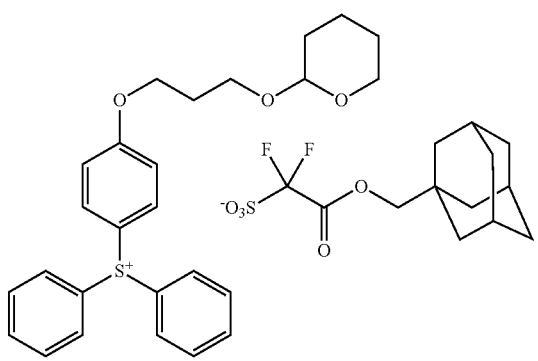
(b-5) 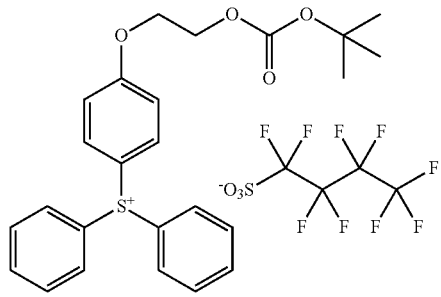
(b-6) 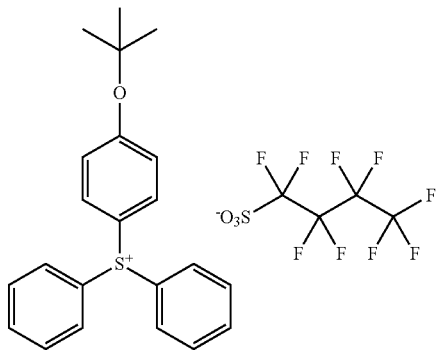
(b-7) 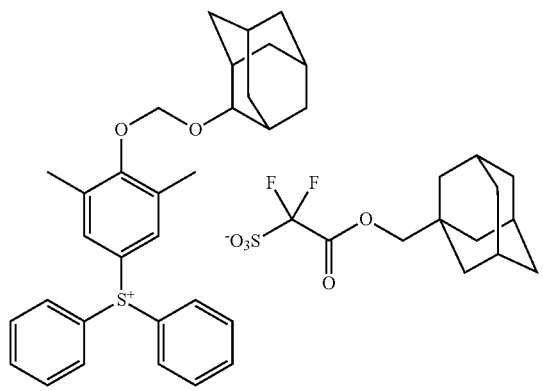
(b-8) 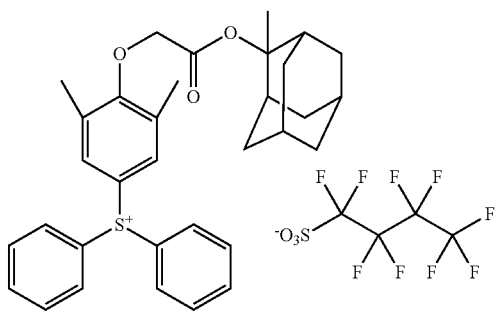

(b-9)
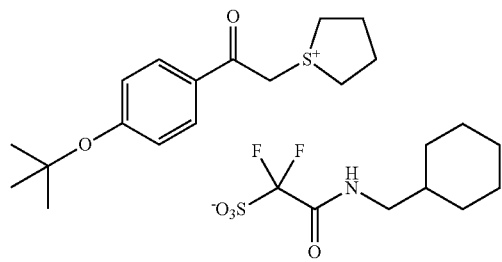
(b-10)
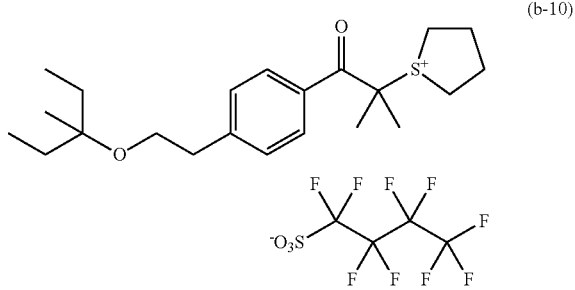
(b-11)
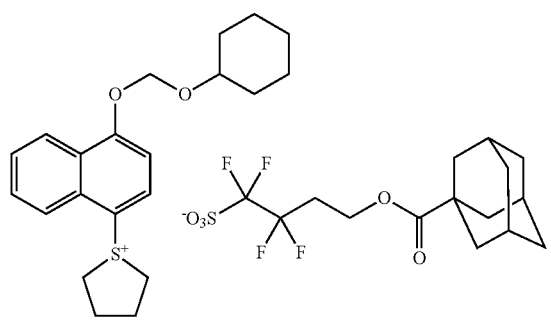
(b-12)
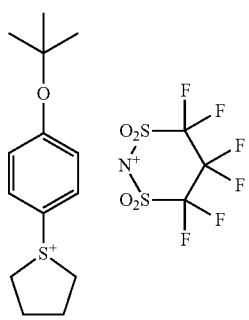
(b-13)
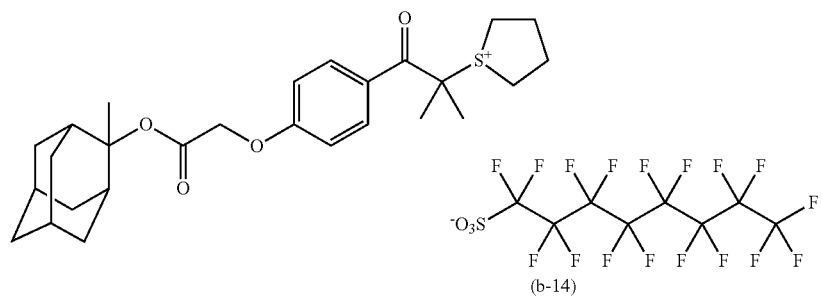
(b-14)
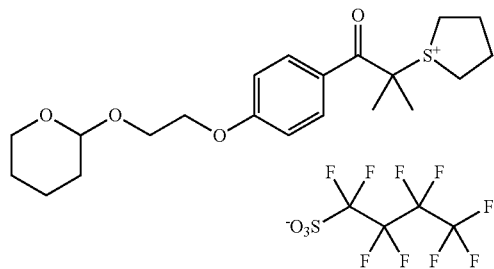
(b-15)
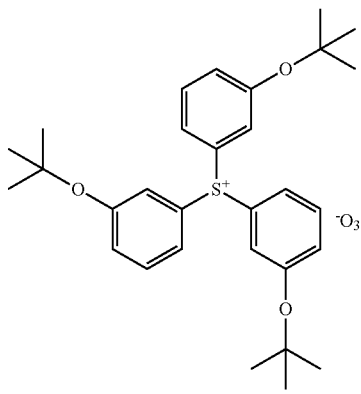
(b-16)
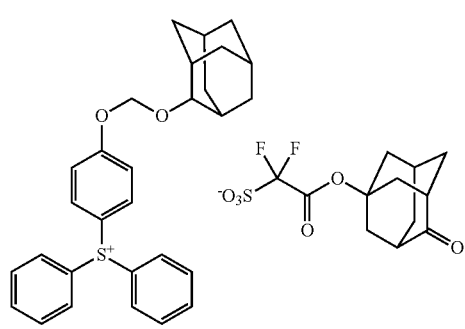
(b-17)
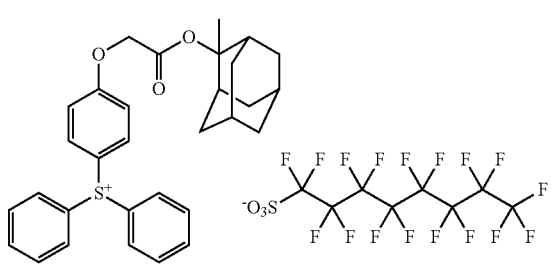

-continued
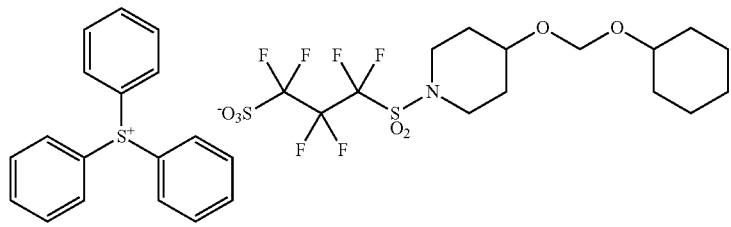
(b-18)
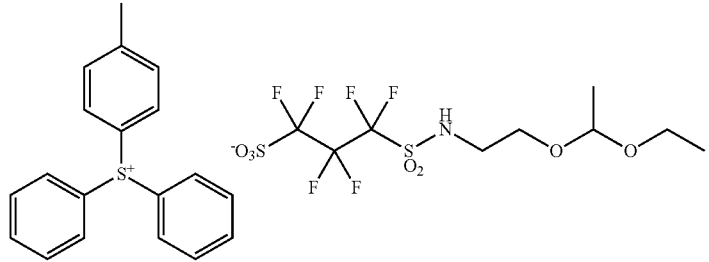
(b-19)
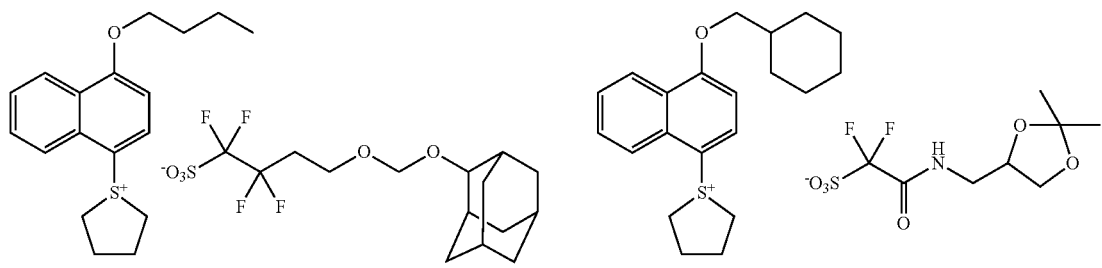
(b-20) (b-21)
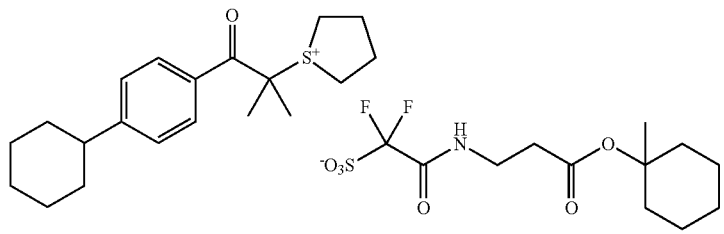
(b-22)
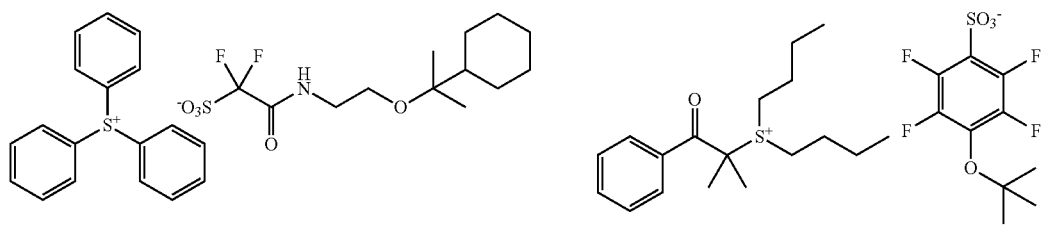
(b-23) (b-24)
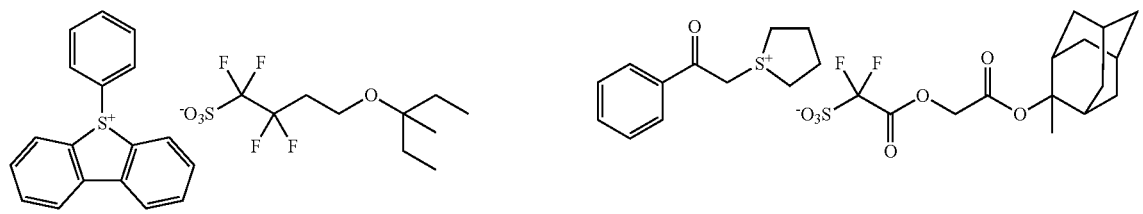
(b-25) (b-26)

-continued
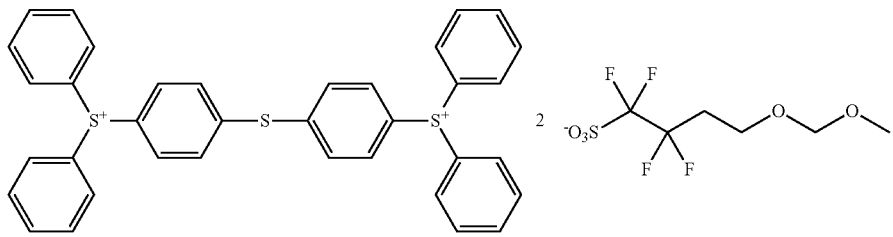
(b-27)
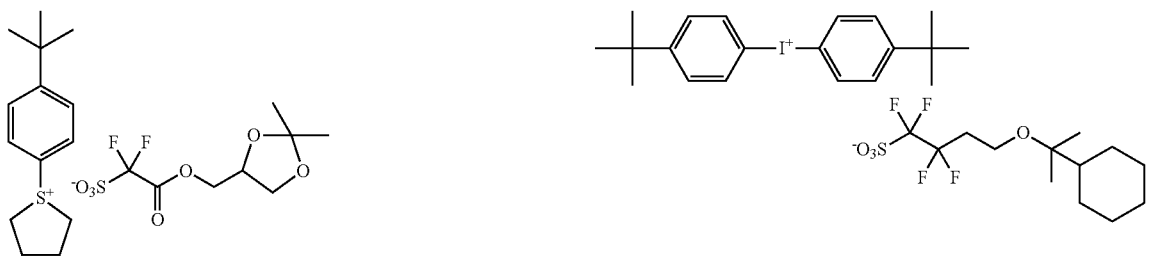
(b-28) (b-29)
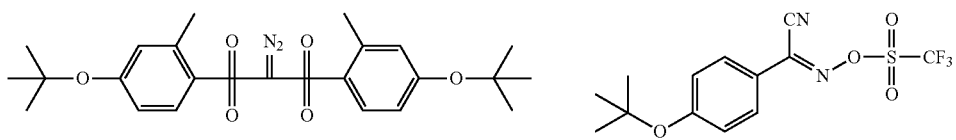
(b-30) (b-31)
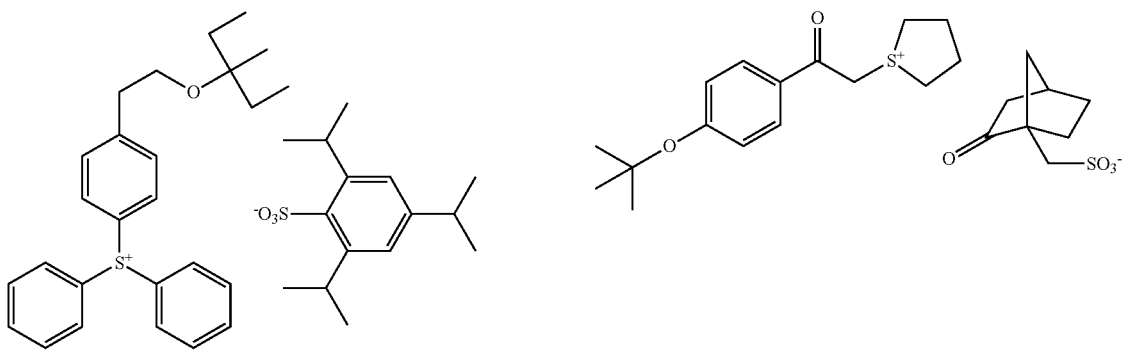
(b-32) (b-33)
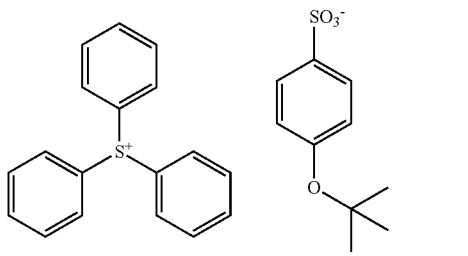
(b-34)
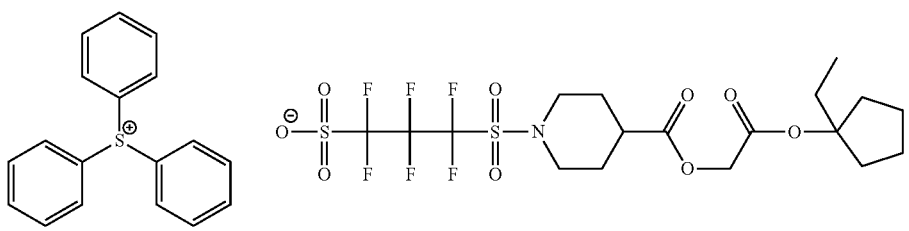
(b-35)

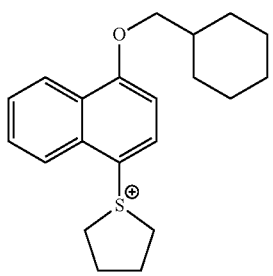 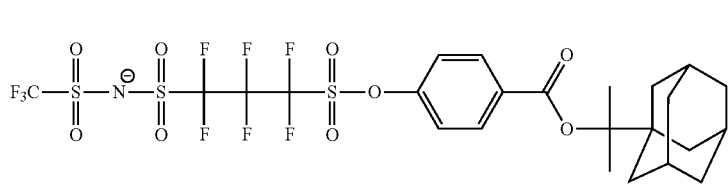

(b-36)

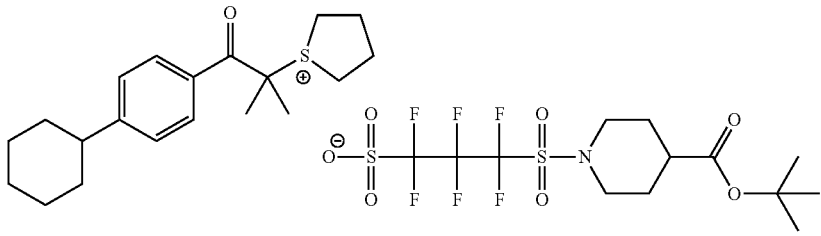

(b-37)

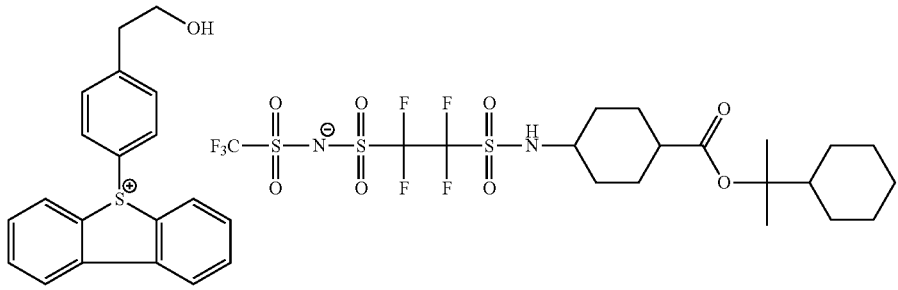

(b-38)

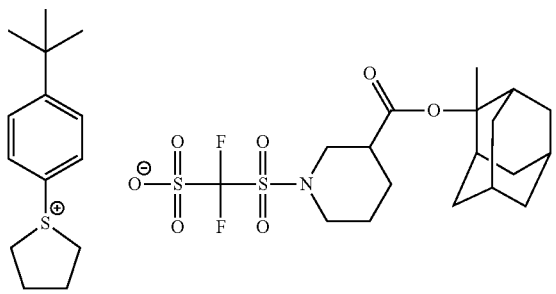

(b-39)

In the actinic ray-sensitive or radiation-sensitive resin composition of the present invention, as the compound (A), one kind of a compound may be used alone, or two or more kinds of compounds may be used in combination, and the content thereof is preferably from 0.1 to 20 mass %, more preferably from 0.5 to 15 mass %, still more preferably from 3 to 12 mass %, based on the entire solid content of the actinic ray-sensitive or radiation-sensitive resin composition.

The actinic ray-sensitive or radiation-sensitive resin composition of the present invention preferably further contains, other than the compound (A), a compound capable of generating an acid upon irradiation with an actinic ray or radiation (hereinafter, sometimes referred to as "combination acid generator").

The combination acid generator other than the compound (A) is described below.

The combination acid generator which can be used may be appropriately selected from a photo-initiator for cationic photopolymerization, a photo-initiator for radical photopolymerization, a photo-decoloring agent for dyes, a photo-discoloring agent, a known compound that generates an acid upon irradiation with an actinic ray or radiation and is used for microresist or the like, and a mixture thereof.

Examples thereof include a diazonium salt, a phosphonium salt, a sulfonium salt, an iodonium salt, imidosulfonate, oxime sulfonate, diazodisulfone, disulfone and o-nitrobenzyl sulfonate.

The combination acid generator is not particularly limited as long as it is a known compound, but preferred compounds include compounds represented by the following formulae (ZI'), (ZII') and (ZIII'):

(ZI')

-continued

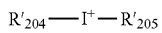
(ZII')

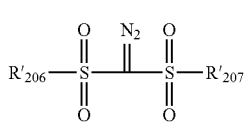
(ZIII')

In formulae (ZI') (ZII') and (ZIII'), R'$_{201}$ to R'$_{207}$ respectively have the same meanings as R$_{201}$ to R$_{207}$ in formulae (ZI), (ZII) and (ZIII), and specific examples and preferred examples are also the same. However, all of R'$_{201}$ to R'$_{207}$ in formulae (ZI') (ZII') and (ZIII') are free from the above-described acid-decomposable group.

Also, in formulae (ZI') and (ZII'), Z$^-$ represents a non-nucleophilic anion (an anion having an extremely low ability of causing a nucleophilic reaction) and has the same meaning as Z$^-$ in formula (ZI) and (ZII), but here, Z$^-$ is free from the above-described acid-decomposable group.

Compounds (ZI'-1), (ZI'-2), (ZI'-3) and (ZI'-4) described below are more preferred as the component (ZI').

The compound (ZI'-1) is an arylsulfonium compound where at least one of R'$_{201}$ to R'$_{203}$ in formula (ZI') is an aryl group, that is, a compound having an arylsulfonium as the cation.

In the arylsulfonium compound, all of R'$_{201}$ to R'$_{203}$ may be an aryl group or a part of R'$_{201}$ to R'$_{203}$ may be an aryl group, with the remaining being an alkyl group or a cycloalkyl group.

Specific examples and preferred examples of the arylsulfonium compound are the same as those described for the compound (ZI-1) except for not having the above-described acid-decomposable group.

The compound (ZI'-2) is a compound where each of R'$_{201}$ to R'$_{203}$ in formula (ZI') independently represents an aromatic ring-free organic group.

Examples of the aromatic ring-free organic group of R'$_{201}$ to R'$_{203}$ are the same as those described for the compound (ZI-2) except for not having the above-described acid-decomposable group.

The compound (ZI'-3) is a compound represented by the following formula (ZI'-3), and this is a compound having a phenacylsulfonium salt structure.

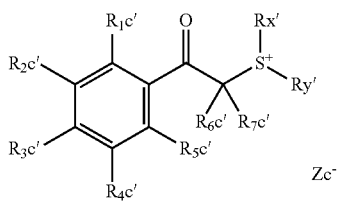
(ZI'-3)

In formula (ZI'-3), each of R$_{1c}$' to R$_{7c}$', Rx' and Ry' independently has the same meaning as R$_{1c}$ to R$_{7c}$, Rx and Ry described above in formula (ZI-3). However, all of R$_{1c}$' to R$_{7c}$', Rx' and Ry' are free from the above-described acid-decomposable group.

Zc'$^-$ represents a non-nucleophilic anion, and examples thereof are the same as those of the non-nucleophilic anion of Z$^-$ in formula (ZI). However, here, the non-nucleophilic anion is free from the above-described acid-decomposable group.

Specific examples of the cation of the compound represented by formula (ZI'-2) or (ZI'-3) are illustrated below.

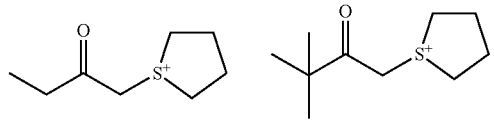
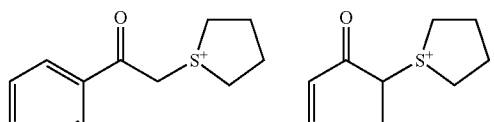
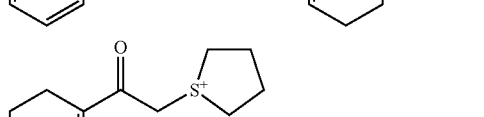
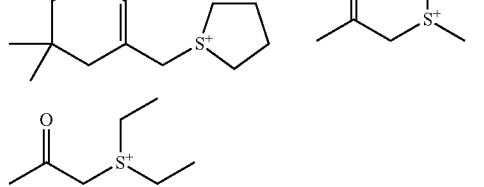
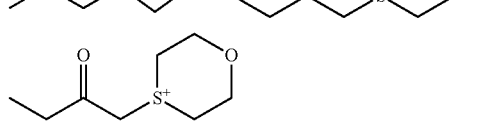
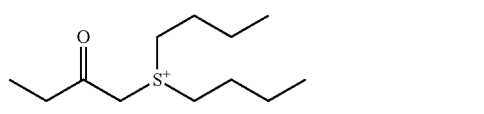
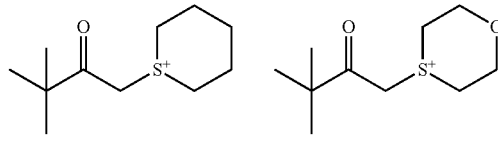
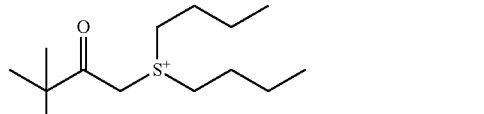
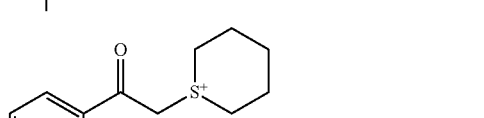
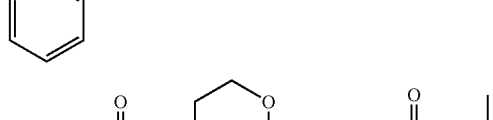
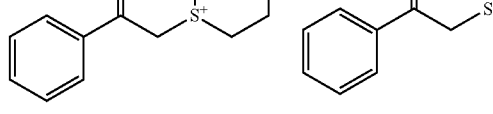

-continued
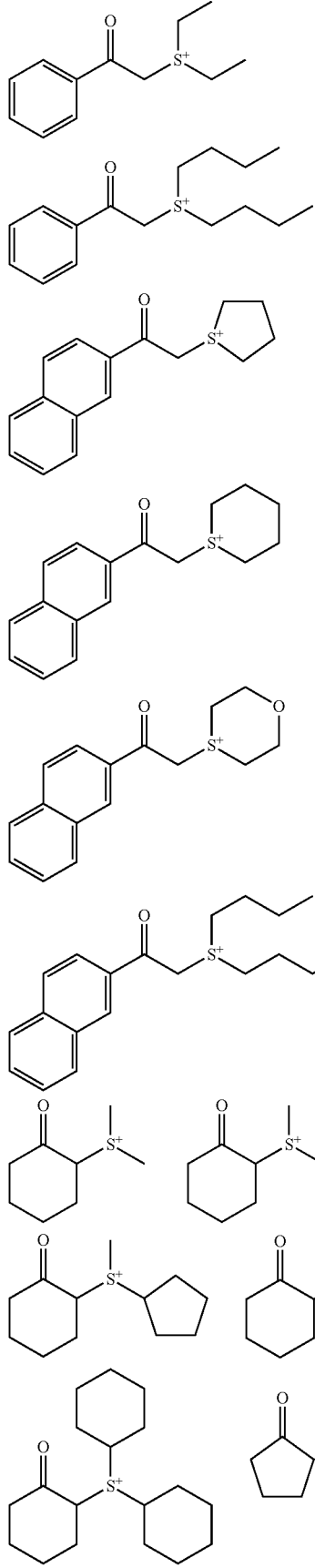
-continued
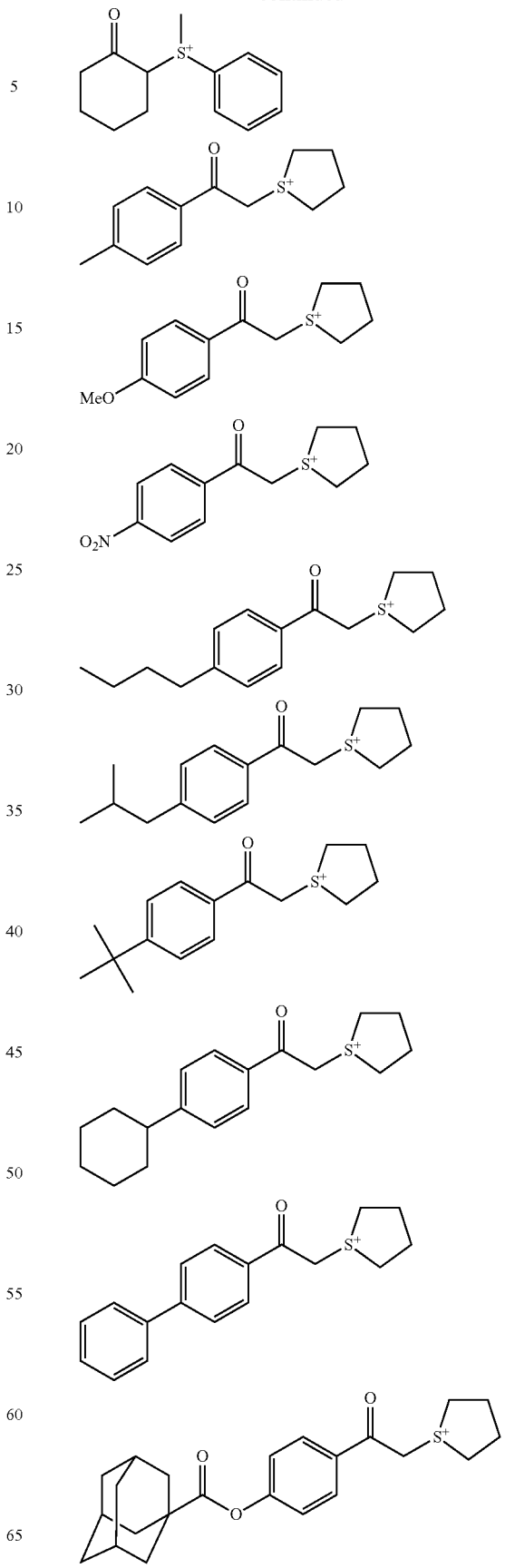

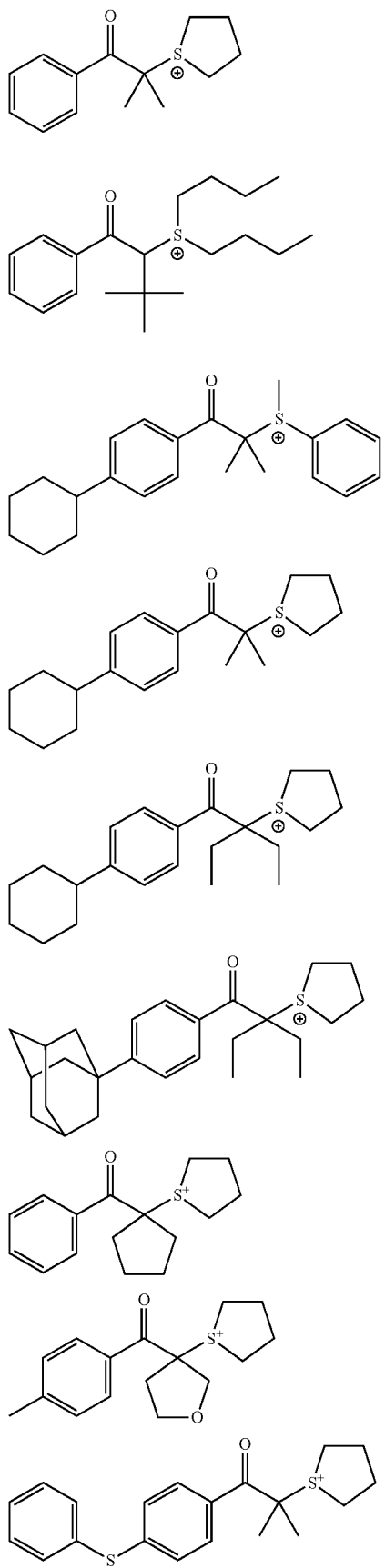
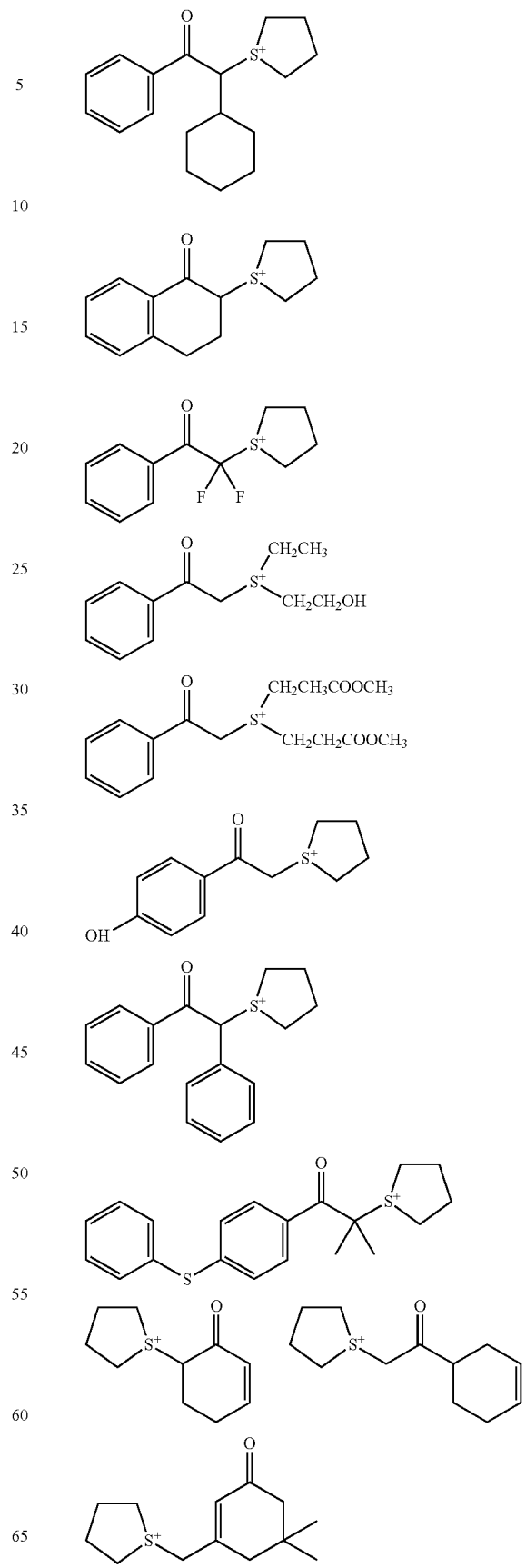

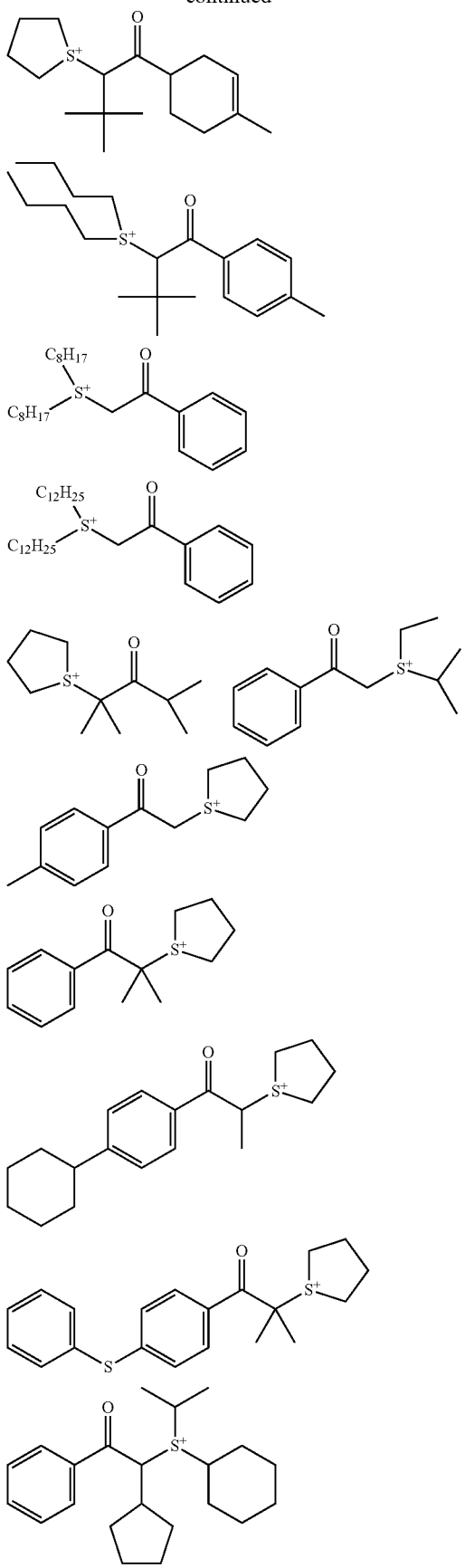
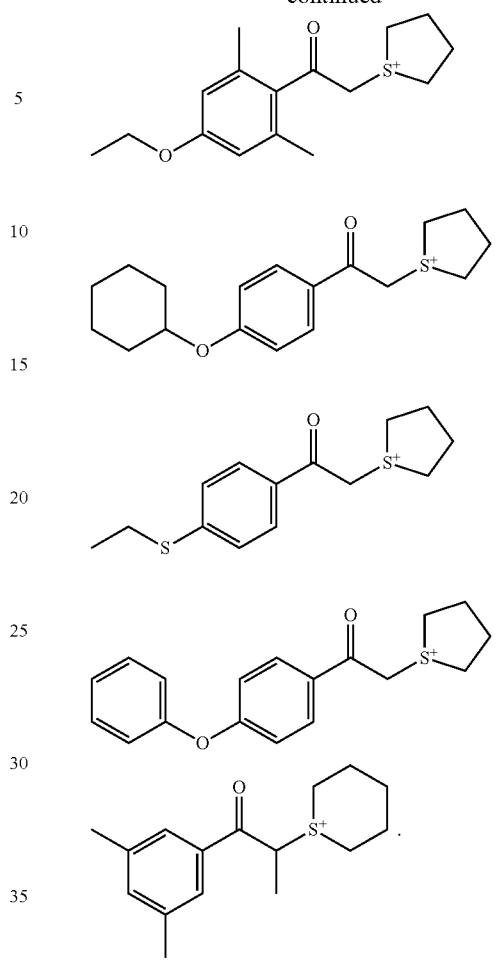

The compound (ZI'-4) is represented by the following formula (ZI'-4):

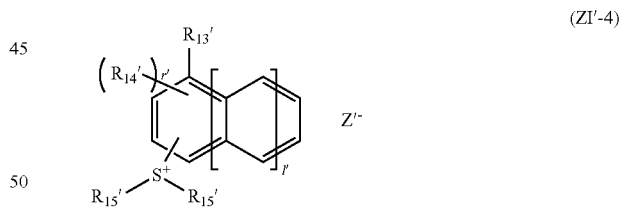

(ZI'-4)

In formula (ZI'-4), each of $R_{13}'$ to $R_{15}'$ independently has the same meaning as $R_{13}$ to $R_{15}$ described above in formula (ZI-4). However, all of $R_{13}'$ to $R_{15}'$ are free from the above-described acid-decomposable group.

l' and r' have the same meanings as l and r described above in formula (ZI-4).

$Z'^-$ represents a non-nucleophilic anion, and examples thereof are the same as those of the non-nucleophilic anion of $Z^-$ in formula (ZI). However, here, the non-nucleophilic anion is free from the above-described acid-decomposable group.

Specific examples of the cation of the compound represented by formula (ZI'-4) are illustrated, below.

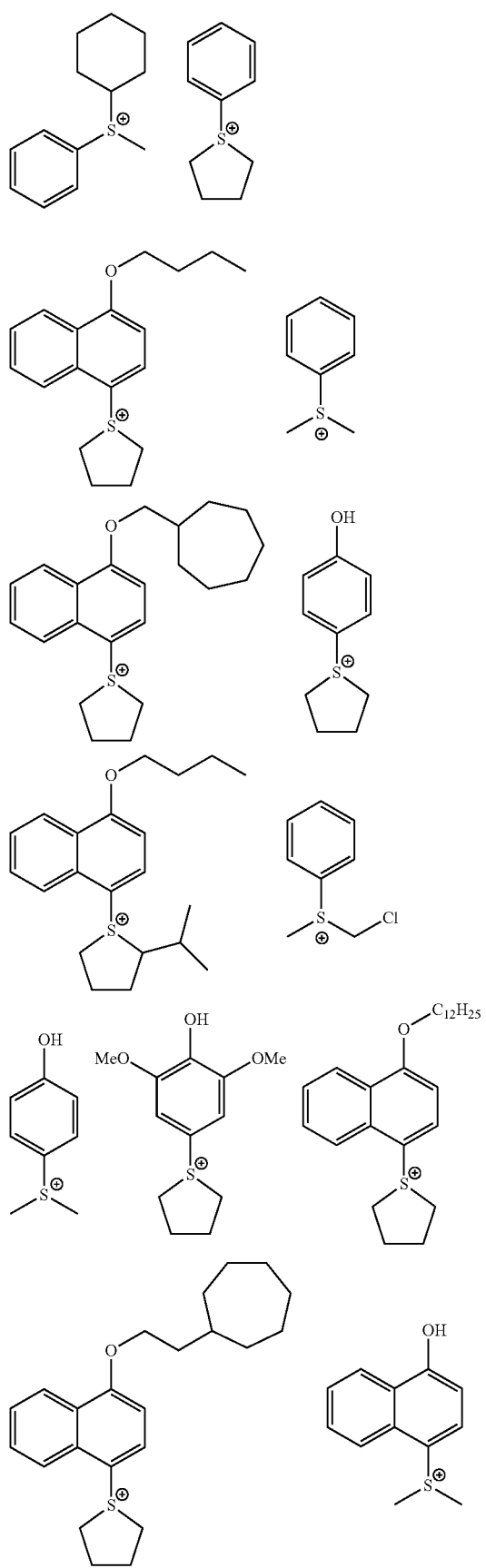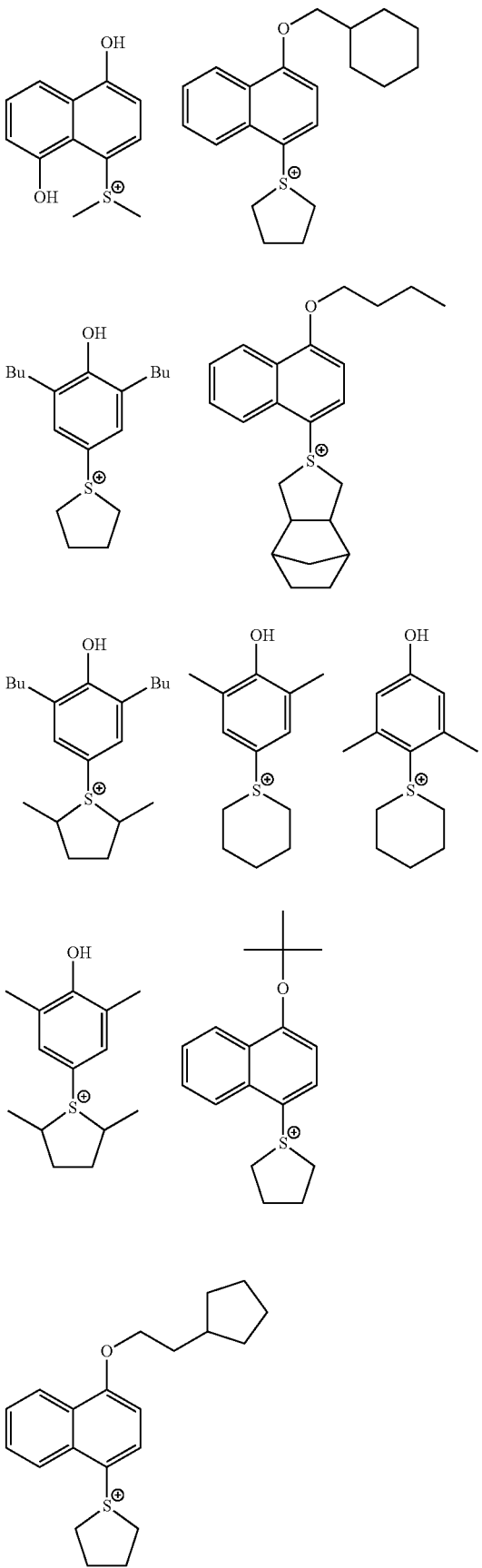

111
-continued
112
-continued
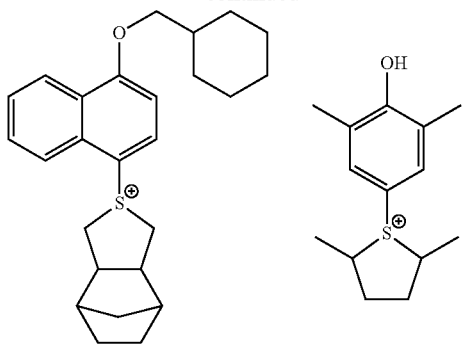
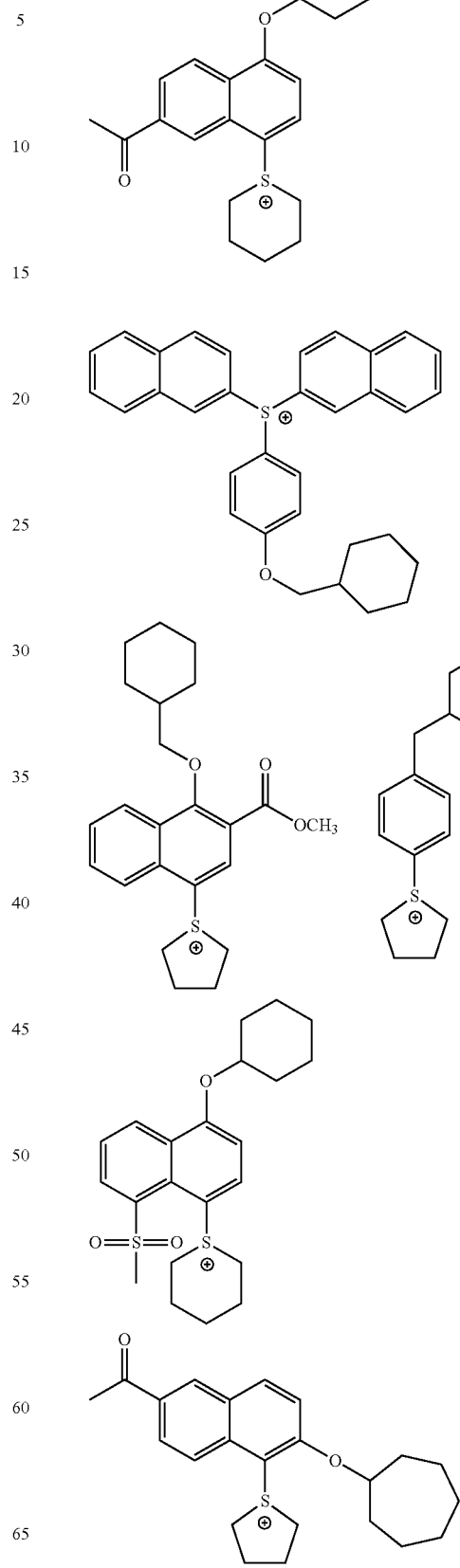

113
-continued
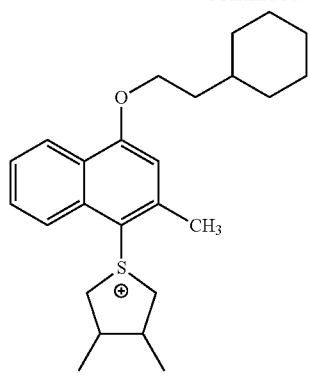
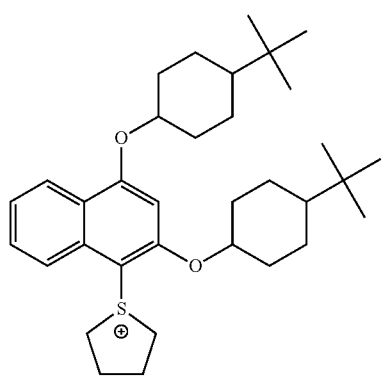
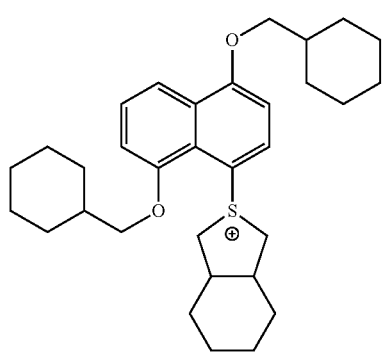
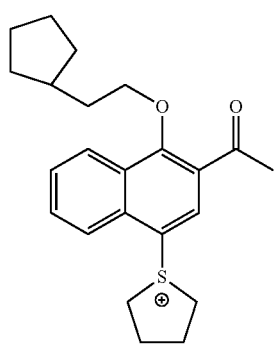
114
-continued
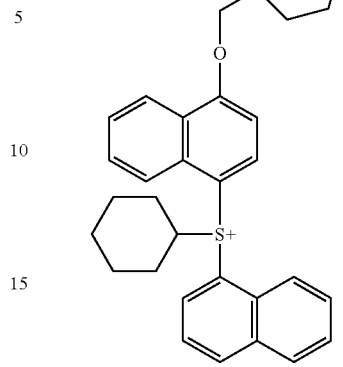
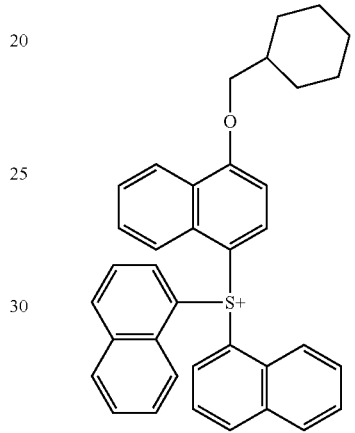
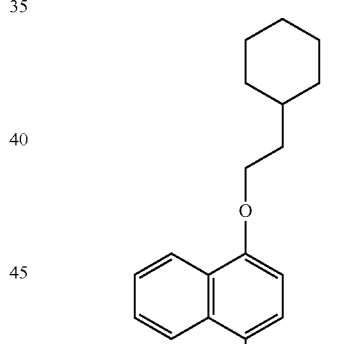
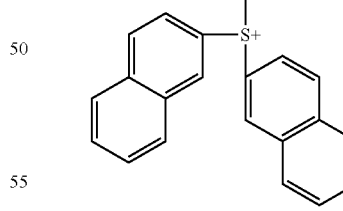 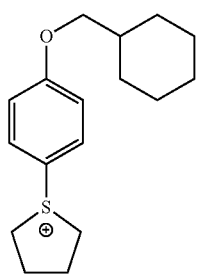
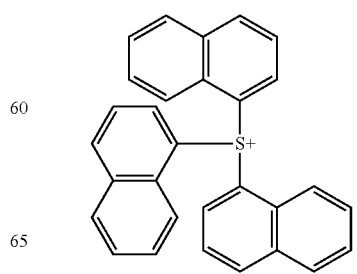

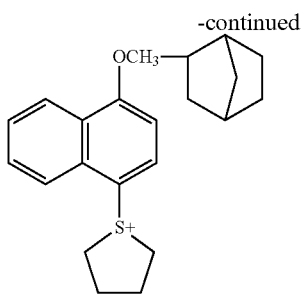

Other examples of the combination acid generator include compounds represented by the following formulae (ZIV'), (ZV') and (ZVI'):

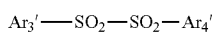 (ZIV')

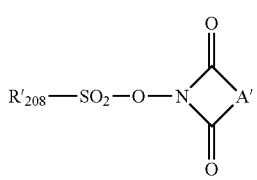 (ZV')

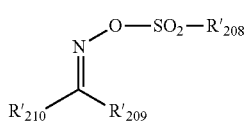 (ZVI')

In formulae (ZV') and (ZVI') Ar'$_3$ and Ar'$_4$ have the same meanings as Ar$_3$ and Ar$_4$ in formula (ZIV) and specific examples are also the same. However, Ar'$_3$ and Ar'$_4$ in formula (ZIV') are free from the above-described acid-decomposable group.

In formulae (ZV') and (ZVI'), A', R'$_{208}$, R'$_{209}$ and R'$_{210}$ have the same meanings as A, R$_{208}$, R$_{209}$ and R$_{210}$ in formulae (ZV) and (ZVI) and specific examples are also the same. However, A', R'$_{208}$, R'$_{209}$ and R'$_{210}$ in formulae (ZV') and (ZVI') are free from the above-described acid-decomposable group.

Among the combination acid generators, more preferred are the compounds represented by formulae (ZI') to (ZIII').

The combination acid generator is preferably a compound capable of generating an acid having one sulfonic acid group or imide group, more preferably a compound capable of generating a monovalent perfluoroalkanesulfonic acid, a compound capable of generating an aromatic sulfonic acid substituted with a monovalent fluorine atom or a fluorine atom-containing group, or a compound capable of generating an imide acid substituted with a monovalent fluorine atom or a fluorine atom-containing group, still more preferably a sulfonium salt of fluoro-substituted alkanesulfonic acid, fluorine-substituted benzenesulfonic acid, fluorine-substituted imide acid or fluorine-substituted methide acid. In particular, the combination acid generator which can be used is preferably a compound capable of generating a fluoro-substituted alkanesulfonic acid, a fluoro-substituted benzenesulfonic acid or a fluoro-substituted imide acid, where pKa of the acid generated is −1 or less, and in this case, the sensitivity is enhanced.

Specific examples of the combination acid generator are illustrated below.

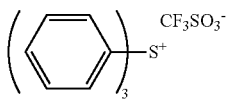 (z1)

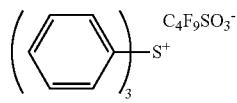 (z2)

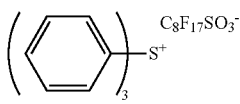 (z3)

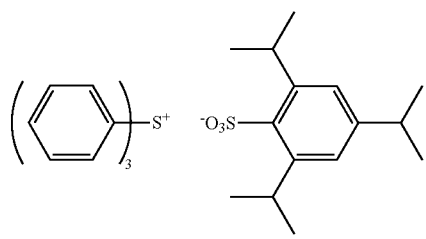 (z4)

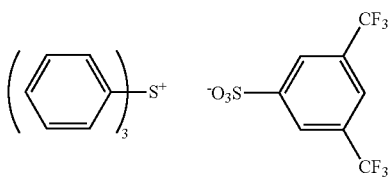 (z5)

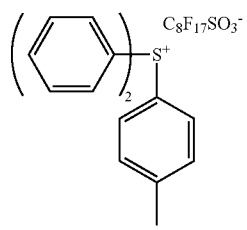 (z6)

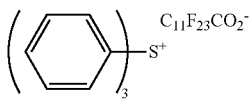 (z7)

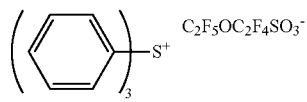 (z8)

-continued
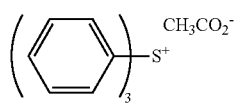 (z9)
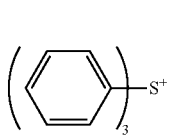 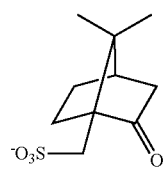 (z10)
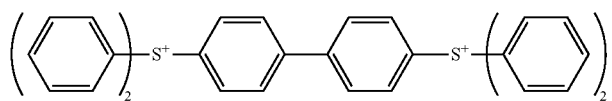 (z11)
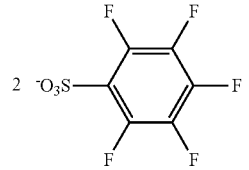
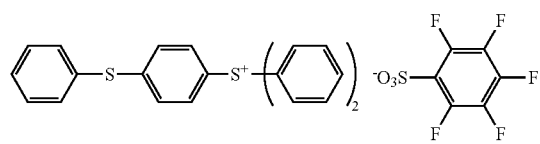 (z12)
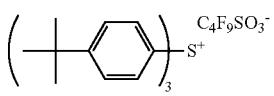 (z13)
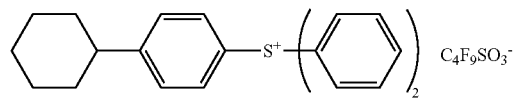 (z14)
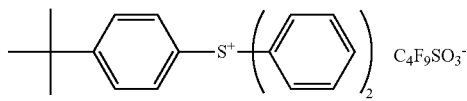 (z15)
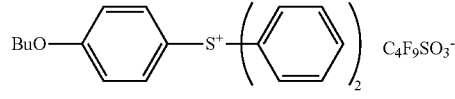 (z16)
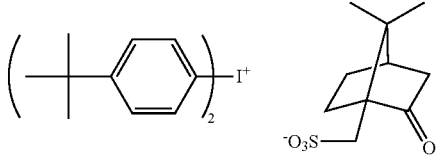 (z17)
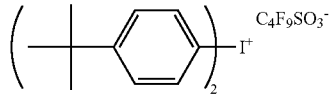 (z18)
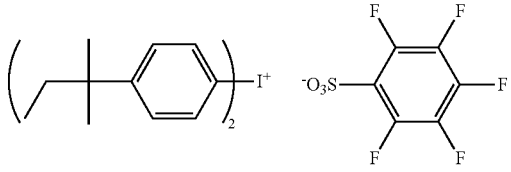 (z19)
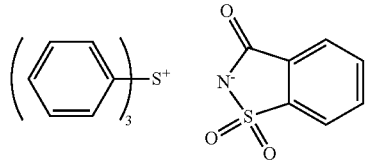 (z20)
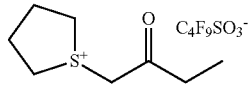 (z21)
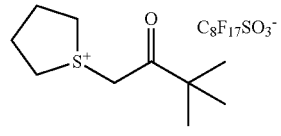 (z22)
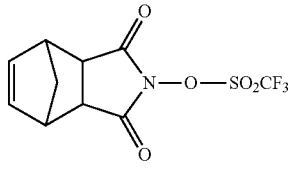 (z23)
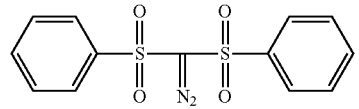 (z24)
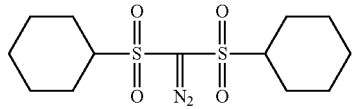 (z25)
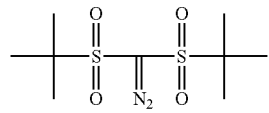 (z26)
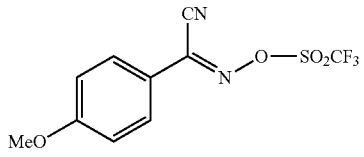 (z27)

-continued
(z28)
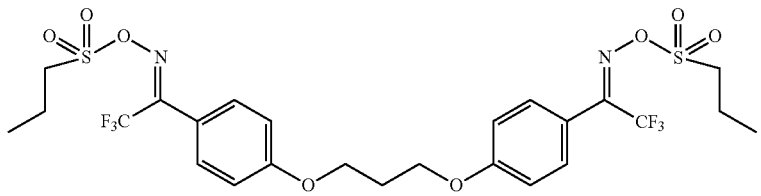
(z29)
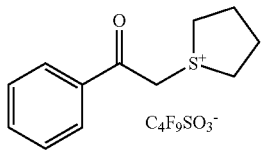
(z30)
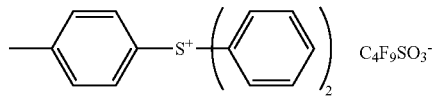
(z31)
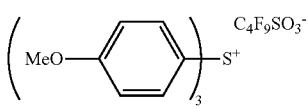
(z32)
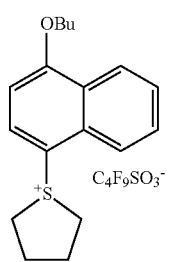
(z33)
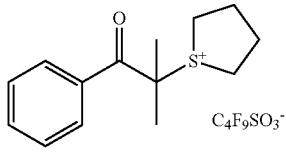
(z34)
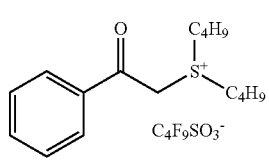
(z35)
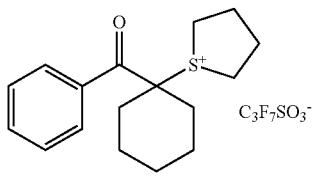
(z36)
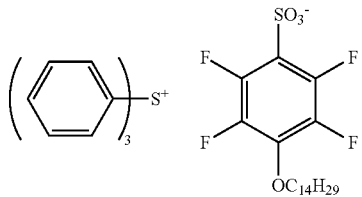
(z37)
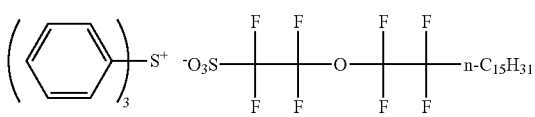
(z38)
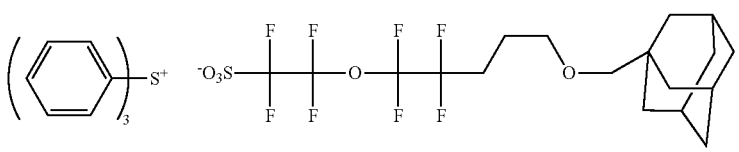
(z39)
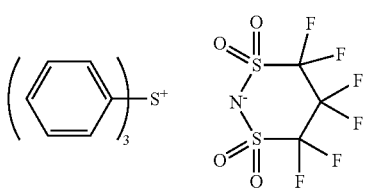
(z40)
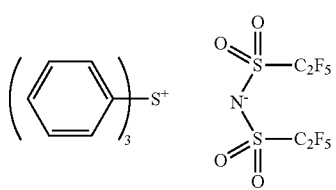

-continued
(z41)
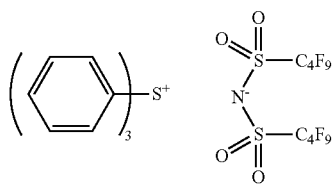
(z42)
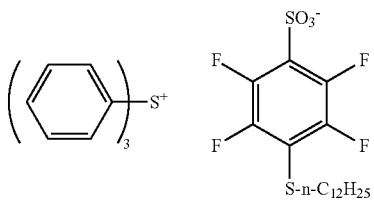
(z43)
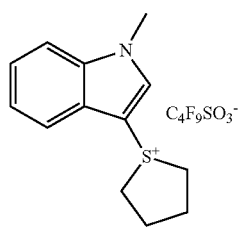
(z44)
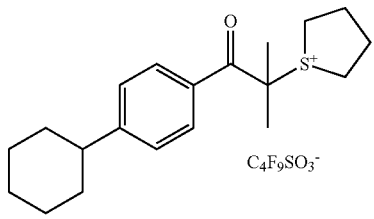
(z45)
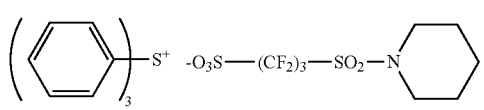
(z46)
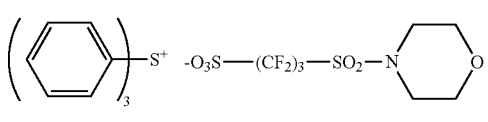
(z47)
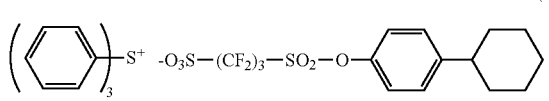
(z48)
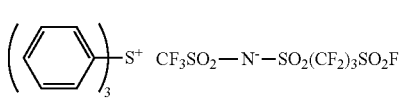
(z49)
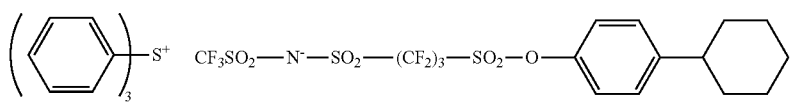
(z50)
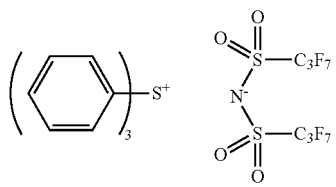
(z51)
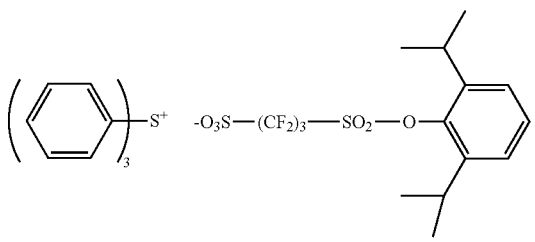
(z52)
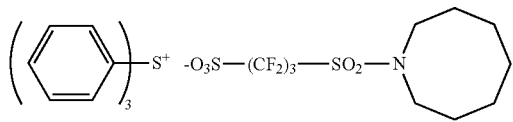
(z53)
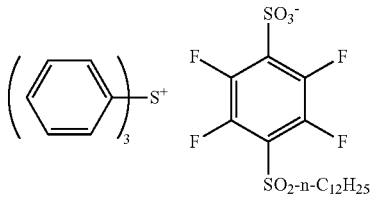
(z54)
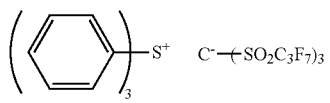
(z55)
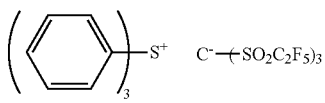
(z56)
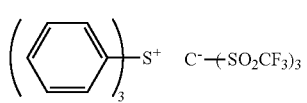
(z57)
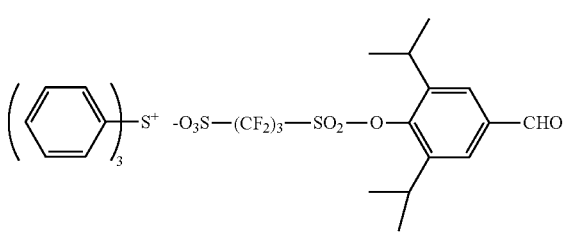

-continued
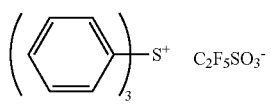(z58)
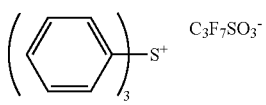(z59)
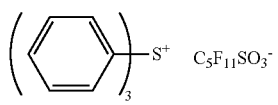(z60)
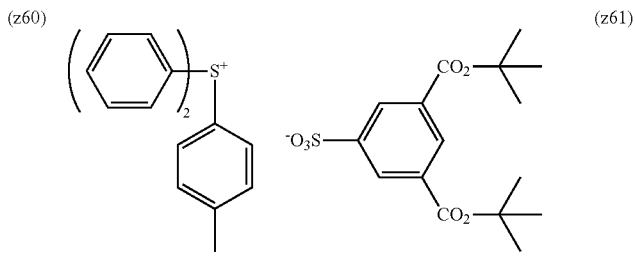(z61)
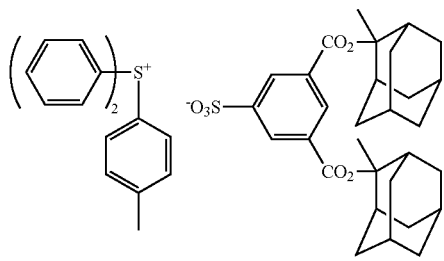(z62)
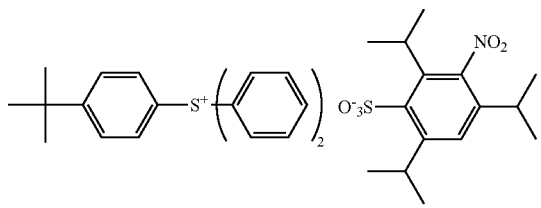(z63)
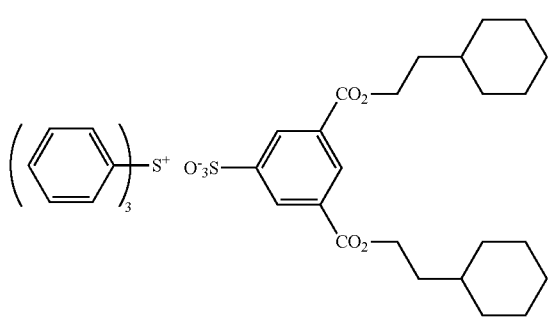(z64)
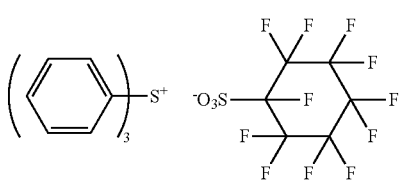(z65)
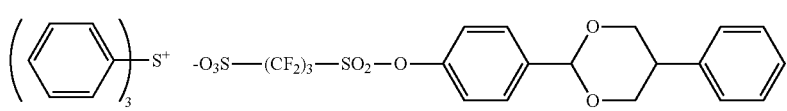(z66)
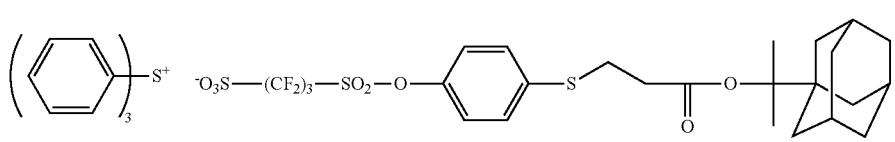(z67)
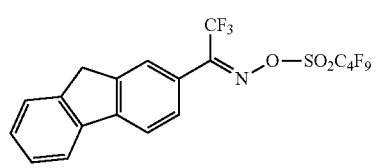(z68)
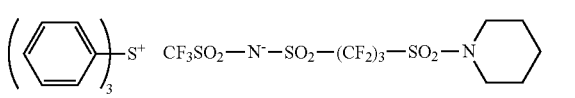(z69)

-continued
(z70)
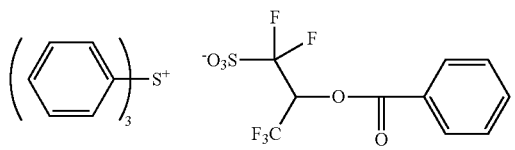
(z71)
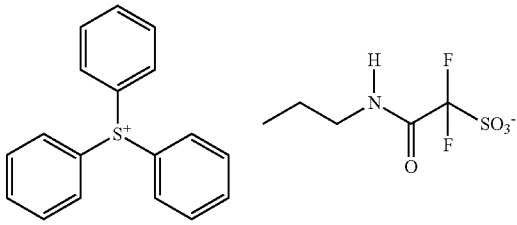
(z72)
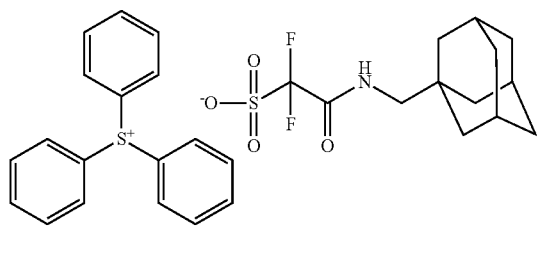
(z73)
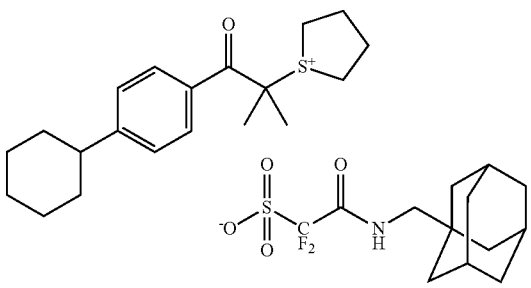
(z74)
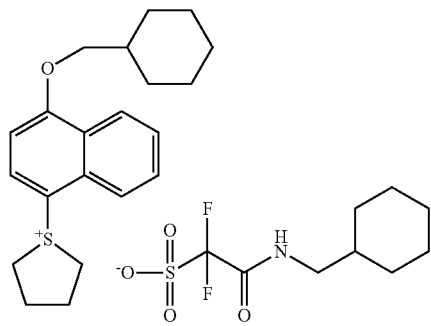
(z75)
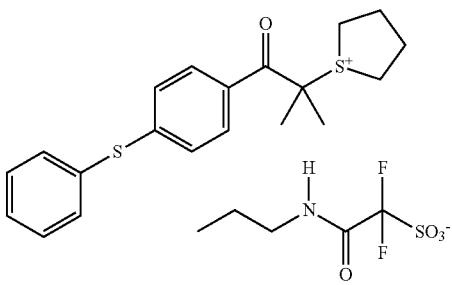
(z76)
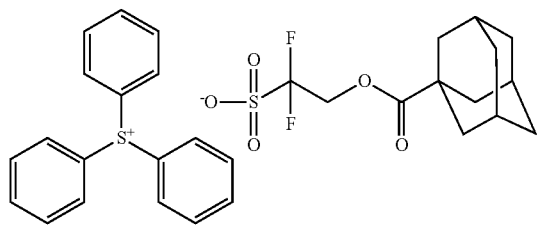
(z77)
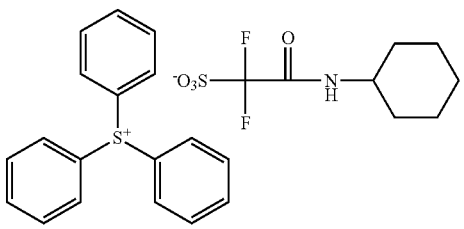
(z78)
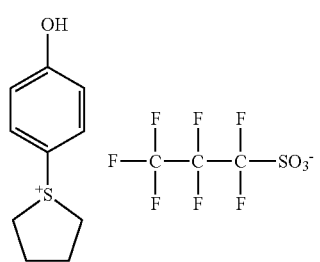
(z79)
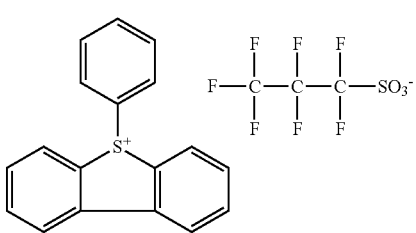

-continued
(z80) 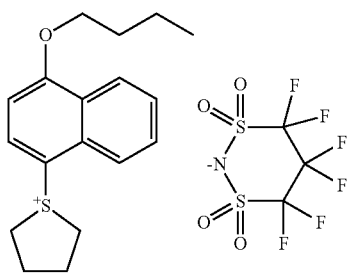
(z81) 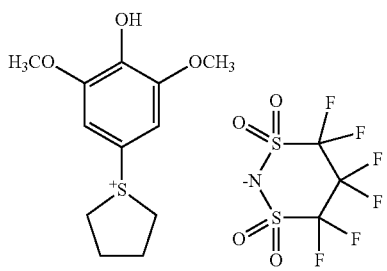
(z82) 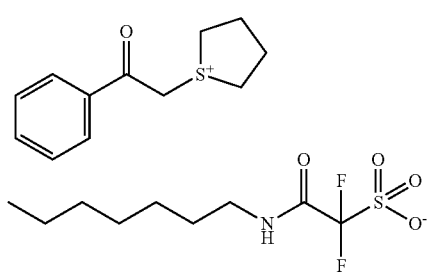
(z83) 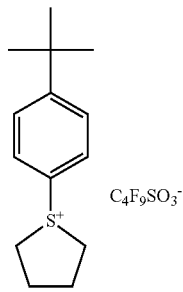
(z84) 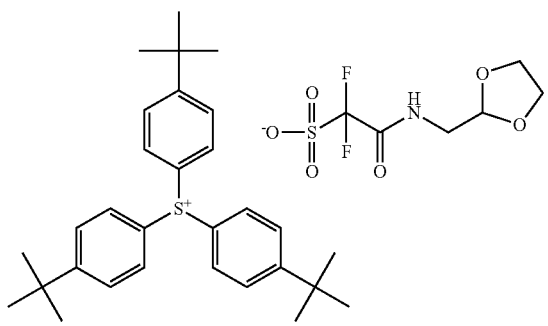
(z85) 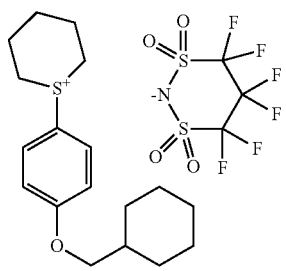
(z86) 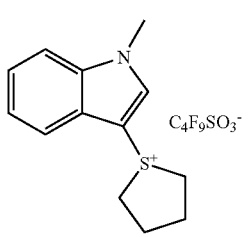
(z87) 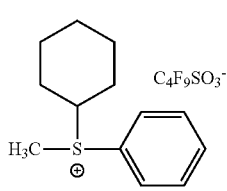
(z88) 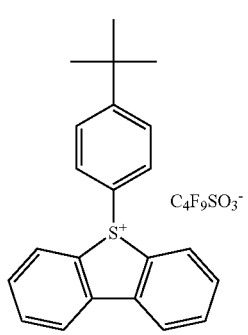
(z89) 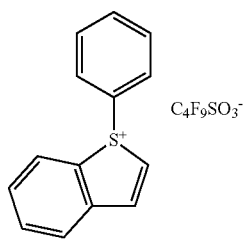

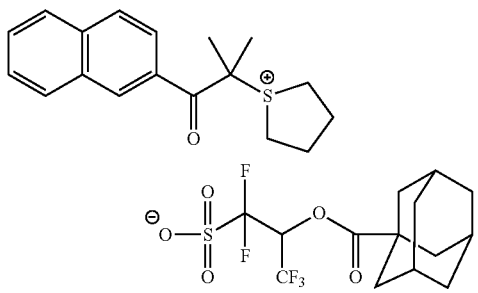 (z90)

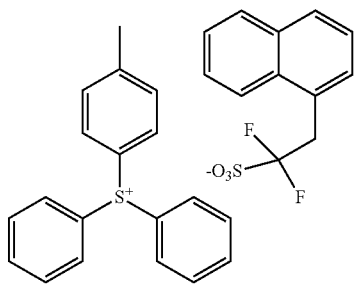 (z91)

The combination acid generator can be synthesized by a known method, for example, can be synthesized in accordance with the method described in JP-A-2007-161707.

As for the combination acid generator, one kind may be used, or two or more kinds may be used in combination.

The content of the combination acid generator in the composition is preferably from 0.05 to 15 mass %, more preferably from 0.1 to 10 mass %, still more preferably from 1 to 6 mass %, based on the entire solid content of the actinic ray-sensitive or radiation-sensitive resin composition.

[3] (c) Solvent

Examples of the solvent which can be used at the preparation of the actinic ray-sensitive or radiation-sensitive resin composition of the present invention include an organic solvent such as alkylene glycol monoalkyl ether carboxylate, alkylene glycol monoalkyl ether, alkyl lactate, alkyl alkoxypropionate, cyclic lactone (preferably having a carbon number of 4 to 10), monoketone compound (preferably having a carbon number of 4 to 10) which may contain a ring, alkylene carbonate, alkyl alkoxyacetate and alkyl pyruvate.

Specific examples of these solvents include those described in paragraphs [0441] to [0455] of U.S. Patent Application Publication 2008/0187860.

In the present invention, a mixed solvent prepared by mixing a solvent containing a hydroxyl group in the structure and a solvent not containing a hydroxyl group may be used as the organic solvent.

The solvent containing a hydroxyl group and the solvent not containing a hydroxyl group may be appropriately selected from the compounds exemplified above, but the solvent containing a hydroxyl group is preferably an alkylene glycol monoalkyl ether, an alkyl lactate or the like, more preferably propylene glycol monomethyl ether (PGME, another name: 1-methoxy-2-propanol) or ethyl lactate. The solvent not containing a hydroxyl group is preferably an alkylene glycol monoalkyl ether acetate, an alkyl alkoxypropionate, a monoketone compound which may contain a ring, a cyclic lactone, an alkyl acetate or the like, more preferably propylene glycol monomethyl ether acetate (PGMEA, another name: 1-methoxy-2-acetoxypropane), ethyl ethoxypropionate, 2-heptanone, γ-butyrolactone, cyclohexanone or butyl acetate, and most preferably propylene glycol monomethyl ether acetate, ethyl ethoxypropionate or 2-heptanone.

The mixing ratio (by mass) of the solvent containing a hydroxyl group and the solvent not containing a hydroxyl group is from 1/99 to 99/1, preferably from 10/90 to 90/10, more preferably from 20/80 to 60/40. A mixed solvent in which the solvent not containing a hydroxyl group accounts for 50 mass % or more is particularly preferred in view of coating uniformity.

The solvent preferably contains propylene glycol monomethyl ether acetate and is preferably a solvent containing propylene glycol monomethyl ether acetate alone or a mixed solvent of two or more kinds of solvents containing propylene glycol monomethyl ether acetate.

[4] (d) Hydrophobic Resin

The actinic ray-sensitive or radiation-sensitive resin composition of the present invention may contain a hydrophobic resin having at least either a fluorine atom or a silicon atom (hereinafter sometimes referred to as a "hydrophobic resin (d)" or simply as a "resin (d)") particularly when the composition is applied to immersion exposure. The hydrophobic resin (d) is unevenly distributed to the film surface layer and when the immersion medium is water, the static/dynamic contact angle on the resist film surface for water as well as the followability of immersion liquid can be enhanced.

The hydrophobic resin (d) is preferably designed, as described above, to be unevenly distributed to the interface but unlike a surfactant, need not have necessarily a hydrophilic group in the molecule and may not contribute to uniform mixing of polar/nonpolar substances.

The hydrophobic resin (d) typically contains a fluorine atom and/or a silicon atom. The fluorine atom and/or silicon atom in the hydrophobic resin (d) may be contained in the main chain of the resin or contained in the side chain.

In the case where the hydrophobic resin (d) contains a fluorine atom, the resin preferably contains, as the fluorine atom-containing partial structure, a fluorine atom-containing alkyl group, a fluorine atom-containing cycloalkyl group or a fluorine atom-containing aryl group.

The fluorine atom-containing alkyl group (preferably having a carbon number of 1 to 10, more preferably from 1 to 4) is a linear or branched alkyl group with at least one hydrogen atom being replaced by a fluorine atom and may further have a substituent other than the fluorine atom.

The fluorine atom-containing cycloalkyl group is a monocyclic or polycyclic cycloalkyl group with at least one hydrogen atom being replaced by a fluorine atom and may further have a substituent other than the fluorine atom.

The fluorine atom-containing aryl group is an aryl group (e.g., phenyl, naphthyl) with at least one hydrogen atom being replaced by a fluorine atom and may further have a substituent other than the fluorine atom.

Preferred examples of the fluorine atom-containing alkyl group, fluorine atom-containing cycloalkyl group and fluorine atom-containing aryl group include the groups represented by the following formulae (F2) to (F4), but the present invention is not limited thereto.

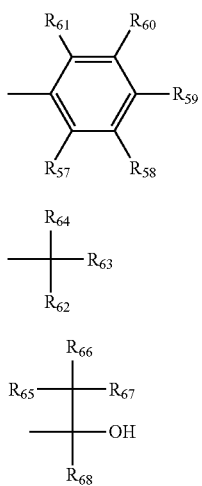

(F2)

(F3)

(F4)

In formulae (F2) to (F4), each of $R_{57}$ to $R_{68}$ independently represents a hydrogen atom, a fluorine atom or an alkyl group (linear or branched). However, each of at least one of $R_{57}$ to $R_{61}$, at least one of $R_{62}$ to $R_{64}$, and at least one of $R_{65}$ to $R_{68}$ independently represents a fluorine atom or an alkyl group (preferably having a carbon number of 1 to 4) with at least one hydrogen atom being replaced by a fluorine atom.

It is preferred that all of $R_{57}$ to $R_{61}$, and $R_{65}$ to $R_{67}$ are a fluorine atom. Each of $R_{62}$, $R_{63}$ and $R_{68}$ is preferably an alkyl group (preferably having a carbon number of 1 to 4) with at least one hydrogen atom being replaced by a fluorine atom, more preferably a perfluoroalkyl group having a carbon number of 1 to 4. $R_{62}$ and $R_{63}$ may combine with each other to form a ring.

Specific examples of the group represented by formula (F2) include p-fluorophenyl group, pentafluorophenyl group and 3,5-di(trifluoromethyl)phenyl group.

Specific examples of the group represented by formula (F3) include trifluoromethyl group, pentafluoropropyl group, pentafluoroethyl group, heptafluorobutyl group, hexafluoroisopropyl group, heptafluoroisopropyl group, hexafluoro(2-methyl)isopropyl group, nonafluorobutyl group, octafluoroisobutyl group, nonafluorohexyl group, nonafluoro-tert-butyl group, perfluoroisopentyl group, perfluorooctyl group, perfluoro(trimethyl)hexyl group, 2,2,3,3-tetrafluorocyclobutyl group and perfluorocyclohexyl group. Among these, hexafluoroisopropyl group, heptafluoroisopropyl group, hexafluoro(2-methyl)isopropyl group, octafluoroisobutyl group, nonafluoro-tert-butyl group and perfluoroisopentyl group are preferred, and hexafluoroisopropyl group and heptafluoroisopropyl group are more preferred.

Specific examples of the group represented by formula (F4) include —C(CF$_3$)$_2$OH, —C(C$_2$F$_5$)$_2$OH, —C(CF$_3$)(CH$_3$)OH and —CH(CF$_3$)OH, with —C(CF$_3$)$_2$OH being preferred.

The fluorine atom-containing partial structure may be bonded directly to the main chain or may be bonded to the main chain through a group selected from the group consisting of an alkylene group, a phenylene group, an ether bond, a thioether bond, a carbonyl group, an ester bond, an amide bond, a urethane bond and a ureylene bond, or a group formed by combining two or more of these groups and bonds.

As the repeating unit having a fluorine atom, those shown below are preferred.

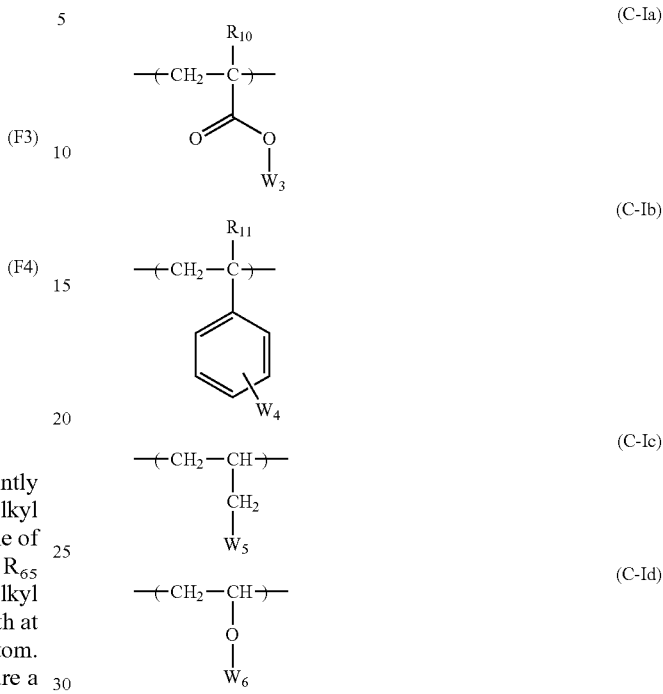

In the formulae, each of $R_{10}$ and $R_{11}$ independently represents a hydrogen atom, a fluorine atom or an alkyl group. The alkyl group is preferably a linear or branched alkyl group having a carbon number of 1 to 4 and may have a substituent, and the alkyl group having a substituent includes, in particular, a fluorinated alkyl group.

Each of $W_3$ to $W_6$ independently represents an organic group having at least one or more fluorine atoms and specifically includes the atomic groups of (F2) to (F4).

Other than these, the hydrophobic resin (d) may contain a unit shown below as the repeating unit having a fluorine atom.

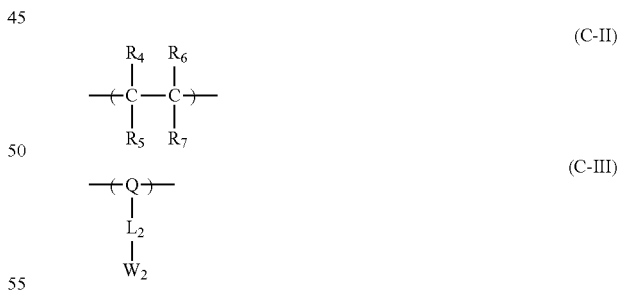

In the formulae, each of $R_4$ to $R_7$ independently represents a hydrogen atom, a fluorine atom or an alkyl group. The alkyl group is preferably a linear or branched alkyl group having a carbon number of 1 to 4 and may have a substituent, and the alkyl group having a substituent includes, in particular, a fluorinated alkyl group.

However, at least one of $R_4$ to $R_7$ represents a fluorine atom. $R_4$ and $R_5$, or $R_6$ and $R_7$ may form a ring.

$W_2$ represents an organic group having at least one fluorine atom and specifically includes the atomic groups of (F2) to (F4).

L₂ represents a single bond or a divalent linking group. The divalent linking group is a substituted or unsubstituted arylene group, a substituted or unsubstituted alkylene group, a substituted or unsubstituted cycloalkylene group, —O—, —SO₂—, —CO—, —N(R)— (wherein R represents a hydrogen atom or an alkyl group), —NHSO₂—, or a divalent linking group formed by combining a plurality of these groups.

Q represents an alicyclic structure. The alicyclic structure may have a substituent and may be monocyclic or polycyclic, and in the case of a polycyclic structure, the structure may be a crosslinked structure. The monocyclic structure is preferably a cycloalkyl group having a carbon number of 3 to 8, and examples thereof include a cyclopentyl group, a cyclohexyl group, a cyclobutyl group and a cyclooctyl group. Examples of the polycyclic structure include a group containing a bicyclo, tricyclo or tetracyclo structure having a carbon number of 5 or more. A cycloalkyl group having a carbon number of 6 to 20 is preferred, and examples thereof include an adamantyl group, a norbornyl group, a dicyclopentyl group, a tricyclodecanyl group and a tetracyclododecyl group. A part of carbon atoms in the cycloalkyl group may be substituted with a heteroatom such as oxygen atom. In particular, Q is preferably a norbornyl group, a tricyclodecanyl group, a tetracyclododecyl group or the like.

Specific examples of the repeating unit containing a fluorine atom are illustrated below, but the present invention is not limited thereto.

In specific examples, $X_1$ represents a hydrogen atom, —$CH_3$, —F or —$CF_3$, and $X_2$ represents —F or —$CF_3$.

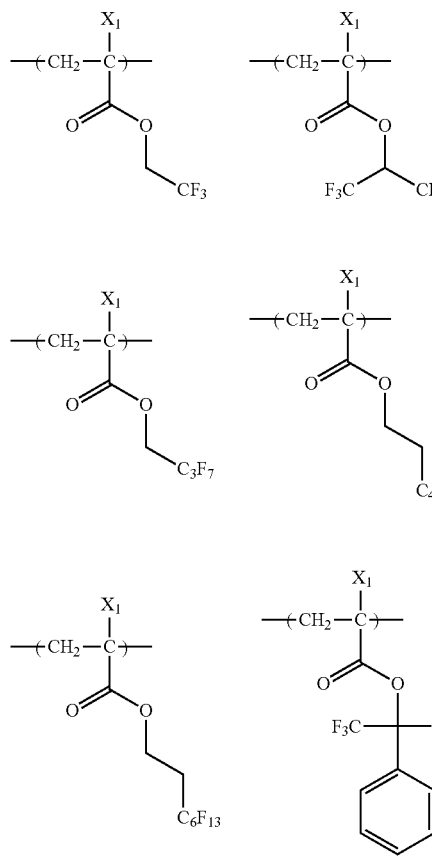

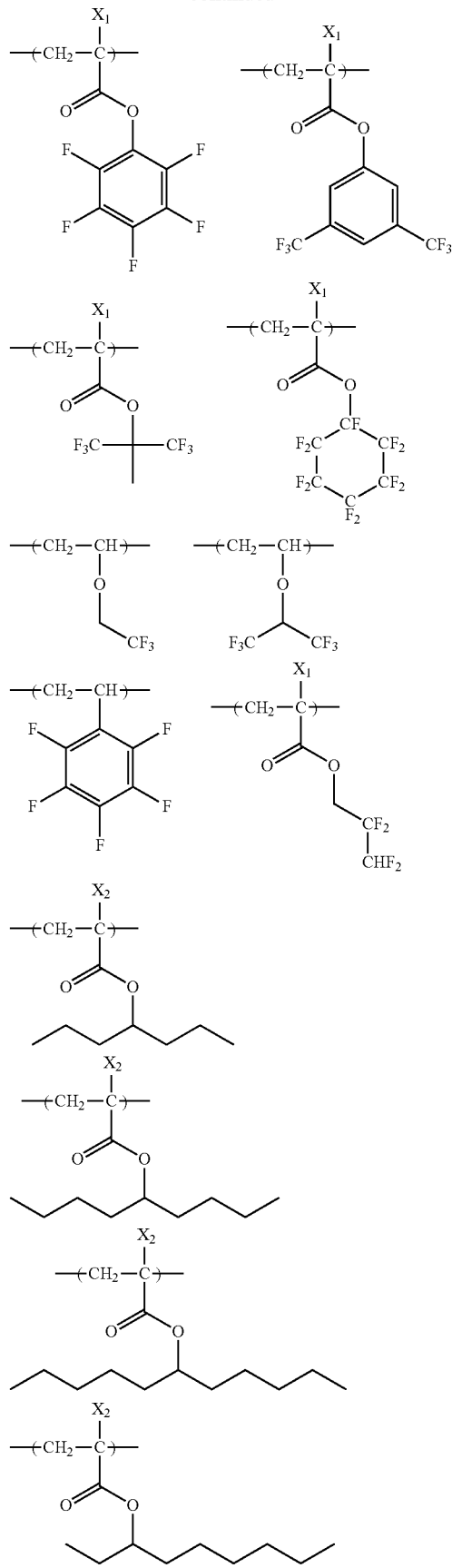

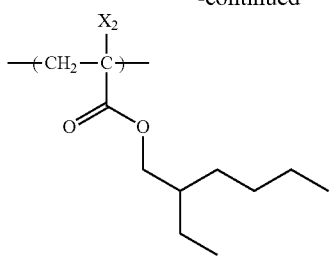
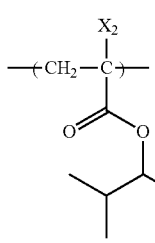
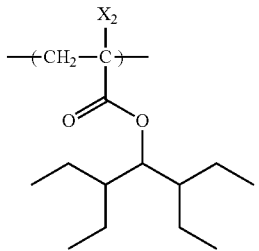
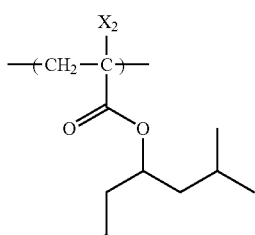
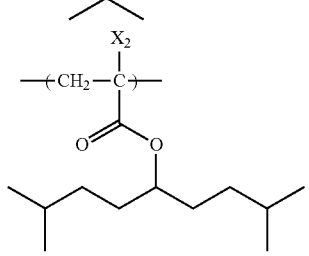
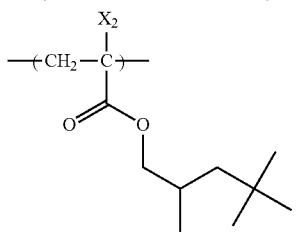
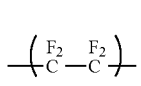
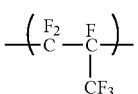
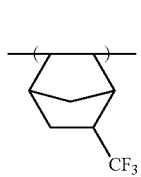
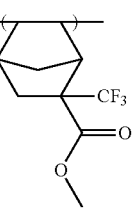

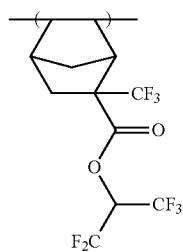

The hydrophobic resin (d) may contain a silicon atom. The resin preferably has, as the silicon atom-containing partial structure, an alkylsilyl structure (preferably a trialkylsilyl group) or a cyclic siloxane structure.

The alkylsilyl structure and cyclic siloxane structure specifically include, for example, the groups represented by the following formulae (CS-1) to (CS-3):

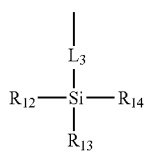

(CS-1)

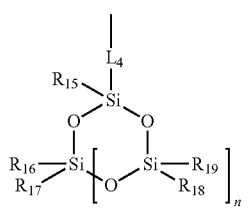

(CS-2)

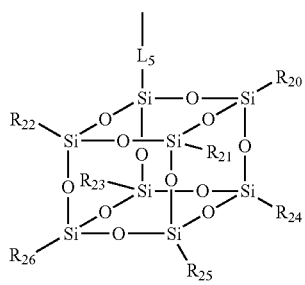

(CS-3)

In formulae (CS-1) to (CS-3), each of $R_{12}$ to $R_{26}$ independently represents a linear or branched alkyl group (preferably having a carbon number of 1 to 20) or a cycloalkyl group (preferably having a carbon number of 3 to 20).

Each of $L_3$ to $L_5$ represents a single bond or a divalent linking group. The divalent linking group is a sole group or a combination of two or more groups (the total carbon number is preferably 12 or less), selected from the group consisting of an alkylene group, a phenylene group, an ether bond, a thioether bond, a carbonyl group, an ester bond, an amide bond, a urethane bond and a urea bond.

n represents an integer of 1 to 5. n is preferably an integer of 2 to 4.

Specific examples of the repeating unit having a group represented by formulae (CS-1) to (CS-3) are illustrated below, but the present invention is not limited thereto. In specific examples, $X_1$ represents a hydrogen atom, —$CH_3$, —F or —$CF_3$.

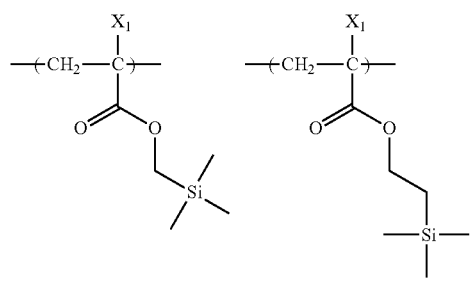
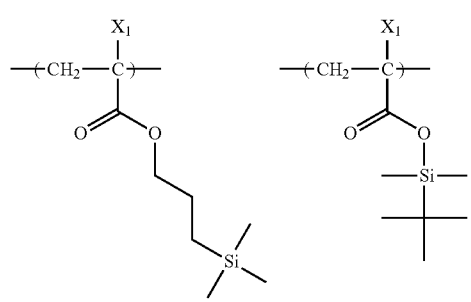
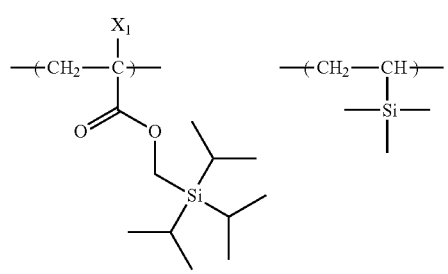
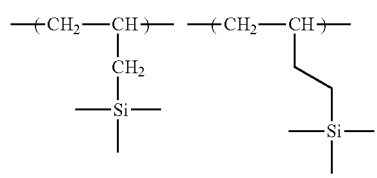
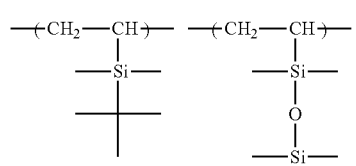
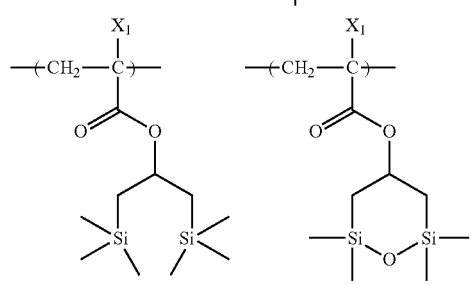
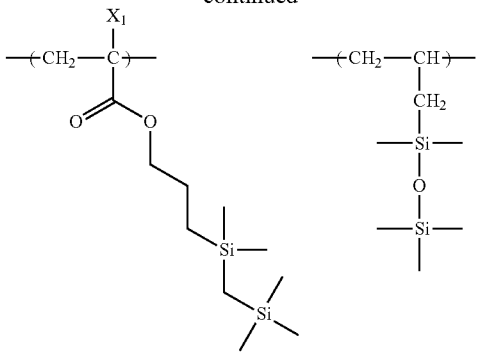
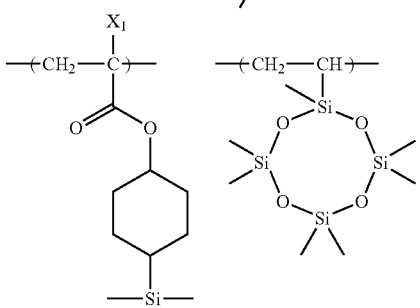
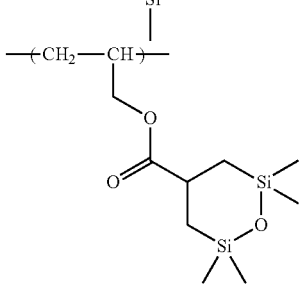
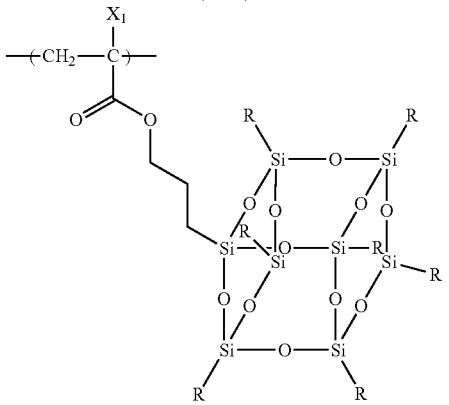
R = $CH_3$, $C_2H_5$, $C_3H_7$, $C_4H_9$
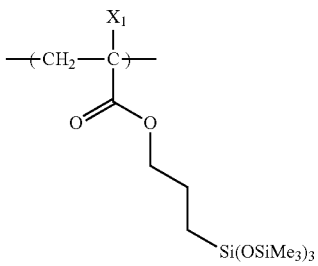
The hydrophobic resin (d) may further contain at least one group selected from the group consisting of the following (x) to (z):

(x) an acid group,
(y) a lactone structure-containing group, an acid anhydride group, or an acid imide group, and
(z) a group capable of decomposing by the action of an add.

Examples of the (x) acid group include a phenolic hydroxyl group, a carboxylic acid group, a fluorinated alcohol group, a sulfonic acid group, a sulfonamide group, a sulfonylimide group, an (alkylsulfonyl)(alkylcarbonyl)methylene group, an (alkylsulfonyl)(alkylcarbonyl)imide group, a bis(alkylcarbonyl)methylene group, a bis(alkylcarbonyl)imide group, a bis(alkylsulfonyl)methylene group, a bis(alkylsulfonyl)imide group, a tris(alkylcarbonyl)methylene group and a tris(alkylsulfonyl)methylene group.

Preferred acid groups include a fluorinated alcohol group (preferably hexafluoroisopropanol group), a sulfonimide group and a bis(alkylcarbonyl)methylene group.

Examples of the repeating unit having (x) an acid group include a repeating unit where an acid group is directly bonded to the main chain of the resin, such as repeating unit by an acrylic acid or a methacrylic acid, and a repeating unit where an acid group is bonded to the main chain of the resin through a linking group. Furthermore, an acid group may be introduced into the terminal of the polymer chain by using an acid group-containing polymerization initiator or chain transfer agent at the polymerization. All of these cases are preferred. The repeating unit having (x) an acid group may have at least either a fluorine atom or a silicon atom.

The content of the repeating unit having (x) an acid group is preferably from 1 to 50 mol %, more preferably from 3 to 35 mol %, still more preferably from 5 to 20 mol %, based on all repeating units in the hydrophobic resin (d).

Specific examples of the repeating unit having (x) an acid group are illustrated below, but the present invention is not limited thereto. In the formulae, Rx represents a hydrogen atom, $CH_3$, $CF_3$ or $CH_2OH$.

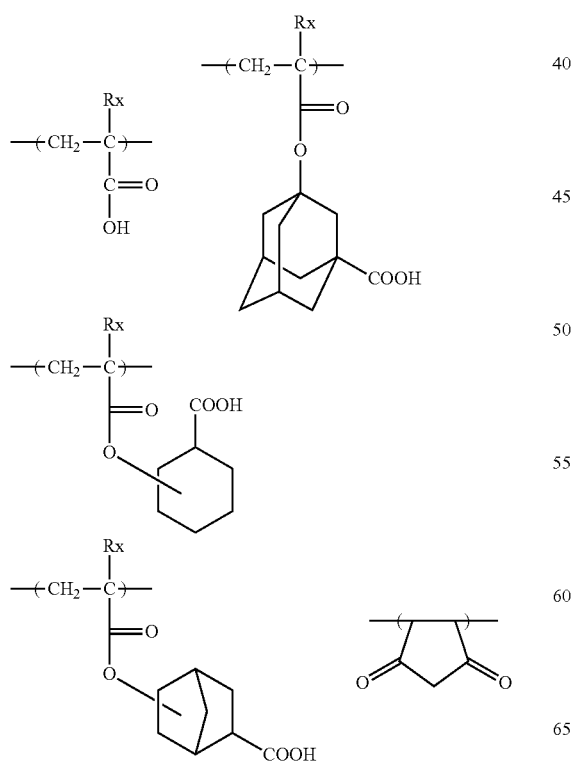

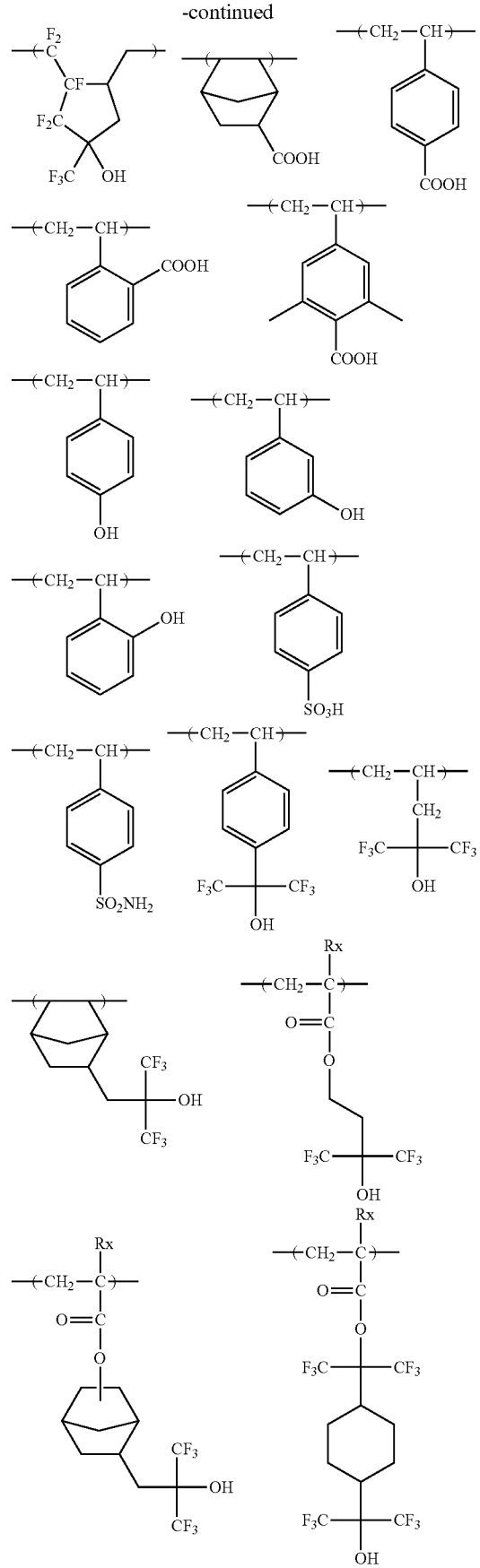

-continued

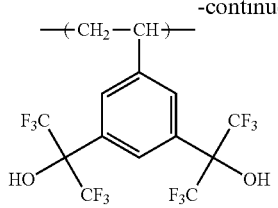

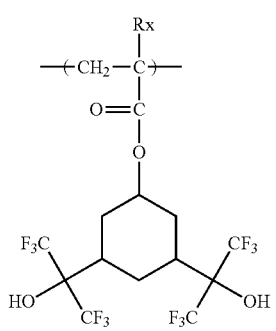

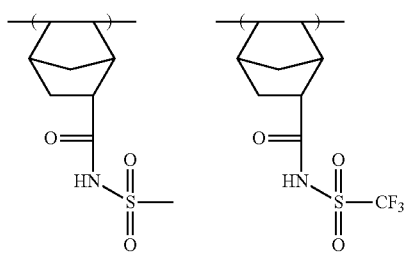

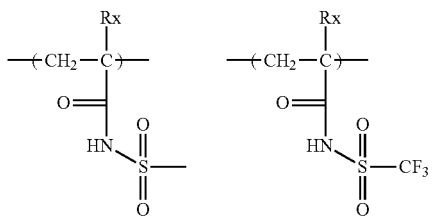

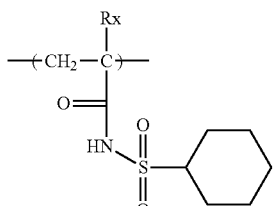

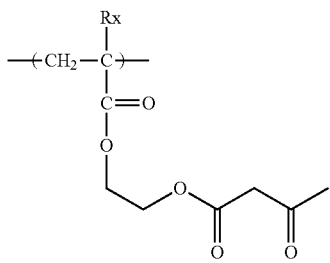

-continued

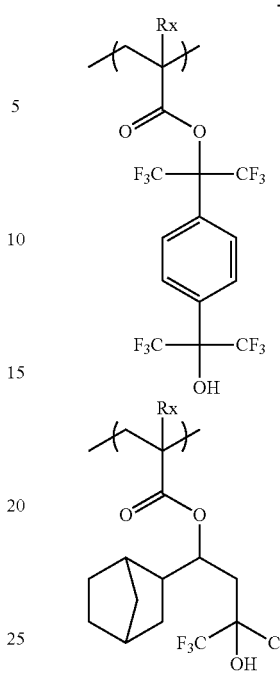

The (y) lactone structure-containing group, acid anhydride group or acid imide group is preferably a lactone structure-containing group.

The repeating unit having such a group is a repeating unit where the group is directly bonded to the main chain of the resin, such as repeating unit by an acrylic acid ester or a methacrylic acid ester. This repeating unit may be also a repeating unit where the group is bonded to the main chain of the resin through a linking group. Alternatively, in this repeating unit, the group may be introduced into the terminal of the resin by using a polymerization initiator or chain transfer agent containing the group at the polymerization.

Examples of the repeating unit having a lactone structure-containing group are the same as those of the repeating unit having a lactone structure described above in the paragraph of (a) acid-decomposable resin.

The content of the repeating unit having a lactone structure-containing group, an acid anhydride group or an acid imide group is preferably from 1 to 100 mol %, more preferably from 3 to 98 mol %, still more preferably from 5 to 95 mol %, based on all repeating units in the hydrophobic resin.

Examples of the repeating unit having (z) a group capable of decomposing by the action of an acid, which is contained in the hydrophobic resin (d), are the same as those of the repeating unit having an acid-decomposable group described for the resin (a). The repeating unit having (z) a group capable of decomposing by the action of an acid may contain at least either a fluorine atom or a silicon atom. The content of the repeating unit having (z) a group capable of decomposing by the action of an acid, in the hydrophobic resin (d), is preferably from 1 to 80 mol %, more preferably from 10 to 80 mol %, still more preferably from 20 to 60 mol %, based on all repeating units in the resin (d).

The hydrophobic resin (d) may further contain a repeating unit represented by the following formula (III):

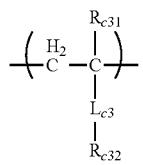
(III)

In formula (III), $R_{c31}$ represents a hydrogen atom, an alkyl group (which may be substituted with a fluorine atom or the like), a cyano group or a —$CH_2$—O-$Rac_2$ group, wherein $Rac_2$ represents a hydrogen atom, an alkyl group or an acyl group. $R_{c31}$ is preferably a hydrogen atom, a methyl group, a hydroxymethyl group or a trifluoromethyl group, more preferably a hydrogen atom or a methyl group.

$R_{c32}$ represents a group having an alkyl group, a cycloalkyl group, an alkenyl group, a cycloalkenyl group or an aryl group. These groups may be substituted with a fluorine atom or a silicon atom-containing group.

$L_{c3}$ represents a single bond or a divalent linking group.

In formula (III), the alkyl group of $R_{c32}$ is preferably a linear or branched alkyl group having a carbon number of 3 to 20.

The cycloalkyl group is preferably a cycloalkyl group having a carbon number of 3 to 20.

The alkenyl group is preferably an alkenyl group having a carbon number of 3 to 20.

The cycloalkenyl group is preferably a cycloalkenyl group having a carbon number of 3 to 20.

The aryl group is preferably an aryl group having a carbon number of 6 to 20, more preferably a phenyl group or a naphthyl group, and these groups may have a substituent.

$R_{c32}$ is preferably an unsubstituted alkyl group or an alkyl group substituted with a fluorine atom.

The divalent linking group of $L_{c3}$ is preferably an alkylene group (preferably having a carbon number of 1 to 5), an ether bond, a phenylene group or an ester bond (a group represented by —COO—).

The content of the repeating unit represented by formula (III) is preferably from 1 to 100 mol %, more preferably from 10 to 90 mol %, still more preferably from 30 to 70 mol %, based on repeating units in the hydrophobic resin.

It is also preferred that the hydrophobic resin (d) further contains a repeating unit represented by the following formula (CII-AB):

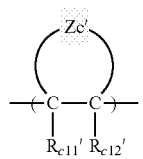
(CII-AB)

In formula (CII-AB), each of $R_{c11}'$ and $R_{c12}'$ independently represents a hydrogen atom, a cyano group, a halogen atom or an alkyl group.

$Z_c'$ represents an atomic group for forming an alicyclic structure containing two carbon atoms (C—C) to which bonded.

The content of the repeating unit represented by formula (CII-AB) is preferably from 1 to 1.00 mol %, more preferably from 10 to 90 mol %, still more preferably from 30 to 70 mol %, based on all repeating units in the hydrophobic resin.

Specific examples of the repeating units represented by formulae (III) and (CII-AB) are illustrated below, but the present invention is not limited thereto. In the formulae, Ra represents H, $CH_3$, $CH_2OH$, $CF_3$ or CN.

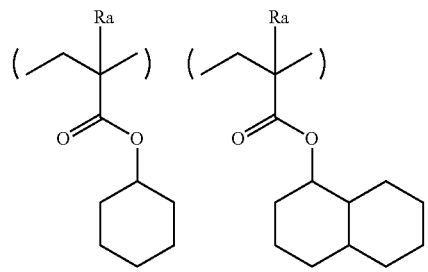

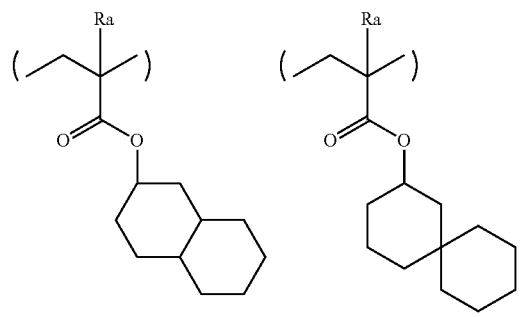

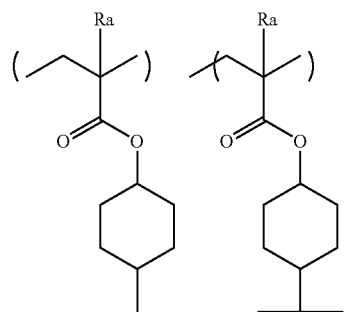

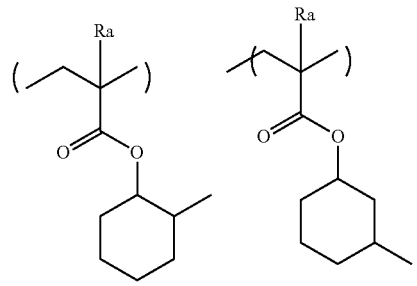

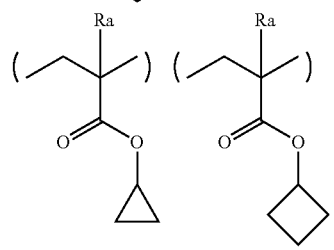

-continued
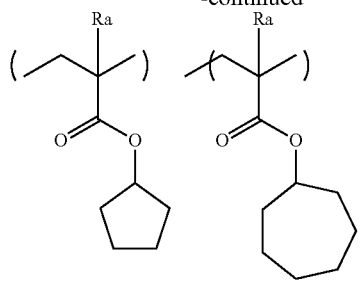
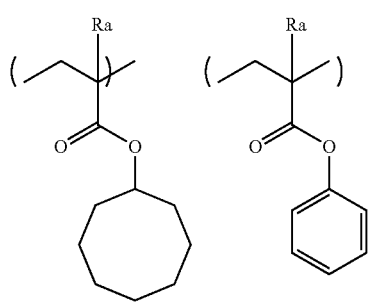
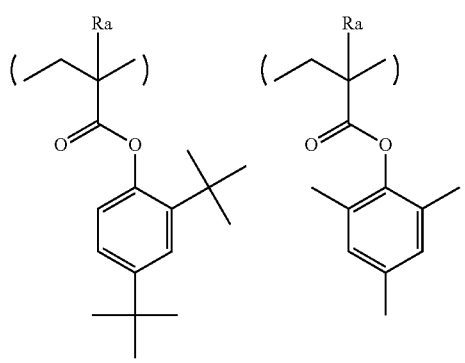
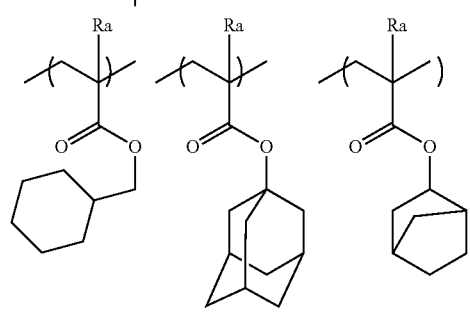
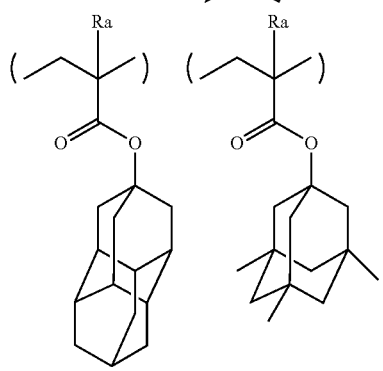
-continued
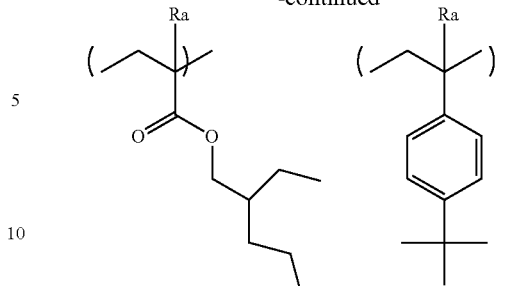
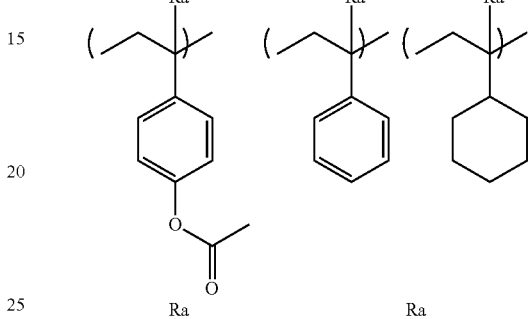
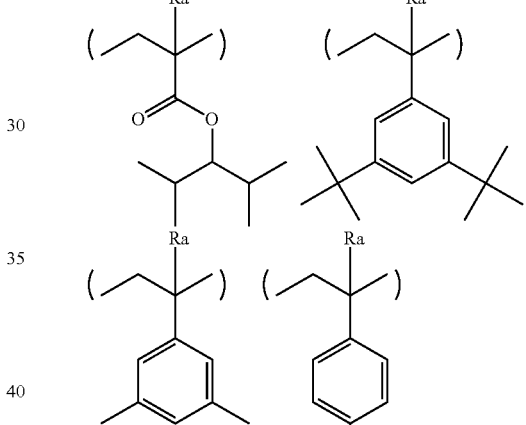
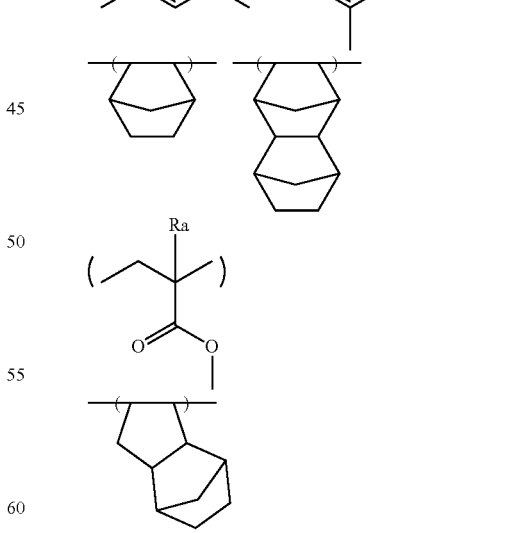
In the case where the hydrophobic resin (d) contains a fluorine atom, the fluorine atom content is preferably from 5 to 80 mass %, more preferably from 10 to 80 mass %, based on the weight average molecular weight of the hydrophobic resin (d). Also, the fluorine atom-containing repeating unit preferably accounts for 10 to 100 mol %, more preferably from 30 to 100 mol %, based on all repeating units contained in the hydrophobic resin (d).

In the case where the hydrophobic resin (d) contains a silicon atom, the silicon atom content is preferably from 2 to 50 mass %, more preferably from 2 to 30 mass %, based on the weight average molecular weight of the hydrophobic resin (d). Also, the silicon atom-containing repeating unit preferably accounts for 10 to 100 mol %, more preferably from 20 to 100 mol %, based on all repeating units contained in the hydrophobic resin (d).

The weight average molecular weight of the hydrophobic resin (d) is preferably from 1,000 to 100,000, more preferably from 1,000 to 50,000, still more preferably from 2,000 to 15,000, in terms of standard polystyrene.

As for the hydrophobic resin (d), one kind of a resin may be used, or a plurality of kinds of resins may be used in combination.

The content of the hydrophobic resin (d) in the composition is preferably from 0.01 to 10 mass %, more preferably from 0.05 to 8 mass %, still more preferably from 0.1 to 5 mass %, based on the entire solid content in the composition of the present invention.

In the hydrophobic resin (d), similarly to the resin (a), it is of course preferred that the content of impurities such as metal is small, but the content of residual monomers or oligomer components is also preferably from 0.01 to 5 mass %, more preferably from 0.01 to 3 mass %, still more preferably from 0.05 to 1 mass %. When these conditions are satisfied, an actinic ray-sensitive or radiation-sensitive resin composition free from extraneous substances in liquid or changes with aging of sensitivity or the like can be obtained. Furthermore, in view of resolution, resist profile, side wall of resist pattern, roughness and the like, the molecular weight distribution (Mw/Mn, sometimes referred to as "polydispersity") is preferably from 1 to 5, more preferably from 1 to 3, still more preferably from 1 to 2.

As for the hydrophobic resin (d), various commercially available products may be used, or the resin may be synthesized by a conventional method (for example, radical polymerization). Examples of the general synthesis method include a batch polymerization method of dissolving monomer species and an initiator in a solvent and heating the solution, thereby effecting the polymerization, and a dropping polymerization method of adding dropwise a solution containing monomer species and an initiator to a heated solvent over 1 to 10 hours. A dropping polymerization method is preferred.

The reaction solvent, the polymerization initiator, the reaction conditions (e.g., temperature, concentration) and the purification method after reaction are the same as those described for the resin (a), but in the synthesis of the hydrophobic resin (d), the concentration during reaction is preferably from 30 to 50 mass %.

Specific examples of the hydrophobic resin (d) are illustrated below. Also, the molar ratio of repeating units (corresponding to repeating units starting from the left), weight average molecular weight and polydispersity of each resin are shown in Tables 1 and 2 later.

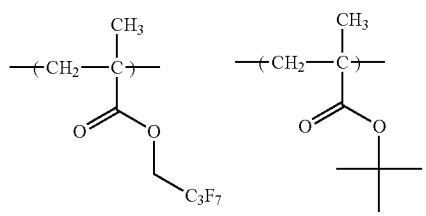
(HR-1)

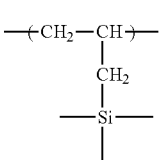
(HR-2)

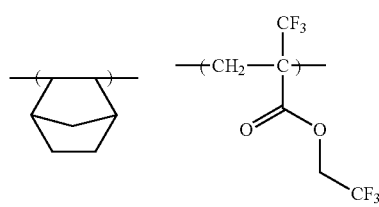
(HR-3)

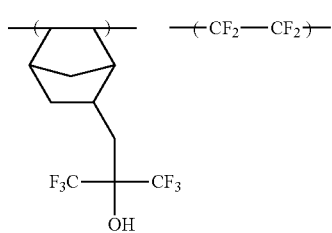
(HR-4)

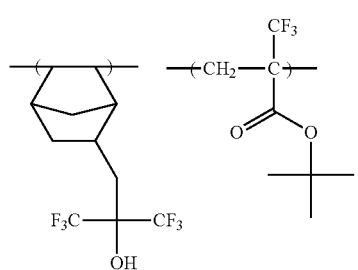
(HR-5)

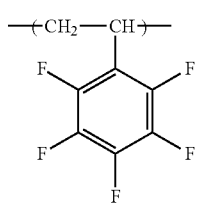
(HR-6)

-continued
(HR-7)
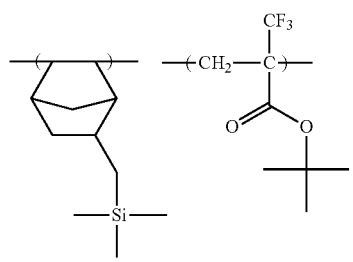
(HR-8)
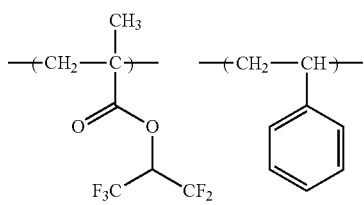
(HR-9)
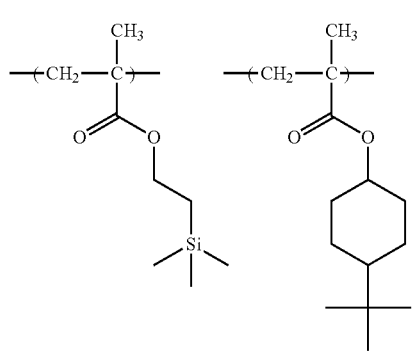
(HR-10)
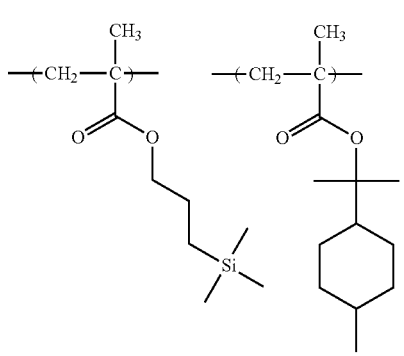
(HR-11)
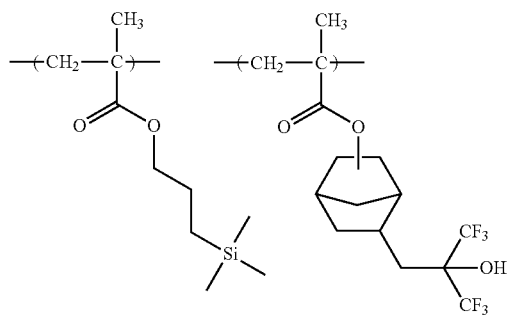
(HR-12)
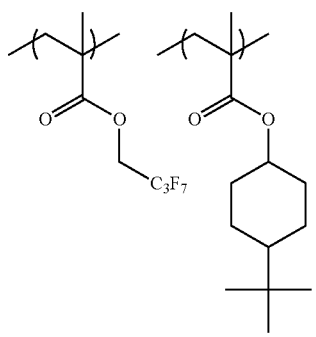
(HR-13)
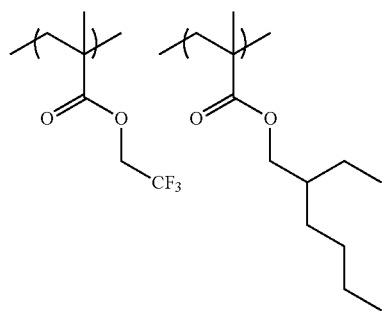
(HR-14)
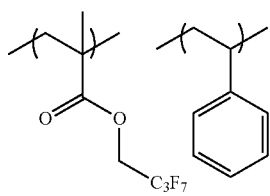
(HR-15)
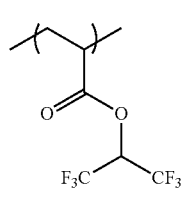
(HR-16)
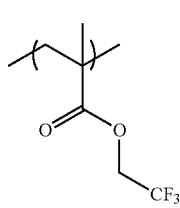

-continued
(HR-17) 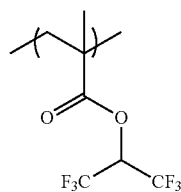
(HR-18) 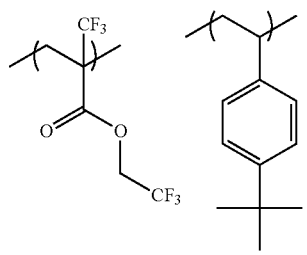
(HR-19) 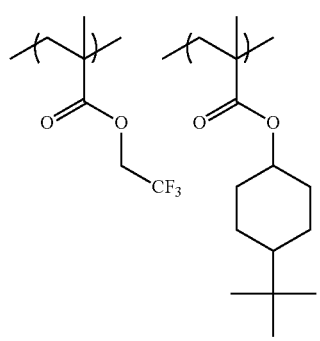
(HR-20) 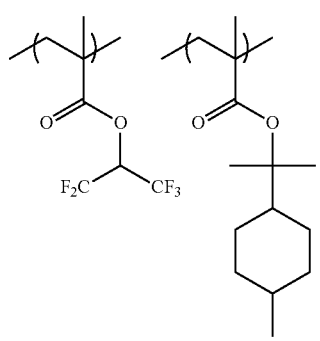
(HR-21) 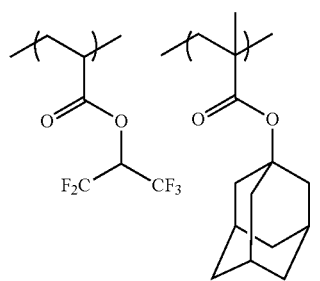
(HR-22) 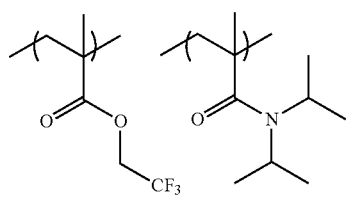
(HR-23) 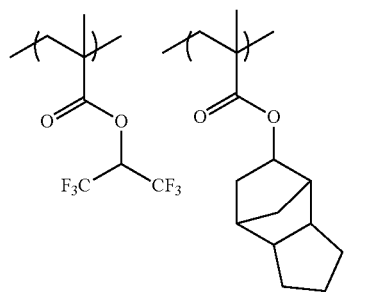
(HR-24) 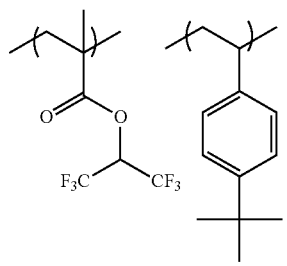
(HR-25) 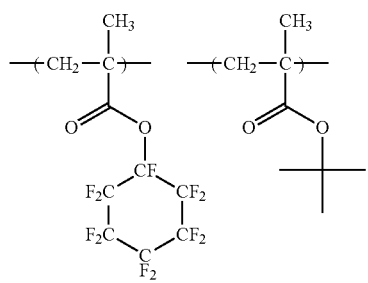
(HR-26) 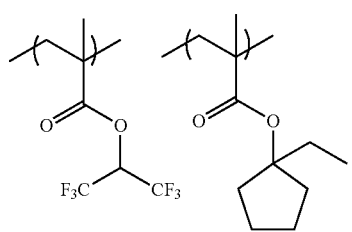

-continued
(HR-27) 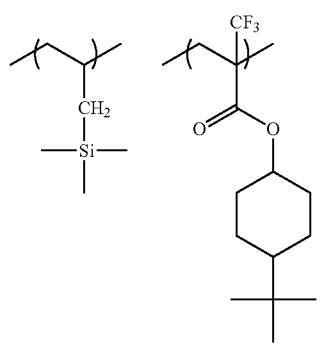
(HR-28) 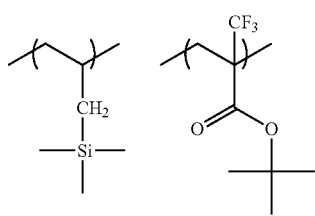
(HR-29) 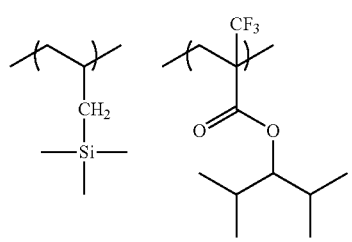
(HR-30) 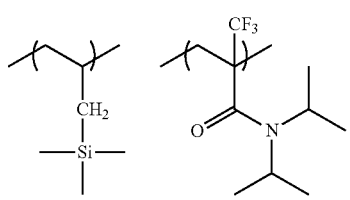
(HR-31) 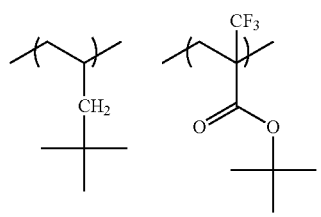
(HR-32) 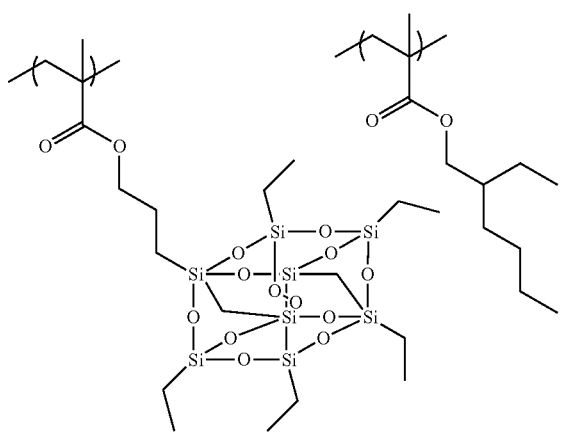
(HR-33) 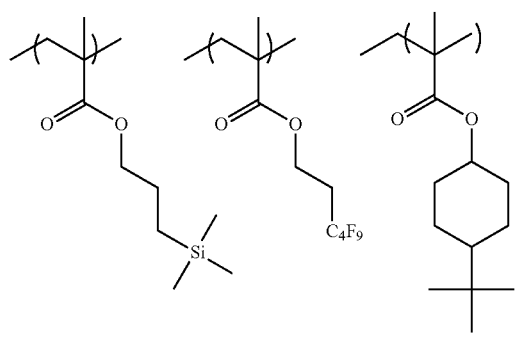
(HR-34) 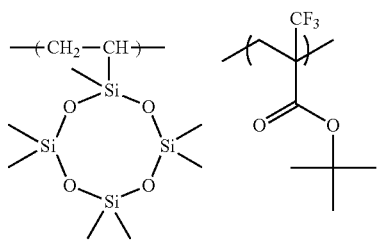

(HR-35)
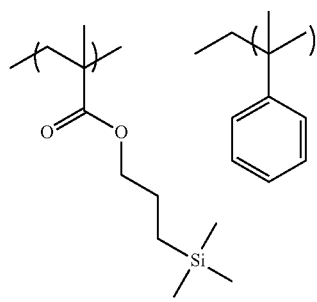
(HR-36)
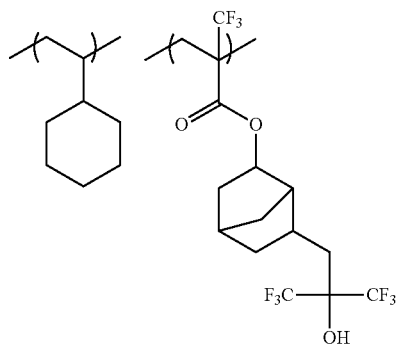
(HR-37)
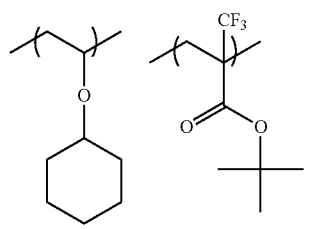
(HR-38)
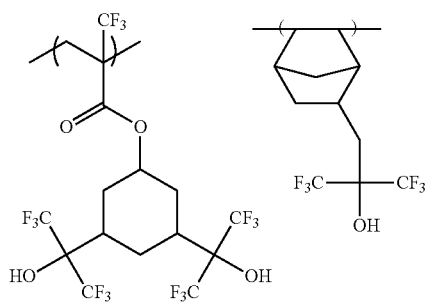
(HR-39)
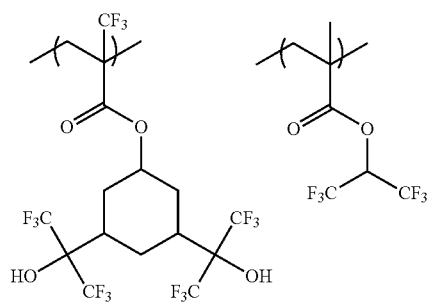
(HR-40)
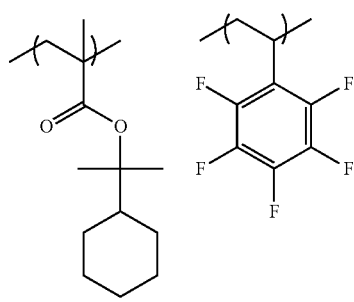
(HR-41)
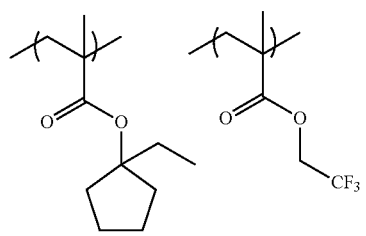
(HR-42)
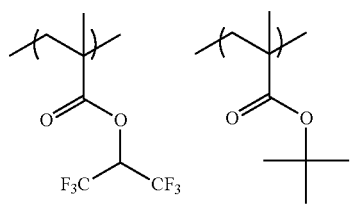
(HR-43)
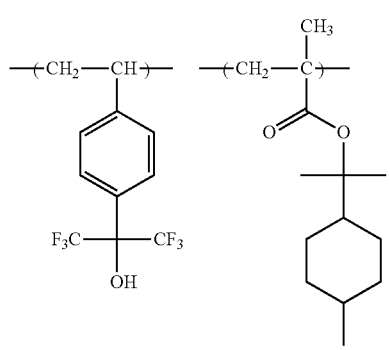
(HR-44)
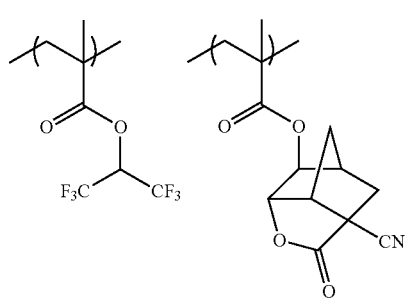

-continued
(HR-45)
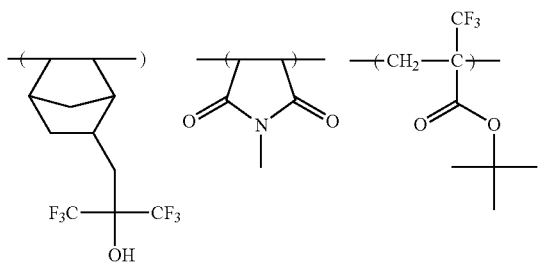
(HR-46)
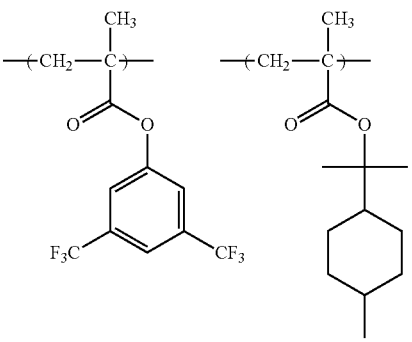
(HR-47)
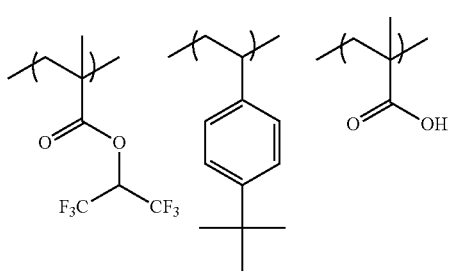
(HR-48)
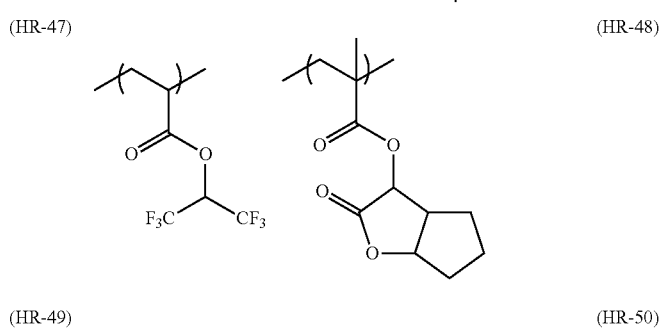
(HR-49)
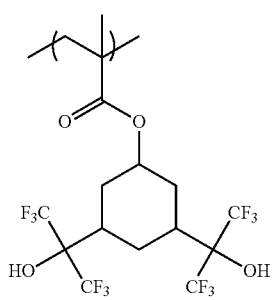
(HR-50)
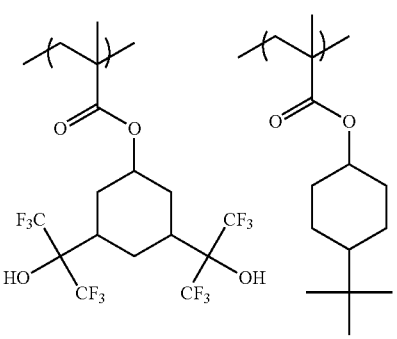
(HR-51)
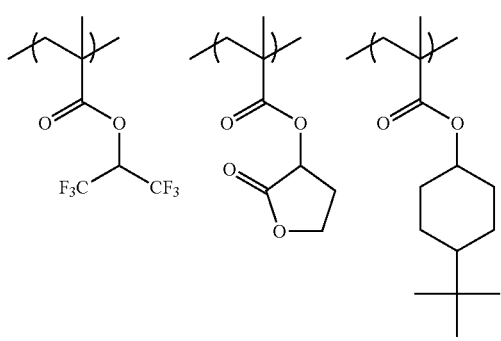
(HR-52)
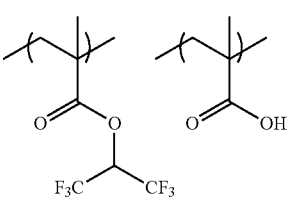
(HR-53)
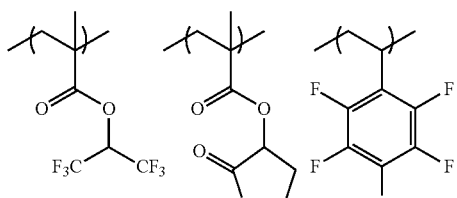
(HR-54)
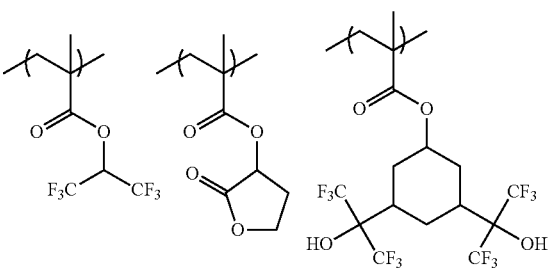

-continued
(HR-55)
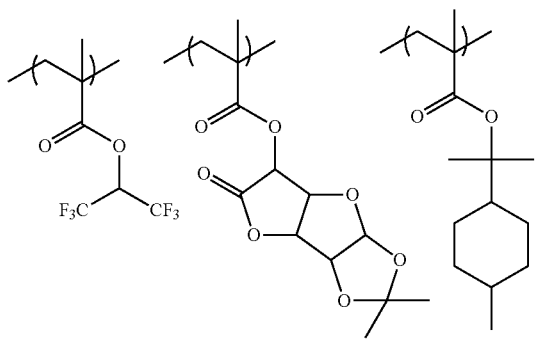
(HR-56)
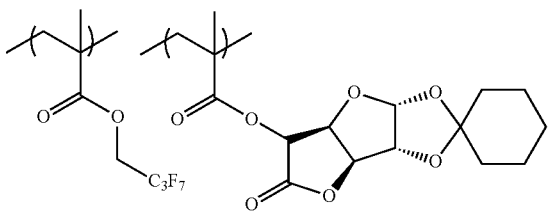
(HR-57)
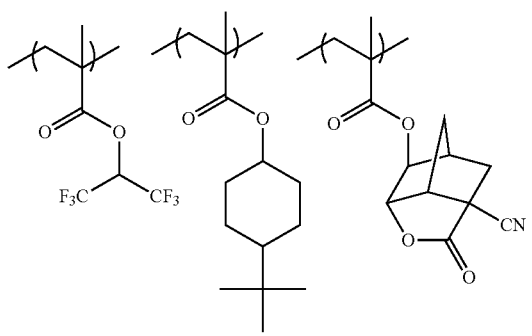
(HR-58)
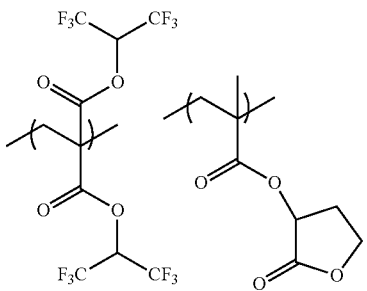
(HR-59)
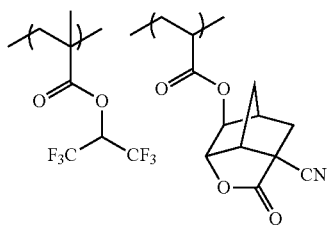
(HR-60)
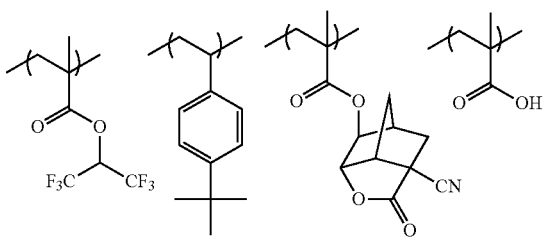
(HR-61)
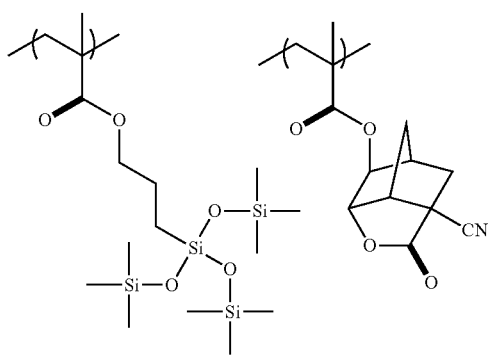
(HR-62)
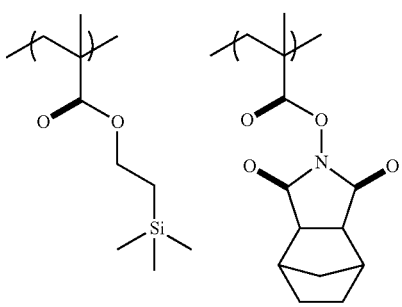
(HR-63)
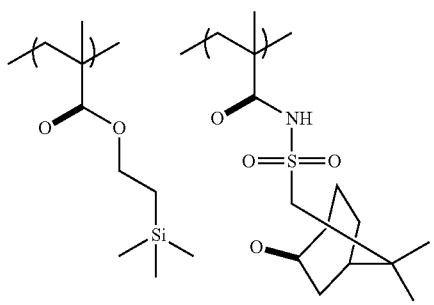
(HR-64)
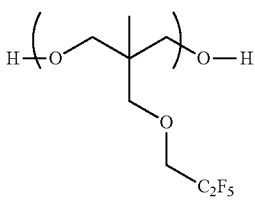

-continued
(HR-65)
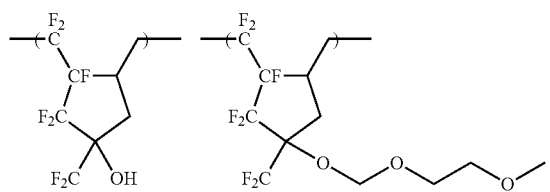
(HR-66)
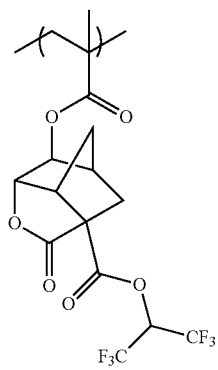
(HR-67)
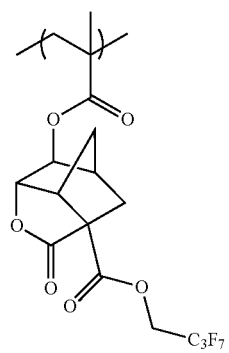
(HR-68)
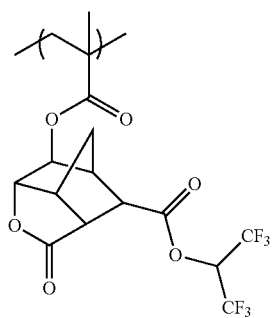
(HR-69)
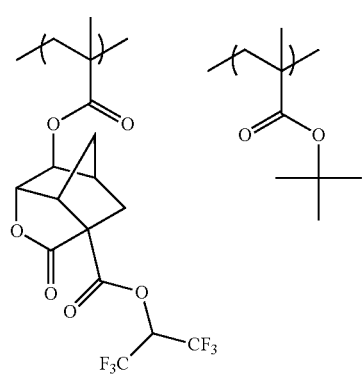
(HR-70)
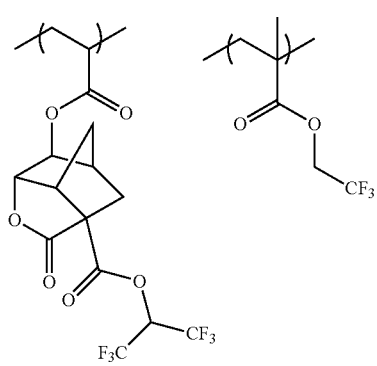
(HR-71)
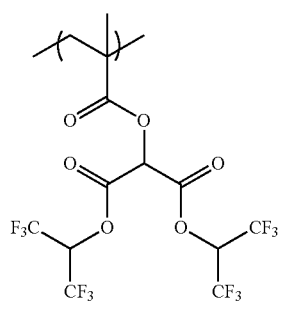
(HR-72)
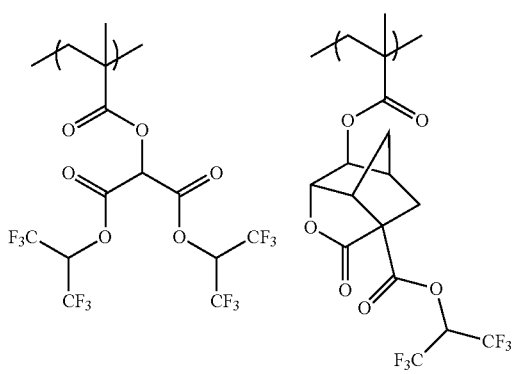

(HR-73)
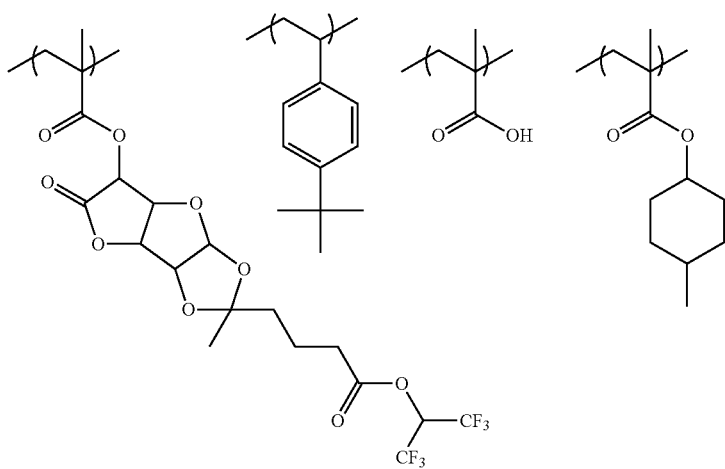
(HR-74)
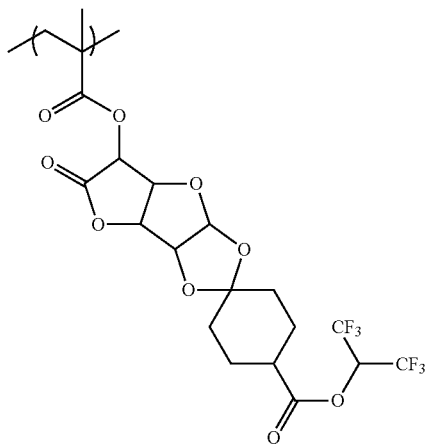
(HR-75)
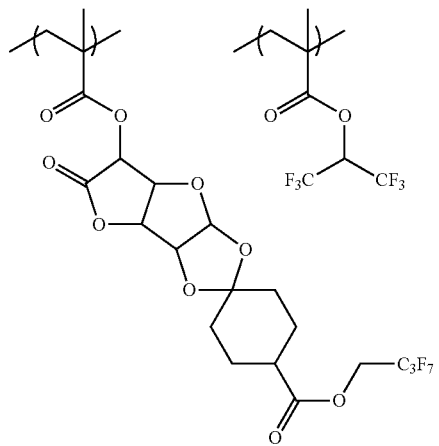
(HR-76)
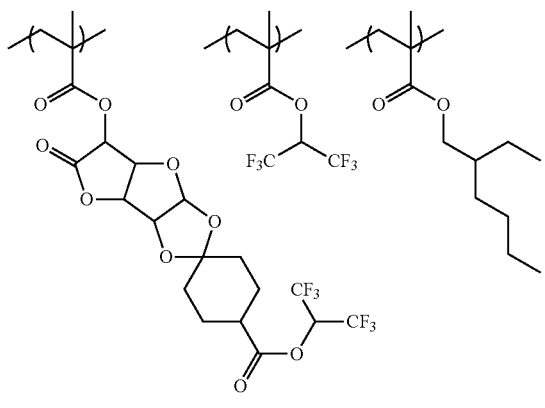
(HR-77)
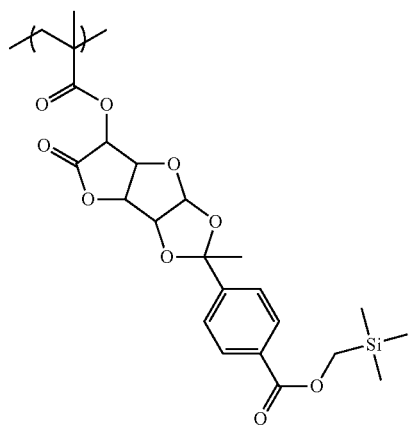

-continued
(HR-78)
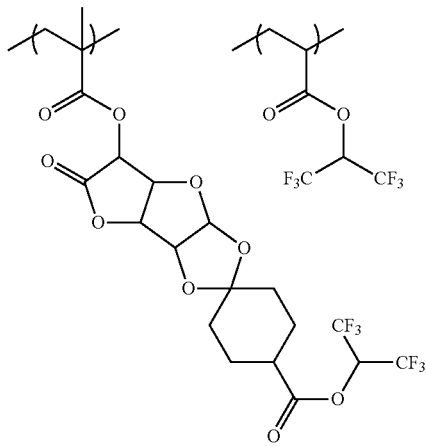
(HR-79)
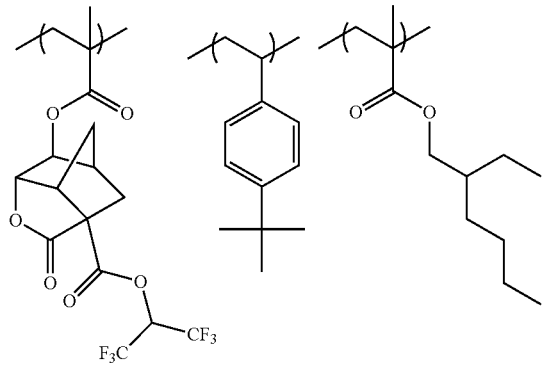
(HR-80)
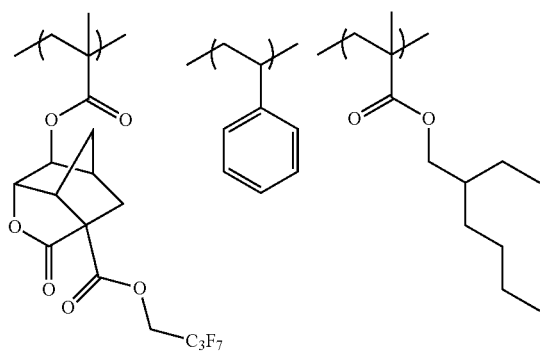
(HR-81)
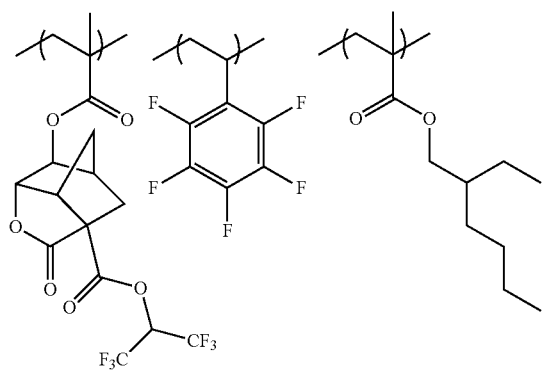
(HR-82)
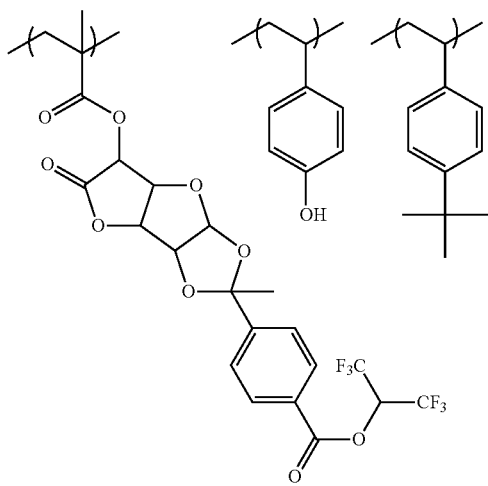
(HR-83)
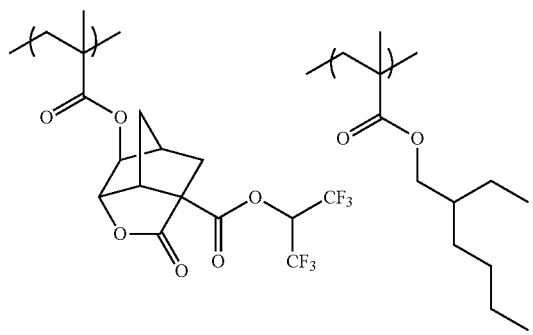

-continued
(HR-84)
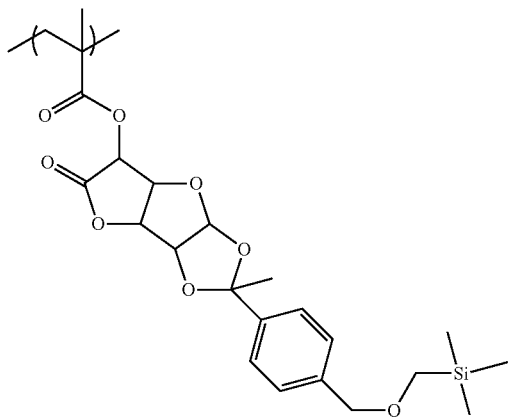
(HR-85)
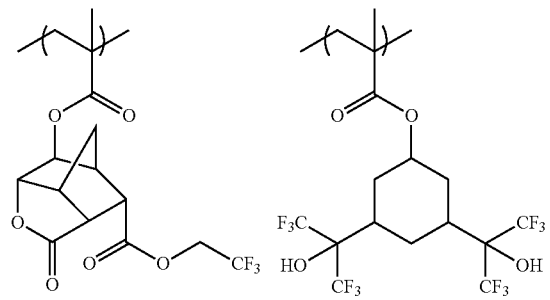
(HR-86)
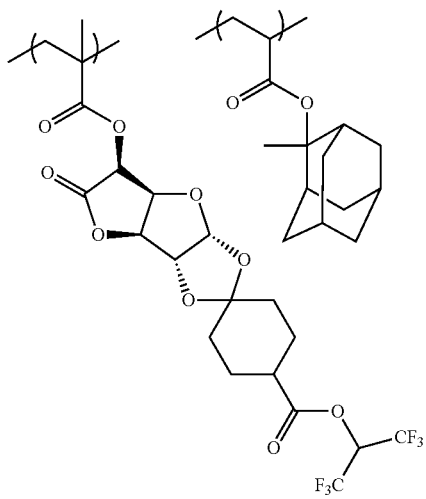
(HR-87)
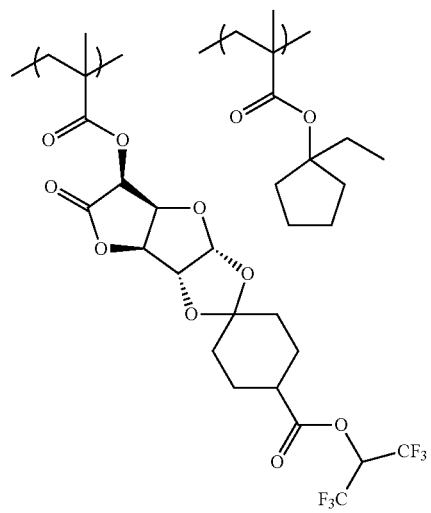
(HR-88)
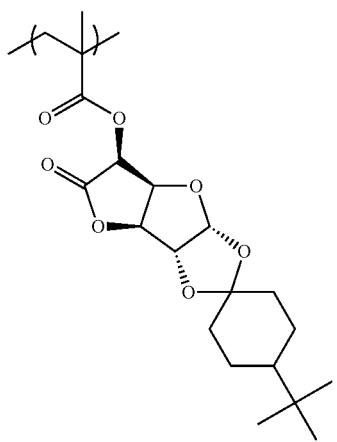
(HR-89)
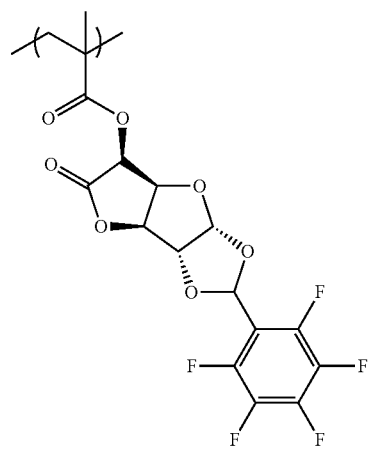

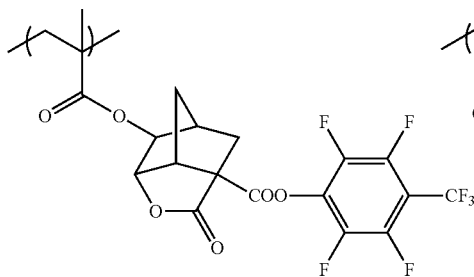
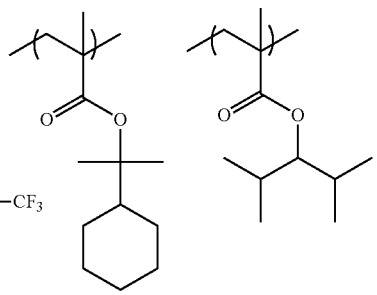

(HR-90)

TABLE 1

| Resin | Composition | Mw | Mw/Mn |
|---|---|---|---|
| HR-1 | 50/50 | 4900 | 1.4 |
| HR-2 | 50/50 | 5100 | 1.6 |
| HR-3 | 50/50 | 4800 | 1.5 |
| HR-4 | 50/50 | 5300 | 1.6 |
| HR-5 | 50/50 | 4500 | 1.4 |
| HR-6 | 100 | 5500 | 1.6 |
| HR-7 | 50/50 | 5800 | 1.9 |
| HR-8 | 50/50 | 4200 | 1.3 |
| HR-9 | 50/50 | 5500 | 1.8 |
| HR-10 | 40/60 | 7500 | 1.6 |
| HR-11 | 70/30 | 6600 | 1.8 |
| HR-12 | 40/60 | 3900 | 1.3 |
| HR-13 | 50/50 | 9500 | 1.8 |
| HR-14 | 50/50 | 5300 | 1.6 |
| HR-15 | 100 | 6200 | 1.2 |
| HR-16 | 100 | 5600 | 1.6 |
| HR-17 | 100 | 4400 | 1.3 |
| HR-18 | 50/50 | 4300 | 1.3 |
| HR-19 | 50/50 | 6500 | 1.6 |
| HR-20 | 30/70 | 6500 | 1.5 |
| HR-21 | 50/50 | 6000 | 1.6 |
| HR-22 | 50/50 | 3000 | 1.2 |
| HR-23 | 50/50 | 5000 | 1.5 |
| HR-24 | 50/50 | 4500 | 1.4 |
| HR-25 | 30/70 | 5000 | 1.4 |
| HR-26 | 50/50 | 5500 | 1.6 |
| HR-27 | 50/50 | 3500 | 1.3 |
| HR-28 | 50/50 | 6200 | 1.4 |
| HR-29 | 50/50 | 6500 | 1.6 |
| HR-30 | 50/50 | 6500 | 1.6 |
| HR-31 | 50/50 | 4500 | 1.4 |
| HR-32 | 30/70 | 5000 | 1.6 |
| HR-33 | 30/30/40 | 6500 | 1.8 |
| HR-34 | 50/50 | 4000 | 1.3 |
| HR-35 | 50/50 | 6500 | 1.7 |
| HR-36 | 50/50 | 6000 | 1.5 |
| HR-37 | 50/50 | 5000 | 1.6 |
| HR-38 | 50/50 | 4000 | 1.4 |
| HR-39 | 20/80 | 6000 | 1.4 |
| HR-40 | 50/50 | 7000 | 1.4 |
| HR-41 | 50/50 | 6500 | 1.6 |
| HR-42 | 50/50 | 5200 | 1.6 |
| HR-43 | 50/50 | 6000 | 1.4 |
| HR-44 | 70/30 | 5500 | 1.6 |
| HR-45 | 50/20/30 | 4200 | 1.4 |
| HR-46 | 30/70 | 7500 | 1.6 |
| HR-47 | 40/58/2 | 4300 | 1.4 |
| HR-48 | 50/50 | 6800 | 1.6 |
| HR-49 | 100 | 6500 | 1.5 |
| HR-50 | 50/50 | 6600 | 1.6 |
| HR-51 | 30/20/50 | 6800 | 1.7 |
| HR-52 | 95/5 | 5900 | 1.6 |
| HR-53 | 40/30/30 | 4500 | 1.3 |
| HR-54 | 50/30/20 | 6500 | 1.8 |
| HR-55 | 30/40/30 | 7000 | 1.5 |
| HR-56 | 60/40 | 5500 | 1.7 |
| HR-57 | 40/40/20 | 4000 | 1.3 |
| HR-58 | 60/40 | 3800 | 1.4 |
| HR-59 | 80/20 | 7400 | 1.6 |

TABLE 1-continued

| Resin | Composition | Mw | Mw/Mn |
|---|---|---|---|
| HR-60 | 40/40/15/5 | 4800 | 1.5 |
| HR-61 | 60/40 | 5600 | 1.5 |
| HR-62 | 50/50 | 5900 | 2.1 |
| HR-63 | 80/20 | 7000 | 1.7 |
| HR-64 | 100 | 5500 | 1.8 |
| HR-65 | 50/50 | 9500 | 1.9 |

TABLE 2

| Resin | Composition | Mw | Mw/Mn |
|---|---|---|---|
| HR-66 | 100 | 6000 | 1.5 |
| HR-67 | 100 | 6000 | 1.4 |
| HR-68 | 100 | 9000 | 1.5 |
| HR-69 | 60/40 | 8000 | 1.3 |
| HR-70 | 80/20 | 5000 | 1.4 |
| HR-71 | 100 | 9500 | 1.5 |
| HR-72 | 40/60 | 8000 | 1.4 |
| HR-73 | 55/30/5/10 | 8000 | 1.3 |
| HR-74 | 100 | 13000 | 1.4 |
| HR-75 | 70/30 | 8000 | 1.3 |
| HR-76 | 50/40/10 | 9500 | 1.5 |
| HR-77 | 100 | 9000 | 1.6 |
| HR-78 | 80/20 | 3500 | 1.4 |
| HR-79 | 90/8/2 | 13000 | 1.5 |
| HR-80 | 85/10/5 | 5000 | 1.5 |
| HR-81 | 80/18/2 | 6000 | 1.5 |
| HR-82 | 50/20/30 | 5000 | 1.3 |
| HR-83 | 90/10 | 8000 | 1.4 |
| HR-84 | 100 | 9000 | 1.6 |
| HR-85 | 80/20 | 15000 | 1.6 |
| HR-86 | 70/30 | 4000 | 1.42 |
| HR-87 | 60/40 | 8000 | 1.32 |
| HR-88 | 100 | 3800 | 1.29 |
| HR-89 | 100 | 6300 | 1.35 |
| HR-90 | 50/40/10 | 8500 | 1.51 |

[5] (e) Basic Compound

The actinic ray-sensitive or radiation-sensitive resin composition of the present invention preferably contains (e) a basic compound so as to reduce the change of performance with aging from exposure to heating.

The basic compound is preferably a compound having a structure represented by the following formulae (A) to (E):

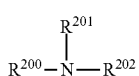

(A)

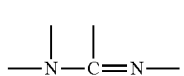

(B)

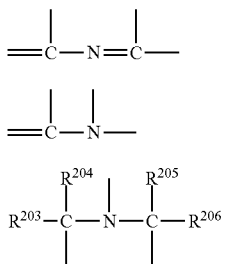

(C)

(D)

(E)

In formulae (A) to (E), each of $R^{200}$, $R^{203}$ and $R^{202}$, which may be the same or different, represents a hydrogen atom, an alkyl group (preferably having a carbon number of 1 to 20), a cycloalkyl group (preferably having a carbon number of 3 to 20) or an aryl group (having a carbon number of 6 to 20), and $R^{201}$ and $R^{202}$ may combine together to form a ring. Each of $R^{203}$, $R^{204}$, $R^{205}$ and $R^{206}$, which may be the same or different, represents an alkyl group having a carbon number of 1 to 20.

As for the alkyl group, the alkyl group having a substituent is preferably an aminoalkyl group having a carbon number of 1 to 20, a hydroxyalkyl group having a carbon number of 1 to 20, or a cyanoalkyl group having a carbon number of 1 to 20.

The alkyl group in formulae (A) and (E) is more preferably unsubstituted.

Preferred examples of the compound include guanidine, aminopyrrolidine, pyrazole, pyrazoline, piperazine, aminomorpholine, aminoalkylmorpholine and piperidine. More preferred examples of the compound include a compound having an imidazole structure, a diazabicyclo structure, an onium hydroxide structure, an onium carboxylate structure, a trialkylamine structure, an aniline structure or a pyridine structure; an alkylamine derivative having a hydroxyl group and/or an ether bond; and an aniline derivative having a hydroxyl group and/or an ether bond.

Examples of the compound having an imidazole structure include imidazole, 2,4,5-triphenylimidazole and benzimidazole. Examples of the compound having a diazabicyclo structure include 1,4-diazabicyclo[2,2,2]octane, 1,5-diazabicyclo[4,3,0]non-5-ene and 1,8-diazabicyclo[5,4,0]undec-7-ene. Examples of the compound having an onium hydroxide structure include a triarylsulfonium hydroxide, a phenacylsulfonium hydroxide, and a 2-oxoalkyl group-containing sulfonium hydroxide, specifically, triphenylsulfonium hydroxide, tris(tert-butylphenyl)sulfonium hydroxide, bis(tert-butylphenyl)iodonium hydroxide, phenacylthiophenium hydroxide and 2-oxopropylthiophenium hydroxide. The compound having an onium carboxylate structure is a compound where the anion moiety of the compound having an onium hydroxide structure replaced by a carboxylate, and examples thereof include an acetate, an adamantane-1-carboxylate and a perfluoroalkyl carboxylate. Examples of the compound having a trialkylamine structure include tri(n-butyl)amine and tri(n-octyl)amine. Examples of the compound having an aniline structure include 2,6-diisopropylaniline, N,N-dimethylaniline, N,N-dibutylaniline and N,N-dihexylaniline. Examples of the alkylamine derivative having a hydroxyl group and/or an ether bond include ethanolamine, diethanolamine, triethanolamine and tris(methoxyethoxyethyl)amine. Examples of the aniline derivative having a hydroxyl group and/or an ether bond include N,N-bis(hydroxyethyl)aniline.

Other preferred basic compounds include a phenoxy group-containing amine compound, a phenoxy group-containing ammonium salt compound, a sulfonic acid ester group-containing amine compound and a sulfonic acid ester group-containing ammonium salt compound.

In the phenoxy group-containing amine compound, phenoxy group-containing ammonium salt compound, sulfonic acid ester group-containing amine compound and sulfonic acid ester group-containing ammonium salt compound, at least one alkyl group is preferably bonded to the nitrogen atom. Also, an oxygen atom is preferably contained in the alkyl chain to form an oxyalkylene group. The number of oxyalkylene groups within the molecule is 1 or more, preferably from 3 to 9, more preferably from 4 to 6. Among oxyalkylene groups, structures of —$CH_2CH_2O$—, —$CH(CH_3)CH_2O$— and —$CH_2CH_2CH_2O$— are preferred.

Specific examples of the phenoxy group-containing amine compound, phenoxy group-containing ammonium salt compound, sulfonic acid ester group-containing amine compound and sulfonic acid ester group-containing ammonium salt compound include, but are not limited to, Compounds (C1-1) to (C3-3) illustrated in paragraph [0066] of U.S. Patent Application Publication 2007/0224539.

In addition, a nitrogen-containing organic compound having a group capable of leaving by the action of an acid, which is a kind of a basic compound, can be also used. Examples of this compound include a compound represented by the following formula (F). Incidentally, the compound represented by the following formula (F) exhibits an effective basicity in the system as a result of elimination of the group capable of leaving by the action of an acid.

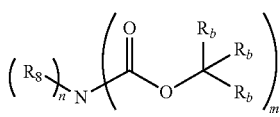

(F)

In formula (F), each Ra independently represents a hydrogen atom, an alkyl group, a cycloalkyl group, an aryl group or an aralkyl group. Also, when n=2, two Ra's may be the same or different, and two Ra's may combine with each other to form a divalent heterocyclic hydrocarbon group (preferably having a carbon number of 20 or less) or a derivative thereof.

Each Rb independently represents a hydrogen atom, an alkyl group, a cycloalkyl group, an aryl group or an aralkyl group, provided that in —C(Rb)(Rb)(Rb), when one or more Rb's are a hydrogen atom, at least one of remaining Rb's is a cyclopropyl group or a 1-alkoxyalkyl group.

At least two Rb's may combine to form an alicyclic hydrocarbon group, an aromatic hydrocarbon group, a heterocyclic hydrocarbon group or a derivative thereof.

n represents an integer of 0 to 2, m represents an integer of 1 to 3, and n+m=3.

In formula (F), each of the alkyl group, cycloalkyl group, aryl group and aralkyl group represented by Ra and Rb may be substitute with a functional group such as hydroxyl group, cyano group, amino group, pyrrolidino group, piperidino group, morpholino group and oxo group, an alkoxy group or a halogen atom.

Examples of the alkyl group, cycloalkyl group, aryl group and aralkyl group (each of these alkyl, cycloalkyl, aryl and aralkyl groups may be substituted with the above-described functional group, an alkoxy group or a halogen atom) of R include:

a group derived from a linear or branched alkane such as methane, ethane, propane, butane, pentane, hexane, heptane, octane, nonane, decane, undecane and dodecane, or a group where the group derived from an alkane is substituted with one or more kinds of or one or more cycloalkyl groups such as cyclobutyl group, cyclopentyl group and cyclohexyl group;

a group derived from a cycloalkane such as cyclobutane, cyclopentane, cyclohexane, cycloheptane, cyclooctane, norbornane, adamantane and noradamantane, or a group where the group derived from a cycloalkane is substituted with one or more kinds of or one or more linear or branched alkyl groups such as methyl group, ethyl group, n-propyl group, i-propyl group, n-butyl group, 2-methylpropyl group, 1-methylpropyl group and tert-butyl group;

a group derived from an aromatic compound such as benzene, naphthalene and anthracene, or a group where the group derived from an aromatic compound is substituted with one or more kinds of or one or more linear or branched alkyl groups such as methyl group, ethyl group, n-propyl group, i-propyl group, n-butyl group, 2-methylpropyl group, 1-methylpropyl group and tert-butyl group;

a group derived from a heterocyclic compound such as pyrrolidine, piperidine, morpholine, tetrahydrofuran, tetrahydropyran, indole, indoline, quinoline, perhydroquinoline, indazole and benzimidazole, or a group where the group derived from a heterocyclic compound is substituted with one or more kinds of or one or more linear or branched alkyl groups or aromatic compound-derived groups; a group where the group derived from a linear or branched alkane or the group derived from a cycloalkane is substituted with one or more kinds of or one or more aromatic compound-derived groups such as phenyl group, naphthyl group and anthracenyl group; and a group where the substituent above is substituted with a functional group such as hydroxyl group, cyano group, amino group, pyrrolidine group, piperidino group, morpholino group and oxo group.

Examples of the divalent heterocyclic hydrocarbon group (preferably having a carbon number of 1 to 20) formed by combining Ra's with each other or a derivative thereof include a group derived from a heterocyclic compound such as pyrrolidine, piperidine, morpholine, 1,4,5,6-tetrahydropyrimidine, 1,2,3,4-tetrahydroquinoline, 1,2,3,6-tetrahydropyridine, homopiperazine, 4-azabenzimidazole, benzotriazole, 5-azabenzotriazole, 1H-1,2,3-triazole, 1,4,7-triazacyclononane, tetrazole, 7-azaindole, indazole, benzimidazole, imidazo[1,2-a]pyridine, (1S,4S)-(+)-2,5-diazabicyclo[2.2.1]heptane, 1,5,7-triazabicyclo[4.4.0]dec-5-ene, indole, indoline, 1,2,3,4-tetrahydroquinoxaline, perhydroquinoline and 1,5,9-triazacyclododecane, and a group where the group derived from a heterocyclic compound is substituted with one or more kinds of or one or more linear or branched alkane-derived groups, cycloalkane-derived groups, aromatic compound-derived groups, heterocyclic compound-derived groups or functional groups such as hydroxyl group, cyano group, amino group, pyrrolidino group, piperidino group, morpholino group and oxo group.

Specific examples particularly preferred in the present invention include N-tert-butoxycarbonyldi-n-octylamine, N-tert-butoxycarbonyldi-n-nonylamine, N-tert-butoxycarbonyldi-n-decylamine, N-tert-butoxycarbonyldicyclohexylamine, N-tert-butoxycarbonyl-1-adamantylamine-tert-butoxycarbonyl-2-adamantylamine, N-tert-butoxycarbonyl-N-methyl-1-adamantylamine, (S)-(−)-1-(tert-butoxycarbonyl)-2-pyrrolidinemethanol, (R)-(+)-1-(tert-butoxycarbonyl)-2-pyrrolidinemethanol, N-tert-butoxycarbonyl-4-hydroxypiperidine, N-tert-butoxycarbonylpyrrolidine, N-tert-butoxycarbonylmorpholine, N-tert-butoxylcarbonylpiperazine, N,N-di-tert-butoxycarbonyl-1-adamantylamine, N,N'-di-tert-butoxycarbonyl-N-methyl-1-adamantylamine, N-tert-butoxycarbonyl-4,4'-diaminodiphenylmethane, N,N'-di-tert-butoxycarbonylhexamethylenediamine, N,N,N',N'-tetra-tert-butoxycarbonylhexamethylenediamine, N,N'-di-tert-butoxy carbonyl-1,7-diaminoheptane, N,N'-di-tert-butoxycarbonyl-1,8-diaminooctane, N,N'-di-tert-butoxycarbonyl-1,9-diaminononane, N,N'-di-tert-butoxycarbonyl-1,10-diaminodecane, N,N'-di-tert butoxycarbonyl-1,12-diaminododecane, N,N'-di-tert-butoxycarbonyl-4,4'-diaminodiphenylmethane, N-tert-butoxycarbonylbenzimidazole, N-tert-butoxycarbonyl-2-methylbenzimidazole and N-tert-butoxycarbonyl-2-phenylbenzimidazole.

As for the compound represented by formula (F), a commercial product may be used, or the compound may be synthesized from a commercially available amine by the method described, for example, in Protective Groups in Organic Synthesis, 4th edition. The compound may be synthesized by the method described, for example, in JP-A-2009-199021, which is a most general method.

The molecular weight of the basic compound is preferably from 250 to 2,000, more preferably from 400 to 1,000. From the standpoint of more reducing LWR, the molecular weight of the basic compound is preferably 400 or more, more preferably 500 or more, still more preferably 600 or more.

One of these basic compounds is used alone, or two or more thereof are used in combination.

The amount of the basic compound used is usually from 0.001 to 10 mass %, preferably from 0.01 to 5 mass %, based on the solid content of the actinic ray-sensitive or radiation-sensitive resin composition.

The ratio between the acid generator and the basic compound used in the composition is preferably acid generator/basic compound (by mol)=from 2.5 to 300. That is, the molar ratio is preferably 2.5 or more in view of sensitivity and resolution and preferably 300 or less from the standpoint of suppressing the reduction in resolution due to thickening of the resist pattern with aging after exposure until heat treatment. The acid generator/basic compound (by mol) is more preferably from 5.0 to 200, still more preferably from 7.0 to 150.

[6] (f) Surfactant

The actinic ray-sensitive or radiation-sensitive resin composition of the present invention may or may not further contain a surfactant and in the case of containing a surfactant, it is preferred to contain any one of fluorine-containing and/or silicon-containing surfactants (a fluorine-containing surfactant, a silicon-containing surfactant or a surfactant containing both a fluorine atom and a silicon atom), or two or more thereof.

By virtue of containing a surfactant, the actinic ray-sensitive or radiation-sensitive resin composition of the present invention can give a resist pattern with good sensitivity, resolution and adherence as well as little development defect when used for exposure to a light source of 250 nm or less, particularly 220 nm or less.

Examples of the fluorine-containing and/or silicon-containing surfactants include the surfactants described in paragraph [0276] of U.S. Patent Application Publication 2008/0248425, such as EFtop EF301 and EF303 (produced by Shin-Akita Kasei K.K.); Florad FC430, 431 and 4430 (produced by Sumitomo 3M Inc.); Megaface F171, F173, F176, F189, F113, F110, F177, F120 and R08 (produced by Dainippon Ink & Chemicals, Inc.); Surflon S-382, SC101, 102, 103, 104, 105 and 106 (produced by Asahi Glass Co., Ltd.); Troysol S-366 (produced by Troy Chemical); GF-300 and GF-150 (produced by Toagosei Chemical Industry Co., Ltd.); Surflon 5-393 (produced by Seimi Chemical Co., Ltd.); EFtop EF121, EF122A, EF122B , RF122C, EF125M, EF135M, EF351, EF352, EF801, EF802 and EF601 (produced by JEMCO Inc.); PF636, PF656, PF6320 and PF6520 (produced by OMNOVA); and FTX-204G, 208G, 218G, 230G, 204D, 208D, 212D, 218D and 222D (produced by NEOS Co., Ltd.). In addition, Polysiloxane Polymer KP-341 (produced by Shin-Etsu Chemical Co., Ltd.) may be also used as the silicon-containing surfactant.

As for the surfactant, other than these known surfactants, a surfactant using a polymer having a fluoro-aliphatic group derived from a fluoro-aliphatic compound which is produced by a telomerization process (also called a telomer process) or an oligomerization process (also called an oligomer process), may be used. The fluoro-aliphatic compound can be synthesized by the method described in JP-A-2002-90991.

Examples of the surfactant coming under this type include Megaface F178, F-470, F-473, F-475, F-476 and F-472 (produced by Dainippon Ink & Chemicals, Inc.), a copolymer of $C_6F_{13}$ group-containing acrylate (or methacrylate) with a (poly(oxyalkylene)) acrylate (or methacrylate), and a copolymer of a $C_3F_7$ group-containing acrylate (or methacrylate) with a (poly(oxyethylene)) acrylate (or methacrylate) and a (poly(oxypropylene)) acrylate (or methacrylate).

In the present invention, a surfactant other than the fluorine-containing and/or silicon-containing surfactants, described in paragraph [0280] of U.S. Patent Application Publication 2008/0248425, may be also used.

One of these surfactants may be used alone, or some of them may be used in combination.

In the case where the actinic ray-sensitive or radiation-sensitive resin composition contains a surfactant, the amount of the surfactant used is preferably from 0.0001 to 2 mass %, more preferably from 0.0005 to 1 mass %, based on the entire amount of the actinic ray-sensitive or radiation-sensitive resin composition (excluding the solvent).

On the other hand, by setting the amount added of the surfactant to 10 ppm or less based on the entire amount of the actinic ray-sensitive or radiation-sensitive resin composition (excluding the solvent), the hydrophobic resin is more unevenly distributed to the surface, so that the resist film surface can be made more hydrophobic and the followability of water at the immersion exposure can be enhanced.

[7] (g) Other Additives

The actinic ray-sensitive or radiation-sensitive resin composition of the present invention may or may not contain an onium carboxylate. Examples of onium carboxylate include those described in paragraphs [0605] and [0606] of U.S. Patent Application Publication No. 2008/0187860.

Such an opium carboxylate can be synthesized by reacting a sulfonium, iodonium or ammonium hydroxide and a carboxylic acid with silver oxide in an appropriate solvent.

In the case where thy actinic ray-sensitive or radiation-sensitive resin composition contains an onium carboxylate, the content thereof is generally from 0.1 to 20 mass %, preferably from 0.5 to 10 mass %, more preferably from 1 to 7 mass %, based on the entire solid content of the composition.

The actinic ray-sensitive or radiation-sensitive resin composition of the present invention may further contain, for example, a dye, a plasticizer, a photosensitizer, a light absorber, an alkali-soluble resin, a dissolution inhibitor, and a compound capable of accelerating dissolution for a developer (for example, a phenol compound having a molecular weight of 1,000 or less, or a carboxyl group-containing alicyclic or aliphatic compound), if desired.

The phenol compound having a molecular weight of 1,000 or less can be easily synthesized by one skilled in the art by referring to the method described, for example, in JP-A-4-122938, JP-A-2-28531, U.S. Pat. No. 4,916,210 and European Patent 219294.

Specific examples of the carboxyl group-containing alicyclic or aliphatic compound include, but are not limited to, a carboxylic acid derivative having asteroid structure, such as cholic acid, deoxycholic acid and lithocholic acid, an adamantanecarboxylic acid derivative, adamantanedicarboxylic acid, a cyclohexanecarboxylic acid and a cyclohexanedicarboxylic acid.

The solid content concentration of the actinic ray-sensitive or radiation-sensitive resin composition of the present invention is usually from 1.0 to 10 mass %, preferably from 2.0 to 5.7 mass %, more preferably from 2.0 to 5.3 mass %. When the solid content concentration is in this range, the resist solution can be uniformly applied on a substrate and moreover, a resist pattern improved in the line edge roughness can be formed. The reasons therefor are not clearly known, but it is considered that by setting the solid content concentration to 10 mass % or less, preferably 5.7 mass % or less, the materials, particularly the photoacid generator, in the resist solution are prevented from aggregation, as a result, a uniform resist film can be formed.

The solid content concentration is a weight percentage of the weight of resist components excluding solvents, based on the total weight of the actinic ray-sensitive or radiation-sensitive resin composition.

[8] Pattern Forming Method

The pattern forming method (negative pattern forming method) of the present invention comprises at least:

(i) a step of forming a film (resist film) from an actinic ray-sensitive or radiation-sensitive resin composition, (ii) a step of exposing the film, and (iii) a step of performing development by using an organic solvent-containing developer.

The resist film is formed from the above-described actinic ray-sensitive or radiation sensitive resin composition of the present invention and, more specifically, is preferably formed on a substrate. In the pattern forming method of the present invention, the step of forming a film from an actinic ray-sensitive or radiation-sensitive resin composition on a substrate, the step of exposing the film, and the development, step can be performed by a generally known method.

The present invention also relates to an actinic ray-sensitive or radiation-sensitive resin composition used for the pattern forming method. That is, the present invention also relates to an actinic ray-sensitive or radiation-sensitive resin composition for organic solvent development, containing (A) a compound capable of generating an acid upon irradiation with an actinic ray or radiation and decomposing by the action of an acid to decrease the solubility for an organic solvent. The term "for organic solvent development" as used herein means to use the composition at least for the step (iii) above.

It is also preferred to include, after film formation, a pre-baking step (PB) before entering the exposure step.

Furthermore, it is also preferred to include a post-exposure baking step (PEB) after the exposure step but before the development step.

As for the heating temperature, both PB and PEB are preferably performed at 70 to 120° C., more preferably at 80 to 110° C.

The heating time is preferably from 30 to 300 seconds, more preferably from 30 to 180 seconds, still more preferably from 30 to 90 seconds.

The heating can be performed using a device attached to an ordinary exposure/developing machine or may be performed using a hot plate or the like.

Thanks to baking, the reaction in the exposed area is accelerated, and the sensitivity and pattern profile are improved.

The light source wavelength of the exposure apparatus for use in the present invention is not limited, but, for example, a KrF excimer laser wavelength (248 nm), an ArF excimer laser wavelength (193 nm) and an $F_2$ excimer laser wavelength (157 nm) are applicable.

In the present invention, an immersion exposure method can be applied in the step of performing exposure.

The immersion exposure method is a technique to increase the resolution, and this is a technique of performing, the exposure by filling a high refractive-index liquid (hereinafter, sometimes referred to as an "immersion liquid") between the projection lens and the sample.

As for the "effect of immersion", assuming that $\lambda_0$ is the wavelength of exposure light in air, n is the refractive index of the immersion liquid for air, θ is the convergence half-angle of beam and $NA_0 = \sin θ$, the resolution and the depth of focus in immersion can be expressed by the following formulae. Here, $k_1$ and $k_2$ are coefficients related to the process.

(Resolution)=$k_1 \cdot (\lambda_0/n)/NA_0$ (Depth of focus)=$\pm k_2 \cdot (\lambda_0/n) NA_0^2$ That is, the effect of immersion is equal to use of an exposure wavelength of 1/n. In other words, in the case of a projection optical system having the same NA, the depth of focus can be made n times larger by the immersion. This is effective for all pattern profiles and furthermore, can be combined with the super-resolution technology under study at present, such as phase-shift method and modified illumination method.

In the case of performing immersion exposure, a step of washing the film surface with an aqueous chemical solution may be performed (1) after forming the film on a substrate but before the step of performing exposure and/or (2) after the step of exposing the film through an immersion liquid but before the step of heating the film.

The immersion liquid is preferably a liquid being transparent to light at the exposure wavelength and having as small a temperature coefficient of refractive index as possible in order to minimize the distortion of an optical image projected on the film. Particularly, when the exposure light source is an ArF excimer laser (wavelength: 193 nm), water is preferably used in view of easy availability and easy handleability in addition to the above-described aspects.

In the case of using water, an additive (liquid) capable of decreasing the surface tension of water and increasing the interface activity may be added in a small ratio. This additive is preferably a liquid that does not dissolve the resist layer on the wafer and at the same time, gives only a negligible effect on the optical coat on the undersurface of the lens element.

Such an additive is preferably, for example, an aliphatic alcohol having a refractive index nearly equal to that of water, and specific examples thereof include methyl alcohol, ethyl alcohol and isopropyl alcohol. By virtue of adding an alcohol having a refractive index nearly equal to that of water, even when the alcohol component in water is evaporated and its content concentration is changed, the change in the refractive index of the liquid as a whole can be advantageously made very small.

On the other hand, if a substance opaque to light at 193 nm or an impurity greatly differing in the refractive index from water is mingled, this incurs distortion of the optical image projected on the resist. Therefore, the water used is preferably distilled water. Furthermore, pure water after filtration through an ion exchange filter or the like may be also used.

In the present invention, the substrate on which the film is formed is not particularly limited, and an inorganic substrate such as silicon, SiN, $SiO_2$ and SiN, a coating-type inorganic substrate such as SOG, or a substrate generally used in the process of producing a semiconductor such as IC or producing a liquid crystal device or a circuit board such as thermal head or in the lithography of other photo-fabrication processes can be used. If desired, an organic antireflection film may be formed between the film and the substrate.

In the case where the pattern forming method of the present invention further includes a step of performing development by using an alkali developer, examples of the alkali developer which can be used include an alkaline aqueous solution of inorganic alkalis such as sodium hydroxide, potassium hydroxide, sodium carbonate, sodium silicate, sodium metasilicate and aqueous ammonia, primary amines such as ethylamine and n-propylamine, secondary amines such as diethylamine and di-n-butylamine, tertiary amines such as triethylamine and methyldiethylamine, alcohol amines such as dimethylethanolamine and triethanolamine, quaternary ammonium salts such as tetramethylammonium hydroxide and tetraethylammonium hydroxide, or cyclic amines such as pyrrole and piperidine.

This alkaline aqueous solution may be also used after adding thereto alcohols and a surfactant each in an appropriate amount.

The alkali concentration of the alkali developer is usually from 0.1 to 20 mass %.

The pH of the alkali developer is usually from 10.0 to 15.0.

In particular, an aqueous solution of 2.38 mass % tetramethylammonium hydroxide is preferred.

As for the rinsing solution in the rinsing treatment performed after the alkali development, pure water is used, and the pure water may be used after adding thereto an appropriate amount of a surfactant.

As for the developer in the step of performing development by using an organic solvent-containing developer (hereinafter, sometimes referred to as an "organic developer"), a polar solvent such as ketone-based solvent, ester-based solvent, alcohol-based solvent, amide-based solvent and ether-based solvent, or a hydrocarbon-based solvent can be used.

Examples of the ketone-based solvent include 1-octanone, 2-octanone, 1-nonanone, 2-nonanone, acetone, 2-heptanone (methyl amyl ketone), 4-heptanone, 1-hexanone, 2-hexanone, diisobutyl ketone, cyclohexanone, methylcyclohexanone, phenylacetone, methyl ethyl ketone, methyl isobutyl ketone, acetyl acetone, acetonyl acetone, ionone, diacetonyl alcohol, acetyl carbinol, acetophenone, methyl naphthyl ketone, isophorone and propylene carbonate.

Examples of the ester-based solvent include methyl acetate, butyl acetate, ethyl acetate, isopropyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl format; ethyl formate, butyl formate, propyl formate, ethyl lactate, butyl lactate and propyl lactate.

Examples of the alcohol-based solvent include an alcohol such as methyl alcohol, ethyl alcohol, n-propyl alcohol, isopropyl alcohol, n-butyl alcohol, sec-butyl alcohol, tert-butyl alcohol, isobutyl alcohol, n-hexyl alcohol, n-heptyl alcohol, n-octyl alcohol and n-decanol; a glycol-based solvent such as ethylene glycol, diethylene glycol and triethylene glycol; and a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether and methoxymethyl butanol.

Examples of the ether-based solvent include dioxane and tetrahydrofuran, in addition to the glycol ether-based solvents above.

Examples of the amide-based solvent which can be used include N-methyl-2-pyrrolidone, N,N-dimethylacetamide, N,N-dimethylformamide, hexamethylphosphoric triamide and 1,3-dimethyl-2-imidazolidinone.

Examples of the hydrocarbon-based solvent include an aromatic hydrocarbon-based solvent such as toluene and xylene, and an aliphatic hydrocarbon-based solvent such as pentane, hexane, octane and decane.

A plurality of these solvents may be mixed, or the solvent may be used by mixing it with a solvent other than those described above or with water. However, in order to sufficiently bring out the effects of the present invention, the water content ratio in the entire developer is preferably less than 10 mass %, and it is more preferred to contain substantially no water.

That is, the amount of the organic solvent used in the organic developer is preferably from 90 to 100 mass %, more preferably from 95 to 100 mass %, based on the entire amount of the developer.

In particular, the organic developer is preferably a developer containing at least one kind of an organic solvent selected from the group consisting of a ketone-based solvent, an ester-based solvent, an alcohol-based solvent, an amide-based solvent and an ether-based solvent.

The vapor pressure at 20° C. of the organic developer is preferably 5 kPa or less, more preferably 3 kPa or less, still more preferably 2 kPa or less. By setting the vapor pressure of the organic developer to 5 kPa or less, evaporation of the developer on a substrate or in a development cup is suppressed and the temperature uniformity in the wafer plane is enhanced, as a result, the dimensional uniformity in the wafer plane is improved.

Specific examples of the solvent having a vapor pressure of 5 kPa or less include a ketone-based solvent such as 1-octanone, 2-octanone, 1-nonanone, 2-nonanone, 2-heptanone(methyl amyl ketone), 4-heptanone, 2-hexanone, diisobutyl ketone, cyclohexanone, methylcyclohexanone, phenylacetone and methyl isobutyl ketone; an ester-based solvent such as butyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, butyl formate, propyl formate, ethyl lactate, butyl lactate and propyl lactate; an alcohol-based solvent such as n-propyl alcohol, isopropyl alcohol, n-butyl alcohol, sec-butyl alcohol, tert-butyl alcohol, isobutyl alcohol, n-hexyl alcohol, n-heptyl alcohol, n-octyl alcohol and n-decanol; a glycol-based solvent such as ethylene glycol, diethylene glycol and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether and methoxymethylbutanol; an ether-based solvent such as tetrahydrofuran; an amide-based solvent, such as N-methyl-2-pyrrolidone, N,N-dimethylacetamide and N,N-dimethylformamide; an aromatic hydrocarbon-based solvent such as toluene and xylene; and an aliphatic hydrocarbon-based solvent such as octane and decane.

Specific examples of the solvent having a vapor pressure of 2 kPa or less that is a particularly preferred range include a ketone-based solvent such as 1-octanone, 2-octanone, 1-nonanone, 2-nonanone, 4-heptanone, 2-hexanone, diisobutyl ketone, cyclohexanone, methylcyclohexanone and phenylacetone; an ester-based solvent such as butyl acetate, amyl, acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, ethyl lactate, butyl lactate and propyl lactate; an alcohol-based solvent such as n-butyl alcohol, sec-butyl alcohol, tert-butyl alcohol, isobutyl alcohol, n-hexyl alcohol, n-heptyl alcohol, n-octyl alcohol and n-decanol; a glycol-based solvent such as ethylene glycol, diethylene glycol and triethylene glycol; a glycol ether-based solvent such as ethylene glycol monomethyl ether, propylene glycol monomethyl ether, ethylene glycol monoethyl ether, propylene glycol monoethyl ether, diethylene glycol monomethyl ether, triethylene glycol monoethyl ether and methoxymethylbutanol; an amide-based solvent such as N-methyl-2-pyrrolidone, N,N-dimethylacetamide and N,N-dimethylformamide; an aromatic hydrocarbon-based solvent such as xylene; and an aliphatic hydrocarbon-based solvent such as octane and decane.

In the organic developer, a surfactant may be added in an appropriate amount, if desired.

The surfactant is not particularly limited but, for example, ionic or nonionic fluorine-containing and/or silicon-containing surfactants can be used. Examples of such fluorine-containing and/or silicon-containing surfactants include surfactants described in JP-A-62-36663. JP-A-61-226746, JP-A-61-226745, JP-A-62-170950, JP-A-63-34540, JP-A-7-230165, JP-A-8-62834, JP-A-9-54432, JP-A-9-5988 and U.S. Pat. Nos. 5,405,720, 5,360,692, 5,529,881, 5,296,330, 5,436,098, 5,576,143, 5,294,511 and 5,824,451. A nonionic surfactant is preferred. The nonionic surfactant is not particularly limited, but use of a fluorine-containing surfactant or a silicon-containing surfactant is more preferred.

The amount of the surfactant used is usually from 0.001 to 5 mass %, preferably from 0.005 to 2 mass %, more preferably from 0.01 to 0.5 mass %, based on the entire amount of the developer.

As regards the developing method, for example, a method of dipping the substrate in a bath filled with the developer for a fixed time (dipping method), a method of raising the developer on the substrate surface by the effect of a surface tension and keeping it still for a fixed time, thereby performing development (puddle method), a method of spraying the developer on the substrate surface (spraying method), and a method of continuously ejecting the developer on the substrate spinning at a constant speed while scanning the developer ejecting nozzle at a constant rate (dynamic dispense method) may be applied.

In the case where the above-described various developing methods include a step of ejecting the developer toward the resist film from a development nozzle of a developing apparatus, the ejection pressure of the developer ejected (the flow velocity per unit area of the developer ejected) is preferably 2 mL/sec/mm$^2$ or less, more preferably 1.5 mL/sec/mm$^2$ or less, still more preferably 1 mL/sec/mm$^2$ or less. The flow velocity has no particular lower limit but in view of throughput, is preferably 0.2 mL/sec/mm$^2$ or more.

By setting the ejection pressure of the ejected developer to the range above, pattern defects attributable to the resist scum after development can be greatly reduced.

Details of this mechanism are not clearly known, but it is considered that thanks to the ejection pressure in the above-described range, the pressure imposed on the resist film by the developer becomes small and the resist film or resist pattern is kept from inadvertent chipping or collapse.

Here, the ejection pressure (mL/sec/mm$^2$) of the developer is a value at the outlet of a development nozzle in a developing apparatus.

Examples of the method for adjusting the ejection pressure of the developer include a method of adjusting the ejection pressure by a pump or the like, and a method of supplying the developer from a pressurized tank and adjusting the pressure to change the ejection pressure.

After the step of performing development by using an organic solvent-containing developer, a step of stopping the development by replacing the solvent with another solvent may be practiced.

A step of rinsing the film with a rinsing solution is preferably provided after the step of performing development by using an organic solvent-containing developer.

The rinsing solution used in the rinsing step after the step of performing development by using an organic solvent-containing developer is not particularly limited as long as it does not dissolve the resist pattern, and a solution containing a general organic solvent may be used. As for the rinsing solution, a rinsing solution containing at least one kind of an organic solvent selected from the group consisting of a hydrocarbon-based solvent, a ketone-based solvent, an ester-based solvent, an alcohol-based solvent, an amide-based solvent and an ether-based solvent is preferably used.

Specific examples of the hydrocarbon-based solvent, ketone-based solvent, ester-based solvent, alcohol-based solvent, amide-based solvent and ether-based solvent are the same as those described above for the organic solvent-containing developer.

After the step of performing development by using an organic solvent-containing developer, more preferably, a step of rinsing the film by using a rinsing solution containing at least one kind of an organic solvent selected from the group consisting of a ketone-based solvent, an ester-based solvent, an alcohol-based solvent and an amide-based solvent is preformed; still more preferably, a step of rinsing the film by using a rinsing solution containing an alcohol-based solvent or an ester-based solvent is performed; yet still more preferably, a step of rinsing the film by using a rinsing solution containing a monohydric alcohol is performed; and most preferably, a step of rinsing the film by using a rinsing solution containing a monohydric alcohol having a carbon number of 5 or more is performed.

The monohydric alcohol used in the rinsing step includes a linear, branched or cyclic monohydric alcohol, and specific examples of the monohydric alcohol which can be used include 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol and 4-octanol. As for the particularly preferred monohydric alcohol having a carbon number of 5 or more, 1-hexanol, 2-hexanol, 4-methyl-2-pentanol, 1-pentanol, 3-methyl-1-butanol and the like can be used.

A plurality of these components may be mixed, or the solvent may be used by mixing it with an organic solvent other than those described above.

The water content ratio in the rinsing solution is preferably 10 mass % or less, more preferably 5 mass % or less, still more preferably 3 mass % or less. By setting the water content ratio to 10 mass % or less, good development characteristics can be obtained.

The vapor pressure at 20° C. of the rinsing solution used after the step of performing development by using an organic solvent-containing developer is preferably from 0.05 to 5 kPa, more preferably from 0.1 to 5 kPa, and most preferably from 0.12 to 3 kPa. By setting the vapor pressure of the rinsing solution to the range from 0.05 to 5 kPa, the temperature uniformity in the wafer plane is enhanced and moreover, swelling due to permeation of the rinsing solution is suppressed, as a result, the dimensional uniformity in the wafer plane is improved.

The rinsing solution may be also used after adding thereto an appropriate amount of a surfactant.

In the rinsing step, the wafer after development using an organic solvent-containing developer is rinsed using the above-described organic solvent-containing rinsing solution. The method for rinsing, treatment is not particularly limited, but examples of the method which can be applied include a method of continuously ejecting the rinsing solution on the substrate spinning at a constant speed (spin coating method), a method of dipping the substrate in a bath filled with the rinsing solution for a fixed time (dipping method), and a method of spraying the rinsing solution on the substrate surface (spraying method). Above all, it is preferred to perform the rinsing treatment by the spin coating method and after the rinsing, remove the rinsing solution from the substrate surface by spinning the substrate at a rotational speed of 2,000 to 4,000 rpm. It is also preferred to include a heating step (Post Bake) after the rinsing step. The developer and rinsing solution remaining between patterns and in the inside of the pattern are removed by the baking. The heating step after the rinsing step is performed at usually from 40 to 160° C., preferably from 70 to 95° C., for usually from 10 seconds to 3 minutes, preferably from 30 to 90 seconds.

EXAMPLES

The present invention is described in greater detail below by referring to Examples, but the present invention should not be construed as being limited thereto.

<Acid-Decomposable Resin>

Resins (P-1) to (P-7) shown below were synthesized as follows.

P-1
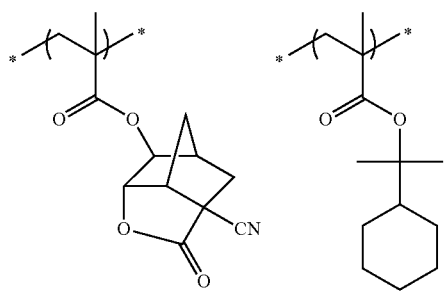
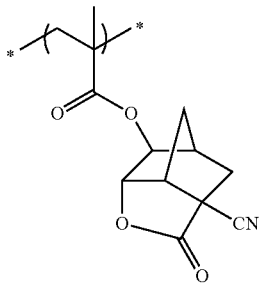
P-2
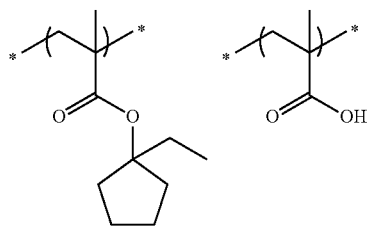
P-3
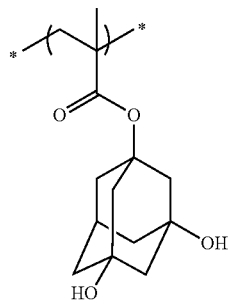
P-4
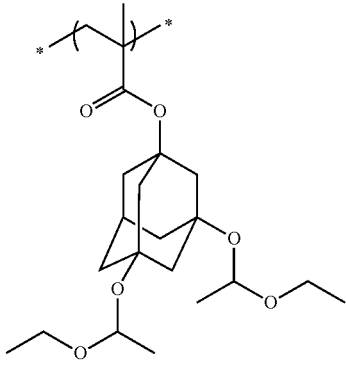
P-5
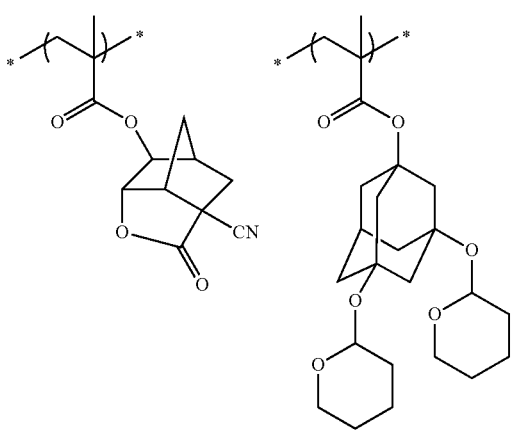
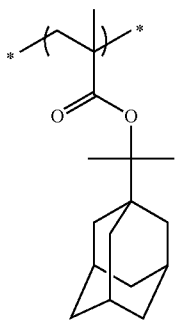

-continued

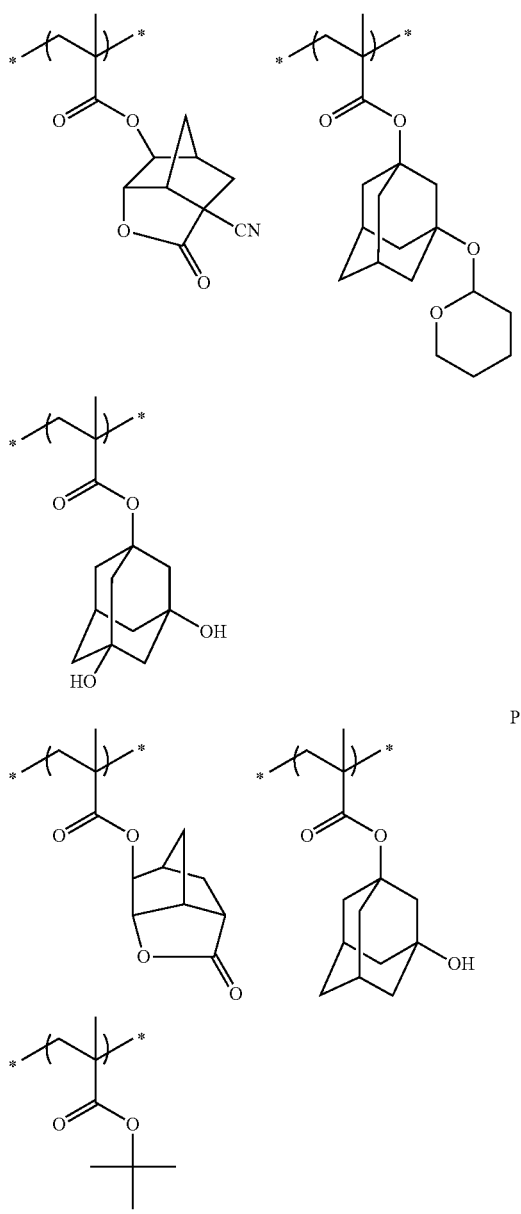

The weight average molecular weight Mw, polydispersity Mw/Mn, and compositional ratio of respective repeating units (molar ratio, corresponding to repeating units from the left) in each of Resins (P-1) to (P-7) are shown together in Table 3 below.

TABLE 3

| Compound No. | Mw | Mw/Mn | Compositional Ratio | | | |
|---|---|---|---|---|---|---|
| P-1 | 9200 | 1.78 | 40 | 60 | | |
| P-2 | 10200 | 1.75 | 35 | 10 | 50 | 5 |
| P-3 | 9500 | 1.68 | 40 | 10 | 30 | 20 |
| P-4 | 6800 | 1.81 | 40 | 60 | | |
| P-5 | 9800 | 1.65 | 40 | 50 | 10 | |
| P-6 | 8300 | 1.72 | 10 | 70 | 20 | |
| P-7 | 12100 | 1.69 | 40 | 10 | 50 | |

[Synthesis Example of Acid-Decomposable Resin]

In a nitrogen stream, a three-neck flask was charged with 200 g of cyclohexanone and heated at 80° C. In this way, Solvent 1 was obtained. Subsequently, monomer-1 shown below (44.5 g) and monomer-2 shown below (56.8 g) were dissolved in cyclohexanone (373 g) to prepare a monomer solution. Furthermore, a solution obtained by adding and dissolving polymerization initiator V-601 (produced by Wako Pure Chemical Industries, Ltd.) in an amount of 6.6 mol % based on the total amount of monomers was added dropwise to Solvent 1 over 6 hours. After the completion of dropwise addition, the reaction was further allowed to proceed at 80° C. for 2 hours. The reaction solution obtained was allowed to cool and then added dropwise to a mixed solvent of 7,736 g of heptane/859 g of ethyl acetate, and the powder precipitated was collected by filtration and dried to obtain 72 g of Resin (P-1), The weight average molecular weight of Resin (P-1) was 9,200, the polydispersity (Mw/Mn) was 1.78, and the compositional ratio measured by $^{13}$C-NMR was 40/60.

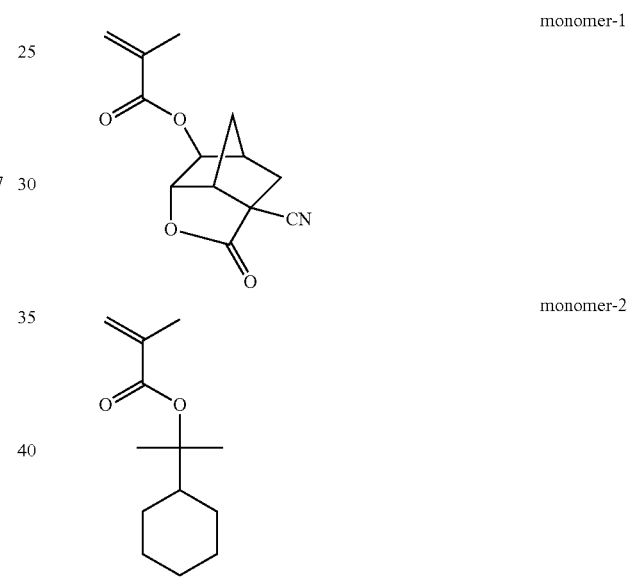

Resins (P-2) to (P-6) were synthesized in the same manner as Resin (P-1). The weight average molecular weight, the polydispersity (Mw/Mn) and the compositional ratio of each of these resins are as shown in Table 3.

<Acid Generator>

Compounds (b-1) to (b-39) illustrated above and Compounds (Cb-1) and (Cb-2) shown below were synthesized as follows.

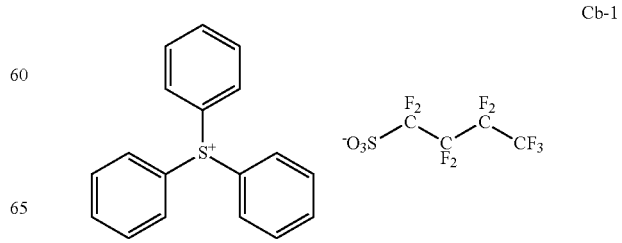

-continued

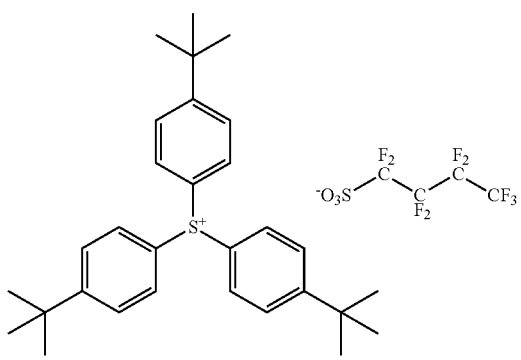

Cb-2

[Synthesis Example of Acid Generator]

Synthesis Example 1

Synthesis of [4-(2-cyclohexyloxymethoxyethyl)phenyl]diphenylsulfonium 1,1,2,2,3,3-hexafluoro-3-(piperidine-1-sulfonyl)-propane-1-sulfonate (b-1)

A solution prepared by dissolving 5.12 g (25.3 mmol) of diphenyl sulfoxide in 25.0 g (152 mmol) of 2-phenylethyl acetate was added dropwise to 10.63 g (50.6 mmol) of trifluoroacetic anhydride at 0 to 5° C., and the resulting mixture was stirred at 0 to 5° C. for 30 minutes. Subsequently, 3.8 g (25.3 mmol) of trifluoromethanesulfonic acid was added dropwise at 0 to 5° C., and the resulting mixture was stirred at 0 to 20° C. for 3 hours. After the reaction, 200 ml of n-hexane was poured, and the system was subjected to decantation and then concentration under reduced pressure.

A solution prepared by dissolving 30 ml of methanol and 3.0 g (76 mmol) of sodium hydroxide in 30 ml of water was added to the oil obtained above, and the resulting mixture was stirred at room temperature for 2 hours. After the reaction, methanol was removed by distillation, and 1 N hydrochloric acid was added until pH reached 2. The obtained aqueous layer was extracted with 40 ml of chloroform, washed with water and concentrated under reduced pressure to obtain 8.40 g (yield: 73%) of (4-hydroxyethyl)benzene-diphenylsulfonium trifluoromethanesulfonate.

$^1$H-NMR (400 MHz in $(CD_3)_2CO$): δ (ppm)=2.8-3.0 (Br, 1H) 2.96 (t, 2H), 3.85 (t, H), 7.4-7.8 (m, 14H).

Thereafter, 7.4 g (16.2 mmol) of the obtained [(4-hydroxyethyl)phenyl]diphenylsulfonium trifluoromethanesulfonate and 2.93 g (22.7 mmol) of diisopropylethylamine were dissolved in 50 ml of tetrahydrofuran, and 2.88 g (19.4 mmol) of chloromethoxycyclohexane was added thereto. The resulting mixture was stirred at 40° C. for 3 hours, and the reaction solution obtained was cooled to room temperature and after adding 200 ml of water, extracted with 200 ml of chloroform. The extract was washed with water, concentrated under reduced pressure and then purified by column chromatography (ethyl acetate/methanol=20/1) to obtain 8.2 g (yield: 89%) of [4-(2-cyclohexyloxymethoxyethyl)phenyl]diphenylsulfonium trifluoromethanesulfonate.

Furthermore, 5.69 g (10 mmol) of the obtained [4-(2-cyclohexyloxymethoxyethyl)phenyl]diphenylsulfonium trifluoromethanesulfonate was dissolved in an aqueous methanol solution, and the resulting solution was passed through an activated anion exchange resin (Amberlite IRA410CL, produced by Aldrich). To the obtained eluate, 4.41 g (10 mmol) of sodium 1,1,2,2,3,3-hexafluoro-3-(piperidine-1-sulfonyl)-propane-1-sulfonate was added, and the resulting mixture was stirred at room temperature for 1 hour. After the reaction, the solvent was removed by distillation, and the residue was dissolved in 50 ml of methylene chloride, washed with water 4 times, concentrated under reduced pressure and then purified by column chromatography (ethyl acetate/methanol 20/1) to obtain 6.2 g (yield: 78%) of [4-(2-cyclohexyloxymethoxyethyl)phenyl]diphenylsulfonium 1,1,2,2,3,3-hexafluoro-3-(piperidine-1-sulfonyl)-propane-1-sulfonate.

$^1$H-NMR (400 MHz in $(CD_3)_2CO$): δ (ppm)=1.0-1.9 (m, 16H), 2.8-3.9 (m, 9H), 4.69 (s, 2H), 7.5-7.8 (m, 14H).

Synthesis Example 2

Synthesis of Compound (b-35)

Compound (b-35) was synthesized according to the following scheme.

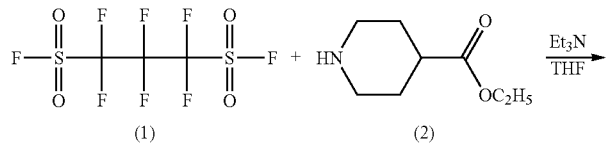

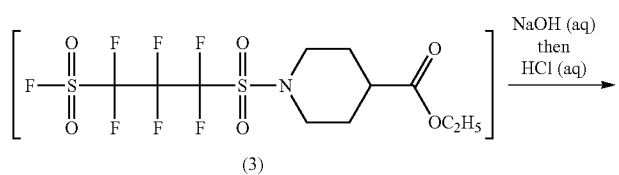

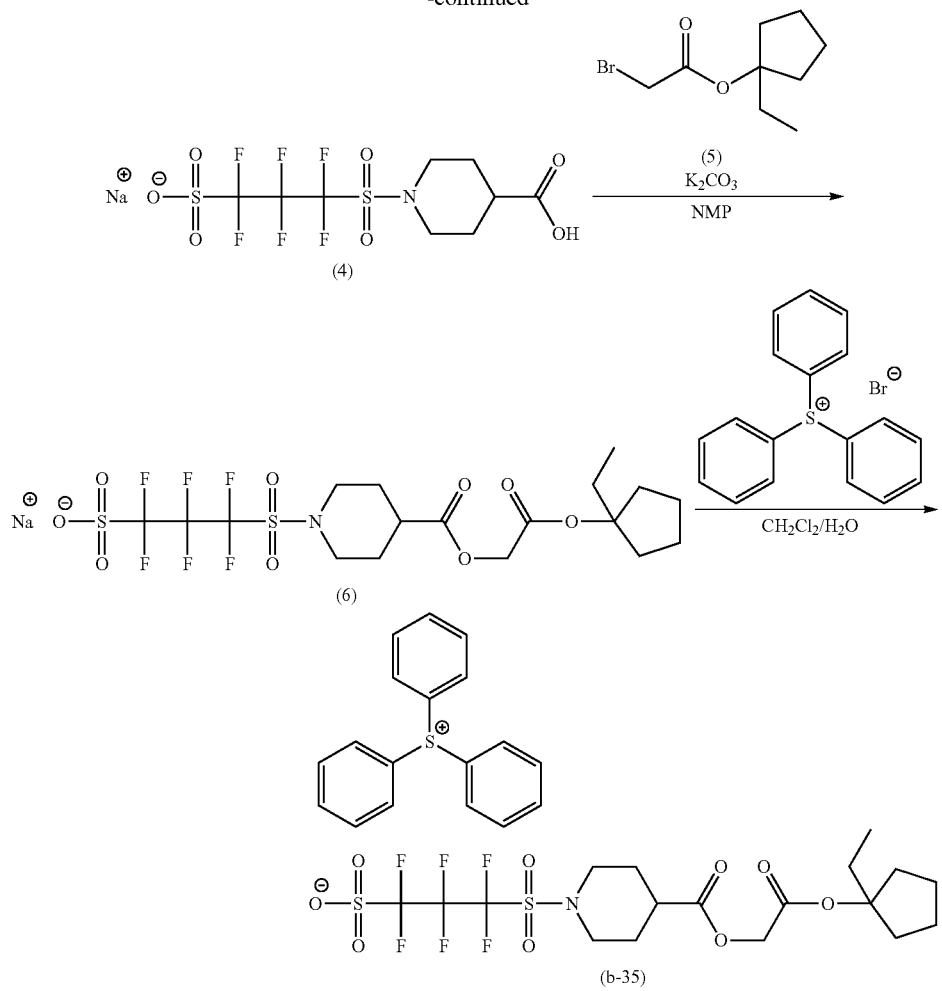

Synthesis of Compound (4):

In a 1,000 ml-volume eggplant-shaped flask, 55 g (174 mmol) of 1,1,2,2,3,3-hexafluoropropane-1,3-disulfonyl difluoride (1) was dissolved in 180 g of THF (tetrahydrofuran) and after cooling in an ice bath, a solution prepared by dissolving 27.3 g (174 mmol) of ethyl isonipecotinate (2) and 35.2 g (358 mmol) of triethylamine in 100 g of THF was added dropwise. After stirring at room temperature for 6 hours, an aqueous sodium hydroxide solution (35 g (87 mmol) of sodium hydroxide, 200 g of water) was added, and the mixed solution was further stirred at room temperature for 4 hours. Thereto, 96 g (1.000 mmol) of methanesulfonic acid was added under cooling in an ice bath and after adding 300 ml of ethyl acetate, the organic layer was separated. The organic layer was washed with 200 g of saturated brine three times and then concentrated to obtain 72 g (162 mmol, 93%, white crystal) of Compound (4).

Synthesis of Compound (5):

In a 1,000 ml-volume eggplant-shaped flask, 10 g (87 mmol) of 1-ethylcyclopentanol and 33 g (217 mmol) of 1,8-diazabicyclo[5.4.0]-7-undecene were dissolved in 200 g of NMP (N-methylpyrrolidone), and 44 g (217 mmol) of bromoacetyl bromide was added dropwise under cooling in an ice bath. The resulting mixture was stirred at room temperature for 4 hours, and the reaction solution was cooled in an ice bath. Thereto, sodium bicarbonate water was slowly added, and 500 ml of hexane was further added. The organic layer was separated, washed with 200 ml of water three times, dried using magnesium sulfate and then concentrated to obtain 24.1 g of Compound (5) as a crude product. Without purifying Compound (5), the next reaction was performed.

Synthesis of Compound (6):

In a 1,000 ml-volume eggplant-shaped flask, 24.1 g of Compound (5) as a crude product and 39 g (87 mmol) of Compound (4) were dissolved in 300 g of NMP, and 12 g (87 mmol) of potassium carbonate was added thereto. The resulting mixture was stirred at room temperature for 2 hours, and 300 g of water and 300 g of ethyl acetate were added to the reaction solution to separate the organic layer. The organic layer was washed with 300 g of water three times and then concentrated to obtain 70.2 g of Compound (6) as a crude product. Without purifying Compound (6), the next reaction was performed.

Synthesis of Compound (b-35):

In a 1,000 ml-volume eggplant-shaped flask, 70.2 g of Compound (6) as a crude product and 30.1 g (87 mmol) of triphenylsulfonium bromide were dissolved in 200 methylene chloride, and 200 g of water was added thereto. The resulting mixture was stirred at room temperature for 3 hours, and the organic layer was separated, washed with 200 g of water three times and concentrated to obtain Compound (b-35) as a crude product. The obtained Compound (b-35) as a crude product was purified using column chromatography to obtain 54.1 g (64.3 mmol, 73.4%, light brown liquid) of Compound (b-35).

$^1$H-NMR (400 MHz, in DMSO-d6): δ (ppm)=7.90-7.75 (m, 15H), 4.61 (s, 2H), 3.90-3.66 (br, 2H), 3.45-3.14 (br, 2H), 2.83-2.75 (m, 1H), 2.09-1.95 (m, 4H), 1.91 (q, 2H), 1.66-1.50 (m, 8H), 0.82 (t, 3H).

Other acid generators were synthesized in the same manner.

<Basic Compound>

Compounds (N-1) to (N-8) shown below were prepared as the basic compound.

N-1
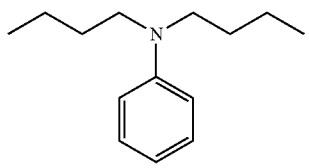

N-2
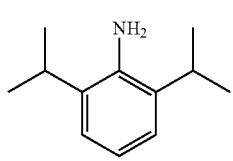

N-3
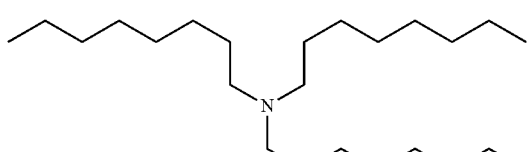

N-4
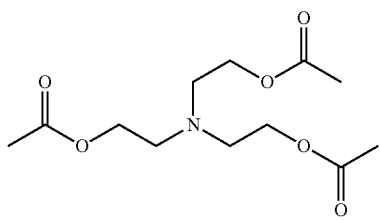

N-5
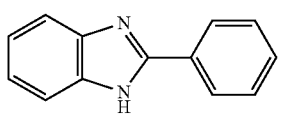

N-6
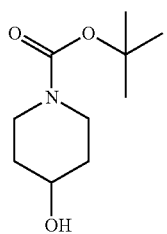

N-7
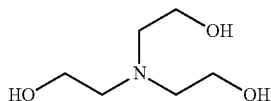

N-8
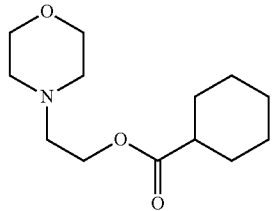

<Hydrophobic Resin>

The hydrophobic resin was appropriately selected from Resins (HR-1) to (HR-90) and used.

Incidentally, Hydrophobic Resin (HR-83) was synthesized based on the description, for example, in U.S. Patent Application Publication No. 2010/0152400 and International Publication Nos. 2010/067905 and 2010/067898.

<Surfactant>

The followings were prepared as the surfactant.
W-1: Megaface F176 (produced by Dainippon Ink & Chemicals, Inc.) (fluorine-containing)
W-2: Megaface R08 (produced by Dainippon Ink & Chemicals, Inc.) (fluorine- and silicon-containing)
W-3: Polysiloxane Polymer KP-341 (produced by Shin-Etsu Chemical Co., Ltd.) (silicon-containing)
W-4: Troysol S-366 (produced by Troy Chemical)
W-5: KH-20 (produced by Asahi Kasei Chemicals Corporation)
W-6: PolyFox PF-6320 (produced by OMNOVA solution inc., fluorine-containing)

<Solvent>

The followings were prepared as the solvent.
(Group a)
SL-1: Propylene glycol monomethyl ether acetate (PGMEA)
SL-2: Propylene glycol monomethyl ether propionate
SL-3: 2-Heptanone
(Group b)
SL-4: Ethyl lactate
SL-5: Propylene glycol monomethyl ether (PGME)
SL-6: Cyclohexanone
(Group c)
SL-7: γ-Butyrolactone
SL-8: Propylene carbonate <Developer>

The followings were prepared as the developer.
SG-1: Butyl acetate
SG-2: Methyl amyl ketone
SG-3: Ethyl-3-ethoxypropionate
SG-4: Pentyl acetate
SG-5: Isopentyl acetate
SG-6: Propylene glycol monomethyl ether acetate
SG-7: Cyclohexane <Rinsing Solution>

SR-1: 4-Methyl-2-pentanol
SR-2: 1-Hexanol
SR-3: Butyl acetate
SR-4: Methyl amyl ketone
SR-5: Ethyl-3-ethoxypropionate <Negative Development>

(Preparation of Resist)

The components shown in Table 4 below were dissolved in the solvent shown in the same Table to give a solid content of 3.5 mass %, and the solution was filtered through a polyethylene filter having a pore size of 0.03 μm to prepare an actinic ray-sensitive or radiation-sensitive resin composition. An organic antireflection film, ARC29SR (produced by Nissan Chemical Industries, Ltd.), was applied on a silicon wafer and baked at 205° C. for 60 seconds to form a 95 nm-thick antireflection film, and the actinic ray-sensitive or radiation-sensitive resin composition was applied thereon and baked (PB) at 100° C. for 60 seconds to form a resist film having a thickness of 100 nm.

The obtained wafer was subjected to pattern exposure using an ArF excimer laser immersion scanner (XT1700i, manufactured by ASML, NA: 1.20, C-Quad, outer sigma: 0.981, inner sigma: 0.895, XY deflection) through an exposure mask (binary mask, line/space=60 nm/60 nm). As the immersion liquid, ultrapure water was used. Thereafter, the wafer was heated (PEB) at 100° C. for 60 seconds, developed by puddling the developer for 30 seconds, rinsed by puddling the rising solution for 30 seconds while throwing off the developer, then spun at a rotational speed of 4,000 rpm for 30 seconds and baked at 90° C. for 60 seconds. In this way, a line-and-space resist pattern with a line width of 60 nm (1:1) was obtained.

(Evaluation of Resist)

[Sensitivity ($E_{opt}$)]

The obtained pattern was observed using a scanning electron microscope (SEM, S-9380II, manufactured by Hitachi Ltd.), and the irradiation energy when resolving a line-and-space resist pattern with a line width of 60 nm (1:1) was taken as Sensitivity ($E_{opt}$) A smaller value indicates higher sensitivity.

[Resolution (Pre-Bridge Dimension)]

In the line-and-space resist pattern with a line width of 60 nm (1:1) at the sensitivity above ($E_{opt}$), the minimum space dimension before generation of a bridge defect was observed by changing the exposure dose. A smaller value indicates less generation of bridge defect and better performance.

[Line Edge Roughness]

In the measurement of line edge roughness (nm), the line-and-space 1/1 pattern with a line width of 60 nm obtained above was observed using a Critical Dimension scanning electron microscope (SEM), the distance from the reference line where the edge should be present was measured at 50 points by a Critical Dimension SEM (S-8840, manufactured by Hitachi, Ltd.) with respect to the longitudinal edge in the range of 5 μm of the line pattern, the standard deviation was obtained, and 3σ was computed. A smaller value indicates better performance.

[Development Time Dependency]

After exposure was performed in the same manner as above with an exposure dose giving the above-described sensitivity, development was performed by puddling the developer, and a value obtained by dividing the difference between the line width when puddling the developer for 30 seconds and the line width when puddling the developer for 60 seconds, by 30 was taken as the development time dependency. A smaller value indicates better performance in terms of development dependency.

(Development time dependency [nm/sec])=((line width [nm] when developed for 60 seconds)−(line width [nm] when developed for 30 seconds))/30 [sec]

These evaluations results are shown in Table 4.

TABLE 4

| Example | Acid-Decomposable Resin | (g) | Acid Generator | (g) | Hydrophobic Resin | (g) | Basic Compound | (g) | Surfactant | (g) | Solvent | (mass ratio) |
|---|---|---|---|---|---|---|---|---|---|---|---|---|
| 1 | P-1 | 10 | b-1 | 0.9 | HR-3 | 0.06 | N-1 | 0.15 | W-2 | 0.05 | SL-1/SL-5 | 60/40 |
| 2 | P-3 | 10 | b-2 | 1 | HR-24 | 0.06 | N-2 | 0.15 | W-3 | 0.04 | SL-1/SL-6 | 80/20 |
| 3 | P-4 | 10 | b-3 | 1.2 | HR-9 | 0.06 | N-3 | 0.15 | W-1 | 0.05 | SL-1/SL-7 | 90/10 |
| 4 | P-5 | 10 | b-4 | 0.8 | HR-26 | 0.06 | N-4 | 0.15 | W-4 | 0.05 | SL-1/SL-5 | 80/20 |
| 5 | P-6 | 10 | b-32 | 1 | HR-3 | 0.06 | N-2 | 0.15 | W-6 | 0.05 | SL-2/SL-5 | 70/30 |
| 6 | P-2 | 10 | b-6 | 1 | HR-24 | 0.06 | N-5 | 0.15 | W-5 | 0.05 | SL-3/SL-4 | 80/20 |
| 7 | P-6 | 10 | b-8 | 0.8 | HR-3 | 0.06 | N-6 | 0.15 | W-6 | 0.06 | SL-1 | 100 |
| 8 | P-3 | 10 | b-11 | 1 | HR-24 | 0.06 | N-7 | 0.15 | W-2 | 0.05 | SL-1/SL-8 | 90/10 |
| 9 | P-2 | 10 | b-15 | 1 | HR-9 | 0.06 | N-8 | 0.15 | W-3 | 0.05 | SL-1/SL-6 | 70/30 |
| 10 | P-4 | 10 | b-18 | 1.2 | HR-26 | 0.06 | N-1 | 0.15 | W-1 | 0.05 | SL-1/SL-5 | 60/40 |
| 11 | P-1 | 10 | b-20 | 0.9 | HR-9 | 0.06 | N-3 | 0.15 | W-4 | 0.05 | SL-1/SL-5/SL-7 | 70/20/10 |
| 12 | P-3 | 10 | b-21 | 0.8 | HR-3 | 0.06 | N-5 | 0.15 | W-5 | 0.05 | SL-1/SL-5 | 70/30 |
| 13 | P-2 | 10 | b-22 | 1 | HR-24 | 0.06 | N-7 | 0.15 | W-6 | 0.05 | SL-3/SL-6 | 70/30 |
| 14 | P-3 | 10 | b-24 | 1 | HR-9 | 0.06 | N-2 | 0.15 | W-2 | 0.05 | SL-2/SL-7 | 90/10 |
| 15 | P-5 | 10 | b-26 | 1 | HR-26 | 0.06 | N-4 | 0.15 | W-3 | 0.05 | SL-1/SL-5 | 60/40 |
| 16 | P-1/P-6 | 5/5 | b-1 | 1 | HR-3 | 0.06 | N-6 | 0.15 | W-1 | 0.05 | SL-1/SL-6 | 60/40 |
| 17 | P-4 | 10 | b-3/b-22 | 0.6/0.4 | HR-24 | 0.06 | N-8 | 0.15 | W-4 | 0.05 | SL-1 | 100 |
| 18 | P-3 | 10 | b-6 | 1 | HR-83/HR-24 | 0.03/0.03 | N-3 | 0.15 | W-5 | 0.05 | SL-1/SL-5 | 80/20 |
| 19 | P-5 | 10 | b-34 | 0.8 | HR-9 | 0.06 | N-3/N-7 | 0.08/0.07 | W-6 | 0.05 | SL-1/SL-4 | 80/20 |
| 20 | P-6 | 10 | b-3 3 | 0.9 | HR-3 | 0.06 | N-4 | 0.15 | W-2/W-3 | 0.02/0.03 | SL-1/SL-5 | 70/30 |
| 21 | P-3 | 10 | b-21/z44 | 0.7/0.3 | HR-3 | 0.06 | N-4 | 0.15 | W-2 | 0.05 | SL-1/SL-6 | 70/30 |
| 22 | P-2 | 10 | b-18 | 1 | None | — | N-7 | 0.15 | W-3 | 0.05 | SL-2/SL-5 | 80/20 |
| 23 | P-3 | 10 | b-22 | 1 | HR-24 | 0.06 | N-4 | 0.15 | None | — | SL-3/SL-7 | 90/10 |
| 24 | P-1 | 10 | b-35 | 1 | HR-24 | 0.06 | N-6 | 0.15 | W-1 | 0.05 | SL-1/SL-5 | 60/40 |
| 25 | P-2 | 10 | b-36 | 1.2 | HR-9 | 0.06 | N-7 | 0.15 | W-4 | 0.05 | SL-1/SL-5 | 60/40 |
| 26 | P-2 | 10 | b-37 | 1.4 | HR-26 | 0.06 | N-5 | 0.15 | W-5 | 0.05 | SL-1/SL-6 | 60/40 |
| 27 | P-7 | 10 | b-38 | 1 | HR-9/HR-24 | 0.04/0.02 | N-1 | 0.15 | W-6 | 0.05 | SL-3/SL-6 | 70/30 |
| 28 | P-1/P-5 | 5/5 | b-39 | 1.1 | HR-3 | 0.06 | N-3 | 0.15 | W-2 | 0.05 | SL-1/SL-8 | 90/10 |
| 29 | P-3 | 10 | b-35/b-37 | 0.7/0.6 | HR-9 | 0.06 | N-7 | 0.15 | W-1 | 0.05 | SL-1/SL-5/SL-7 | 70/20/10 |

TABLE 4-continued

| Comparative Example | | | | | | | | | | | | |
|---|---|---|---|---|---|---|---|---|---|---|---|---|
| 1 | P-1 | 10 | Cb-1 | 1 | HR-24 | 0.06 | N-5 | 0.15 | W-3 | 0.05 | SL-1/SL-6 | 80/20 |
| 2 | P-1 | 10 | Cb-2 | 1 | HR-3 | 0.06 | N-6 | 0.15 | W-6 | 0.05 | SL-1/SL-5 | 60/40 |

| | Developer | (mass ratio) | Rinsing Solution | (mass ratio) | Sensitivity [mJ/cm$^2$] | Pre-Bridge Dimension [nm] | Line Edge Roughness [nm] | Development Time Dependency [nm/sec] |
|---|---|---|---|---|---|---|---|---|
| Example | | | | | | | | |
| 1 | SG-1 | 100 | SR-1 | 100 | 28.4 | 28 | 7.7 | 0.16 |
| 2 | SG-2 | 100 | SR-2 | 100 | 31.0 | 29 | 7.6 | 0.15 |
| 3 | SG-1 | 100 | SR-1/SR-3 | 80/20 | 29.2 | 28 | 7.7 | 0.17 |
| 4 | SG-3 | 100 | SR-5 | 100 | 30.5 | 28 | 7.6 | 0.16 |
| 5 | SG-1 | 100 | SR-3 | 100 | 30.1 | 28 | 7.6 | 0.17 |
| 6 | SG-5 | 100 | SR-1 | 100 | 25.3 | 32 | 7.9 | 0.18 |
| 7 | SG-6 | 100 | SR-2 | 100 | 27.7 | 31 | 7.9 | 0.18 |
| 8 | SG-2/SG-7 | 80/20 | SR-1 | 100 | 27.5 | 29 | 7.8 | 0.19 |
| 9 | SG-1/SG-3 | 60/40 | SR4/SR-4 | 70/30 | 30.1 | 30 | 8.0 | 0.18 |
| 10 | SG-1 | 100 | SR-1 | 100 | 28.8 | 29 | 7.9 | 0.19 |
| 11 | SG-1 | 100 | SR-1/SR-5 | 90/10 | 26.9 | 30 | 7.9 | 0.17 |
| 12 | SG-1/SG-2 | 40/60 | None | — | 25.6 | 28 | 7.9 | 0.19 |
| 13 | SG-3/SG-7 | 70/30 | SR-1 | 100 | 29.8 | 31 | 8.0 | 0.17 |
| 14 | SG-4 | 100 | SR-2 | 100 | 30.9 | 30 | 7.8 | 0.20 |
| 15 | SG-1/SG-7 | 90/10 | SR-1 | 100 | 32.0 | 31 | 7.8 | 0.18 |
| 16 | SG-2/SG-3 | 50/50 | SR-1/SR-3 | 70/30 | 27.4 | 28 | 7.6 | 0.16 |
| 17 | SG-1 | 100 | SR-1 | 100 | 30.1 | 29 | 7.8 | 0.18 |
| 18 | SG-3 | 100 | SR-2 | 100 | 28.6 | 28 | 7.9 | 0.17 |
| 19 | SG-2 | 100 | SR-1/SR-5 | 80/20 | 29.1 | 30 | 8.0 | 0.19 |
| 20 | SG-4 | 100 | SR-3 | 100 | 31.9 | 30 | 7.9 | 0.18 |
| 21 | SG-5 | 100 | SR-1 | 100 | 32.2 | 32 | 8.0 | 0.20 |
| 22 | SG-2 | 100 | SR-2 | 100 | 31.2 | 31 | 7.9 | 0.18 |
| 23 | SG-5 | 100 | SR-5 | 100 | 27.5 | 29 | 8.0 | 0.19 |
| 24 | SG-1 | 100 | SR-2 | 100 | 26.9 | 30 | 7.9 | 0.12 |
| 25 | SG-2 | 100 | SR-1 | 100 | 28.6 | 28 | 7.5 | 0.18 |
| 26 | SG-1 | 100 | SR-1/SR-4 | 70/30 | 31.9 | 28 | 7.3 | 0.18 |
| 27 | SG-3 | 100 | SR-1 | 100 | 27.5 | 30 | 7.8 | 0.17 |
| 28 | SG-1 | 100 | SR-1 | 100 | 30.1 | 29 | 7.6 | 0.16 |
| 29 | SG-6 | 100 | SR-3 | 100 | 29.8 | 29 | 7.4 | 0.13 |
| Comparative Example | | | | | | | | |
| 1 | SG-1 | 100 | SR-1 | 100 | 30.2 | 38 | 8.5 | 0.27 |
| 2 | SG-1 | 100 | SR-1 | 100 | 35.2 | 43 | 7.8 | 0.32 |

As apparent from the results in Table 4, in Comparative Example 1 not using an acid generator according to the present invention, the resolution (pre-bridge dimension), line edge roughness and development time dependency are poor. Also, in Comparative Example 2 using an acid generator where the cation moiety has an alkyl group as the substituent and the hydrophobicity is thereby enhanced, the line edge roughness is improved, but the sensitivity, resolution (pre-bridge dimension) and development time dependency are poor.

On the other hand, in Examples 1 to 29 using the acid generator according to the present invention, excellent performance is exhibited in all of resolution (pre-bridge dimension), line edge roughness and development time dependency.

Furthermore, in Examples 1 to 5 and 16 using an acid generator having an alcoholic hydroxyl group in the cation moiety, particularly excellent performance is exhibited in all of pre-bridge dimension, line edge roughness and development time dependency.

INDUSTRIAL APPLICABILITY

According to the present invention, a pattern forming method ensuring excellent performance in terms of resolution such as pre-bridge dimension, roughness such as line edge roughness, and development time dependency, and an actinic ray-sensitive or radiation-sensitive resin composition and a resist film each used for the pattern forming method, can be provided.

This application is based on Japanese patent application Nos. JP 2010-145618 filed on Jun. 25, 2010, and JP 2010-286766 filed on Dec. 22, 2010, the entire contents of which are hereby incorporated by reference, the same as if set forth at length.

The invention claimed is:
1. A pattern forming method, comprising:
(i) forming a film from an actinic ray-sensitive or radiation-sensitive resin composition that contains (A) a compound capable of generating an acid upon irradiation with an actinic ray or radiation and decomposing by an action of an acid to decrease a solubility of the compound (A) for an organic solvent, said compound being capable of decomposing an acid-decomposable structure;
(ii) exposing the film; and
(iii) performing development by using a developer containing an organic solvent, wherein the compound (A) is a compound represented by the following formula (II-4) or (II-5):

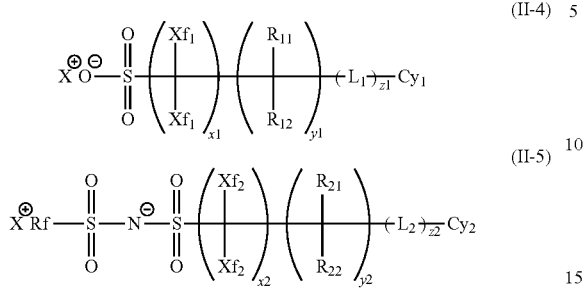

wherein each X⁺ independently represents a counter cation;
Rf represents an alkyl group having at least one fluorine atom, a cycloalkyl group having at least one fluorine atom, or an aryl group having at least one fluorine atom;
each of $Xf_1$ and $Xf_2$ independently represents a fluorine atom or an alkyl group substituted with at least one fluorine atom;
each of $R_{11}$, $R_{12}$, $R_{21}$ and $R_{22}$ independently represents a hydrogen atom, a fluorine atom or an alkyl group, and when a plurality of $R_{11}$'s, $R_{12}$'s, $R_{21}$'s or $R_{22}$'s are present, each may be the same as or different from every others;
each $L_1$ in formula (II-4) represents a divalent linking group selected from the group consisting of —COO—, —OCO—, —CO—, —O—, —S—, —SO—, —SO$_2$—, an alkylene group, a cycloalkylene group, an alkenylene group, and a linking group formed by combining a plurality of these members, provided that at least one of $L_1$ is —COO—, and when a plurality of $L_1$'s is present, each may be the same as or different from every other;
each $L_2$ in formula (II-5) represents a divalent linking group selected from the group consisting of —COO—, —OCO—, —CO—, —O—, —S—, —SO—, —SO$_2$—, an alkylene group, a cycloalkylene group, an alkenylene group, and a linking group formed by combining a plurality of these members, and when a plurality of $L_2$'s are present, each may be the same as or different from every other;
each of $Cy_1$ and $Cy_2$ independently represents an alicyclic group, an aryl group or a heterocyclic group;
provided that at least one of $Xf_1$, $R_{11}$, $R_{12}$, $L_1$ and $Cy_1$ is substituted with a group having a structure in which a moiety capable of decomposing by an action of an acid to produce an alcoholic hydroxyl group or a carboxyl group is protected with a leaving group capable of decomposing and leaving by an action of an acid; and that at least one of $Xf_2$, $R_{21}$, $R_{22}$, $L_2$, $Cy_2$ and Rf is substituted with a group having a structure in which a moiety capable of decomposing by an action of an acid to produce an alcoholic hydroxyl group or a carboxyl group is protected with a leaving group capable of decomposing and leaving by an action of an acid;
each of x1 and x2 independently represents an integer of 1 to 20;
each of y1 and y2 independently represents an integer of 0 to 10;
z1 represents an integer of 1 to 10; and
z2 represents an integer of 0 to 10;

wherein the moiety capable of decomposing by an action of an acid to produce a hydroxyl group or a carboxyl group is represented by at least one formula selected from the group consisting of the following formulas (I-1) and (I-5):

wherein
in formula (I-1), each $R_1$ independently represents a hydrogen atom or a monovalent organic group, and two $R_1$'s may combine with each other to form a ring; and $R_2$ represents a monovalent organic group, and one $R_1$ and $R_2$ may combine with each other to form a ring;
in formula (I-5), each $R_7$ independently represents a hydrogen atom or a monovalent organic group, and $R_7$'s may combine with each other to form a ring; and
in formulae (I-1) and (I-5), * represents a bond.

2. The pattern forming method according to claim 1, wherein the content of the organic solvent contained in the developer containing the organic solvent is from 90 to 100 mass % based on the entire amount of the developer.

3. The pattern forming method according to claim 1, wherein exposure in the step (ii) is immersion exposure.

4. The pattern forming method according to claim 1, wherein the developer containing an organic solvent is a developer containing at least one kind of an organic solvent selected from the group consisting of a ketone-based solvent, an ester-based solvent, an alcohol-based solvent, an amide-based solvent and an ether-based solvent.

5. The pattern forming method according to claim 1, wherein the moiety capable of decomposing by an action of an acid to produce a hydroxyl group or a carboxyl group is represented by formula (I-1).

6. The pattern forming method according to claim 1, wherein the resist composition further contains a resin including a repeating unit having a lactone structure and represented by the following formula (III):

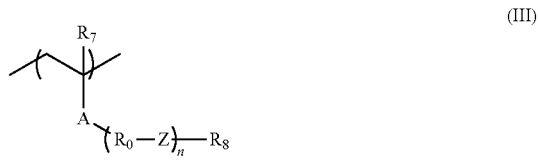

wherein A represents an ester bond of the structure —COO— or an amido bond of the structure —CONH—;
each $R_0$ independently represents an alkylene group, a cycloalkylene group or a combination thereof;

each Z independently represents a single bond, an ether bond, an ester bond, an amide bond, a urethane bond of the structure

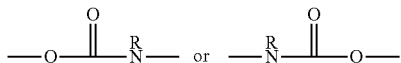

or a urea bond of the structure

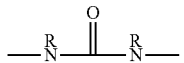

wherein each R independently represents a hydrogen atom, an alkyl group, a cycloalkyl group or an aryl group;
$R_8$ represents a monovalent organic group having a lactone structure;
n represents an integer of from 1 to 5; and
$R_7$ represents a hydrogen atom, a halogen atom or an alkyl group.

7. The pattern forming method according to claim 1, wherein the developer containing an organic solvent is butyl acetate.

8. A pattern forming method, comprising:
(i) forming a film from an actinic ray-sensitive or radiation-sensitive resin composition that contains (A) a compound capable of generating an acid upon irradiation with an actinic ray or radiation and decomposing by an action of an acid to decrease a solubility of the compound (A) for an organic solvent, said compound being capable of decomposing an acid-decomposable structure;
(ii) exposing the film; and
(iii) performing development by using a developer containing an organic solvent,
wherein the compound (A) is a compound represented by the following formula (II-4) or (II-5):

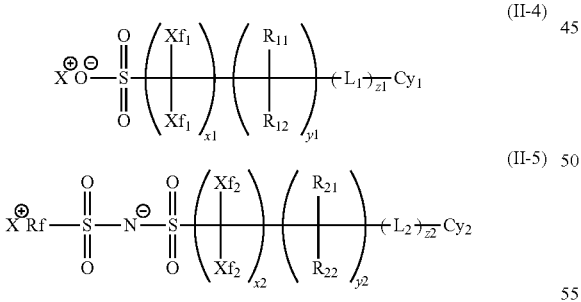

wherein each $X^+$ independently represents a counter cation;
Rf represents an alkyl group having at least one fluorine atom, a cycloalkyl group having at least one fluorine atom, or an aryl group having at least one fluorine atom;
each of $Xf_1$ and $Xf_2$ independently represents a fluorine atom or an alkyl group substituted with at least one fluorine atom;
each of $R_{11}$, $R_{12}$, $R_{21}$ and $R_{22}$ independently represents a hydrogen atom, a fluorine atom or an alkyl group, and when a plurality of $R_{11}$'s, $R_{12}$'s, $R_{21}$'s or $R_{22}$'s are present, each may be the same as or different from every others;
each $L_1$ in formula (II-4) represents a divalent linking group selected from the group consisting of —COO—, —OCO—, —S—, —SO—, —SO$_2$—, an alkylene group, a cycloalkylene group, an alkenylene group, and a linking group formed by combining a plurality of these members, and when a plurality of $L_1$'s is present, each may be the same as or different from every other;
each $L_2$ in formula (II-5) represents a divalent linking group selected from the group consisting of —COO—, —OCO—, —CO—, —O—, —S—, —SO—, —SO$_2$—, an alkylene group, a cycloalkylene group, an alkenylene group, and a linking group formed by combining a plurality of these members, and when a plurality of $L_2$'s are present, each may be the same as or different from every other;
each of $Cy_1$ and $Cy_2$ independently represents an alicyclic group, an aryl group or a heterocyclic group;
provided that at least one of $Xf_1$, $R_{11}$, $R_{12}$, $L_1$ and $Cy_1$ is substituted with a group having a structure in which a moiety capable of decomposing by an action of an acid to produce an alcoholic hydroxyl group or a carboxyl group is protected with a leaving group capable of decomposing and leaving by an action of an acid; and that at least one of $Xf_2$, $R_{21}$, $R_{22}$, $L_2$, $Cy_2$ and Rf is substituted with a group having a structure in which a moiety capable of decomposing by an action of an acid to produce an alcoholic hydroxyl group or a carboxyl group is protected with a leaving group capable of decomposing and leaving by an action of an acid;
each of x1 and x2 independently represents an integer of 1 to 20;
each of y1 and y2 independently represents an integer of 0 to 10; and
each of z1 and z2 independently represents an integer of 0 to 10;
wherein the moiety capable of decomposing by an action of an acid to produce a hydroxyl group or a carboxyl group is represented by at least one formula selected from the group consisting of the following formulas (I-1) and (I-5):

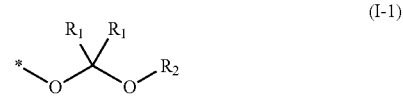

wherein
in formula (I-1), each $R_1$ independently represents a hydrogen atom or a monovalent organic group, and two $R_1$'s may combine with each other to form a ring; and
$R_2$ represents a monovalent organic group, and one $R_1$ and $R_2$ may combine with each other to form a ring;
in formula (I-5), each $R_7$ independently represents a hydrogen atom or a monovalent organic group, and $R_7$'s may combine with each other to form a ring; and
in formulae (I-1) and (I-5), * represents a bond.

9. The pattern forming method according to claim 1, wherein $Cy_1$ represents a heterocyclic group.

* * * * *